(12) United States Patent
Gonda et al.

(10) Patent No.: US 10,894,819 B2
(45) Date of Patent: Jan. 19, 2021

(54) COMPOSITIONS AND METHODS FOR TREATING HIV/AIDS WITH IMMUNOTHERAPY

(71) Applicant: LENTIGEN TECHNOLOGY, INC., Gaithersburg, MD (US)

(72) Inventors: Kim Anthony Gonda, Gaithersburg, MD (US); Dina Schneider, Potomac, MD (US); Rimas Orentas, Seattle, WA (US); Boro Dropulic, Ellicott City, MD (US)

(73) Assignee: LENTIGEN TECHNOLOGY, INC., Gaithersburg, MD (US)

( * ) Notice: Subject to any disclaimer, the term of this patent is extended or adjusted under 35 U.S.C. 154(b) by 0 days.

(21) Appl. No.: 16/228,077

(22) Filed: Dec. 20, 2018

(65) Prior Publication Data

US 2019/0202895 A1 Jul. 4, 2019

Related U.S. Application Data

(60) Provisional application No. 62/608,479, filed on Dec. 20, 2017, provisional application No. 62/660,819, filed on Apr. 20, 2018.

(51) Int. Cl.
| | | |
|---|---|---|
| *C07K 16/10* | (2006.01) | |
| *C07K 14/705* | (2006.01) | |
| *A61P 35/00* | (2006.01) | |
| *A61P 31/18* | (2006.01) | |
| *A61K 35/17* | (2015.01) | |
| *C07K 14/725* | (2006.01) | |
| *A61K 39/00* | (2006.01) | |
| *A61K 38/00* | (2006.01) | |

(52) U.S. Cl.
CPC .......... *C07K 16/1063* (2013.01); *A61K 35/17* (2013.01); *A61P 31/18* (2018.01); *A61P 35/00* (2018.01); *C07K 14/7051* (2013.01); *C07K 14/70517* (2013.01); *C07K 14/70578* (2013.01); *A61K 38/00* (2013.01); *A61K 2039/505* (2013.01); *C07K 2317/31* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC ............ C07K 14/7051; C07K 2319/03; C07K 2317/622; C12N 5/0636; C12N 2510/00; C12N 2501/515; C12N 5/0647; C12N 2501/2302; C12N 5/0638; C12N 2501/998; C12N 2510/02; C12N 2511/00; C12N 2501/23; C12N 2502/99; C12N 5/0646; C12N 9/1205; C12N 9/22; C12N 2502/11; C12N 2740/16043; C12N 15/00; C12N 15/102; C12N 15/86; C12N 15/87; C12N 2501/599; C12N 2740/15043; C12N 2740/16033; C12N 2740/16111; C12N 2800/22; C12N 2840/20; C12N 7/00; A61K 35/17; A61K 2039/5156; A61K 48/005; A61K 2039/5158; A61K 35/28; A61K 45/06; A61K 39/0011; A61K 2035/124; A61K 2039/585; A61K 38/00; A61K 39/21; A61K 2039/505; A61K 2039/572; A61K 31/675; A61K 38/1774; A61K 39/42; A61K 39/395; A61K 38/177; A61P 31/18; A61P 31/06; A61P 31/14; A61P 35/00
USPC ....................................................... 424/93.21
See application file for complete search history.

(56) References Cited

U.S. PATENT DOCUMENTS

| | | | |
|---|---|---|---|
| 2013/0108636 A1 * | 5/2013 | Dimitrov | C07K 16/1063 |
| | | | 424/134.1 |
| 2015/0037334 A1 * | 2/2015 | Kufer | C07K 16/2809 |
| | | | 424/134.1 |
| 2016/0039904 A1 | 2/2016 | Dimitrov | |
| 2017/0267739 A1 * | 9/2017 | Berger | A61K 48/005 |
| 2018/0208645 A1 | 7/2018 | Orentas | |

FOREIGN PATENT DOCUMENTS

| | | | | |
|---|---|---|---|---|
| WO | WO-0040616 A1 * | 7/2000 | | A61K 47/62 |
| WO | WO-2011146891 A2 * | 11/2011 | | C07K 16/1063 |
| WO | WO 2014150748 | 9/2014 | | |
| WO | WO-2014150748 A2 * | 9/2014 | | C07K 14/70514 |
| WO | WO 2015/017755 | 2/2015 | | |
| WO | WO 2015/077789 | 5/2015 | | |
| WO | WO 2016153572 | 9/2016 | | |

OTHER PUBLICATIONS

Hale, et al., "Engineering HIV-resistant, anti-HIV chimeric antigen receptor T cells," Mol. Ther., 2017, 25(3):570-579.

(Continued)

*Primary Examiner* — Janet L Epps-Smith

(74) *Attorney, Agent, or Firm* — Serge Sira, Esq.; Gregory J. Hwa, Esq.; Fish & Richardson P.C.

(57) ABSTRACT

Chimeric antigen receptors (CARs) containing HIV envelope antigen binding domains are disclosed. Nucleic acids, recombinant expression vectors, host cells, antigen binding fragments, and pharmaceutical compositions, relating to the CARs are also disclosed. Methods of treating or preventing HIV-infection in a subject, and methods of making CAR T cells are also disclosed. Results of treating or preventing HIV-infection, and results of making CAR T cells are also disclosed.

18 Claims, 62 Drawing Sheets

Specification includes a Sequence Listing.

(56) References Cited

OTHER PUBLICATIONS

International Search Report and Written Opinion in PCT Application No. PCT/US2018/066744, dated Jun. 10, 2019, 14 pages.
Liu, et al., "Novel CD4-based bispecific chimeric antigen receptor designed for enhanced anti-HIV potency and absence of HIV entry receptor activity," J. Virol., 2015, 89(13):6685-6694.
PCT International Preliminary Report on Patentability in International Application. No. PCT/US2018/066744, dated Jun. 23, 2020, 10 pages.
Chen, et al., "Exceptionally Potent and Broadly Cross Reactive, Bispecific Multivalent HIV-1 Inhibitors Based on Single Human CD4 and Antibody Domains," J. Virol., 2014, 88(2):1125-1139.
Qi et al., "HIV-1 gp41-targeting fusion inhibitory peptides enhance the gp120-targeting protein-mediated inactivation of HIV-1 virions" Emerging Microbes & Infections, 2017, 6(6):e59.
Wilkie, et al., "Dual targeting of ErbB2 and MUC1 in breast cancer using chimeric antigen receptors engineered to provide complementary signaling," J. Clin. Immunol., 2012, 32:1059-1070.

* cited by examiner

FIG. 1
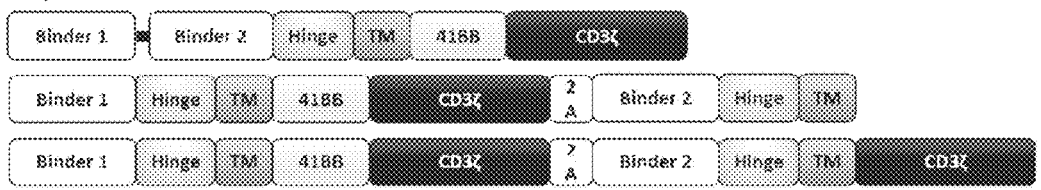
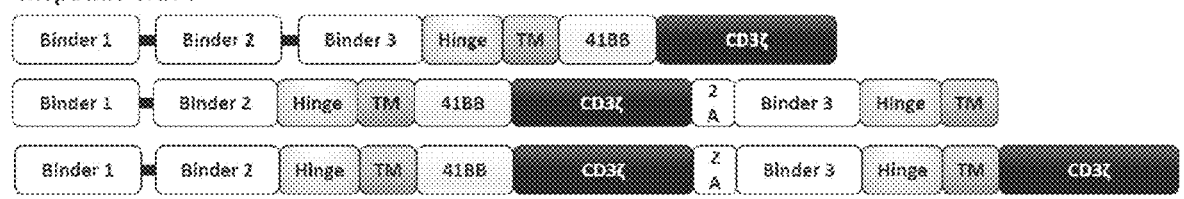

FIG. 2A

LTG1944: LP-mD1.22-CD8TM-41BB-CD3zeta nucleic acid sequence (SEQ ID NO: 39)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGA GGACTCGGATACCTACATCTGCGAA
GTGGAGGACCAGAAGGAGGAGGTGCAGCTGGTGGTGGTGGGGGCGGCCGCAAC
TACCACCCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCTGAGGAGGAAGAGGGGGGATGCGAA
CTGCGCGTCAAGTTCTCACGGTCCGCCGACGCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAA
CTCCAGAAAGACAAGATGGCGGAAGCCTACTCAGAAATCGGGATGAAGGGAGA
GCGGAGGAGGGGAAAGGGTCACGACGGGCTGTACCAGGGACTGAGCACCGCCA
CTAAGGATACCTACGATGCCTTGCATATGCAAGCACTCCACCCCGGTAG

LTG1944: LP-mD1.22-CD8TM-41BB-CD3zeta amino acid sequence (SEQ ID NO: 40)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGAAATTTPAPRPPTPAPTIASQPLSLRPEACRPAAGGAVHTRGLDFACDIY
IWAPLAGTCGVLLLSLVITLYCKRGRKKL LYIFKQPFMRPVQTTQEEDGCSCRFPEEE
EGGCELRVKFSRSADAPAYQQGQNQLYNELNLGRREEYDVLDKRRGRDPEMGGKP
RRKNPQEGLYNELQKDKMAEAYSEIGM KGERRRGKGHDGLYQGLSTATKDTYDAL
HMQALPPR

FIG. 2B

LTG1945: LP-m36.4-CD8TM-41BB-CD3zeta nucleic acid sequence (SEQ ID NO: 41)

ATGCTTCTCCTGGTCACCTCCCTGCTCCTCTGCGAACTGCCTCACCCTGCCTTCCT
TCTGATTCCTGACACCCAGGTGCAGCTGGTGCAGTCTGGGGGAGGCTTGGTACA
GCCTGGAGGGTCCCTGAGACTCTCCTGTGCAGCCTCTGCTTTCGATTTCTCTGATT
ATGAAATGAGCTGGGTCCGCGAGGCTCCAGGGAAGGGGCTGGAGTGGATTGGG
GAAATCAATGATAGTGGAAACACCATTTACAATCCGTCCCTCAAGAGTCGAGTC
ACCATCTCCAGAGACAATTCCAAGAACACACTGTATCTGCAAATGAACACCCTG
AGAGCCGAGGACACAGCCATATATTACTGTGCGATATATGGTGGTAACTCCGGG
GGAGAGTACTGGGGCCAGGGCACCCTGGTCACCGTCTCCTCAGCGGCCGCAACT
ACCACCCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAACTCCAGAAAGACAAGATGGCGGAAGCCT
ACTCAGAAATCGGGATGAAGGGAGAGCGGAGGAGGGAAAGGGTCACGACGGG
CTGTACCAGGGACTGAGCACCGCCACTAAGGATACCTACGATGCCTTGCATATG
CAAGCACTCCCACCCCGGTAG

LTG1945: LP-m36.4-CD8TM-41BB-CD3zeta amino acid sequence (SEQ ID NO: 42)

MLLLVTSLLLCELPHPAFLLIPDTQVQLVQSGGGLVQPGGSLRLSCAASAFDFSDYE
MSWVREAPGKGLEWIGEINDSGNTIYNPSLKSRVTISRDNSKNTLYLQMNTLRAEDT
AIYYCAIYGGNSGGEYWGQGTLVTVSSAAATTTPAPRPPTPAPTIASQPLSLRPEACR
PAAGGAVHTRGLDFACDIYIWAPLAGTCGVLLLSLVITLYCKRGRKKLLYIFKQPFM
RPVQTTQEEDGCSCRFPEEEEGGCELRVKFSRSADAPAYQQGQNQLYNELNLGRRE
EYDVLDKRRGRDPEMGGKPRRKNPQEGLYNELQKDKMAEAYSEIGMKGERRRGK
GHDGLYQGLSTATKDTYDALHMQALPPR

FIG. 2C

LTG2328: LP-C46-CD8TM-41BB-CD3zeta nucleic acid sequence (SEQ ID NO: 43)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGCGGCCGC
AACTACCACCCCTGCCCCTCGGCCGCCGACTCCGGCCCCAACCATCGCAAGCCA
ACCCCTCTCCTTGCGCCCCGAAGCTTGCCGCCCGGCCGCGGGTGGAGCCGTGCAT
ACCCGGGGGCTGGACTTTGCCTGCGATATCTACATTTGGGCCCCGCTGGCCGGCA
CTTGCGGCGTGCTCCTGCTGTCGCTGGTCATCACCCTTTACTGCAAGAGGGGCCG
GAAGAAGCTGCTTTACATCTTCAAGCAGCCGTTCATGCGGCCCGTGCAGACGAC
TCAGGAAGAGGACGGATGCTCGTGCAGATTCCCTGAGGAGGAAGAGGGGGGAT
GCGAACTGCGCGTCAAGTTCTCACGGTCCGCCGACGCCCCCGCATATCAACAGG
GCCAGAATCAGCTCTACAACGAGCTGAACCTGGGAAGGAGAGAGGAGTACGAC
GTGCTGGACAAGCGACGCGGACGCGACCCGGAGATGGGGGGGAAACCACGGCG
GAAAAACCCTCAGGAAGGACTGTACAACGAACTCCAGAAAGACAAGATGGCGG
AAGCCTACTCAGAAATCGGGATGAAGGGAGAGCGGAGGAGGGGAAAGGGTCAC
GACGGGCTGTACCAGGGACTGAGCACCGCCACTAAGGATACCTACGATGCCTTG
CATATGCAAGCACTCCCACCCCGGTAG

LTG2328: LP-C46-CD8TM-41BB-CD3zeta amino acid sequence (SEQ ID NO: 44)

MLLLVTSLLLCELPHPAFLLIPDTWMEWDREINNYTSLIHSLIEESQNQQEKNEQELL
ELDKWASLWNWFAAATTTPAPRPPTPAPTIASQPLSLRPEACRPAAGGAVHTRGLDF
ACDIYIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRRGRDPE
MGGKPRRKNPQEGLYNELQKDKMAEAYSEIGMKGERRRGKGHDGLYQGLSTATK
DTYDALHMQALPPR

FIG. 2D

LTG2325: LP-mD1.22-L1-m36.4-CD8TM-41BB-CD3zeta nucleic acid sequence (SEQ ID NO: 47)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGA GGACTCGGATACCTACATCTGCGAA
GTGGAGGACCAGAAGGAGGAGGTGCAGCTGGTGGTGGTGGGCGGCGGAGGCGG
GTCACAGGTGCAGCTGGTGCAGTCTGGGGGAGGCTTGGTACAGCCTGGAGGGTC
CCTGAGACTCTCCTGTGCAGCCTCTGCTTTCGATTTCTCTGATTATGAAATGAGCT
GGGTCCGCGAGGCTCCAGGGAAGGGGCTGGAGTGGATTGGGGAAATCAATGAT
AGTGGAAACACCATTTACAATCCGTCCCTCAAGAGTCGAGTCACCATCTCCAGA
GACAATTCCAAGAACACACTGTATCTGCAAATGAACACCCTGAGAGCCGAGGAC
ACAGCCATATATTACTGTGCGATATATGGTGGTAACTCCGGGGGAGAGTACTGG
GGCCAGGGCACCCTGGTCACCGTCTCCTCAGCGGCCGCAACTACCACCCCTGCCC
CTCGGCCGCCGACTCCGGCCCCAACCATCGCAAGCCAACCCCTCTCCTTGCGCCC
CGAAGCTTGCCGCCCGGCCGCGGGTGGAGCCGTGCATACCCGGGGGCTGGACTT
TGCCTGCGATATCTACATTTGGGCCCCGCTGGCCGGCACTTGCGGCGTGCTCCTG
CTGTCGCTGGTCATCACCCTTTACTGCAAGAGGGGCCGGAAGAAGCTGCTTTACA
TCTTCAAGCAGCCGTTCATGCGGCCCGTGCAGACGACTCAGGAAGAGGACGGAT
GCTCGTGCAGATTCCCTGAGGAGGAAGAGGGGGGATGCGAACTGCGCGTCAAGT
TCTCACGGTCCGCCGACGCCCCCGCATATCAACAGGGCCAGAATCAGCTCTACA
ACGAGCTGAACCTGGGAAGGAGAGAGGAGTACGACGTGCTGGACAAGCGACGC
GGACGCGACCCGGAGATGGGGGGGAAACCACGGCGGAAAAACCCTCAGGAAGG
ACTGTACAACGAACTCCAGAAAGACAAGATGGCGGAAGCCTACTCAGAAATCG
GGATGAAGGGAGAGCGGAGGAGGGGAAAGGGTCACGACGGGCTGTACCAGGGA
CTGAGCACCGCCACTAAGGATACCTACGATGCCTTGCATATGCAAGCACTCCCA
CCCCGGTAG

LTG2325: LP-mD1.22-L1-m36.4-CD8TM-41BB-CD3zeta amino acid sequence (SEQ ID NO: 48)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSQVQLVQSGGGLVQPGGSLRLSCAASAFDFSDYEMSWVREAPG
KGLEWIGEINDSGNTIYNPSLKSRVTISRDNSKNTLYLQMNTLRAEDTAIYYCAIYGG
NSGGEYWGQGTLVTVSSAAATTTPAPRPPTPAPTIASQPLSLRPEACRPAAGGAVHT
RGLDFACDIYIWAPLAGTCGVLLLSLVITLYCKRGRKKLLYIFKQPFMRPVQTTQEED
GCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLST
ATKDTYDALHMQALPPR

FIG. 2E

LTG2313: LP-mD1.22-L2-m36.4-CD8TM-41BB-CD3zeta nucleic acid sequence (SEQ ID NO: 51)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGAGGTGGCGG
TTCAGGCGGAGGGGGGAGTCAGGTGCAGCTGGTGCAGTCTGGGGGAGGCTTGGT
ACAGCCTGGAGGGTCCCTGAGACTCTCCTGTGCAGCCTCTGCTTTCGATTTCTCT
GATTATGAAATGAGCTGGGTCCGCGAGGCTCCAGGGAAGGGGCTGGAGTGGATT
GGGGAAATCAATGATAGTGGAAACACCATTTACAATCCGTCCCTCAAGAGTCGA
GTCACCATCTCCAGAGACAATTCCAAGAACACACTGTATCTGCAAATGAACACC
CTGAGAGCCGAGGACACAGCCATATATTACTGTGCGATATATGGTGGTAACTCC
GGGGGAGAGTACTGGGGCCAGGGCACCCTGGTCACCGTCTCCTCAGCGGCCGCA
ACTACCACCCCTGCCCCTCGGCCGCCGACTCCGGCCCCAACCATCGCAAGCCAA
CCCCTCTCCTTGCGCCCCGAAGCTTGCCGCCCGGCCGCGGGTGGAGCCGTGCATA
CCCGGGGGCTGGACTTTGCCTGCGATATCTACATTTGGGCCCCGCTGGCCGGCAC
TTGCGGCGTGCTCCTGCTGTCGCTGGTCATCACCCTTTACTGCAAGAGGGGCCGG
AAGAAGCTGCTTTACATCTTCAAGCAGCCGTTCATGCGGCCCGTGCAGACGACTC
AGGAAGAGGACGGATGCTCGTGCAGATTCCCTGAGGAGGAAGAGGGGGATGC
GAACTGCGCGTCAAGTTCTCACGGTCCGCCGACGCCCCGCATATCAACAGGGC
CAGAATCAGCTCTACAACGAGCTGAACCTGGGAAGGAGAGAGGAGTACGACGT
GCTGGACAAGCGACGCGGACGCGACCCGGAGATGGGGGGGAAACCACGGCGGA
AAAACCCTCAGGAAGGACTGTACAACGAACTCCAGAAAGACAAGATGGCGGAA
GCCTACTCAGAAATCGGGATGAAGGGAGAGCGGAGGAGGGGAAAGGGTCACGA
CGGGCTGTACCAGGGACTGAGCACCGCCACTAAGGATACCTACGATGCCTTGCA
TATGCAAGCACTCCCACCCCGGTAG

LTG2313: LP-mD1.22-L2-m36.4-CD8TM-41BB-CD3zeta amino acid sequence (SEQ ID NO: 52)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSQVQLVQSGGGLVQPGGSLRLSCAASAFDFSDYEMSWV
REAPGKGLEWIGEINDSGNTIYNPSLKSRVTISRDNSKNTLYLQMNTLRAEDTAIYYC
AIYGGNSGGEYWGQGTLVTVSSAAATTTPAPRPPTPAPTIASQPLSLRPEACRPAAGG
AVHTRGLDFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGL
YQGLSTATKDTYDALHMQALPPR

FIG. 2F

LTG1946 LP-mD1.22-L3-m36.4-CD8TM-41BB-CD3zeta nucleic acid sequence (SEQ ID NO: 55)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGAGGTGGCGG
TTCAGGCGGAGGGGGGAGTGGAGGTGGGGGAAGCCAGGTGCAGCTGGTGCAGT
CTGGGGGAGGCTTGGTACAGCCTGGAGGGTCCCTGAGACTCTCCTGTGCAGCCT
CTGCTTTCGATTTCTCTGATTATGAAATGAGCTGGGTCCGCGAGGCTCCAGGGAA
GGGGCTGGAGTGGATTGGGGAAATCAATGATAGTGGAAACACCATTTACAATCC
GTCCCTCAAGAGTCGAGTCACCATCTCCAGAGACAATTCCAAGAACACACTGTA
TCTGCAAATGAACACCCTGAGAGCCGAGGACACAGCCATATATTACTGTGCGAT
ATATGGTGGTAACTCCGGGGGAGAGTACTGGGGCCAGGGCACCCTGGTCACCGT
CTCCTCAGCGGCCGCAACTACCACCCCTGCCCCTCGGCCGCCGACTCCGGCCCCA
ACCATCGCAAGCCAACCCCTCTCCTTGCGCCCCGAAGCTTGCCGCCCGGCCGCGG
GTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTAC
TGCAAGAGGGGCCGGAAGAAGCTGCTTTACATCTTCAAGCAGCCGTTCATGCGG
CCCGTGCAGACGACTCAGGAAGAGGACGGATGCTCGTGCAGATTCCCTGAGGAG
GAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAG
AGAGGAGTACGACGTGCTGGACAAGCGACGCGGACGCGACCCGGAGATGGGGG
GGAAACCACGGCGGAAAAACCCTCAGGAAGGACTGTACAACGAACTCCAGAAA
GACAAGATGGCGGAAGCCTACTCAGAAATCGGGATGAAGGGAGAGCGGAGGAG
GGGAAAGGGTCACGACGGGCTGTACCAGGGACTGAGCACCGCCACTAAGGATA
CCTACGATGCCTTGCATATGCAAGCACTCCCACCCCGGTAG

LTG1946: LP-mD1.22-L3-m36.4-CD8TM-41BB-CD3zeta amino acid sequence (SEQ ID NO: 56)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSQVQLVQSGGGLVQPGGSLRLSCAASAFDFSDY
EMSWVREAPGKGLEWIGEINDSGNTIYNPSLKSRVTISRDNSKNTLYLQMNTLRAED
TAIYYCAIYGGNSGGEYWGQGTLVTVSSAAATTTPAPRPPTPAPTIASQPLSLRPEAC
RPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGERRRG
KGHDGLYQGLSTATKDTYDALHMQALPPR

FIG. 2G

LTG2326: LP-mD1.22-L4-m36.4-CD8TM-41BB-CD3zeta nucleic acid sequence (SEQ ID NO: 59)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGCGGAGGCGG
GTCAGGTGGCGGTGGTAGTGGCGGTGGCGGTTCAGGCGGTGGTGGGAGTCAGGT
GCAGCTGGTGCAGTCTGGGGGAGGCTTGGTACAGCCTGGAGGGTCCCTGAGACT
CTCCTGTGCAGCCTCTGCTTTCGATTTCTCTGATTATGAAATGAGCTGGGTCCGCG
AGGCTCCAGGGAAGGGGCTGGAGTGGATTGGGGAAATCAATGATAGTGGAAAC
ACCATTTACAATCCGTCCCTCAAGAGTCGAGTCACCATCTCCAGAGACAATTCCA
AGAACACACTGTATCTGCAAATGAACACCCTGAGAGCCGAGGACACAGCCATAT
ATTACTGTGCGATATATGGTGGTAACTCCGGGGGAGAGTACTGGGGCCAGGGCA
CCCTGGTCACCGTCTCCTCAGCGGCCGCAACTACCACCCCTGCCCCTCGGCCGCC
GACTCCGGCCCCAACCATCGCAAGCCAACCCCTCTCCTTGCGCCCCGAAGCTTGC
CGCCCGGCCGCGGGTGGAGCCGTGCATACCCGGGGGCTGGACTTTGCCTGCGAT
ATCTACATTTGGGCCCCGCTGGCCGGCACTTGCGGCGTGCTCCTGCTGTCGCTGG
TCATCACCCTTTACTGCAAGAGGGGCCGGAAGAAGCTGCTTTACATCTTCAAGCA
GCCGTTCATGCGGCCCGTGCAGACGACTCAGGAAGAGGACGGATGCTCGTGCAG
ATTCCCTGAGGAGGAAGAGGGGGGATGCGAACTGCGCGTCAAGTTCTCACGGTC
CGCCGACGCCCCCGCATATCAACAGGGCCAGAATCAGCTCTACAACGAGCTGAA
CCTGGGAAGGAGAGAGGAGTACGACGTGCTGGACAAGCGACGCGGACGCGACC
CGGAGATGGGGGGGAAACCACGGCGGAAAAACCCTCAGGAAGGACTGTACAAC
GAACTCCAGAAAGACAAGATGGCGGAAGCCTACTCAGAAATCGGGATGAAGGG
AGAGCGGAGGAGGGGAAAGGGTCACGACGGGCTGTACCAGGGACTGAGCACCG
CCACTAAGGATACCTACGATGCCTTGCATATGCAAGCACTCCCACCCCGGTAG

LTG2326 LP-mD1.22-L4-m36.4-CD8TM-41BB-CD3zeta amino acid sequence (SEQ ID NO: 60)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSQVQLVQSGGGLVQPGGSLRLSCAASAF
DFSDYEMSWVREAPGKGLEWIGEINDSGNTIYNPSLKSRVTISRDNSKNTLYLQMNT
LRAEDTAIYYCAIYGGNSGGEYWGQGTLVTVSSAAATTTPAPRPPTPAPTIASQPLSL
RPEACRPAAGGAVHTRGLDFACDIYIWAPLAGTCGVLLLSLVITLYCKRGRKKLLYI
FKQPFMRPVQTTQEEDGCSCRFPEEEEGGCELRVKFSRSADAPAYQQGQNQLYNEL
NLGRREEYDVLDKRRGRDPEMGGKPRRKNPQEGLYNELQKDKMAEAYSEIGMKGE
RRRGKGHDGLYQGLSTATKDTYDALHMQALPPR

FIG. 2H

LTG1947: LP-mD1.22-L5-m36.4-CD8TM-41BB-CD3zeta nucleic acid sequence (SEQ ID NO: 63)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGCGGAGGCGG
GTCAGGTGGCGGTGGTAGTGGCGGTGGCGGTTCAGGCGGTGGTGGGAGTGGGGG
AGGAGGCAGCCAGGTGCAGCTGGTGCAGTCTGGGGGAGGCTTGGTACAGCCTGG
AGGGTCCCTGAGACTCTCCTGTGCAGCCTCTGCTTTCGATTTCTCTGATTATGAAA
TGAGCTGGGTCCGCGAGGCTCCAGGGAAGGGGCTGGAGTGGATTGGGGAAATCA
ATGATAGTGGAAACACCATTTACAATCCGTCCCTCAAGAGTCGAGTCACCATCTC
CAGAGACAATTCCAAGAACACACTGTATCTGCAAATGAACACCCTGAGAGCCGA
GGACACAGCCATATATTACTGTGCGATATATGGTGGTAACTCCGGGGGAGAGTA
CTGGGGCCAGGGCACCCTGGTCACCGTCTCCTCAGCGGCCGCAACTACCACCCCT
GCCCCTCGGCCGCCGACTCCGGCCCCAACCATCGCAAGCCAACCCCTCTCCTTGC
GCCCCGAAGCTTGCCGCCCGGCCGCGGGTGGAGCCGTGCATACCCGGGGGCTGG
ACTTTGCCTGCGATATCTACATTTGGGCCCCGCTGGCCGGCACTTGCGGCGTGCT
CCTGCTGTCGCTGGTCATCACCCTTTACTGCAAGAGGGGCCGGAAGAAGCTGCTT
TACATCTTCAAGCAGCCGTTCATGCGGCCCGTGCAGACGACTCAGGAAGAGGAC
GGATGCTCGTGCAGATTCCTGAGGAGGAAGAGGGGGGATGCGAACTGCGCGTC
AAGTTCTCACGGTCCGCCGACGCCCCCGCATATCAACAGGGCCAGAATCAGCTC
TACAACGAGCTGAACCTGGGAAGGAGAGAGGAGTACGACGTGCTGGACAAGCG
ACGCGGACGCGACCCGGAGATGGGGGGGAAACCACGGCGGAAAAACCCTCAGG
AAGGACTGTACAACGAACTCCAGAAAGACAAGATGGCGGAAGCCTACTCAGAA
ATCGGGATGAAGGGAGAGCGGAGGAGGGGAAAGGGTCACGACGGGCTGTACCA
GGGACTGAGCACCGCCACTAAGGATACCTACGATGCCTTGCATATGCAAGCACT
CCCACCCCGGTAGCCTAGGATTTGTACGCGTAATCAACCTCTGGATTACAAAATT
TGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTC
CTCCTTGTATAAATCCTGGTTGCTGTCTCTTTATGAGGAGTTGTGGCCCGTTGTCA
GGCAACGTGGCGTGGTGTGCACTGTGTTTGCTGA

LTG1947: LP-mD1.22-L5-m36.4-CD8TM-41BB-CD3zeta amino acid sequence (SEQ ID NO: 64)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSGGGGSQVQLVQSGGGLVQPGGSLRLSC
AASAFDFSDYEMSWVREAPGKGLEWIGEINDSGNTIYNPSLKSRVTISRDNSKNTLY
LQMNTLRAEDTAIYYCAIYGGNSGGEYWGQGTLVTVSSAAATTTPAPRPPTPAPTIA
SQPLSLRPEACRPAAGGAVHTRGLDFACDIYIWAPLAGTCGVLLLSLVITLYCKRGR
KKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEI
GMKGERRRGKGHDGLYQGLSTATKDTYDALHMQALPPR

FIG. 21

LTG1948: LP-m36.4-L3-mD1.22-CD8TM-41BB-CD3zeta nucleic acid sequence (SEQ ID NO: 67)

ATGCTTCTCCTGGTCACCTCCCTGCTCCTCTGCGAACTGCCTCACCCTGCCTTCCT
TCTGATTCCTGACACCCAGGTGCAGCTGGTGCAGTCTGGGGGAGGCTTGGTACA
GCCTGGAGGGTCCCTGAGACTCTCCTGTGCAGCCTCTGCTTTCGATTTCTCTGATT
ATGAAATGAGCTGGGTCCGCGAGGCTCCAGGGAAGGGGCTGGAGTGGATTGGG
GAAATCAATGATAGTGGAAACACCATTTACAATCCGTCCCTCAAGAGTCGAGTC
ACCATCTCCAGAGACAATTCCAAGAACACACTGTATCTGCAAATGAACACCCTG
AGAGCCGAGGACACAGCCATATATTACTGTGCGATATATGGTGGTAACTCCGGG
GGAGAGTACTGGGGCCAGGGCACCCTGGTCACCGTCTCCTCAGGAGGTGGCGGT
TCAGGCGGAGGGGGGAGTGGAGGTGGGGGAAGCAAGAAAGTCGTGTACGGAAA
GAAGGGAGACACTGTGGAGCTGACCTGTACCGCAAGCCAGAAGAAGAACATCC
AGTTCCACTGGAAGAACTCCAACCAAATCAAGATCCTGGGGAACCAGGGTTCCT
TCCTGACTAAGGGACCCTCAAAGCTGAACGACCGCGTGGATAGCAGACGCTCCC
TGTGGGACCAGGGAAACTTCCCGCTTATCATTAAGAACCTCAAACCTGAGGACT
CGGATACCTACATCTGCGAAGTGGAGGACCAGAAGGAGGAGGTGCAGCTGGTG
GTGGTGGGCGCGGCCGCAACTACCACCCCTGCCCCTCGGCCGCCGACTCCGGCC
CCAACCATCGCAAGCCAACCCCTCTCCTTGCGCCCCGAAGCTTGCCGCCCGGCCG
CGGGTGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTTCATG
CGGCCCGTGCAGACGACTCAGGAAGAGGACGGATGCTCGTGCAGATTCCCTGAG
GAGGAAGAGGGGGGATGCGAACTGCGCGTCAAGTTCTCACGGTCCGCCGACGCC
CCCGCATATCAACAGGGCCAGAATCAGCTCTACAACGAGCTGAACCTGGGAAGG
AGAGAGGAGTACGACGTGCTGGACAAGCGACGCGGACGCGACCCGGAGATGGG
GGGGAAACCACGGCGGAAAAACCCTCAGGAAGGACTGTACAACGAACTCCAGA
AAGACAAGATGGCGGAAGCCTACTCAGAAATCGGGATGAAGGGAGAGCGGAGG
AGGGGAAAGGGTCACGACGGGCTGTACCAGGGACTGAGCACCGCCACTAAGGA
TACCTACGATGCCTTGCATATGCAAGCACTCCCACCCCGGTAG

LTG1948: LP-m36.4-L3-mD1.22-CD8TM-41BB-CD3zeta amino acid sequence (SEQ ID NO: 68)

MLLLVTSLLLCELPHPAFLLIPDTQVQLVQSGGGLVQPGGSLRLSCAASAFDFSDYE
MSWVREAPGKGLEWIGEINDSGNTIYNPSLKSRVTISRDNSKNTLYLQMNTLRAEDT
AIYYCAIYGGNSGGEYWGQGTLVTVSSGGGGSGGGGSGGGGSKKVVYGKKGDTVE
LTCTASQKKNIQFHWKNSNQIKILGNQGSFLTKGPSKLNDRVDSRRSLWDQGNFPLII
KNLKPEDSDTYICEVEDQKEEVQLVVVGAAATTTPAPRPPTPAPTIASQPLSLRPEAC
RPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGERRRG
KGHDGLYQGLSTATKDTYDALHMQALPPR

FIG. 2J

LTG2303: LP-mD1.22-CD8TM-41BB-CD3zeta-F2AF-LP2-m36.4-TNFRSF19TM-CD3zeta2 nucleic acid sequence (SEQ ID NO: 71)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGGGCGGCCGCAAC
TACCACCCTGCCCCTCGGCCGCCGACTCCGGCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAACTCCAGAAAGACAAGATGGCGGAAGCCT
ACTCAGAAATCGGGATGAAGGGAGAGCGGAGGAGGGGAAAGGGTCACGACGGG
CTGTACCAGGGACTGAGCACCGCCACTAAGGATACCTACGATGCCTTGCATATG
CAAGCACTCCCACCCCGGCGCGCGAAACGCAGCGGCAGCGGCGCGACCAACTTT
AGCCTGCTGAAACAGGCGGGCGATGTGGAAGAAAACCCGGGCCCGCGAGCAAA
GAGGATGGGAATTCAGGGGGGTTCCGTGCTCTTTGGCTTGCTCCTGGTCCTGGCA
GTGTTTTGTCACTCGGGACACAGCCTGCAGCAGGTGCAGCTGGTGCAGTCTGGG
GGAGGCTTGGTACAGCCTGGAGGGTCCCTGAGACTCTCCTGTGCAGCCTCTGCTT
TCGATTTCTCTGATTATGAAATGAGCTGGGTCCGCGAGGCTCCAGGGAAGGGGC
TGGAGTGGATTGGGGAAATCAATGATAGTGGAAACACCATTTACAATCCGTCCC
TCAAGAGTCGAGTCACCATCTCCAGAGACAATTCCAAGAACACACTGTATCTGC
AAATGAACACCCTGAGAGCCGAGGACACAGCCATATATTACTGTGCGATATATG
GTGGTAACTCCGGGGGAGAGTACTGGGGCCAGGGCACCCTGGTCACCGTCTCCT
CACCGGCTCCACGACCACCCACTCCAGCCCCAACGATTGCGAGCCAACCTCTCA
GTCTTCGGCCCGAGGCTTGCAGGCCAGCCGCAGGAGGAGCAGTGCACACCCGAG
GACTGGATTTCGATACCGCACTGGCGGCCGTGATCTGTAGCGCCCTGGCCACCGT
GCTGCTGGCGCTGCTCATCCTTTGCGTGATCTACTGCAAGCGGCAGCGGGTTAAA
TTCTCCCGCAGCGCAGACGCACCCGCCTACCAGCAAGGACAGAATCAGCTCTAC
AACGAACTGAACCTTGGTAGGAGAGAAGAATATGATGTTCTCGACAAGCGCAGA
GGGAGAGATCCAGAGATGGGTGGGAAGCCGCAACGCCGGAAAAACCCACAAGA
GGGACTGTACAATGAATTGCAGAAAGATAAGATGGCCGAGGCTTACTCAGAAAT
CGGAATGAAGGGGGAGCGGCGGAGGGGCAAGGGACATGATGGTCTCTACCAAG
GGCTTTCAACCGCTACTAAGGACACTTATGACGCACTCCACATGCAGGCGCTGCC
TCCGCGATAA

LTG2303: LP-mD1.22-CD8TM-41BB-CD3zeta-F2AF-LP2-m36.4-TNFRSF19TM-CD3zeta2 amino acid sequence (SEQ ID NO: 72)

FIG. 2J cont.

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGAAATTTPAPRPPTPAPTIASQPLSLRPEACRPAAGGAVHTRGLDFACDIY
IWAPLAGTCGVLLLSLVITLYCKRGRKKL LYIFKQPFMRPVQTTQEEDGCSCRFPEEE
EGGCELRVKFSRSADAPAYQQGQNQLYNELNLGRREEYDVLDKRRGRDPEMGGKP
RRKNPQEGLYNELQKDKMAEAYSEIGM KGERRRGKGHDGLYQGLSTATKDTYDAL
HMQALPPRRAKRSGSGATNFSLLKQAGDVEENPGPRAKRMGIQGGSVLFGLLLVLA
VFCHSGHSLQQVQLVQSGGGLVQPGGSLRLSCAASAFDFSDYEMSWVREAPGKGLE
WIGEINDSGNTIYNPSLKSRVTISRDNSKNTLYLQMNTLRAEDTAIYYCAIYGGNSGG
EYWGQGTLVTVSSPAPRPPTPAPTIASQPLSLRPEACRPAAGGAVHTRGLDFDTALA
AVICSALATVLLALLILCVIYCKRQRVKFSRSADAPAYQQGQNQLYNELNLGRREEY
DVLDKRRGRDPEMGGKPQRRKNPQEGLYNELQKDKMAEAYSEIGMKGERRRGKG
HDGLYQGLSTATKDTYDALHMQALPPR

FIG. 2K

LTG2322: LP-mD1.22-CD8TM-41BB-CD3zeta-F2AF-LP2-m36.4-TNFRSF19TM nucleic acid sequence (SEQ ID NO: 73)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGGGCGGCCGCAAC
TACCACCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAACTCCAGAAAGACAAGATGGCGGAAGCCT
ACTCAGAAATCGGGATGAAGGGAGAGCGGAGGAGGGGAAAGGGTCACGACGGG
CTGTACCAGGGACTGAGCACCGCCACTAAGGATACCTACGATGCCTTGCATATG
CAAGCACTCCCACCCCGGCGCGCGAAACGCAGCGGCAGCGGCGCGACCAACTTT
AGCCTGCTGAAACAGGCGGGCGATGTGGAAGAAAACCCGGGCCCGCGAGCAAA
GAGGATGGGAATTCAGGGGGGTTCCGTGCTCTTTGGCTTGCTCCTGGTCCTGGCA
GTGTTTTGTCACTCGGGACACAGCCTGCAGCAGGTGCAGCTGGTGCAGTCTGGG
GGAGGCTTGGTACAGCCTGGAGGGTCCCTGAGACTCTCCTGTGCAGCCTCTGCTT
TCGATTTCTCTGATTATGAAATGAGCTGGGTCCGCGAGGCTCCAGGGAAGGGGC
TGGAGTGGATTGGGGAAATCAATGATAGTGGAAACACCATTTACAATCCGTCCC
TCAAGAGTCGAGTCACCATCTCCAGAGACAATTCCAAGAACACACTGTATCTGC
AAATGAACACCCTGAGAGCCGAGGACACAGCCATATATTACTGTGCGATATATG
GTGGTAACTCCGGGGGAGAGTACTGGGGCCAGGGCACCCTGGTCACCGTCTCCT
CACCGGCTCCACGACCACCCACTCCAGCCCCAACGATTGCGAGCCAACCTCTCA
GTCTTCGGCCCGAGGCTTGCAGGCCAGCCGCAGGAGGAGCAGTGCACACCCGAG
GACTGGATTTCGATACCGCACTGGCGGCCGTGATCTGTAGCGCCCTGGCCACCGT
GCTGCTGGCGCTGCTCATCCTTTGCGTGATCTACTGCAAGCGGCAGTAG

LTG2322: LP-mD1.22-CD8TM-41BB-CD3zeta-F2AF-LP2-m36.4-TNFRSF19TM amino acid sequence (SEQ ID NO: 74)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGAAATTTPAPRPPTPAPTIASQPLSLRPEACRPAAGGAVHTRGLDFACDIY
IWAPLAGTCGVLLLSLVITLYCKRGRKKL LYIFKQPFMRPVQTTQEEDGCSCRFPEEE
EGGCELRVKFSRSADAPAYQQGQNQLYNELNLGRREEYDVLDKRRGRDPEMGGKP
RRKNPQEGLYNELQKDKMAEAYSEIGM KGERRRGKGHDGLYQGLSTATKDTYDAL
HMQALPPRRAKRSGSGATNFSLLKQAGDVEENPGPRAKRMGIQGGSVLFGLLLVLA

FIG. 2K cont.

VFCHSGHSLQQVQLVQSGGGLVQPGGSLRLSCAASAFDFSDYEMSWVREAPGKGLE
WIGEINDSGNTIYNPSLKSRVTISRDNSKNTLYLQMNTLRAEDTAIYYCAIYGGNSGG
EYWGQGTLVTVSSPAPRPPTPAPTIASQPLSLRPEACRPAAGGAVHTRGLDFDTALA
AVICSALATVLLALLILCVIYCKRQ

FIG. 2L

LTG2314: LP-mD1.22-L3-C46-CD8TM-41BB-CD3zeta nucleic acid sequence (SEQ ID NO: 77)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGAGGTGGCGG
TTCAGGCGGAGGGGGGAGTGGAGGTGGGGGAAGCTGGATGGAATGGGATCGCG
AAATCAACAACTACACCTCCCTGATTCACTCCCTGATTGAGGAATCCCAGAATCA
ACAGGAGAAGAACGAACAAGAGCTTCTGGAGCTGGACAAATGGGCCTCCCTGTG
GAACTGGTTCGCGGCCGCAACTACCACCCCTGCCCCTCGGCCGCCGACTCCGGCC
CCAACCATCGCAAGCCAACCCCTCTCCTTGCGCCCCGAAGCTTGCCGCCCGGCCG
CGGGTGGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCACCCTT
TACTGCAAGAGGGGCCGGAAGAAGCTGCTTTACATCTTCAAGCAGCCGTTCATG
CGGCCCGTGCAGACGACTCAGGAAGAGGACGGATGCTCGTGCAGATTCCCTGAG
GAGGAAGAGGGGGGATGCGAACTGCGCGTCAAGTTCTCACGGTCCGCCGACGCC
CCCGCATATCAACAGGGCCAGAATCAGCTCTACAACGAGCTGAACCTGGGAAGG
AGAGAGGAGTACGACGTGCTGGACAAGCGACGCGGACGCGACCCGGAGATGGG
GGGGAAACCACGGCGGAAAAACCCTCAGGAAGGACTGTACAACGAACTCCAGA
AAGACAAGATGGCGGAAGCCTACTCAGAAATCGGGATGAAGGGAGAGCGGAGG
AGGGGAAAGGGTCACGACGGGCTGTACCAGGGACTGAGCACCGCCACTAAGGA
TACCTACGATGCCTTGCATATGCAAGCACTCCCACCCCGGTAG

LTG2314: LP-mD1.22-L3-C46-CD8TM-41BB-CD3zeta amino acid sequence (SEQ ID NO: 78)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSWMEWDREINNYTSLIHSLIEESQNQQEKNEQEL
LELDKWASLWNWFAAATTTPAPRPPTPAPTIASQPLSLRPEACRPAAGGAVHTRGLD
FACDIYIWAPLAGTCGVLLLSLVITLYCKRGRKKLLYIFKQPFMRPVQTTQEEDGCSC
RFPEEEEGGCELRVKFSRSADAPAYQQGQNQLYNELNLGRREEYDVLDKRRGRDPE
MGGKPRRKNPQEGLYNELQKDKMAEAYSEIGMKGERRRGKGHDGLYQGLSTATK
DTYDALHMQALPPR

FIG. 2M

LTG2315: LP-mD1.22-L5-C46-CD8TM-41BB-CD3zeta nucleic acid sequence (SEQ ID NO: 81)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGCGGAGGCGG
GTCAGGTGGCGGTGGTAGTGGCGGTGGCGGTTCAGGCGGTGGTGGGAGTGGGGG
AGGAGGCAGCTGGATGGAATGGGATCGCGAAATCAACAACTACACCTCCCTGAT
TCACTCCCTGATTGAGGAATCCCAGAATCAACAGGAGAAGAACGAACAAGAGCT
TCTGGAGCTGGACAAATGGGCCTCCCTGTGGAACTGGTTCGCGGCCGCAACTAC
CACCCCTGCCCCTCGGCCGCCGACTCCGGCCCCAACCATCGCAAGCCAACCCCTC
TCCTTGCGCCCCGAAGCTTGCCGCCCGGCCGCGGGTGGAGCCGTGCATACCCGG
GGGCTGGACTTTGCCTGCGATATCTACATTTGGGCCCCGCTGGCCGGCACTTGCG
GCGTGCTCCTGCTGTCGCTGGTCATCACCCTTTACTGCAAGAGGGGCCGGAAGA
AGCTGCTTTACATCTTCAAGCAGCCGTTCATGCGGCCCGTGCAGACGACTCAGGA
AGAGGACGGATGCTCGTGCAGATTCCCTGAGGAGGAAGAGGGGGATGCGAAC
TGCGCGTCAAGTTCTCACGGTCCGCCGACGCCCCGCATATCAACAGGGCCAGA
ATCAGCTCTACAACGAGCTGAACCTGGGAAGGAGAGAGGAGTACGACGTGCTGG
ACAAGCGACGCGGACGCGACCCGGAGATGGGGGGGAAACCACGGCGGAAAAAC
CCTCAGGAAGGACTGTACAACGAACTCCAGAAAGACAAGATGGCGGAAGCCTA
CTCAGAAATCGGGATGAAGGGAGAGCGGAGGAGGGGAAAGGGTCACGACGGGC
TGTACCAGGGACTGAGCACCGCCACTAAGGATACCTACGATGCCTTGCATATGC
AAGCACTCCCACCCCGGTAG

LTG2315: LP-mD1.22-L5-C46-CD8TM-41BB-CD3zeta amino acid sequence (SEQ ID NO: 82)

MLLLVTSLLLCELPHPAFLLIPDTKKVVYGKKGDTVELTCTASQKKNI
QFHWKNSNQIKILGNQGSFLTKGPSKLNDRVDSRRSLWDQGNFPLIIKNL
KPEDSDTYICEVEDQKEEVQLVVVGGGGSGGGGSGGGGSGGGGSGGGGS
WMEWDREINNYTSLIHSLIEESQNQQEKNEQELLELDKWASLWNWFAAAT
TTPAPRPPTPAPTIASQPLSLRPEACRPAAGGAVHTRGLDFACDIYIWAP
LAGTCGVLLLSLVITLYCKRGRKKLLYIFKQPFMRPVQTTQEEDGCSCRF
PEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLY
QGLSTATKDTYDALHMQALPPR

FIG. 2N

LTG2316: LP-C46-L3-mD1.22-CD8TM-41BB-CD3zeta nucleic acid sequence (SEQ ID NO: 85)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGCGGAGG
GGGGAGTGGAGGTGGCGGTTCAGGAGGTGGGGGAAGCAAGAAAGTCGTGTACG
GAAAGAAGGGAGACACTGTGGAGCTGACCTGTACCGCAAGCCAGAAGAAGAAC
ATCCAGTTCCACTGGAAGAACTCCAACCAAATCAAGATCCTGGGGAACCAGGGT
TCCTTCCTGACTAAGGGACCCTCAAAGCTGAACGACCGCGTGGATAGCAGACGC
TCCCTGTGGGACCAGGGAAACTTCCCGCTTATCATTAAGAACCTCAAACCTGAG
GACTCGGATACCTACATCTGCGAAGTGGAGGACCAGAAGGAGGAGGTGCAGCTG
GTGGTGGTGGGCGCGGCCGCAACTACCACCCCTGCCCCTCGGCCGCCGACTCCG
GCCCCAACCATCGCAAGCCAACCCCTCTCCTTGCGCCCCGAAGCTTGCCGCCCGG
CCGCGGGTGGAGCCGTGCATACCCGGGGGCTGGACTTTGCCTGCGATATCTACA
TTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTC
ATGCGGCCCGTGCAGACGACTCAGGAAGAGGACGGATGCTCGTGCAGATTCCCT
GAGGAGGAAGAGGGGGGATGCGAACTGCGCGTCAAGTTCTACGGTCCGCCGA
CGCCCCCGCATATCAACAGGGCCAGAATCAGCTCTACAACGAGCTGAACCTGGG
AAGGAGAGAGGAGTACGACGTGCTGGACAAGCGACGCGGACGCGACCCGGAGA
TGGGGGGGAAACCACGGCGGAAAAACCCTCAGGAAGGACTGTACAACGAACTC
CAGAAAGACAAGATGGCGGAAGCCTACTCAGAAATCGGGATGAAGGGAGAGCG
GAGGAGGGGAAAGGGTCACGACGGGCTGTACCAGGGACTGAGCACCGCCACTA
AGGATACCTACGATGCCTTGCATATGCAAGCACTCCCACCCCGGTAG

LTG2316: LP-C46-L3-mD1.22-CD8TM-41BB-CD3zeta amino acid sequence (SEQ ID NO: 86)

MLLLVTSLLLCELPHPAFLLIPDTWMEWDREINNYTSLIHSLIEESQNQQEKNEQELL
ELDKWASLWNWFGGGGSGGGGSGGGGSKKVVYGKKGDTVELTCTASQKKNIQFH
WKNSNQIKILGNQGSFLTKGPSKLNDRVDSRRSLWDQGNFPLIIKNLKPEDSDTYICE
VEDQKEEVQLVVVGAAATTTPAPRPPTPAPTIASQPLSLRPEACRPAAGGAVHTRGL
DFACDIYIWAPLAGTCGVLLLSLVITLYCKRGRKKLLYIFKQPFMRPVQTTQEEDGCS
CRFPEEEEGGCELRVKFSRSADAPAYQQGQNQLYNELNLGRREEYDVLDKRRGRDP
EMGGKPRRKNPQEGLYNELQKDKMAEAYSEIGMKGERRRGKGHDGLYQGLSTAT
KDTYDALHMQALPPR

FIG. 20

LTG2317: LP-C46-L5-mD1.22-CD8TM-41BB-CD3zeta nucleic acid sequence (SEQ ID NO: 89)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGCGGAGG
GGGGAGTGGAGGTGGCGGTTCAGGAGGTGGGGGAAGCGGTGGCGGTGGTAGTG
GCGGTGGCGGTTCAAAGAAAGTCGTGTACGGAAAGAAGGGAGACACTGTGGAG
CTGACCTGTACCGCAAGCCAGAAGAAGAACATCCAGTTCCACTGGAAGAACTCC
AACCAAATCAAGATCCTGGGGAACCAGGGTTCCTTCCTGACTAAGGGACCCTCA
AAGCTGAACGACCGCGTGGATAGCAGACGCTCCCTGTGGGACCAGGGAAACTTC
CCGCTTATCATTAAGAACCTCAAACCTGAGGACTCGGATACCTACATCTGCGAA
GTGGAGGACCAGAAGGAGGAGGTGCAGCTGGTGGTGGTGGGCGCGGCCGCAAC
TACCACCCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAACTCCAGAAAGACAAGATGGCGGAAGCCT
ACTCAGAAATCGGGATGAAGGGAGAGCGGAGGAGGGGAAAGGGTCACGACGGG
CTGTACCAGGGACTGAGCACCGCCACTAAGGATACCTACGATGCCTTGCATATG
CAAGCACTCCCACCCCGGTAG

LTG2317: LP-C46-L5-mD1.22-CD8TM-41BB-CD3zeta amino acid sequence (SEQ ID NO: 90)

MLLLVTSLLLCELPHPAFLLIPDTWMEWDREINNYTSLIHSLIEESQNQQEKNEQELL
ELDKWASLWNWFGGGSGGGGSGGGGSGGGGSGGGGSKKVVYGKKGDTVELTC
TASQKKNIQFHWKNSNQIKILGNQGSFLTKGPSKLNDRVDSRRSLWDQGNFPLIIKN
LKPEDSDTYICEVEDQKEEVQLVVVGAAATTTPAPRPPTPAPTIASQPLSLRPEACRP
AAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYQQGQNQLYNELNLGRREE
YDVLDKRRGRDPEMGGKPRRKNPQEGLYNELQKDKMAEAYSEIGMKGERRRGKG
HDGLYQGLSTATKDTYDALHMQALPPR

FIG. 2P

LTG2318: LP-mD1.22-L3-m36.4-L3-C46-CD8TM-41BB-CD3zeta nucleic acid sequence
(SEQ ID NO: 93)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGAGGTGGCGG
TTCAGGCGGAGGGGGGAGTGGAGGTGGGGGAAGCCAGGTGCAGCTGGTGCAGT
CTGGGGGAGGCTTGGTACAGCCTGGAGGGTCCCTGAGACTCTCCTGTGCAGCCT
CTGCTTTCGATTTCTCTGATTATGAAATGAGCTGGGTCCGCGAGGCTCCAGGGAA
GGGGCTGGAGTGGATTGGGGAAATCAATGATAGTGGAAACACCATTTACAATCC
GTCCCTCAAGAGTCGAGTCACCATCTCCAGAGACAATTCCAAGAACACACTGTA
TCTGCAAATGAACACCCTGAGAGCCGAGGACACAGCCATATATTACTGTGCGAT
ATATGGTGGTAACTCCGGGGGAGAGTACTGGGGCCAGGGCACCCTGGTCACCGT
CTCCTCAGGTGGAGGGGGCTCTGGCGGTGGAGGGTCCGGGGGAGGTGGCTCGTG
GATGGAATGGGATCGCGAAATCAACAACTACACCTCCCTGATTCACTCCCTGATT
GAGGAATCCCAGAATCAACAGGAGAAGAACGAACAAGAGCTTCTGGAGCTGGA
CAAATGGGCCTCCCTGTGGAACTGGTTCGCGGCCGCAACTACCACCCCTGCCCCT
CGGCCGCCGACTCCGGCCCCAACCATCGCAAGCCAACCCCTCTCCTTGCGCCCCG
AAGCTTGCCGCCCGGCCGCGGGTGGAGCCGTGCATACCCGGGGGCTGGACTTTG
CCTGCGATATCTACATTTGGGCCCCGCTGGCCGGCACTTGCGGCGTGCTCCTGCT
GTCGCTGGTCATCACCCTTTACTGCAAGAGGGGCCGGAAGAAGCTGCTTTACATC
TTCAAGCAGCCGTTCATGCGGCCCGTGCAGACGACTCAGGAAGAGGACGGATGC
TCGTGCAGATTCCTGAGGAGGAAGAGGGGGGATGCGAACTGCGCGTCAAGTTC
TCACGGTCCGCCGACGCCCCCGCATATCAACAGGGCCAGAATCAGCTCTACAAC
GAGCTGAACCTGGGAAGGAGAGAGGAGTACGACGTGCTGGACAAGCGACGCGG
ACGCGACCCGGAGATGGGGGGGAAACCACGGCGGAAAAACCCTCAGGAAGGAC
TGTACAACGAACTCCAGAAAGACAAGATGGCGGAAGCCTACTCAGAAATCGGG
ATGAAGGGAGAGCGGAGGAGGGGAAAGGGTCACGACGGGCTGTACCAGGGACT
GAGCACCGCCACTAAGGATACCTACGATGCCTTGCATATGCAAGCACTCCCACC
CCGGTAGC

LTG2318: LP-mD1.22-L3-m36.4-L3-C46-CD8TM-41BB-CD3zeta amino acid sequence
(SEQ ID NO: 94)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSQVQLVQSGGGLVQPGGSLRLSCAASAFDFSDY
EMSWVREAPGKGLEWIGEINDSGNTIYNPSLKSRVTISRDNSKNTLYLQMNTLRAED
TAIYYCAIYGGNSGGEYWGQGTLVTVSSGGGGSGGGGSGGGGSWMEWDREINNYT
SLIHSLIEESQNQQEKNEQELLELDKWASLWNWFAAATTTPAPRPPTPAPTIASQPLS
LRPEACRPAAGGAVHTRGLDFACDIYIWAPLAGTCGVLLLSLVITLYCKRGRKKLLY
IFKQPFMRPVQTTQEEDGCSCRFPEEEEGGCELRVKFSRSADAPAYQQGQNQLYNEL

FIG. 2P Cont.

NLGRREEYDVLDKRRGRDPEMGGKPRRKNPQEGLYNELQKDKMAEAYSEIGMKGE
RRRGKGHDGLYQGLSTATKDTYDALHMQALPPR

FIG. 2Q

LTG2319: LP-mD1.22-L3-C46-L3-m36.4-CD8TM-41BB-CD3zeta nucleic acid sequence
(SEQ ID NO: 97)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGA GGACTCGGATACCTACATCTGCGAA
GTGGAGGACCAGAAGGAGGAGGTGCAGCTGGTGGTGGTGGGCGGAGGTGGCGG
TTCAGGCGGAGGGGGGAGTGGAGGTGGGGGAAGCTGGATGGAATGGGATCGCG
AAATCAACAACTACACCTCCCTGATTCACTCCCTGATTGAGGAATCCCAGAATCA
ACAGGAGAAGAACGAACAAGAGCTTCTGGAGCTGGACAAATGGGCCTCCCTGTG
GAACTGGTTCGGTGGAGGGGGCTCTGGCGGTGGAGGGTCCGGGGGAGGTGGCTC
GCAGGTGCAGCTGGTGCAGTCTGGGGGAGGCTTGGTACAGCCTGGAGGGTCCCT
GAGACTCTCCTGTGCAGCCTCTGCTTTCGATTTCTCTGATTATGAAATGAGCTGG
GTCCGCGAGGCTCCAGGGAAGGGGCTGGAGTGGATTGGGAAATCAATGATAGT
GGAAACACCATTTACAATCCGTCCCTCAAGAGTCGAGTCACCATCTCCAGAGAC
AATTCCAAGAACACACTGTATCTGCAAATGAACACCCTGAGAGCCGAGGACACA
GCCATATATTACTGTGCGATATATGGTGGTAACTCCGGGGGAGAGTACTGGGGC
CAGGGCACCCTGGTCACCGTCTCCTCAGCGGCCGCAACTACCACCCCTGCCCCTC
GGCCGCCGACTCCGGCCCCAACCATCGCAAGCCAACCCCTCTCCTTGCGCCCCGA
AGCTTGCCGCCCGGCCGCGGGTGGAGCCGTGCATACCCGGGGGCTGGACTTTGC
CTGCGATATCTACATTTGGGCCCCGCTGGCCGGCACTTGCGGCGTGCTCCTGCTG
TCGCTGGTCATCACCCTTTACTGCAAGAGGGGCCGGAAGAAGCTGCTTTACATCT
TCAAGCAGCCGTTCATGCGGCCCGTGCAGACGACTCAGGAAGAGGACGGATGCT
CGTGCAGATTCCCTGAGGAGGAAGAGGGGGGATGCGAACTGCGCGTCAAGTTCT
CACGGTCCGCCGACGCCCCCGCATATCAACAGGGCCAGAATCAGCTCTACAACG
AGCTGAACCTGGGAAGGAGAGAGGAGTACGACGTGCTGGACAAGCGACGCGGA
CGCGACCCGGAGATGGGGGGGAAACCACGGCGGAAAAACCCTCAGGAAGGACT
GTACAACGAACTCCAGAAAGACAAGATGGCGGAAGCCTACTCAGAAATCGGGA
TGAAGGGAGAGCGGAGGAGGGGAAAGGGTCACGACGGGCTGTACCAGGGACTG
AGCACCGCCACTAAGGATACCTACGATGCCTTGCATATGCAAGCACTCCCACCC
CGGTAG

LTG2319: LP-mD1.22-L3-C46-L3-m36.4-CD8TM-41BB-CD3zeta amino acid sequence
(SEQ ID NO: 98)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSWMEWDREINNYTSLIHSLIEESQNQQEKNEQEL
LELDKWASLWNWFGGGGSGGGGSGGGGSQVQLVQSGGGLVQPGGSLRLSCAASA
FDFSDYEMSWVREAPGKGLEWIGEINDSGNTIYNPSLKSRVTISRDNSKNTLYLQMN
TLRAEDTAIYYCAIYGGNSGGEYWGQGTLVTVSSAAATTTPAPRPPTPAPTIASQPLS
LRPEACRPAAGGAVHTRGLDFACDIYIWA PLAGTCGVLLLSLVITLYCKRGRKKLLY
IFKQPFMRPVQTTQEEDGCSCRFPEEEEGGCELRVKFSRSADAPAYQQGQNQLYNEL

FIG. 2Q Cont.

NLGRREEYDVLDKRRGRDPEMGGKPRRKNPQEGLYNELQKDKMAEAYSEIGMKGE
RRRGKGHDGLYQGLSTATKDTYDALHMQALPPR

FIG. 2R

LTG2320: LP-C46-L3-mD1.22-L3-m36.4-CD8TM-41BB-CD3zeta nucleic acid sequence
(SEQ ID NO: 101)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGTGGAGG
GGGCTCTGGCGGTGGAGGGTCCGGGGGAGGTGGCTCGAAGAAAGTCGTGTACGG
AAAGAAGGGAGACACTGTGGAGCTGACCTGTACCGCAAGCCAGAAGAAGAACA
TCCAGTTCCACTGGAAGAACTCCAACCAAATCAAGATCCTGGGGAACCAGGGTT
CCTTCCTGACTAAGGGACCCTCAAAGCTGAACGACCGCGTGGATAGCAGACGCT
CCCTGTGGGACCAGGGAAACTTCCCGCTTATCATTAAGAACCTCAAACCTGAGG
ACTCGGATACCTACATCTGCGAAGTGGAGGACCAGAAGGAGGAGGTGCAGCTGG
TGGTGGTGGGCGGAGGTGGCGGTTCAGGCGGAGGGGGGAGTGGAGGTGGGGGA
AGCCAGGTGCAGCTGGTGCAGTCTGGGGGAGGCTTGGTACAGCCTGGAGGGTCC
CTGAGACTCTCCTGTGCAGCCTCTGCTTTCGATTTCTCTGATTATGAAATGAGCTG
GGTCCGCGAGGCTCCAGGGAAGGGGCTGGAGTGGATTGGGGAAATCAATGATA
GTGGAAACACCATTTACAATCCGTCCCTCAAGAGTCGAGTCACCATCTCCAGAG
ACAATTCCAAGAACACACTGTATCTGCAAATGAACACCCTGAGAGCCGAGGACA
CAGCCATATATTACTGTGCGATATATGGTGGTAACTCCGGGGGAGAGTACTGGG
GCCAGGGCACCCTGGTCACCGTCTCCTCAGCGGCCGCAACTACCACCCCTGCCCC
TCGGCCGCCGACTCCGGCCCCAACCATCGCAAGCCAACCCCTCTCCTTGCGCCCC
GAAGCTTGCCGCCCGGCCGCGGGTGGAGCCGTGCATACCCGGGGGCTGGACTTT
GCCTGCGATATCTACATTTGGGCCCCGCTGGCCGGCACTTGCGGCGTGCTCCTGC
TGTCGCTGGTCATCACCCTTTACTGCAAGAGGGGCCGGAAGAAGCTGCTTTACAT
CTTCAAGCAGCCGTTCATGCGGCCCGTGCAGACGACTCAGGAAGAGGACGGATG
CTCGTGCAGATTCCCTGAGGAGGAAGAGGGGGGATGCGAACTGCGCGTCAAGTT
CTCACGGTCCGCCGACGCCCCCGCATATCAACAGGGCCAGAATCAGCTCTACAA
CGAGCTGAACCTGGGAAGGAGAGAGGAGTACGACGTGCTGGACAAGCGACGCG
GACGCGACCCGGAGATGGGGGGGAAACCACGGCGGAAAAACCCTCAGGAAGGA
CTGTACAACGAACTCCAGAAAGACAAGATGGCGGAAGCCTACTCAGAAATCGG
GATGAAGGGAGAGCGGAGGAGGGGAAAGGGTCACGACGGGCTGTACCAGGGAC
TGAGCACCGCCACTAAGGATACCTACGATGCCTTGCATATGCAAGCACTCCCAC
CCCGGTAG

LTG2320: LP-C46-L3-mD1.22-L3-m36.4-CD8TM-41BB-CD3zeta amino acid sequence
(SEQ ID NO: 102)

MLLLVTSLLLCELPHPAFLLIPDTWMEWDREINNYTSLIHSLIEESQNQQEKNEQELL
ELDKWASLWNWFGGGGSGGGGSGGGGSKKVVYGKKGDTVELTCTASQKKNIQFH
WKNSNQIKILGNQGSFLTKGPSKLNDRVDSRRSLWDQGNFPLIIKNLKPEDSDTYICE
VEDQKEEVQLVVVGGGGSGGGGSGGGGSQVQLVQSGGGLVQPGGSLRLSCAASA
FDFSDYEMSWVREAPGKGLEWIGEINDSGNTIYNPSLKSRVTISRDNSKNTLYLQMN
TLRAEDTAIYYCAIYGGNSGGEYWGQGTLVTVSSAAATTTPAPRPPTPAPTIASQPLS
LRPEACRPAAGGAVHTRGLDFACDIYIWA PLAGTCGVLLLSLVITLYCKRGRKKLLY
IFKQPFMRPVQTTQEEDGCSCRFPEEEEGGCELRVKFSRSADAPAYQQGQNQLYNEL

FIG. 2R Cont.

NLGRREEYDVLDKRRGRDPEMGGKPRRKNPQEGLYNELQKDKMAEAYSEIGMKGE
RRRGKGHDGLYQGLSTATKDTYDALHMQALPPR

FIG. 2S

LTG2323: LP-mD1.22-L3-m36.4-CD8TM-41BB-CD3zeta-F2AF-LP2-C46-TNFRSF19TM
nucleic acid sequence (SEQ ID NO: 105)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGGGAGGTGGCGG
TTCAGGCGGAGGGGGGAGTGGAGGTGGGGAAGCCAGGTGCAGCTGGTGCAGT
CTGGGGGAGGCTTGGTACAGCCTGGAGGGTCCCTGAGACTCTCCTGTGCAGCCT
CTGCTTTCGATTTCTCTGATTATGAAATGAGCTGGGTCCGCGAGGCTCCAGGGAA
GGGGCTGGAGTGGATTGGGGAAATCAATGATAGTGGAAACACCATTTACAATCC
GTCCCTCAAGAGTCGAGTCACCATCTCCAGAGACAATTCCAAGAACACACTGTA
TCTGCAAATGAACACCCTGAGAGCCGAGGACACAGCCATATATTACTGTGCGAT
ATATGGTGGTAACTCCGGGGAGAGTACTGGGGCCAGGGCACCCTGGTCACCGT
CTCCTCAGCGGCCGCAACTACCACCCCTGCCCCTCGGCCGCCGACTCCGGCCCCA
ACCATCGCAAGCCAACCCCTCTCCTTGCGCCCCGAAGCTTGCCGCCCGGCCGCGG
GTGGAGCCGTGCATACCCGGGGGCTGGACTTTGCCTGCGATATCTACATTTGGGC
CCCGCTGGCCGGCACTTGCGGCGTGCTCCTGCTGTCGCTGGTCATCACCCTTTAC
TGCAAGAGGGGCCGGAAGAAGCTGCTTTACATCTTCAAGCAGCCGTTCATGCGG
CCCGTGCAGACGACTCAGGAAGAGGACGGATGCTCGTGCAGATTCCCTGAGGAG
GAAGAGGGGGGATGCGAACTGCGCGTCAAGTTCTCACGGTCCGCCGACGCCCCC
GCATATCAACAGGGCCAGAATCAGCTCTACAACGAGCTGAACCTGGGAAGGAG
AGAGGAGTACGACGTGCTGGACAAGCGACGCGGACGCGACCCGGAGATGGGGG
GGAAACCACGGCGGAAAAACCCTCAGGAAGGACTGTACAACGAACTCCAGAAA
GACAAGATGGCGGAAGCCTACTCAGAAATCGGGATGAAGGGAGAGCGGAGGAG
GGGAAAGGGTCACGACGGGCTGTACCAGGGACTGAGCACCGCCACTAAGGATA
CCTACGATGCCTTGCATATGCAAGCACTCCCACCCCGGCGCGCGAAACGCAGCG
GCAGCGGCGCGACCAACTTTAGCCTGCTGAAACAGGCGGGCGATGTGGAAGAA
AACCCGGGCCCGCGAGCAAAGAGGATGGGAATTCAGGGGGGTTCCGTGCTCTTT
GGCTTGCTCCTGGTCCTGGCAGTGTTTGTCACTCGGGACACAGCCTGCAGTGGA
TGGAATGGGATCGCGAAATCAACAACTACACCTCCCTGATTCACTCCCTGATTGA
GGAATCCCAGAATCAACAGGAGAAGAACGAACAAGAGCTTCTGGAGCTGGACA
AATGGGCCTCCCTGTGGAACTGGTTCCCGGCTCCACGACCACCCACTCCAGCCCC
AACGATTGCGAGCCAACCTCTCAGTCTTCGGCCCGAGGCTTGCAGGCCAGCCGC
AGGAGGAGCAGTGCACACCCGAGGACTGGATTTCGATACCGCACTGGCGGCCGT
GATCTGTAGCGCCCTGGCCACCGTGCTGCTGGCGCTGCTCATCCTTTGCGTGATC
TACTGCAAGCGGCAGTAG

LTG2323: LP-mD1.22-L3-m36.4-CD8TM-41BB-CD3zeta-F2AF-C46-TNFRSF19TM
amino acid sequence (SEQ ID NO: 106)

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSQVQLVQSGGGLVQPGGSLRLSCAASAFDFSDY

FIG. 2S Cont.

EMSWVREAPGKGLEWIGEINDSGNTIYNPSLKSRVTISRDNSKNTLYLQMNTLRAED
TAIYYCAIYGGNSGGEYWGQGTLVTVSSAAATTTPAPRPPTPAPTIASQPLSLRPEAC
RPAAGGAVHTRGLDFACDIYIWAPLAGTCGVLLLSLVITLYCKRGRKKLLYIFKQPF
MRPVQTTQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGERRRG
KGHDGLYQGLSTATKDTYDALHMQALPPRRAKRSGSGATNFSLLKQAGDVEENPG
PRAKRMGIQGGSVLFGLLLVLAVFCHSGHS LQWMEWDREINNYTSLIHSLIEESQNQ
QEKNEQELLELDKWASLWNWFPAPRPPTPAPTIASQPLSLRPEACRPAAGGAVHTRG
LDFDTALAAVICSALATVLLALLILCVIYCKRQ

FIG. 2T

LTG2329: LP-C46-L3-mD1.22-CD8TM-41BB-CD3zeta-F2AF-LP2-m36.4-TNFRSF19TM-CD3zeta2 nucleic acid sequence (SEQ ID NO: 107)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGCGGAGG
GGGGAGTGGAGGTGGCGGTTCAGGAGGTGGGGGAAGCAAGAAAGTCGTGTACG
GAAAGAAGGGAGACACTGTGGAGCTGACCTGTACCGCAAGCCAGAAGAAGAAC
ATCCAGTTCCACTGGAAGAACTCCAACCAAATCAAGATCCTGGGGAACCAGGGT
TCCTTCCTGACTAAGGGACCCTCAAAGCTGAACGACCGCGTGGATAGCAGACGC
TCCCTGTGGGACCAGGGAAACTTCCCGCTTATCATTAAGAACCTCAAACCTGAG
GACTCGGATACCTACATCTGCGAAGTGGAGGACCAGAAGGAGGAGGTGCAGCTG
GTGGTGGTGGGCGCGGCCGCAACTACCACCCTGCCCCTCGGCCGCCGACTCCG
GCCCCAACCATCGCAAGCCAACCCCTCTCCTTGCGCCCCGAAGCTTGCCGCCCGG
CCGCGGGTGGAGCCGTGCATACCCGGGGCTGGACTTTGCCTGCGATATCTACA
TTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTC
ATGCGGCCCGTGCAGACGACTCAGGAAGAGGACGGATGCTCGTGCAGATTCCCT
GAGGAGGAAGAGGGGGGATGCGAACTGCGCGTCAAGTTCTCACGGTCCGCCGA
CGCCCCCGCATATCAACAGGGCCAGAATCAGCTCTACAACGAGCTGAACCTGGG
AAGGAGAGAGGAGTACGACGTGCTGGACAAGCGACGCGGACGCGACCCGGAGA
TGGGGGGGAAACCACGGCGGAAAAACCCTCAGGAAGGACTGTACAACGAACTC
CAGAAAGACAAGATGGCGGAAGCCTACTCAGAAATCGGGATGAAGGGAGAGCG
GAGGAGGGGAAAGGGTCACGACGGGCTGTACCAGGGACTGAGCACCGCCACTA
AGGATACCTACGATGCCTTGCATATGCAAGCACTCCCACCCCGGCGCGCGAAAC
GCAGCGGCAGCGGCGCGACCAACTTTAGCCTGCTGAAACAGGCGGGCGATGTGG
AAGAAAACCCGGGCCCGCGAGCAAAGAGGATGGGAATTCAGGGGGGTTCCGTG
CTCTTTGGCTTGCTCCTGGTCCTGGCAGTGTTTGTCACTCGGGACACAGCCTGCA
GCAGGTGCAGCTGGTGCAGTCTGGGGGAGGCTTGGTACAGCCTGGAGGGTCCCT
GAGACTCTCCTGTGCAGCCTCTGCTTTCGATTTCTCTGATTATGAAATGAGCTGG
GTCCGCGAGGCTCCAGGGAAGGGGCTGGAGTGGATTGGGGAAATCAATGATAGT
GGAAACACCATTTACAATCCGTCCCTCAAGAGTCGAGTCACCATCTCCAGAGAC
AATTCCAAGAACACACTGTATCTGCAAATGAACACCCTGAGAGCCGAGGACACA
GCCATATATTACTGTGCGATATATGGTGGTAACTCCGGGGGAGAGTACTGGGGC
CAGGGCACCCTGGTCACCGTCTCCTCACCGGCTCCACGACCACCCACTCCAGCCC
CAACGATTGCGAGCCAACCTCTCAGTCTTCGGCCCGAGGCTTGCAGGCCAGCCG
CAGGAGGAGCAGTGCACACCCGAGGACTGGATTCGATACCGCACTGGCGGCCG
TGATCTGTAGCGCCCTGGCCACCGTGCTGCTGGCGCTGCTCATCCTTTGCGTGAT
CTACTGCAAGCGGCAGCGGGTTAAATTCTCCCGCAGCGCAGACGCACCCGCCTA
CCAGCAAGGACAGAATCAGCTCTACAACGAACTGAACCTTGGTAGGAGAGAAG
AATATGATGTTCTCGACAAGCGCAGAGGGAGAGATCCAGAGATGGGTGGGAAG
CCGCAACGCCGGAAAAACCCACAAGAGGGACTGTACAATGAATTGCAGAAAGA
TAAGATGGCCGAGGCTTACTCAGAAATCGGAATGAAGGGGGAGCGGCGGAGGG
GCAAGGGACATGATGGTCTCTACCAAGGGCTTTCAACCGCTACTAAGGACACTT
ATGACGCACTCCACATGCAGGCGCTGCCTCCGCGATAA

FIG. 2T Cont.

LTG2329: LP-C46-L3-mD1.22-CD8TM-41BB-CD3zeta-F2AF-LP2-m36.4-TNFRSF19TM-CD3zeta2 amino acid sequence (SEQ ID NO: 108)

MLLLVTSLLLCELPHPAFLLIPDTWMEWDREINNYTSLIHSLIEESQNQQEKNEQELL
ELDKWASLWNWFGGGGSGGGGSGGGGSKKVVYGKKGDTVELTCTASQKKNIQFH
WKNSNQIKILGNQGSFLTKGPSKLNDRVDSRRSLWDQGNFPLIIKNLKPEDSDTYICE
VEDQKEEVQLVVVGAAATTTPAPRPPTPAPTIASQPLSLRPEACRPAAGGAVHTRGL
DFACDIYIWAPLAGTCGVLLLSLVITLYCKRGRKKLLYIFKQPFMRPVQTTQEEDGCS
CRFPEEEEGGCELRVKFSRSADAPAYQQGQNQLYNELNLGRREEYDVLDKRRGRDP
EMGGKPRRKNPQEGLYNELQKDKMAEAYSEIGMKGERRRGKGHDGLYQGLSTAT
KDTYDALHMQALPPRRAKRSGSGATNFSLLKQAGDVEENPGPRAKRMGIQGGSVLF
GLLLVLAVFCHSGHSLQQVQLVQSGGGLVQPGGSLRLSCAASAFDFSDYEMSWVRE
APGKGLEWIGEINDSGNTIYNPSLKSRVTISRDNSKNTLYLQMNTLRAEDTAIYYCAI
YGGNSGGEYWGQGTLVTVSSPAPRPPTPAPTIASQPLSLRPEACRPAAGGAVHTRGL
DFDTALAAVICSALATVLLALLILCVIYCKRQRVKFSRSADAPAYQQGQNQLYNELN
LGRREEYDVLDKRRGRDPEMGGKPQRRKNPQEGLYNELQKDKMAEAYSEIGMKGE
RRRGKGHDGLYQGLSTATKDTYDALHMQALPPR

FIG. 2U

LTG2330: LP-C46-L5-mD1.22-CD8TM-4IBB-CD3zeta-F2AF-LP2-m36.4-TNFRSF19TM-CD3zeta2 nucleic acid sequence (SEQ ID NO: 109)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGCGGAGG
GGGGAGTGGAGGTGGCGGTTCAGGAGGTGGGGGAAGCGGTGGCGGTGGTAGTG
GCGGTGGCGGTTCAAAGAAAGTCGTGTACGGAAAGAAGGGAGACACTGTGGAG
CTGACCTGTACCGCAAGCCAGAAGAAGAACATCCAGTTCCACTGGAAGAACTCC
AACCAAATCAAGATCCTGGGGAACCAGGGTTCCTTCCTGACTAAGGGACCCTCA
AAGCTGAACGACCGCGTGGATAGCAGACGCTCCCTGTGGGACCAGGGAAACTTC
CCGCTTATCATTAAGAACCTCAAACCTGAGGACTCGGATACCTACATCTGCGAA
GTGGAGGACCAGAAGGAGGAGGTGCAGCTGGTGGTGGTGGGCGCGGCCGCAAC
TACCACCCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAACTCCAGAAAGACAAGATGGCGGAAGCCT
ACTCAGAAATCGGGATGAAGGGAGAGCGGAGGAGGGAAAGGGTCACGACGGG
CTGTACCAGGGACTGAGCACCGCCACTAAGGATACCTACGATGCCTTGCATATG
CAAGCACTCCACCCCGGCGCGCGAAACGCAGCGGCAGCGGCGCGACCAACTTT
AGCCTGCTGAAACAGGCGGGCGATGTGGAAGAAAACCCGGGCCCGCGAGCAAA
GAGGATGGGAATTCAGGGGGGTTCCGTGCTCTTTGGCTTGCTCCTGGTCCTGGCA
GTGTTTTGTCACTCGGGACACAGCCTGCAGCAGGTGCAGCTGGTGCAGTCTGGG
GGAGGCTTGGTACAGCCTGGAGGGTCCCTGAGACTCTCCTGTGCAGCCTCTGCTT
TCGATTTCTCTGATTATGAAATGAGCTGGGTCCGCGAGGCTCCAGGGAAGGGGC
TGGAGTGGATTGGGGAAATCAATGATAGTGGAAACACCATTTACAATCCGTCCC
TCAAGAGTCGAGTCACCATCTCCAGAGACAATTCCAAGAACACACTGTATCTGC
AAATGAACACCCTGAGAGCCGAGGACACAGCCATATATTACTGTGCGATATATG
GTGGTAACTCCGGGGGAGAGTACTGGGGCCAGGGCACCCTGGTCACCGTCTCCT
CACCGGCTCCACGACCACCCACTCCAGCCCCAACGATTGCGAGCCAACCTCTCA
GTCTTCGGCCCGAGGCTTGCAGGCCAGCCGCAGGAGGAGCAGTGCACACCCGAG
GACTGGATTTCGATACCGCACTGGCGGCCGTGATCTGTAGCGCCCTGGCCACCGT
GCTGCTGGCGCTGCTCATCCTTTGCGTGATCTACTGCAAGCGGCAGCGGGTTAAA
TTCTCCCGCAGCGCAGACGCACCCGCCTACCAGCAAGGACAGAATCAGCTCTAC
AACGAACTGAACCTTGGTAGGAGAGAAGAATATGATGTTCTCGACAAGCGCAGA
GGGAGAGATCCAGAGATGGGTGGGAAGCCGCAACGCCGGAAAAACCCACAAGA
GGGACTGTACAATGAATTGCAGAAAGATAAGATGGCCGAGGCTTACTCAGAAAT
CGGAATGAAGGGGGAGCGGCGGAGGGGCAAGGGACATGATGGTCTCTACCAAG
GGCTTTCAACCGCTACTAAGGACACTTATGACGCACTCCACATGCAGGCGCTGCC
TCCGCGATAA

FIG. 2U Cont.

LTG2330: LP-C46-L5-mD1.22-CD8TM-41BB-CD3zeta-F2AF-LP2-m36.4-TNFRSF19TM-CD3zeta2 amino acid sequence (SEQ ID NO: 110)

MLLLVTSLLLCELPHPAFLLIPDTWMEWDREINNYTSLIHSLIEESQNQQEKNEQELL
ELDKWASLWNWFGGGGSGGGGSGGGGSGGGGSGGGGSKKVVYGKKGDTVELTC
TASQKKNIQFHWKNSNQIKILGNQGSFLTKGPSKLNDRVDSRRSLWDQGNFPLIIKN
LKPEDSDTYICEVEDQKEEVQLVVVGAAATTTPAPRPPTPAPTIASQPLSLRPEACRP
AAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYQQGQNQLYNELNLGRREE
YDVLDKRRGRDPEMGGKPRRKNPQEGLYNELQKDKMAEAYSEIGMKGERRRGKG
HDGLYQGLSTATKDTYDALHMQALPPRRAKRSGSGATNFSLLKQAGDVEENPGPR
AKRMGIQGGSVLFGLLLVLAVFCHSGHSLQQVQLVQSGGGLVQPGGSLRLSCAASA
FDFSDYEMSWVREAPGKGLEWIGEINDSGNTIYNPSLKSRVTISRDNSKNTLYLQMN
TLRAEDTAIYYCAIYGGNSGGEYWGQGTLVTVSSPAPRPPTPAPTIASQPLSLRPEAC
RPAAGGAVHTRGLDFDTALAAVICSALATVLLALLILCVIYCKRQRVKFSRSADAPA
YQQGQNQLYNELNLGRREEYDVLDKRRGRDPEMGGKPQRRKNPQEGLYNELQKD
KMAEAYSEIGMKGERRRGKGHDGLYQGLSTATKDTYDALHMQALPPR

FIG. 2V

LTG2331: LP-C46-L3-mD1.22-CD8TM-41BB-CD3zeta-F2AF-LP2-m36.4-TNFRSF19TM nucleic acid sequence (SEQ ID NO: 113)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGCGGAGG
GGGGAGTGGAGGTGGCGGTTCAGGAGGTGGGGGAAGCAAGAAAGTCGTGTACG
GAAAGAAGGGAGACACTGTGGAGCTGACCTGTACCGCAAGCCAGAAGAAGAAC
ATCCAGTTCCACTGGAAGAACTCCAACCAAATCAAGATCCTGGGGAACCAGGGT
TCCTTCCTGACTAAGGGACCCTCAAAGCTGAACGACCGCGTGGATAGCAGACGC
TCCCTGTGGGACCAGGGAAACTTCCCGCTTATCATTAAGAACCTCAAACCTGAG
GACTCGGATACCTACATCTGCGAAGTGGAGGACCAGAAGGAGGAGGTGCAGCTG
GTGGTGGTGGGCGCGGCCGCAACTACCACCCCTGCCCCTCGGCCGCCGACTCCG
GCCCCAACCATCGCAAGCCAACCCCTCTCCTTGCGCCCCGAAGCTTGCCGCCCGG
CCGCGGGTGGAGCCGTGCATACCCGGGGCTGGACTTTGCCTGCGATATCTACA
TTTGGGCCCCGCTGGCCGGCACTTGCGGCGTGCTCCTGCTGTCGCTGGTCATCAC
CCTTTACTGCAAGAGGGGCCGGAAGAAGCTGCTTTACATCTTCAAGCAGCCGTTC
ATGCGGCCCGTGCAGACGACTCAGGAAGAGGACGGATGCTCGTGCAGATTCCCT
GAGGAGGAAGAGGGGGGATGCGAACTGCGCGTCAAGTTCTCACGGTCCGCCGA
CGCCCCCGCATATCAACAGGGCCAGAATCAGCTCTACAACGAGCTGAACCTGGG
AAGGAGAGAGGAGTACGACGTGCTGGACAAGCGACGCGGACGCGACCCGGAGA
TGGGGGGGAAACCACGGCGGAAAAACCCTCAGGAAGGACTGTACAACGAACTC
CAGAAAGACAAGATGGCGGAAGCCTACTCAGAAATCGGGATGAAGGGAGAGCG
GAGGAGGGGAAAGGGTCACGACGGGCTGTACCAGGGACTGAGCACCGCCACTA
AGGATACCTACGATGCCTTGCATATGCAAGCACTCCCACCCCGGCGCGCGAAAC
GCAGCGGCAGCGGCGCGACCAACTTTAGCCTGCTGAAACAGGCGGGCGATGTGG
AAGAAAACCCGGGCCCGCGAGCAAAGAGGATGGGAATTCAGGGGGGTTCCGTG
CTCTTTGGCTTGCTCCTGGTCCTGGCAGTGTTTGTCACTCGGGACACAGCCTGCA
GCAGGTGCAGCTGGTGCAGTCTGGGGGAGGCTTGGTACAGCCTGGAGGGTCCCT
GAGACTCTCCTGTGCAGCCTCTGCTTTCGATTTCTCTGATTATGAAATGAGCTGG
GTCCGCGAGGCTCCAGGGAAGGGGCTGGAGTGGATTGGGAAATCAATGATAGT
GGAAACACCATTTACAATCCGTCCCTCAAGAGTCGAGTCACCATCTCCAGAGAC
AATTCCAAGAACACACTGTATCTGCAAATGAACACCCTGAGAGCCGAGGACACA
GCCATATATTACTGTGCGATATATGGTGGTAACTCCGGGGGAGAGTACTGGGGC
CAGGGCACCCTGGTCACCGTCTCCTCACCGGCTCCACGACCACCCACTCCAGCCC
CAACGATTGCGAGCCAACTCTCAGTCTTCGGCCCGAGGCTTGCAGGCCAGCCG
CAGGAGGAGCAGTGCACACCCGAGGACTGGATTTCGATACCGCACTGGCGGCCG
TGATCTGTAGCGCCCTGGCCACCGTGCTGCTGGCGCTGCTCATCCTTTGCGTGAT
CTACTGCAAGCGGCAGTAG

LTG2331: LP-C46-L3-mD1.22-CD8TM-41BB-CD3zeta-F2AF-LP2-m36.4-TNFRSF19TM amino acid sequence (SEQ ID NO: 114)

MLLLVTSLLLCELPHPAFLLIPDTWMEWDREINNYTSLIHSLIEESQNQQEKNEQELL
ELDKWASLWNWFGGGSGGGGSGGGGSKKVVYGKKGDTVELTCTASQKKNIQFH
WKNSNQIKILGNQGSFLTKGPSKLNDRVDSRRSLWDQGNFPLIIKNLKPEDSDTYICE

FIG. 2V Cont.

VEDQKEEVQLVVVGAAATTTPAPRPPTPAPTIASQPLSLRPEACRPAAGGAVHTRGL
DFACDIYIWAPLAGTCGVLLLSLVITLYCKRGRKKLLYIFKQPFMRPVQTTQEEDGCS
CRFPEEEEGGCELRVKFSRSADAPAYQQGQNQLYNELNLGRREEYDVLDKRRGRDP
EMGGKPRRKNPQEGLYNELQKDKMAEAYSEIGMKGERRRGKGHDGLYQGLSTAT
KDTYDALHMQALPPRRAKRSGSGATNFSLLKQAGDVEENPGPRAKRMGIQGGSVLF
GLLLVLAVFCHSGHSLQQVQLVQSGGGLVQPGGSLRLSCAASAFDFSDYEMSWVRE
APGKGLEWIGEINDSGNTIYNPSLKSRVTISRDNSKNTLYLQMNTLRAEDTAIYYCAI
YGGNSGGEYWGQGTLVTVSSPAPRPPTPAPTIASQPLSLRPEACRPAAGGAVHTRGL
DFDTALAAVICSALATVLLALLILCVIYCKRQ

FIG. 2W

LTG2332: LP-C46-L5-mD1.22-CD8TM-41BB-CD3zeta-F2AF-LP2-m36.4-TNFRSF19TM nucleic acid sequence (SEQ ID NO: 117)

ATGCTTCTCCTGGTCACCTCCCTGCTCCTCTGCGAACTGCCTCACCCTGCCTTCCT
TCTGATTCCTGACACCTGGATGGAATGGGATCGCGAAATCAACAACTACACCTC
CCTGATTCACTCCCTGATTGAGGAATCCCAGAATCAACAGGAGAAGAACGAACA
AGAGCTTCTGGAGCTGGACAAATGGGCCTCCCTGTGGAACTGGTTCGGCGGAGG
GGGGAGTGGAGGTGGCGGTTCAGGAGGTGGGGGAAGCGGTGGCGGTGGTAGTG
GCGGTGGCGGTTCAAAGAAAGTCGTGTACGGAAAGAAGGGAGACACTGTGGAG
CTGACCTGTACCGCAAGCCAGAAGAAGAACATCCAGTTCCACTGGAAGAACTCC
AACCAAATCAAGATCCTGGGGAACCAGGGTTCCTTCCTGACTAAGGGACCCTCA
AAGCTGAACGACCGCGTGGATAGCAGACGCTCCCTGTGGGACCAGGGAAACTTC
CCGCTTATCATTAAGAACCTCAAACCTGAGGACTCGGATACCTACATCTGCGAA
GTGGAGGACCAGAAGGAGGAGGTGCAGCTGGTGGTGGTGGGCGCGGCCGCAAC
TACCACCCCTGCCCCTCGGCCGCCGACTCCGGCCCCAACCATCGCAAGCCAACCC
CTCTCCTTGCGCCCCGAAGCTTGCCGCCCGGCCGCGGGTGGAGCCGTGCATACCC
GGGGGCTGGACTTTGCCTGCGATATCTACATTTGGGCCCCGCTGGCCGGCACTTG
CGGCGTGCTCCTGCTGTCGCTGGTCATCACCCTTTACTGCAAGAGGGGCCGGAAG
AAGCTGCTTTACATCTTCAAGCAGCCGTTCATGCGGCCCGTGCAGACGACTCAGG
AAGAGGACGGATGCTCGTGCAGATTCCTGAGGAGGAAGAGGGGGGATGCGAA
CTGCGCGTCAAGTTCTCACGGTCCGCCGACGCCCCCGCATATCAACAGGGCCAG
AATCAGCTCTACAACGAGCTGAACCTGGGAAGGAGAGAGGAGTACGACGTGCTG
GACAAGCGACGCGGACGCGACCCGGAGATGGGGGGGAAACCACGGCGGAAAAA
CCCTCAGGAAGGACTGTACAACGAACTCCAGAAAGACAAGATGGCGGAAGCCT
ACTCAGAAATCGGGATGAAGGGAGAGCGGAGGAGGGGAAAGGGTCACGACGGG
CTGTACCAGGGACTGAGCACCGCCACTAAGGATACCTACGATGCCTTGCATATG
CAAGCACTCCCACCCCGGCGCGCGAAACGCAGCGGCAGCGGCGCGACCAACTTT
AGCCTGCTGAAACAGGCGGGCGATGTGGAAGAAAACCCGGGCCCGCGAGCAAA
GAGGATGGGAATTCAGGGGGGTTCCGTGCTCTTTGGCTTGCTCCTGGTCCTGGCA
GTGTTTTGTCACTCGGGACACAGCCTGCAGCAGGTGCAGCTGGTGCAGTCTGGG
GGAGGCTTGGTACAGCCTGGAGGGTCCCTGAGACTCTCCTGTGCAGCCTCTGCTT
TCGATTTCTCTGATTATGAAATGAGCTGGGTCCGCGAGGCTCCAGGGAAGGGGC
TGGAGTGGATTGGGGAAATCAATGATAGTGGAAACACCATTTACAATCCGTCCC
TCAAGAGTCGAGTCACCATCTCCAGAGACAATTCCAAGAACACACTGTATCTGC
AAATGAACACCCTGAGAGCCGAGGACACAGCCATATATTACTGTGCGATATATG
GTGGTAACTCCGGGGGAGAGTACTGGGGCCAGGGCACCCTGGTCACCGTCTCCT
CACCGGCTCCACGACCACCCACTCCAGCCCCAACGATTGCGAGCCAACCTCTCA
GTCTTCGGCCCGAGGCTTGCAGGCCAGCCGCAGGAGGAGCAGTGCACACCCGAG
GACTGGATTTCGATACCGCACTGGCGGCCGTGATCTGTAGCGCCCTGGCCACCGT
GCTGCTGGCGCTGCTCATCCTTTGCGTGATCTACTGCAAGCGGCAGTAG

LTG2332: LP-C46-L5-mD1.22-CD8TM-41BB-CD3zeta-F2AF-LP2-m36.4-TNFRSF19TM amino acid sequence (SEQ ID NO: 118)

FIG. 2W Cont.

MLLLVTSLLLCELPHPAFLLIPDTWMEWDREINNYTSLIHSLIEESQNQQEKNEQELL
ELDKWASLWNWFGGGGSGGGGSGGGGSGGGGSGGGGSKKVVYGKKGDTVELTC
TASQKKNIQFHWKNSNQIKILGNQGSFLTKGPSKLNDRVDSRRSLWDQGNFPLIIKN
LKPEDSDTYICEVEDQKEEVQLVVVGAAATTTPAPRPPTPAPTIASQPLSLRPEACRP
AAGGAVHTRGLDFACDIYIWAPLAGTCGVLLLSLVITLYCKRGRKKLLYIFKQPFMR
PVQTTQEEDGCSCRFPEEEEGGCELRVKFSRSADAPAYQQGQNQLYNELNLGRREE
YDVLDKRRGRDPEMGGKPRRKNPQEGLYNELQKDKMAEAYSEIGMKGERRRGKG
HDGLYQGLSTATKDTYDALHMQALPPRRAKRSGSGATNFSLLKQAGDVEENPGPR
AKRMGIQGGSVLFGLLLVLAVFCHSGHSLQQVQLVQSGGGLVQPGGSLRLSCAASA
FDFSDYEMSWVREAPGKGLEWIGEINDSGNTIYNPSLKSRVTISRDNSKNTLYLQMN
TLRAEDTAIYYCAIYGGNSGGEYWGQGTLVTVSSPAPRPPTPAPTIASQPLSLRPEAC
RPAAGGAVHTRGLDFDTALAAVICSALATVLLALLILCVIYCKRQ

FIG. 2X

LTG2334: LP-mD1.22-L5-m36.4-CD8TM-41BB-CD3zeta-F2AF-LP2-C46-TNFRSF19TM nucleic acid sequence (SEQ ID NO: 121)

ATGCTTCTCCTGGTCACCTCCCTGCTCCTCTGCGAACTGCCTCACCCTGCCTTCCT
TCTGATTCCTGACACCAAGAAAGTCGTGTACGGAAAGAAGGGAGACACTGTGGA
GCTGACCTGTACCGCAAGCCAGAAGAAGAACATCCAGTTCCACTGGAAGAACTC
CAACCAAATCAAGATCCTGGGGAACCAGGGTTCCTTCCTGACTAAGGGACCCTC
AAAGCTGAACGACCGCGTGGATAGCAGACGCTCCCTGTGGGACCAGGGAAACTT
CCCGCTTATCATTAAGAACCTCAAACCTGAGGACTCGGATACCTACATCTGCGAA
GTGGAGGACCAGAAGGAGGAGGTGCAGCTGGTGGTGGTGGGCGGCGGAGGCGG
GTCAGGTGGCGGTGGTAGTGGCGGTGGCGGTCAGGCGGTGGTGGGAGTGGGGG
AGGAGGCAGCCAGGTGCAGCTGGTGCAGTCTGGGGGAGGCTTGGTACAGCCTGG
AGGGTCCCTGAGACTCTCCTGTGCAGCCTCTGCTTTCGATTTCTCTGATTATGAAA
TGAGCTGGGTCCGCGAGGCTCCAGGGAAGGGGCTGGAGTGGATTGGGGAAATCA
ATGATAGTGGAAACACCATTTACAATCCGTCCCTCAAGAGTCGAGTCACCATCTC
CAGAGACAATTCCAAGAACACACTGTATCTGCAAATGAACACCCTGAGAGCCGA
GGACACAGCCATATATTACTGTGCAGATATATGGTGGTAACTCCGGGGGAGAGTA
CTGGGGCCAGGGCACCCTGGTCACCGTCTCCTCAGCGGCCGCAACTACCACCCCT
GCCCCTCGGCCGCCGACTCCGGCCCCAACCATCGCAAGCCAACCCCTCTCCTTGC
GCCCCGAAGCTTGCCGCCCGGCCGCGGGTGGAGCCGTGCATACCCGGGGGCTGG
ACTTTGCCTGCGATATCTACATTTGGGCCCCGCTGGCCGGCACTTGCGGCGTGCT
CCTGCTGTCGCTGGTCATCACCCTTTACTGCAAGAGGGGCCGGAAGAAGCTGCTT
TACATCTTCAAGCAGCCGTTCATGCGGCCCGTGCAGACGACTCAGGAAGAGGAC
GGATGCTCGTGCAGATTCCCTGAGGAGGAAGAGGGGGGATGCGAACTGCGCGTC
AAGTTCTCACGGTCCGCCGACGCCCCCGCATATCAACAGGGCCAGAATCAGCTC
TACAACGAGCTGAACCTGGGAAGGAGAGAGGAGTACGACGTGCTGGACAAGCG
ACGCGGACGCGACCCGGAGATGGGGGGGAAACCACGGCGGAAAAACCCTCAGG
AAGGACTGTACAACGAACTCCAGAAAGACAAGATGGCGGAAGCCTACTCAGAA
ATCGGGATGAAGGGAGAGCGGAGGAGGGGAAAGGGTCACGACGGGCTGTACCA
GGGACTGAGCACCGCCACTAAGGATACCTACGATGCCTTGCATATGCAAGCACT
CCCACCCCGGCGCGCGAAACGCAGCGGCAGCGGCGCGACCAACTTTAGCCTGCT
GAAACAGGCGGGCGATGTGGAAGAAAACCCGGGCCCGCGAGCAAAGAGGATGG
GAATTCAGGGGGGTTCCGTGCTCTTTGGCTTGCTCCTGGTCCTGGCAGTGTTTTGT
CACTCGGGACACAGCCTGCAGTGGATGGAATGGGATCGCGAAATCAACAACTAC
ACCTCCCTGATTCACTCCCTGATTGAGGAATCCAGAATCAACAGGAGAAGAAC
GAACAAGAGCTTCTGGAGCTGGACAAATGGGCCTCCCTGTGGAACTGGTTCCCG
GCTCCACGACCACCCACTCCAGCCCCAACGATTGCGAGCCAACCTCTCAGTCTTC
GGCCCGAGGCTTGCAGGCCAGCCGCAGGAGGAGCAGTGCACACCCGAGGACTG
GATTTCGATACCGCACTGGCGGCCGTGATCTGTAGCGCCCTGGCCACCGTGCTGC
TGGCGCTGCTCATCCTTTGCGTGATCTACTGCAAGCGGCAGTAG

LTG2334: LP-mD1.22-L5-m36.4-CD8TM-41BB-CD3zeta-F2AF-C46-TNFRSF19TM amino acid sequence (SEQ ID NO: 122)

FIG. 2X Cont.

MLLLVTSLLLCELPHPAFLLIPDTKKVVYGKKGDTVELTCTASQKKNIQFHWKNSNQ
IKILGNQGSFLTKGPSKLNDRVDSRRSLWDQGNFPLIIKNLKPEDSDTYICEVEDQKE
EVQLVVVGGGGSGGGGSGGGGSGGGGSGGGGSQVQLVQSGGGLVQPGGSLRLSC
AASAFDFSDYEMSWVREAPGKGLEWIGEINDSGNTIYNPSLKSRVTISRDNSKNTLY
LQMNTLRAEDTAIYYCAIYGGNSGGEYWGQGTLVTVSSAAATTTPAPRPPTPAPTIA
SQPLSLRPEACRPAAGGAVHTRGLDFACDIYIWAPLAGTCGVLLLSLVITLYCKRGR
KKLLYIFKQPFMRPVQTTQEEDGCSCRFPEEEEGGCELRVKFSRSADAPAYQQGQNQ
LYNELNLGRREEYDVLDKRRGRDPEMGGKPRRKNPQEGLYNELQKDKMAEAYSEI
GMKGERRRGKGHDGLYQGLSTATKDTYDALHMQALPPRRAKRSGSGATNFSLLKQ
AGDVEENPGPRAKRMGIQGGSVLFGLLLVLAVFCHSGHSLQWMEWDREINNYTSLI
HSLIEESQNQQEKNEQELLELDKWASLWNWFPAPRPPTPAPTIASQPLSLRPEACRPA
AGGAVHTRGLDFDTALAAVICSALATVLLALLILCVIYCKRQ

FIG. 4B     FIG. 4C

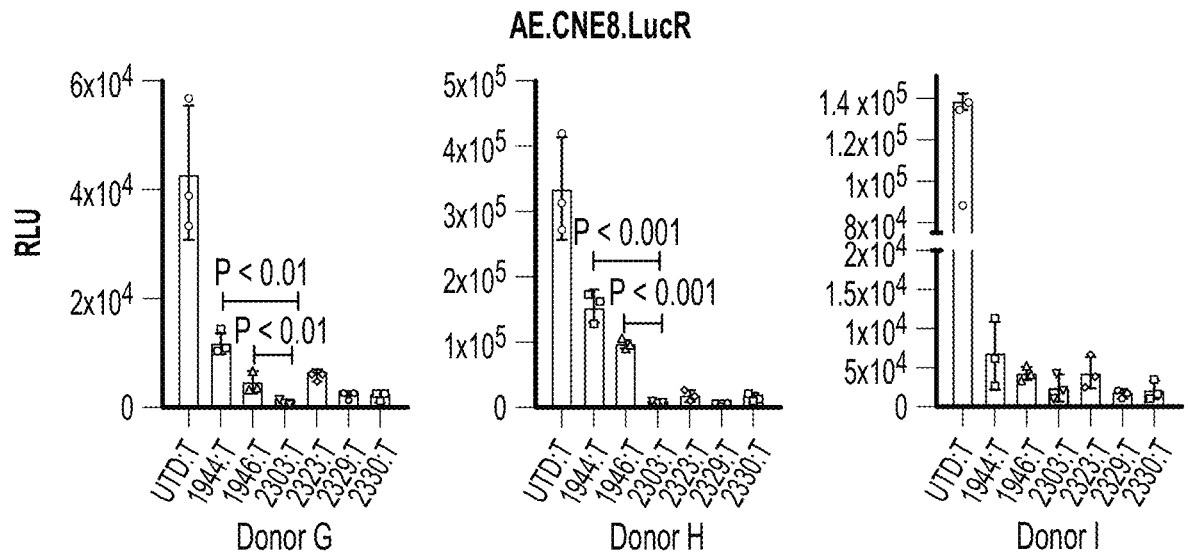
FIG. 14J
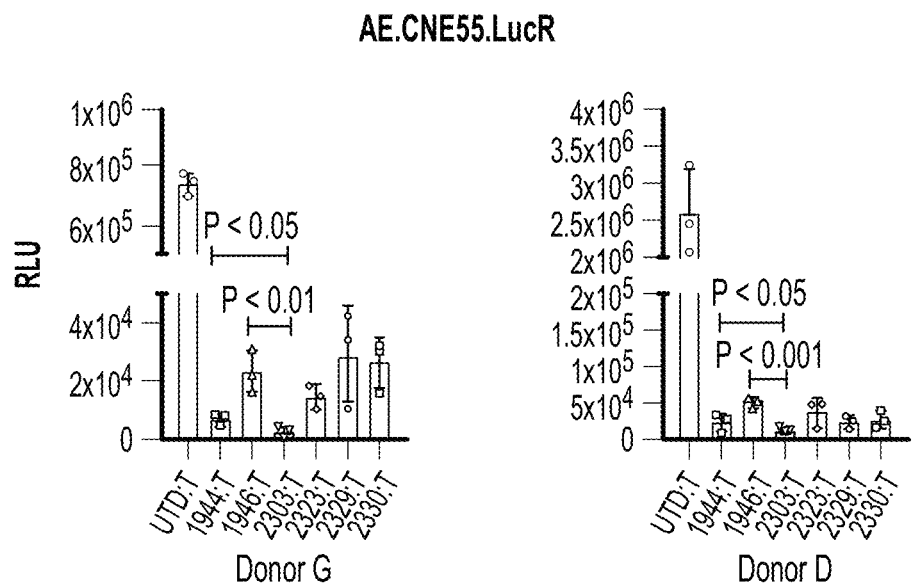
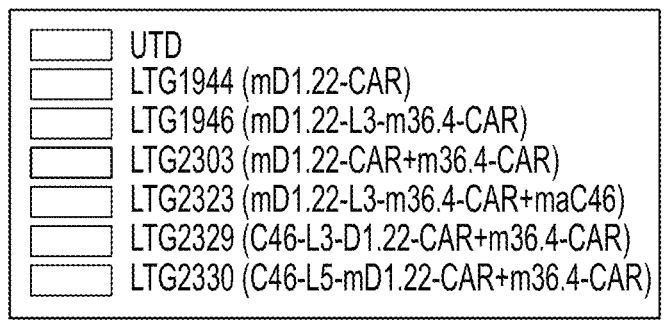
FIG. 14K

| | HIV-1 Strain | Clade | Geographic Location | VRC01 Neutralization | Mono | Bispecific | | Trispecific | | |
|---|---|---|---|---|---|---|---|---|---|---|
| | | | | | 1944 | 1946 | 2303 | 2323 | 2329 | 2330 |
| 1 | BaL | B | USA | Sensitive | -1.95 | -2.20 | -2.87 | -2.64 | -2.66 | -2.56 |
| 2 | NL4-3 | B | Clone | Sensitive | -0.73 | -1.62 | -2.34 | -1.75 | -3.01 | -2.70 |
| 3 | SF162 | B | USA | Sensitive | -1.63 | -2.08 | -2.77 | -2.60 | -2.00 | -2.03 |
| 4 | CAP45 | C | Malawi/East Africa | Partially Resistant | -2.00 | -1.79 | -2.66 | -1.67 | -2.91 | -2.49 |
| 5 | C.Du172.17 | C | S. Africa | Resistant | -1.14 | -1.26 | -1.95 | -1.56 | -2.05 | -2.49 |
| 6 | C.Du422.1 | C | S. Africa | Resistant | -1.24 | -1.39 | -2.19 | -1.46 | -2.21 | -2.15 |
| 7 | GX1632_S2_B10 | G | Spain/NW Africa | Sensitive | -1.81 | -1.77 | -2.10 | -1.79 | -2.28 | -2.25 |
| 8 | AC.246F3 | AC | Tanzania/Africa | Sensitive | -1.35 | -1.29 | -1.93 | -1.18 | -1.96 | -1.87 |
| 9 | AE.CNE8 | AE | S. China/Thailand | Sensitive | -0.73 | -1.00 | -1.88 | -1.20 | -1.73 | -1.51 |
| 10 | AE.CNE55 | AE | S. China/Thailand | Sensitive | -2.02 | -1.59 | -2.55 | -1.76 | -1.71 | -1.70 |
| 11 | BC.CH119.1 | BC | China | Partially Resistant | -1.43 | -1.30 | -1.93 | -1.48 | -2.09 | -2.07 |

Log Inhibition
- <-0.99 log
- -1 to -1.49 log
- -1.50 to -1.99 log
- -2.00 to -2.49 log
- -2.50 to -3.00 log

FIG. 15

| HIV-1 Strain | Clade | Geographic Location | VRC01 Neutralization | Mono | Bispecific | | Trispecific | | |
|---|---|---|---|---|---|---|---|---|---|
| | | | | 1944 | 1946 | 2303 | 2323 | 2329 | 2330 |
| 1 | BaL | B | USA | Sensitive | 80.43 | 99.25 | 99.71 | 99.54 | 99.25 | 99.69 |
| 2 | NL4-3 | B | Clone | Sensitive | 72.76 | 97.13 | 99.32 | 97.84 | 99.88 | 99.7 |
| 3 | SF162 | B | USA | Sensitive | 97.52 | 99.13 | 99.4 | 99.23 | 98.95 | 99.01 |
| 4 | CAP45 | C | Malawi/East Africa | Partially Resistant | 98.35 | 98.09 | 99.71 | 95.53 | 99 | 99.34 |
| 5 | C.Du172.17 | C | S. Africa | Resistant | 92.2 | 92.73 | 98.24 | 94.45 | 98.53 | 99.54 |
| 6 | C.Du422.1 | C | S. Africa | Resistant | 93.14 | 94.47 | 99.06 | 94.76 | 99.09 | 98.98 |
| 7 | GX1632_S2_B10 | G | Spain/NW Africa | Sensitive | 98.12 | 98.03 | 99.04 | 97.95 | 99.24 | 99.18 |
| 8 | AC.246F3 | AC | Tanzania/Africa | Sensitive | 95.05 | 91.66 | 96.47 | 88 | 98.11 | 96.5 |
| 9 | AE.CNE8 | AE | S. China/Thailand | Sensitive | 73.5 | 85.5 | 98.59 | 92.47 | 97.5 | 96.53 |
| 10 | AE.CNE55 | AE | S. China/Thailand | Sensitive | 99.04 | 97.39 | 99.72 | 98.25 | 97.51 | 97.63 |
| 11 | BC.CH119.1 | BC | China | Partially Resistant | 93.79 | 92.08 | 96.34 | 95.38 | 96.91 | 99.51 |

% inhibition: <95.99%, 96-96.99%, 97-97.99%, 98-98.99%, >99%

FIG. 16

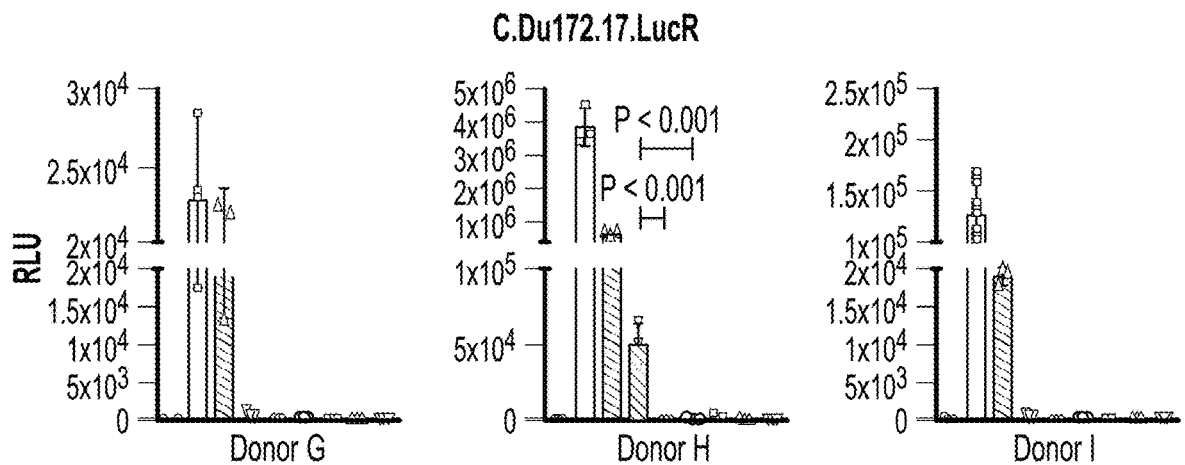
FIG. 18D
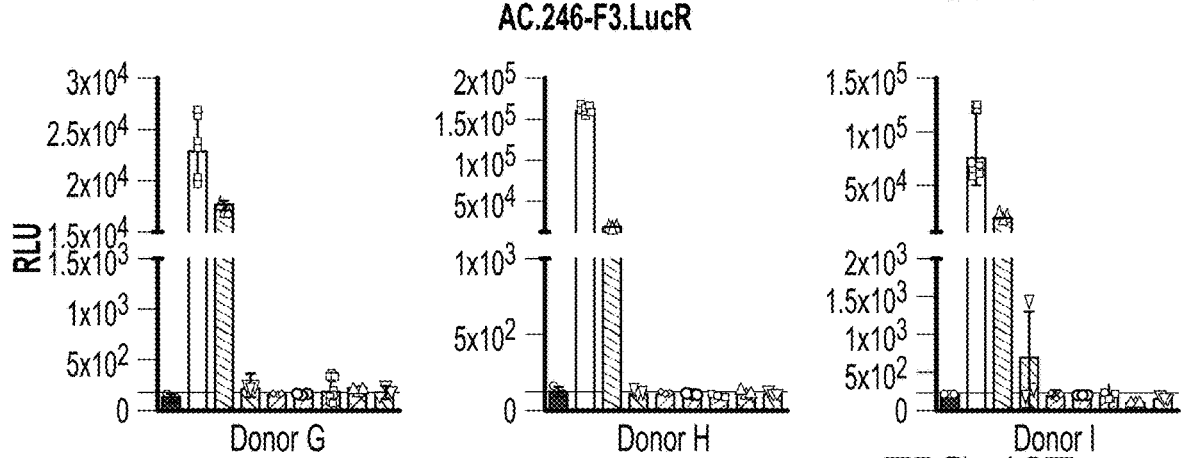
FIG. 18E
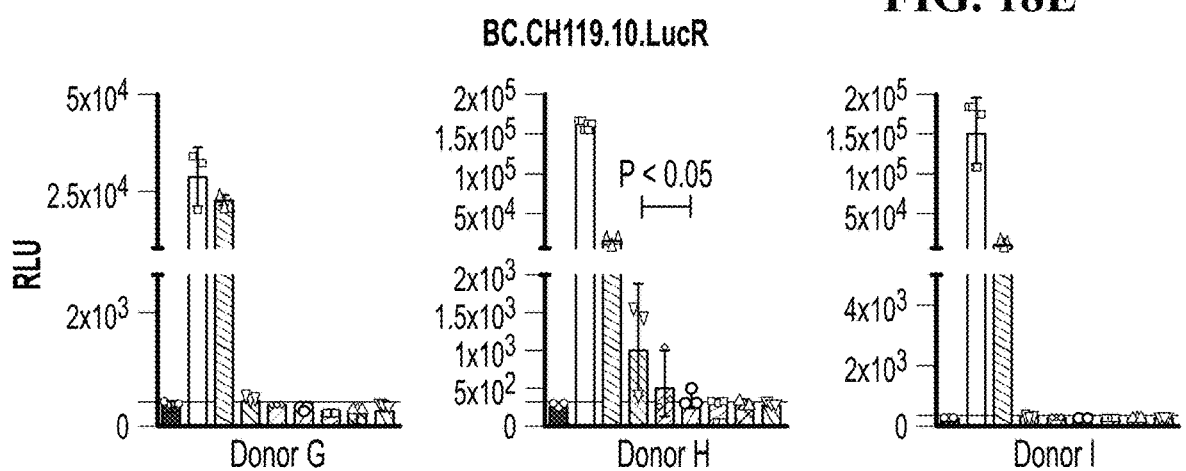
FIG. 18F
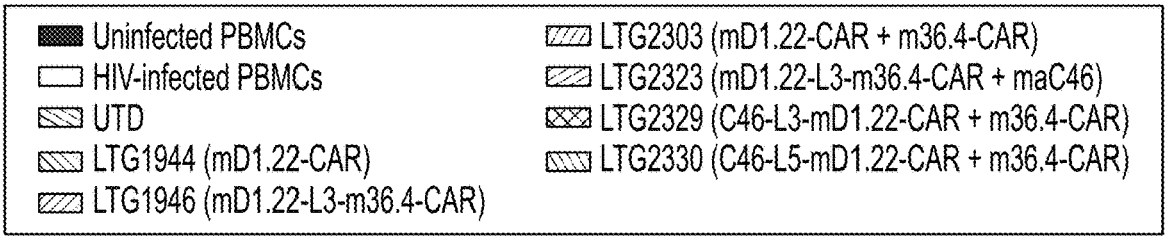

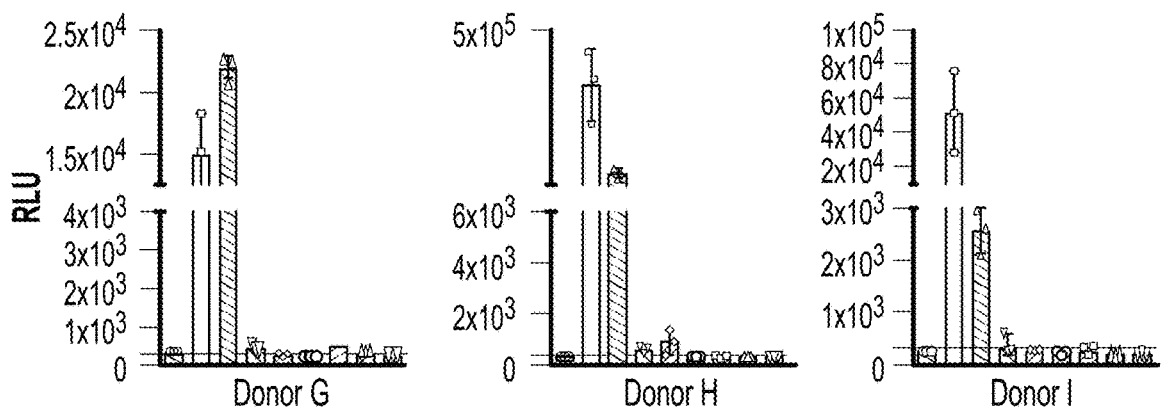
FIG. 18G
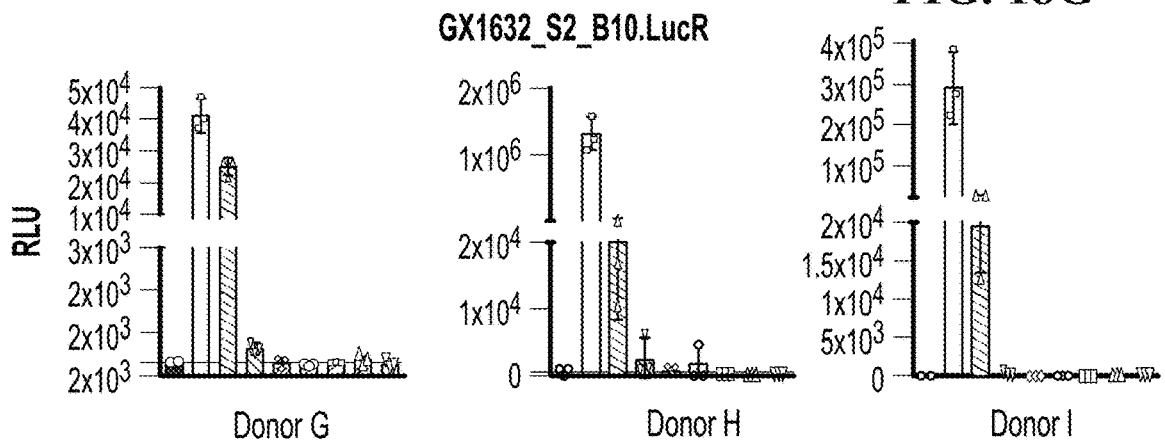
FIG. 18H
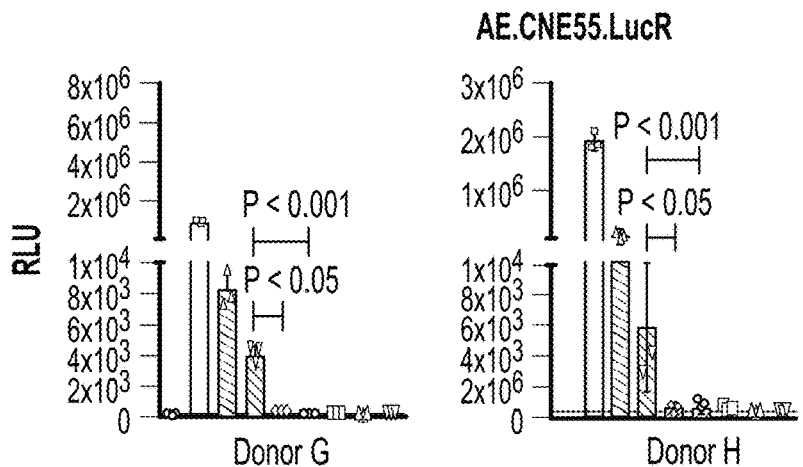
FIG. 18I
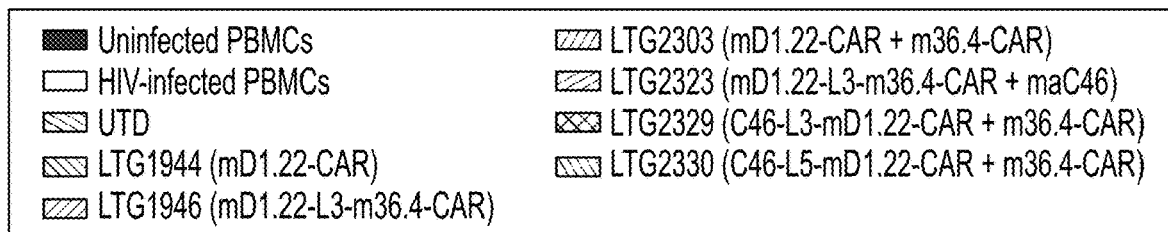

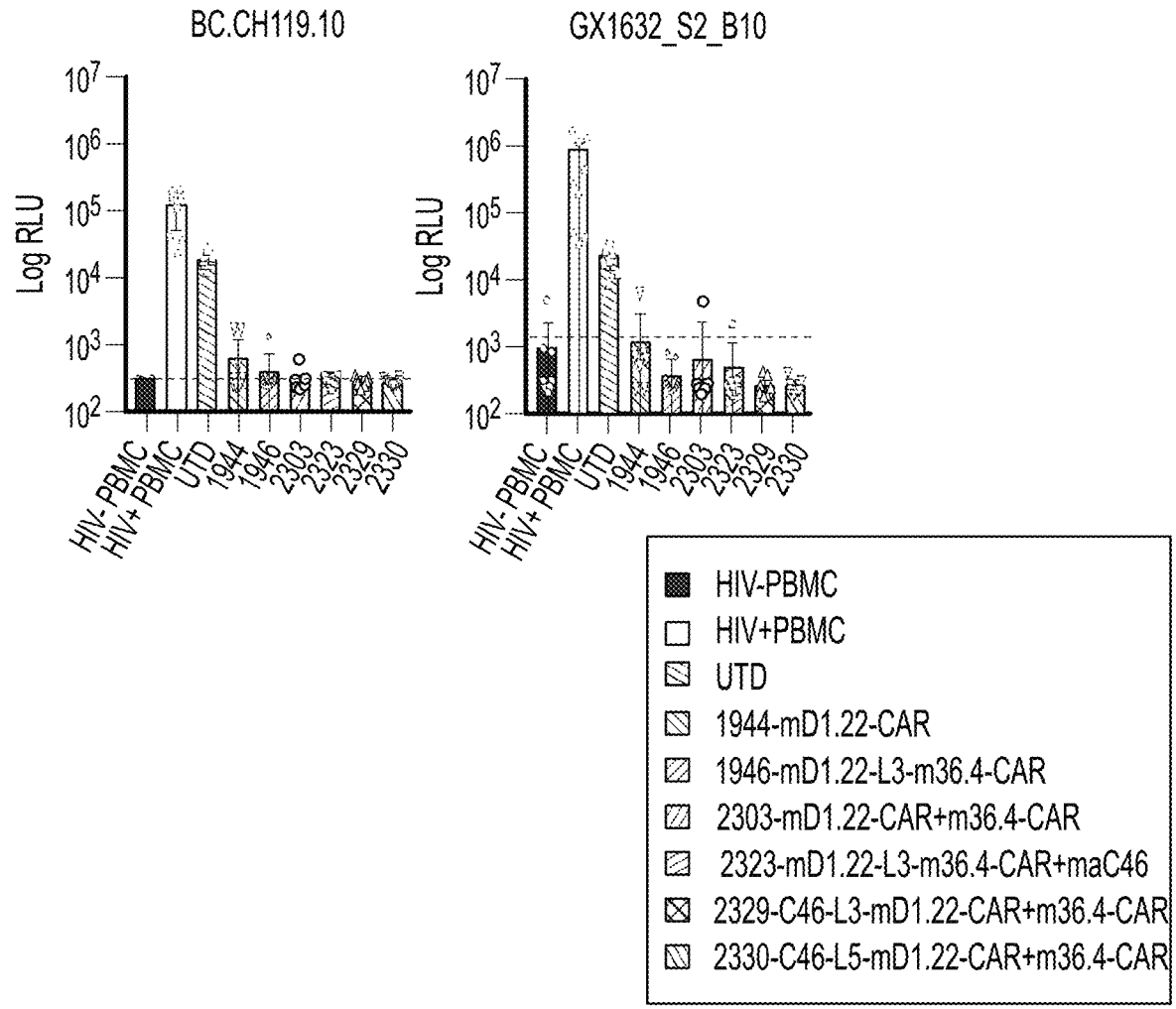
FIG. 18J(Cont...)

COMPOSITIONS AND METHODS FOR TREATING HIV/AIDS WITH IMMUNOTHERAPY

CROSS-REFERENCE TO RELATED APPLICATIONS

This application claims the benefit of priority under 35 U.S.C. Section 119(e) to U.S. Provisional Patent Application No. 62/608,479, filed on Dec. 20, 2017, U.S. Provisional Patent Application No. 62/660,819, filed on Apr. 20, 2018, the entire contents of each of which are incorporated herein by reference.

SEQUENCE LISTING

The instant application contains a Sequence Listing which has been submitted electronically in ASCII format and is hereby incorporated by reference in its entirety. The ASCII copy, created on Dec. 18, 2018, is named SequenceListing.txt and is 232 kilobytes in size.

STATEMENT REGARDING FEDERALLY SPONSORED RESEARCH OR DEVELOPMENT

Not applicable

FIELD OF THE DISCLOSURE

This application relates to the field of disease associated with infection with the human immunodeficiency virus/acquired immunodeficiency syndrome (HIV, HIV/AIDS), particularly to protein binding domains and chimeric antigen receptors (CARs) containing such binding domains and methods of use thereof.

BACKGROUND

Infection with Human Immunodeficiency Virus (HIV) remains a major threat to human health. In 2016, 1.0 million people died from HIV-related causes globally, and an estimated 36.7 million people are living with HIV. Fifty-four percent of adults and 43% of children living with HIV are currently receiving lifelong anti-retroviral drug-based therapy (ART). There is no cure for HIV infection, however ART has allowed many to live long and productive lives (all data from WHO Fact sheet, updated July 2017). Long-term anti-retroviral therapy (ART) can lead to increased chances of severe toxicities and co-morbidities such as, lipodystrophy, insulin resistance, cardiovascular disease, and organ failure. In addition, long-term ART can lead to emergence of HIV resistance and reduced drug efficacy. Although ART is successful in controlling infection, it is not a cure.

HIV infection can be blocked by inhibiting its ability to enter and replicate in the host. As an alternative to ART, several HIV therapies have been attempted that are based on passive immunotherapy using HIV-1 specific broadly neutralizing antibodies to inhibit and control HIV infection (reviewed in Margolis et al., Immunol Rev 2017; 275: 313-323). These therapies have exceptional breadth and potency against diverse HIV clades in vitro. However, these monotherapies when applied in vivo are not fully effective and are met with several challenges such as antibody stability (reviewed in Boesch et al., Current Opinion in HIV and AIDS 2015, 10(3):160-169), lack of virologic control (Bar et al., N Engl J Med 2016; 375:2037-2050), HIV resistance (Wu et al., Journal of Virology 2012; 86:5844-5853), and persistence of the latent HIV reservoir (reviewed in Margolis et al., Immunol Rev 2017; 275:313-323).

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Oncoimmunology 2013; 2 (4):e23621). The antigen-binding motif of a CAR is commonly fashioned after a single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D or CD4) also have been engineered into CARs. Alternate cell targets for CAR expression (such as NK or gamma-delta T cells) are also under development (Brown C E et al., Clin Cancer Res. 2012; 18(8):2199-209; Lehner M et al. PLoS One. 2012; 7 (2):e31210). There remains significant work to be done with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some cellular targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was also used in third-generation CARs containing CD137 (4-1BB) signaling motifs (Zhao Y et al J Immunol. 2009; 183 (9): 5563-74). With the advent of new technology, the activation of T cells with beads linked to anti-CD3 and anti-CD28 antibodies, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-CARs targeting B cell precursor ALL, Blood. 2013; 121 (7):1165-74; Kochenderfer J N et al., Blood 2012; 119 (12):2709-20). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured, for example the inclusion of the cytokines IL-2, IL-7, and/or IL-15 (Kaiser A D et al. Cancer Gene Ther. 2015; 22(2):72-78).

T-cell-based immunotherapy featuring CARs has become a new frontier in synthetic biology in both cancer therapy and in therapy for infectious diseases. Multiple promoters and gene products can be introduced into primary lymphocytes using gene engineering techniques such as the use of lentivirus-based gene vectors (LV). Engineering T cells with LV expressing CARs are envisioned to steer these highly potent cells to sites of HIV-infection and HIV-reactivation from latency, where CAR-engineered T cells can both evade HIV infection by inhibiting fusion with HIV virions or infected cells and also mediate effective killing of cells expressing the viral envelope protein and thus eliminating HIV-infected cells and thus the viral reservoir.

The "Berlin patient" (an HIV-infected bone marrow transplant patient that received hematopoietic stem cells (HSC) from a CCR5 variant donor) is the only reported case of an HIV cure, and in principle demonstrates that HIV eradication is achievable. One major barrier in the search for an HIV cure is the ability of HIV to persist in a latent state within cellular reservoirs in the host. One approach called "shock and kill" exploits latency reversing agents (LRAs) to reactivate the latent HIV reservoir. These agents "shock" the latently infected cell to reactivate the virus at the epigenetic level. When combined with immunotherapies that effectively "kill" HIV-infected cells, this combinatorial approach has been proposed as a pathway towards a HIV cure.

Previously tested immunotherapies using CAR strategies for HIV include fusing the CD4-receptor or a broadly-neutralizing antibody domain (bnAb) to transmembrane and the intracellular domain of the CD3zeta chain. In the late 1990s, first-generation anti-HIV CARs were constructed with the extracellular region of the CD4 receptor (CD4-zeta) and demonstrated to be highly effective in eliminating HIV-infected cells in vitro (Tran et al., The Journal of Immunology 1995; 155:(2)1000-1009; Yang et al., PNAS 1997; 94(21):11478-11483). However, in vivo they showed no significant control over HIV infection and were possibly susceptible to HIV infection themselves (reviewed in Lam et al. Immunotherapy 2013, 5(4):404-414). Similarly, CARs engineered with bnAbs have also shown promising results in vitro. In 2015, one group reported that an anti-HIV CAR consisting of the CD4 receptor fused to a bnAb (17b) effectively kills HIV-infected cells while resisting infection (Liu et al., J. Virol. 2015; 89:13 10 6685-6694). One major drawback with developing CARs with bnAbs is that they require further engineering to account for reduced therapeutic effectiveness (Bar et al., N Engl J Med 2016; 375:2037-2050; Sievers et al., Current Opinion in HIV and AIDS; 2015: 10(3), 151-159). Furthermore, this approach may lead to undesired viral escape (Wu et al., Journal of Virology 2012; 86:5844-5853; Barr et al. N Engl J Med 2016; 375:2037-2050; Lynch et al., 2015 Journal of Virology; 89(8): 4201-4213).

With regard to clinical experience with CAR-transduced T cells for HIV, the first clinical trials almost two decades ago were done using CAR-T for HIV. The clinical trials demonstrated that anti-HIV CAR-T therapies are safe and have exceptional in vivo persistence (Mitsuyasu et al., Blood 2000; 96(3): 785-793; Deeks et al., Mol Ther. 2002; 5:788). One striking finding was that despite only modest control of HIV viremia, modified-CAR T-cells trafficked to tissues that harbor the latent HIV reservoir (Mitsuyasu et al., Blood 2000; 96(3): 785-793). This is a major advantage over non-CAR approaches and suggests that CAR-T actively engages in immunosurveillance activities. Since then, studies suggest that CAR-T may also be able to reactivate the latent HIV reservoir of chronically-infected cells through cytokine release (Sahu et al., Virology 2013; 446(0): 268-275). These findings have strong implications for a HIV cure and support the rationale for developing improved anti-HIV CAR-T therapies.

New HIV therapies combining HIV-1 entry or fusion inhibitors to form a Chimeric Antigen Receptor (Anti-HIV CAR) is another attractive approach to effectively target and subsequently kill HIV-infected cells. The advantage of this approach is that in the absence of ART, anti-HIV CARs have the potential to mediate immunosurveillance of the latent HIV reservoir while effectively eliminating HIV infected cells. Furthermore, combining multiple entry and/or fusion inhibitors makes it harder for HIV to infect the CAR-modified T cell and to thereby undergo further replication and develop resistance. Therefore, newly developed anti-HIV CAR therapies especially those containing more than one inhibitor have strong implications toward a functional cure.

There is an urgent and long felt need in the art for discovering novel compositions and methods for treatment of HIV/AIDS using an approach that can exhibit specific and efficacious anti-HIV disease effect without the aforementioned short comings.

The present invention addresses these needs by providing CAR compositions and therapeutic methods that can be used to treat HIV and other diseases and/or conditions. In particular, the present invention as disclosed and described herein provides CARs that may be used for the treatment of diseases, disorders or conditions associated with expression of HIV envelope protein in which CARs contain multiple HIV antigen binding domains that exhibit a high surface expression on transduced T cells, exhibit a high degree of cytolysis of HIV-infected cells, and in which the transduced T cells demonstrate in vivo expansion and persistence.

SUMMARY

Novel anti-HIV envelope protein antibodies or antigen binding domains thereof and chimeric antigen receptors (CARs) that contain such anti-HIV envelope protein antigen binding domains are provided herein, as well as host cells (e.g., T cells) expressing the receptors, and nucleic acid molecules encoding the receptors. The CARs exhibit a high level of surface expression on transduced T cells, exert a high degree of cytolysis, and with the ability of transduced T cells to expand and persist in vivo. Methods of using the disclosed CARs, host cells, and nucleic acid molecules are also provided, for example, to treat HIV infection or AIDS, or HIV-related cancers in a patient.

In one aspect, improved second generation CARs are provided herein comprising three unique classes of HIV peptide inhibitors (mD1.22, m36.4, and C46 peptide). When these domains are engineered in certain orientations within the context of an HIV Chimeric Antigen Receptor, they form a novel collection of highly potent bispecific (a combination of two HIV inhibitors) and trispecific (a combination of three HIV inhibitors) anti-HIV CARs. The anti-HIV CARs provided herein are designed to destroy HIV-infected cells while conferring protection to the CAR T-cell.

Thus, in one aspect, an isolated polynucleotide encoding an anti-HIV envelope protein (anti-HIV binder, or simply anti-HIV) or a fragment thereof is provided comprising a nucleic acid sequence selected from the group consisting of SEQ ID NOs: 1, 3, and 5.

In another aspect, an isolated polynucleotide encoding an anti-HIV envelope protein linked to a second anti-HIV envelope protein, or a fragment thereof is provided comprising a nucleic acid sequence selected from the group consisting of SEQ ID NOs: 45, 49, 53, 57, 61, 65, 75, 79, 83, and 87.

In another aspect, an isolated polynucleotide encoding an anti-HIV envelope protein is expressed in a cell encoding a second anti-HIV envelope protein, or fragment thereof is provided comprising a nucleic acid sequence consisting of SEQ ID NO: 69.

In yet another aspect, an isolated polynucleotide encoding an anti-HIV envelope protein linked to two additional anti-HIV envelope proteins, or a fragment thereof is provided comprising a nucleic acid sequence selected from the group consisting of SEQ ID NOs: 91, 95, and 99.

In another aspect, an isolated polynucleotide encoding an anti-HIV envelope protein linked to another anti-HIV envelope protein expressed in a cell where another such anti-HIV envelope protein is expressed comprising a nucleic acid sequence selected from the group consisting of SEQ ID NOs: 103, 111, 115, and 119.

In one embodiment, an isolated polynucleotide encoding a fully human anti-HIV antibody or a fragment thereof is provided, wherein the antibody or a fragment thereof comprises a fragment selected from the group consisting of a Fab fragment, a F(ab')$_2$ fragment, a Fv fragment, and a single chain Fv (ScFv).

In one embodiment, an isolated polynucleotide encoding an anti-HIV antibody or a fragment thereof or another anti-HIV binding protein is provided, wherein the antibody or a fragment thereof, comprises an amino acid sequence selected from the group consisting of SEQ ID NOs: 2, 4, and 6.

In another embodiment, an isolated polynucleotide encoding an anti-HIV antibody or a fragment thereof or other anti-HIV binding protein is provided, wherein the antibody or a fragment thereof, or other anti-HIV binding protein is linked to a second such anti-HIV binder comprised of an amino acid sequence selected from the group consisting of SEQ ID NOs: 46, 50, 54, 58, 62, 66, 76, 80, 84, and 88.

In yet another embodiment, an isolated polynucleotide encoding an anti-HIV antibody or a fragment thereof or other anti-HIV binding protein is provided, wherein the antibody or a fragment thereof, or other anti-HIV binding protein is expressed in a cell that contains a second anti-HIV binder comprised of an amino acid sequence comprising SEQ ID NO: 70. In yet another embodiment, an isolated polynucleotide encoding an anti-HIV antibody or a fragment thereof or other anti-HIV binding protein is provided, wherein the antibody or a fragment thereof, or other anti-HIV binding protein is linked to two additional such anti-HIV binders comprised of an amino acid sequence selected from the group consisting of SEQ ID NOs: 92, 96, and 100.

In another embodiment, an isolated polynucleotide encoding an anti-HIV envelope protein linked to another anti-HIV envelope protein expressed in a cell where another such anti-HIV envelope proteins is expressed comprising an amino acid sequence selected from the group consisting of SEQ ID NOs: 104, 112, 116, and 120.

In one aspect, an isolated nucleic acid molecule encoding a CAR is provided comprising, from N-terminus to C-terminus, at least one HIV antigen binding domain encoded by a nucleotide sequence comprising a nucleic acid sequence selected from the group consisting of SEQ ID NOs: 1, 3, and 5; at least one transmembrane domain; and at least one intracellular signaling domain.

In one embodiment, an isolated nucleic acid molecule encoding the CAR is provided wherein the encoded extracellular HIV antigen binding domain comprises at least one single chain variable fragment of an antibody or a minimized single antibody domain (for example VH-only) that binds to the HIV envelope protein.

In another embodiment, an isolated nucleic acid molecule encoding the CAR is provided wherein the encoded extracellular HIV antigen binding domain comprises at least one heavy chain variable region of an antibody that binds to HIV.

In yet another embodiment, an isolated nucleic acid molecule encoding the CAR is provided wherein the encoded CAR extracellular HIV antigen binding domain further comprises at least one lipocalin-based antigen binding antigen (anticalins) that binds to HIV.

In yet another embodiment, an isolated nucleic acid molecule encoding a CAR is provided wherein the encoded CAR extracellular HIV antigen binding domain is comprised of a single immunoglobulin domain, such as a VH-only domain, or a similar single chain Ig-like binding moiety.

In one embodiment, an isolated nucleic acid molecule is provided wherein the encoded extracellular HIV antigen binding domain is connected to the transmembrane domain by a linker domain.

In another embodiment, an isolated nucleic acid molecule encoding the CAR is provided wherein the encoded HIV extracellular antigen binding domain is preceded by a sequence encoding a leader or signal peptide.

In yet another embodiment, an isolated nucleic acid molecule encoding the CAR is provided comprising at least one HIV antigen binding domain encoded by a nucleotide sequence comprising a nucleic acid sequence selected from the group consisting of SEQ ID NOs: 1, 3, and 5, and wherein the CAR additionally encodes an extracellular antigen binding domain which targets an antigen that includes, but is not limited to, a HIV latency-associated antigen (e.g., CD32a), Hepatitis B Virus (HBV) surface antigen (HBsAg), Hepatitis C Virus (HCV) E2 protein, Cytomegalovirus (CMV) glycoprotein B, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, TSLPR, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD32a ScFv antigen binding domain, anti-HBsAg ScFv antigen binding domain, an anti-HCV E2 ScFv antigen binding domain, an anti-CMV glycoprotein B ScFv antigen binding domain, an anti-CD19 ScFv antigen binding domain, an anti-CD20 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-TSLPR ScFv antigen binding domain an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a single linker or spacer domain.

In another aspect, the CARs provided herein that contain more than one HIV antigen binder, may contain two, three or four linker or spacer domains.

In one embodiment, an isolated nucleic acid molecule encoding the CAR is provided wherein the extracellular HIV antigen binding domain, the intracellular signaling domain, or both are connected to the transmembrane domain by a linker or spacer domain.

In one aspect, an isolated nucleic acid molecule encoding the CAR is provided wherein the extracellular HIV antigen binding domains are connected to one another or the transmembrane domain by nucleic acid sequence encoding a linker or spacer domain selected from the group consisting of SEQ ID NOs: 9, 23, 25, 27, 29, and 31.

In one embodiment, an isolated nucleic acid molecule encoding the CAR is provided wherein the extracellular HIV antigen binding domains are connected to one another or the transmembrane domain by a linker or spacer domain by amino acid sequence selected from the group consisting of SEQ ID NOs: 10, 24, 26, 28, 30, and 32.

In one aspect, an isolated nucleic acid molecule encoding the CAR is provided wherein the extracellular HIV antigen binding domains are connected to one another or the transmembrane domain by nucleic acid sequence encoding a linker or spacer domain that contains furin cleavage sites flanking a translational skip site as exemplified in SEQ ID NOs: 33.

In one embodiment, an isolated nucleic acid molecule encoding the CAR is provided wherein the extracellular HIV antigen binding domains are connected to one another or the transmembrane domain by a linker or spacer domain that contains furin cleavage sites flanking a translational skip site comprised of amino acid sequence as exemplified by SEQ ID NOs: 34.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD83, CD86, CD134, CD137, CD154, TNFRSF19, or a combination thereof.

In yet another embodiment, an isolated nucleic acid molecule encoding the CAR is provided wherein the encoded intracellular signaling domain further comprises a CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In yet another embodiment, where more than one HIV antigen binders may be expressed on two different transmembrane proteins in the same cell, the two proteins may express identical intracellular signaling domains, different signaling domains, or one may express no signaling domains.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 35 or SEQ ID NO: 37.

In yet another embodiment, an isolated nucleic acid molecule encoding the CAR is provided wherein the encoded leader sequence comprises the amino acid sequence of SEQ ID NO: 36 or SEQ ID NO: 38.

In one aspect, a CAR is provided herein comprising, from N-terminus to C-terminus, at least one HIV antigen binding domain, at least one transmembrane domain, and at least one intracellular signaling domain.

In one embodiment, a CAR is provided wherein the extracellular HIV antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, TNFRSF19, or a combination thereof.

In some embodiments, the CAR is provided wherein CAR additionally encodes an extracellular antigen binding domain comprising a HIV latency-associated antigen (e.g., CD32a), Hepatitis B Virus (HBV) surface antigen (HBsAg), Hepatitis C Virus (HCV) E2 protein, Cytomegalovirus (CMV) glycoprotein B, CD19, CD20, ROR1, mesothelin, CD33, CD38, CD123 (IL3RA), CD138, BCMA (CD269), GPC2, GPC3, FGFR4, TSLPR, c-Met, PSMA, Glycolipid F77, EGFRvIII, GD-2, TSLPR, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD32a ScFv antigen binding domain, anti-HBsAg ScFv antigen binding domain, an anti-HCV E2 ScFv antigen binding domain, an anti-CMV glycoprotein B ScFv antigen binding domain, an anti-CD19 ScFv antigen binding domain, an anti-CD20 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, anti-TSLPR ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESO-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 39 (LTG1944, LP-mD1.22-CD8TM-41BB-CD3zeta nucleic acid sequence (FIG. 2A)). In one embodiment, the nucleic acid sequence encodes a CAR comprising the amino acid sequence of SEQ ID NO: 40 (LTG1944, LP-mD1.22-CD8TM-41BB-CD3zeta CAR amino acid sequence (FIG. 2A)).

In another embodiment, the nucleic acid sequence encoding a CAR comprises the nucleic acid sequence of SEQ ID NO: 41 (LTG1945, LP-m36.4-CD8TM-41BB-CD3zeta CAR nucleic acid sequence (FIG. 2B)). In one embodiment, the nucleic acid sequence encodes a CAR comprising the amino acid sequence of SEQ ID NO: 42 (LTG1945, LP-m36.4-CD8TM-41BB-CD3zeta CAR amino acid sequence (FIG. 2B)).

In another embodiment, the nucleic acid sequence encoding a CAR comprises the nucleic acid sequence of SEQ ID NO: 43 (LTG2328, LP-C46-CD8TM-41BB-CD3zeta CAR nucleotide sequence (FIG. 2C)). In one embodiment, the nucleic acid sequence encodes a CAR comprising the amino acid sequence of SEQ ID NO: 44 (LTG2328, LP-C46-CD8TM-41BB-CD3zeta CAR amino acid sequence (FIG. 2C)).

In another embodiment, the nucleic acid sequence encoding a CAR comprises the nucleic acid sequence of SEQ ID NO: 47 (LTG2325, LP-mD1.22-L1-m36.4-CD8TM-41BB-CD3zeta CAR nucleic acid sequence (FIG. 2D)). In one embodiment, the nucleic acid sequence encodes a CAR comprising the amino acid sequence of SEQ ID NO: 48 (LTG2325, LP-mD1.22-L1-m36.4-CD8TM-41BB-CD3zeta CAR amino acid sequence (FIG. 2D)).

In another embodiment, the nucleic acid sequence encoding a CAR comprises the nucleic acid sequence of SEQ ID NO: 51 (LTG2313, LP-mD1.22-L2-m36.4-CD8TM-41BB-CD3zeta CAR nucleic acid sequence (FIG. 2E)). In one embodiment, the nucleic acid sequence encodes a CAR comprising the amino acid sequence of SEQ ID NO: 52 (LTG2313, LP-mD1.22-L2-m36.4-CD8TM-41BB-CD3zeta CAR amino acid sequence (FIG. 2E)).

In another embodiment, the nucleic acid sequence encoding a CAR comprises the nucleic acid sequence of SEQ ID NO: 55 (LTG1946, LP-mD1.22-L3-m36.4-CD8TM-41BB-CD3zeta CAR nucleic acid sequence (FIG. 2F)). In one embodiment, the nucleic acid sequence encodes a CAR comprising the amino acid sequence of SEQ ID NO: 56 (LTG1946, LP-mD1.22-L3-m36.4-CD8TM-41BB-CD3zeta CAR amino acid sequence (FIG. 2F)).

In another embodiment, the nucleic acid sequence encoding a CAR comprises the nucleic acid sequence of SEQ ID NO: 59 (LTG2326, LP-mD1.22-L4-m36.4-CD8TM-41BB-CD3zeta CAR nucleic acid sequence (FIG. 2G)). In one embodiment, the nucleic acid sequence encodes a CAR comprising the amino acid sequence of SEQ ID NO: 60 (LTG2326, LP-mD1.22-L4-m36.4-CD8TM-41BB-CD3zeta CAR amino acid sequence (FIG. 2G)).

In another embodiment, the nucleic acid sequence encoding a CAR comprises the nucleic acid sequence of SEQ ID NO: 63 (LTG1947, LP-mD1.22-L5-m36.4-CD8TM-41BB-CD3zeta CAR nucleic acid sequence (FIG. 2H)). In one embodiment, the nucleic acid sequence encodes a CAR comprising the amino acid sequence of SEQ ID NO: 64 (LTG1947, LP-mD1.22-L5-m36.4-CD8TM-41BB-CD3zeta CAR amino acid sequence (FIG. 2H)).

In another embodiment, the nucleic acid sequence encoding a CAR comprises the nucleic acid sequence of SEQ ID NO: 67 (LTG1948, LP-m36.4-L3-mD1.22-CD8TM-41BB-CD3zeta CAR nucleic acid sequence (FIG. 2I)). In one embodiment, the nucleic acid sequence encodes a CAR comprising the amino acid sequence of SEQ ID NO: 68 (LTG1948, LP-m36.4-L3-mD1.22-CD8TM-41BB-CD3zeta CAR amino acid sequence (FIG. 2I)).

In another embodiment, the nucleic acid sequence encoding a CAR comprises the nucleic acid sequence of SEQ ID NO: 71 (LTG2303, LP-mD1.22-CD8TM-41BB-CD3zeta-F2AF-m36.4-TNFRSF19TM-CD3zeta2 CAR nucleic acid sequence (FIG. 2J)). In one embodiment, the nucleic acid sequence encodes a CAR comprising the amino acid sequence of SEQ ID NO: 72 (LTG2303, LP-mD1.22-CD8TM-41BB-CD3zeta-F2AF-m36.4-TNFRSF19TM-CD3zeta2 CAR amino acid sequence (FIG. 2J)).

In another embodiment, the nucleic acid sequence encoding a CAR comprises the nucleic acid sequence of SEQ ID NO: 73 (LTG2322, LP-mD1.22-CD8TM-41BB-CD3zeta-F2AF-m36.4-TNFRSF19TM CAR nucleic acid sequence (FIG. 2K)). In one embodiment, the nucleic acid sequence encodes a CAR comprising the amino acid sequence of SEQ ID NO: 74 (LTG2322, LP-mD1.22-CD8TM-41BB-CD3zeta-F2AF-m36.4-TNFRSF19TM CAR amino acid sequence (FIG. 2K)).

In another embodiment, the nucleic acid sequence encoding a CAR comprises the nucleic acid sequence of SEQ ID NO: 77 (LTG2314, LP-mD1.22-L3-C46-CD8TM-41BB-CD3zeta CAR nucleic acid sequence (FIG. 2L)). In one embodiment, the nucleic acid sequence encodes a CAR comprising the amino acid sequence of SEQ ID NO: 78 (LTG2314, LP-mD1.22-L3-C46-CD8TM-41BB-CD3zeta CAR amino acid sequence (FIG. 2L)).

In another embodiment, the nucleic acid sequence encoding a CAR comprises the nucleic acid sequence of SEQ ID NO: 81 (LTG2315, LP-mD1.22-L5-C46-CD8TM-41BB-CD3zeta CAR nucleic acid sequence (FIG. 2M)). In one embodiment, the nucleic acid sequence encodes a CAR comprising the amino acid sequence of SEQ ID NO: 82 (LTG2315, LP-mD1.22-L5-C46-CD8TM-41BB-CD3zeta CAR amino acid sequence (FIG. 2M)).

In another embodiment, the nucleic acid sequence encoding a CAR comprises the nucleic acid sequence of SEQ ID NO: 85 (LTG2316, LP-C46-L3-mD1.22-CD8TM-41BB-CD3zeta CAR nucleic acid sequence (FIG. 2N)). In one embodiment, the nucleic acid sequence encodes a CAR comprising the amino acid sequence of SEQ ID NO: 86 (LTG2316, LP-C46-L3-mD1.22-CD8TM-41BB-CD3zeta CAR amino acid sequence (FIG. 2N)).

In another embodiment, the nucleic acid sequence encoding a CAR comprises the nucleic acid sequence of SEQ ID NO: 89 (LTG2317, LP-C46-L5-mD1.22-CD8TM-41BB-CD3zeta CAR nucleic acid sequence (FIG. 2O)). In one embodiment, the nucleic acid sequence encodes a CAR comprising the amino acid sequence of SEQ ID NO: 90 (LTG2317, LP-C46-L5-mD1.22-CD8TM-41BB-CD3zeta CAR amino acid sequence (FIG. 2O)).

In another embodiment, the nucleic acid sequence encoding a CAR comprises the nucleic acid sequence of SEQ ID NO: 93 (LTG2318, LP-mD1.22-L3-m36.4-L3-C46-CD8TM-41BB-CD3zeta CAR nucleic acid sequence (FIG. 2P)). In one embodiment, the nucleic acid sequence encodes a CAR comprising the amino acid sequence of SEQ ID NO:

94 (LTG2318, LP-mD1.22-L3-m36.4-L3-C46-CD8TM-41BB-CD3zeta CAR amino acid sequence (FIG. 2P)).

In another embodiment, the nucleic acid sequence encoding a CAR comprises the nucleic acid sequence of SEQ ID NO: 97 (LTG2319, LP-mD1.22-L3-C46-L3-m36.4-CD8TM-41BB-CD3zeta CAR nucleic acid sequence (FIG. 2Q)). In one embodiment, the nucleic acid sequence encodes a CAR comprising the amino acid sequence of SEQ ID NO: 98 (LTG2319, LP-mD1.22-L3-C46-L3-m36.4-CD8TM-41BB-CD3zeta CAR amino acid sequence (FIG. 2Q)).

In another embodiment, the nucleic acid sequence encoding a CAR comprises the nucleic acid sequence of SEQ ID NO: 101 (LTG2320, LP-C46-L3-mD1.22-L3-m36.4-CD8TM-41BB-CD3zeta CAR nucleic acid sequence (FIG. 2R)). In one embodiment, the nucleic acid sequence encodes a CAR comprising the amino acid sequence of SEQ ID NO: 102 (LTG2320, LP-C46-L3-mD1.22-L3-m36.4-CD8TM-41BB-CD3zeta CAR amino acid sequence (FIG. 2R)).

In another embodiment, the nucleic acid sequence encoding a CAR comprises the nucleic acid sequence of SEQ ID NO: 105 (LTG2323, LP-mD1.22-L3-m36.4-CD8TM-41BB-CD3zeta-F2AF-C46-TNFRSF19TM CAR nucleic acid sequence (FIG. 2S)). In one embodiment, the nucleic acid sequence encodes a CAR comprising the amino acid sequence of SEQ ID NO: 106 (LTG2323, LP-mD1.22-L3-m36.4-CD8TM-41BB-CD3zeta-F2AF-C46-TNFRSF19TM CAR amino acid sequence (FIG. 2S)).

In another embodiment, the nucleic acid sequence encoding a CAR comprises the nucleic acid sequence of SEQ ID NO: 107 (LTG2329, LP-C46-L3-mD1.22-CD8TM-41BB-CD3zeta-F2AF-m36.4-TNFRSF19TM-CD3zeta2 CAR nucleic acid sequence (FIG. 2T)). In one embodiment, the nucleic acid sequence encodes a CAR comprising the amino acid sequence of SEQ ID NO: 108 (LTG2329, LP-C46-L3-mD1.22-CD8TM-41BB-CD3zeta-F2AF-m36.4-TNFRSF19TM-CD3zeta2 CAR amino acid sequence (FIG. 2T)).

In another embodiment, the nucleic acid sequence encoding a CAR comprises the nucleic acid sequence of SEQ ID NO: 109 (LTG2330, LP-C46-L5-mD1.22-CD8TM-41BB-CD3zeta-F2AF-m36.4-TNFRSF19TM-CD3zeta2 CAR nucleic acid sequence (FIG. 2U)). In one embodiment, the nucleic acid sequence encodes a CAR comprising the amino acid sequence of SEQ ID NO: 110 (LTG2330, LP-C46-L5-mD1.22-CD8TM-41BB-CD3zeta-F2AF-m36.4-TNFRSF19TM-CD3zeta2 CAR amino acid sequence (FIG. 2U)).

In another embodiment, the nucleic acid sequence encoding a CAR comprises the nucleic acid sequence of SEQ ID NO: 113 (LTG2331, LP-C46-L3-mD1.22-CD8TM-CD3zeta-F2AF-m36.4-TNFRSF19TM CAR nucleic acid sequence (FIG. 2V)). In one embodiment, the nucleic acid sequence encodes a CAR comprising the amino acid sequence of SEQ ID NO: 114 (LTG2331, LP-C46-L3-mD1.22-CD8TM-CD3zeta-F2AF-m36.4-TNFRSF19TM CAR amino acid sequence (FIG. 2V)).

In another embodiment, the nucleic acid sequence encoding a CAR comprises the nucleic acid sequence of SEQ ID NO: 117 (LTG2332, LP-C46-L5-mD1.22-CD8TM-41BB-CD3zeta-F2AF-m36.4-TNFRSF19TM CAR nucleic acid sequence (FIG. 2W)). In one embodiment, the nucleic acid sequence encodes a CAR comprising the amino acid sequence of SEQ ID NO: 118 (LTG2332, LP-C46-L5-mD1.22-CD8TM-41BB-CD3zeta-F2AF-m36.4-TNFRSF19TM CAR amino acid sequence (FIG. 2W)).

In another embodiment, the nucleic acid sequence encoding a CAR comprises the nucleic acid sequence of SEQ ID NO: 121 (LTG2334, LP-mD1.22-L5-m36.4-CD8TM-41BB-CD3zeta-F2AF-C46-TNFRSF19TM CAR nucleic acid sequence (FIG. 2X)). In one embodiment, the nucleic acid sequence encodes a CAR comprising the amino acid sequence of SEQ ID NO: 122 (LTG2334, LP-mD1.22-L5-m36.4-CD8TM-41BB-CD3zeta-F2AF-C46-TNFRSF19TM CAR amino acid sequence (FIG. 2X)).

In one aspect, the CARs disclosed herein are modified to express or contain a detectable marker for use in diagnosis, monitoring, and/or predicting the treatment outcome such as for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentiviral vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter, a synthetic promoter, or any combination thereof.

In yet another embodiment, the vector expressing the CAR can be further modified to include one or more operative elements to control the expression or function of CAR T cells (e.g., inducible homo-/hetero-dimerized CAR), or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD). In another aspect, host cells including the nucleic acid molecule encoding the CAR are also provided. In some embodiments, the host cell is a T cell, such as a primary T cell obtained from a subject. In one embodiment, the host cell is a CD8$^+$ T cell.

In yet another aspect, a pharmaceutical composition is provided comprising an anti-HIV effective amount of a population of human T cells, wherein the T cells comprise a nucleic acid sequence that encodes a CAR, wherein the CAR comprises at least one extracellular antigen binding domain comprising an anti-HIV antigen binding domain or combination of domains comprising the amino acid sequence of SEQ ID NO. 2, 4, 6, or combination of domains comprising the amino acid sequence of SEQ ID NO. 46, 50, 54, 58, 62, 66, 70, 76, 80, 84, 88, 92, 96, 100, 104, 112, 116, and 120, at least one linker domain, at least one transmembrane domain, and at least one intracellular signaling domain, wherein the T cells are T cells of a human having an HIV infection, or T cells intended to be administered to a patient having HIV/AIDS.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD83, CD86, CD134, CD137, CD154, TNFRSF19, or a combination thereof.

In another embodiment, a pharmaceutical composition is provided wherein the human disease includes infection with HIV/AIDS or HIV-associated cancers including an adult carcinoma comprising oral and pharynx cancer (tongue, mouth, pharynx, head and neck), carcinomas associated with infection with Kaposi's sarcoma virus (HHV8), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-HIV effective amount of a population of human T cells of a human having HIV/AIDS, and HIV-associated malignancy such a leukemia, leukemia of the CNS, sarcoma, Kaposi's sarcoma, or infectious sequelae associated with HIV/AIDS wherein the infection is refractory or non-responsive to one or more highly active anti-retroviral therapies (ART) and/or chemotherapies that have failed to completely eradicate the HIV/AIDS or HIV-associated malignancy, respectively. The use of CAR-modified T cells also includes the situation wherein the viral reservoir is reactivated or allowed to progress in order to decrease the ratio of latently to actively infected cells including withdrawal of ART (therapeutic holiday), or active induction by agents that methylate or demethylate promoter elements, activate cell activation pathways, or mimic epigenetic signals that activate latent virus to express the envelope protein and thus become a CAR targets.

In another aspect, methods of making CAR-containing T cells (hereinafter "CAR-T cells") are provided. The methods include transducing a T cell with a vector or nucleic acid molecule encoding a disclosed CAR that specifically binds HIV envelope protein, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of HIV envelope on a cell, is provided comprising a) contacting the cell with a human anti-HIV antibody or fragment thereof, wherein the antibody or a fragment thereof comprises an amino acid sequence selected from the group consisting of SEQ ID NOs: 2, 4, 6, 46, 50, 54, 58, 62, 66, 70, 76, 80, 84, 88, 92, 96, 100, 104, 112, 116, and 120; and b) detecting the presence of HIV envelope wherein the presence of HIV envelope protein diagnoses for the disease, disorder or condition associated with HIV/AIDS.

In one embodiment, the disease, disorder or condition associated with the expression of HIV is any AIDS-defining illness, including Candidiasis of the esophagus, bronchi, trachea, or lungs and mouth (thrush), Cervical cancer, invasive, Coccidioidomycosis, disseminated or extrapulmonary, Cryptococcosis, extrapulmonary, Cryptosporidiosis, chronic intestinal (greater than one month's duration), Cytomegalovirus disease (other than liver, spleen, or nodes), Cytomegalovirus retinitis (with loss of vision), Encephalopathy, HIV related, Herpes simplex: chronic ulcer(s) (more than 1 month in duration); or bronchitis, pneumonitis, or esophagitis, Histoplasmosis, disseminated or extrapulmonary, Isosporiasis, chronic intestinal (more than 1 month in duration), Kaposi sarcoma, Lymphoma, Burkitt's (or equivalent term), Lymphoma, immunoblastic (or equivalent term), Lymphoma, primary, of brain, *Mycobacterium avium* complex or *M kansasii*, disseminated or extrapulmonary, *Mycobacterium tuberculosis*, any site (pulmonary or extrapulmonary), *Mycobacterium*, other species or unidentified species, disseminated or extrapulmonary, *Pneumocystis jiroveci* pneumonia, Pneumonia, recurrent, Progressive multifocal leukoencephalopathy, *Salmonella* septicemia, recurrent, Toxoplasmosis of brain, Wasting syndrome due to HIV (source: Revised classification system for HIV infection and expanded surveillance case definition for AIDS among adolescents and adults. Morbidity and Mortality Weekly Report, Dec. 18, 1992/41 (RR-17), 1993). These may occur co-incident with cancer including hematopoietic cancer, myelodysplastic syndrome pancreatic cancer, head and neck cancer, cutaneous tumors, minimal residual disease (MRD) in ALL, AML, adult B cell malignancies including, CLL, CML, NHL, pediatric B cell malignancies (including B lineage ALL), multiple myeloma lung cancer, breast cancer, ovarian cancer, prostate cancer, colon cancer, melanoma or other hematological cancer and solid tumors, or any combination thereof.

In another embodiment, a method of diagnosing, prognosing, or determining risk of an HIV-related disease in a mammal, is provided comprising detecting the expression of HIV envelope in a sample derived from the mammal comprising: a) contacting the sample with a human anti-HIV antibody or fragment thereof, wherein the antibody or a fragment thereof comprises an amino acid sequence selected from the group consisting of SEQ ID NOs: 2, 4, 6, 46, 50, 54, 58, 62, 66, 70, 76, 80, 84, 88, 92, 96, 100, 104, 112, 116, and 120; and b) detecting the presence of HIV wherein the presence of HIV diagnoses for an HIV-related disease in the mammal.

In another embodiment, a method of inhibiting HIV-dependent T cell inhibition, is provided comprising contacting a cell with a human anti-HIV antibody or fragment thereof, wherein the antibody or a fragment thereof comprises an amino acid sequence selected from the group consisting of SEQ ID NOs: 2, 4, 6, 46, 50, 54, 58, 62, 66, 70, 76, 80, 84, 88, 92, 96, 100, 104, 112, 116, and 120. In one embodiment, the cell is selected from the group consisting of HIV-expressing cells, HIV-susceptible cells, and any combination thereof.

In another embodiment, a method of blocking T-cell inhibition mediated by an HIV-expressing cell and altering infected tissues to inhibit HIV pathogenesis in a mammal, is provided comprising administering to the mammal an effective amount of a composition comprising an isolated anti-HIV antibody or fragment thereof, wherein the antibody or a fragment thereof comprises an amino acid sequence selected from the group consisting of SEQ ID NOs: 2, 4, 6, 46, 50, 54, 58, 62, 66, 70, 76, 80, 84, 88, 92, 96, 100, 104, 112, 116, and 120. In one embodiment, the cell is selected from the group consisting of an HIV envelope expressing cell, HIV-infected cells or tissues, HIV-susceptible cells and tissues, and any combination thereof.

In another embodiment, a method of inhibiting, suppressing or preventing immunosuppression of an anti-HIV response in a mammal, is provided comprising administering to the mammal an effective amount of a composition comprising an isolated anti-HIV antibody or fragment thereof, wherein the antibody or a fragment thereof comprises an amino acid sequence selected from the group consisting of SEQ ID NOs: 2, 4, 6, 46, 50, 54, 58, 62, 66, 70, 76, 80, 84, 88, 92, 96, 100, 104, 112, 116, and 120. In one embodiment, the antibody or fragment thereof inhibits the interaction between a first cell with a T cell, wherein the first cell is selected from the group consisting of an HIV-expressing cell, HIV-infected cells or tissues, and any combination thereof.

In another aspect, a method is provided for inducing an anti-HIV immunity in a mammal comprising administering to the mammal a therapeutically effective amount of a T cell transduced with vector or nucleic acid molecule encoding a disclosed CAR.

In another embodiment, a method of treating or preventing HIV infection in a mammal is provided comprising administering to the mammal one or more of the disclosed CARs, in an amount effective to treat or prevent HIV infection in the mammal. The method includes administering to the subject a therapeutically effective amount of host cells expressing a disclosed CAR that specifically binds HIV and/or one or more of the aforementioned antigens, under conditions sufficient to form an immune complex of the antigen binding domain on the CAR and the extracellular domain of HIV and/or one or more of the aforementioned antigens in the subject.

In yet another embodiment, a method is provided for treating a mammal having a disease, disorder or condition associated with an elevated expression of an HIV antigen, the method comprising administering to the subject a pharmaceutical composition comprising an anti-HIV effective amount of a population of T cells, wherein the T cells comprise a nucleic acid sequence that encodes a CAR, wherein the CAR includes at least one extracellular HIV antigen binding domain comprising the amino acid sequence of SEQ ID NOs. 2, 4, 6, 46, 50, 54, 58, 62, 66, 70, 76, 80, 84, 88, 92, 96, 100, 104, 112, 116, and 120 or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a CAR, wherein the CAR comprises at least one HIV antigen binding domain comprising the amino acid sequence of SEQ ID NOs. 2, 4, 6, 46, 50, 54, 58, 62, 66, 70, 76, 80, 84, 88, 92, 96, 100, 104, 112, 116, and 120 or any combination thereof, at least one linker or spacer domain, at least one transmembrane domain, at least one intracellular signaling domain, wherein the T cells are T cells of the subject having HIV infection or T cells to be administered to such a patient. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD19, CD22, Mesothelin, CD33, CD37, CD64, CD80, CD83, CD86, CD134, CD137, CD154, TNFRSF16, TNFRSF19, or a combination thereof.

In yet another embodiment, a method is provided for generating a persisting population of genetically engineered T cells in a human diagnosed with HIV infection. In one embodiment, the method comprises administering to a human a T cell genetically engineered to express a CAR wherein the CAR comprises at least one HIV antigen binding domain comprising the amino acid sequence of SEQ ID NOs. 2, 4, 6, 46, 50, 54, 58, 62, 66, 70, 76, 80, 84, 88, 92, 96, 100, 104, 112, 116, and 120 or any combination thereof, at least one transmembrane domain, and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned infections, cancers, diseases, disorders or conditions associated with an elevated expression of a HIV antigen that may be treated or prevented or ameliorated using one or more of the CARs disclosed herein.

In yet another aspect, each of the aforementioned bispecific and/or trispecific anti-HIV CARs may be used in an adoptive T-cell immunotherapy in an amount effective to either inhibit, suppress or prevent immunosuppression of an anti-HIV response in a mammal, or to treat, or prevent HIV infection in said mammal, wherein the mammal receives the adoptive T-cell immunotherapy with either no prior anti-retroviral therapy (ART) treatment regimens being required, or to effectively substantially reduce the number of ART treatment regimens required from approximately 10% to 99%.

In yet another aspect, a kit is provided for making a CAR T-cell as described supra or for preventing, treating, or ameliorating any of the infections, cancers, diseases, disorders or conditions associated with an elevated expression of a HIV antigen in a subject as described supra, comprising a container comprising any one of the nucleic acid molecules, vectors, host cells, or compositions disclosed supra or any combination thereof, and instructions for using the kit.

While the disclosure provided herein has initially focused on the generation of CARs utilizing HIV envelope protein antigen binding fragments thereof, it is predicted that the CARs, T Cell Receptors (TCRs) or nucleic acid sequences, polypeptides and methods of use thereof may be also employed with HIV protein other than the HIV envelope protein antigen binding fragments specifically elucidated herein, and are therefore meant to specifically include any HIV-derived protein associated with a latent or productive HIV infection, including, and not by way of limitation, Rev, Tat, Vif, Nef, Vpu, Vpr, Gag, Pol, Protease, Nucleocapsid, Matrix, Capsid, Integrase, and/or Reverse Transcriptase, or any combination thereof.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIG. 1 depicts a schematic of the general domain structure of CARs with novel extracellular HIV antigen binding domain sequences. Monospecific CAR-T (top construct) are composed of an extracellular HIV-binding domain (binder 1), a hinge and transmembrane domain (for example CD8 hinge/spacer and CD8 transmembrane domain (TM), an intracellular signaling CD137 costimulatory domain (41BB) and CD3zeta signaling domain. Bispecific CAR-T (center three constructs) are composed of two binders joined by a linker (black line) linked to hinge and transmembrane domains and intracellular signaling domains (41BB, CD3zeta), or a single binder (binder 1) linked to a hinge/TM and intracellular signaling domains, followed by a 2A ribosomal skip site, then followed by a second binder (binder 2) linked to only a hinge/linker and transmembrane, or a hinge/linker transmembrane domain linked to a second intracellular CD3zeta sequence. Trispecific CAR-T (bottom three constructs) are composed of either three linked anti-HIV binders linked together to a single hinge/transmembrane sequence and intracellular signaling sequences (41BB and CD3zeta) or two binders linked to each other and then to a hinge/transmembrane sequence followed by intracellular signaling motifs followed by a 2A ribosomal skip site and then linked to either the third binder (binder 3) and hinge/transmembrane sequence only or hinge/transmembrane followed by CD3zeta intracellular signaling sequence.

FIGS. 2A-X depict several CARs containing novel extracellular HIV antigen binding domain sequences. The general scheme for the CARs includes, from the N terminus to the C terminus, a Signal peptide, anti-HIV binder(s), extracellular linker, transmembrane, 4-1BB, CD3 zeta. Bispecific and trispecific CAR constructs are also exemplified.

FIG. 2A depicts a lentiviral vector expressing the CAR containing the LTG1944 (LP-mD1.22-CD8TM-41BB-CD3zeta) nucleic acid sequence (SEQ ID NO: 39) and the encoded amino acid sequence (SEQ ID NO: 40).

FIG. 2B depicts a lentiviral vector expressing the CAR containing the LTG1945 (LP-m36.4-CD8TM-41BB-CD3zeta) nucleic acid sequence (SEQ ID NO: 41) and the encoded amino acid sequence (SEQ ID NO: 42).

FIG. 2C depicts a lentiviral vector expressing the CAR containing the LTG2328 (LP-C46-CD8TM-41BB-CD3zeta) nucleotide sequence (SEQ ID NO: 43) and the encoded amino acid sequence (SEQ ID NO: 44).

FIG. 2D depicts a lentiviral vector expressing the CAR containing the LTG2325 (LP-mD1.22-L1-m36.4-CD8TM-41BB-CD3zeta) nucleic acid sequence (SEQ ID NO: 47) and the encoded amino acid sequence (SEQ ID NO: 48).

FIG. 2E depicts a lentiviral vector expressing the CAR containing the LTG2313 (LP-mD1.22-L2-m36.4-CD8TM-41BB-CD3zeta) nucleic acid sequence (SEQ ID NO: 51) and the encoded amino acid sequence (SEQ ID NO: 52).

FIG. 2F depicts a lentiviral vector expressing the CAR containing the LTG1946 (LP-mD1.22-L3-m36.4-CD8TM-41BB-CD3zeta) nucleic acid sequence (SEQ ID NO: 55) and the encoded amino acid sequence (SEQ ID NO: 56).

FIG. 2G depicts a lentiviral vector expressing the CAR containing the LTG2326 (LP-mD1.22-L4-m36.4-CD8TM-41BB-CD3zeta) nucleic acid sequence (SEQ ID NO: 59) and the encoded amino acid sequence (SEQ ID NO: 60).

FIG. 2H depicts a lentiviral vector expressing the CAR containing the LTG1947 (LP-mD1.22-L5-m36.4-CD8TM-41BB-CD3zeta) nucleic acid sequence (SEQ ID NO: 63) and the encoded amino acid sequence (SEQ ID NO: 64).

FIG. 2I depicts a lentiviral vector expressing the CAR containing the LTG1948 (LP-m36.4-L3-mD1.22-CD8TM-41BB-CD3zeta) nucleic acid sequence (SEQ ID NO: 67) and the encoded amino acid sequence (SEQ ID NO: 68).

FIG. 2J depicts a lentiviral vector expressing the CAR containing the LTG2303 (LP-mD1.22-CD8TM-41BB-CD3zeta-F2AF-m36.4-TNFRSF19TM-CD3zeta2) nucleic acid sequence (SEQ ID NO: 71) and the encoded amino acid sequence (SEQ ID NO: 72).

FIG. 2K depicts a lentiviral vector expressing the CAR containing the LTG2322 (LP-mD1.22-CD8TM-41BB-CD3zeta-F2AF-m36.4-TNFRSF19TM) nucleic acid sequence (SEQ ID NO: 73) and the encoded amino acid sequence (SEQ ID NO: 74).

FIG. 2L depicts a lentiviral vector expressing the CAR containing the LTG2314 (LP-mD1.22-L3-C46-CD8TM-41BB-CD3zeta) nucleic acid sequence (SEQ ID NO: 77) and the encoded amino acid sequence (SEQ ID NO: 78).

FIG. 2M depicts a lentiviral vector expressing the CAR containing the LTG2315 (LP-mD1.22-L5-C46-CD8TM-41BB-CD3zeta) nucleic acid sequence (SEQ ID NO: 81) and the encoded amino acid sequence (SEQ ID NO: 82).

FIG. 2N depicts a lentiviral vector expressing the CAR containing the LTG2316 (LP-C46-L3-mD1.22-CD8TM-41BB-CD3zeta) nucleic acid sequence (SEQ ID NO: 85) and the encoded amino acid sequence (SEQ ID NO: 86).

FIG. 2O depicts a lentiviral vector expressing the CAR containing the LTG2317 (LP-C46-L5-mD1.22-CD8TM-41BB-CD3zeta) nucleic acid sequence (SEQ ID NO: 89) and the encoded amino acid sequence (SEQ ID NO: 90).

FIG. 2P depicts a lentiviral vector expressing the CAR containing the LTG2318 (LP-mD1.22-L3-m36.4-L3-C46-CD8TM-41BB-CD3zeta) nucleic acid sequence (SEQ ID NO: 93) and the encoded amino acid sequence (SEQ ID NO: 94).

FIG. 2Q depicts a lentiviral vector expressing the CAR containing the LTG2319 (LP-mD1.22-L3-C46-L3-m36.4-CD8TM-41BB-CD3zeta) nucleic acid sequence (SEQ ID NO: 97) and the encoded amino acid sequence (SEQ ID NO: 98).

FIG. 2R depicts a lentiviral vector expressing the CAR containing the LTG2320 (LP-C46-L3-mD1.22-L3-m36.4-CD8TM-41BB-CD3zeta) nucleic acid sequence (SEQ ID NO: 101) and the encoded amino acid sequence (SEQ ID NO: 102).

FIG. 2S depicts a lentiviral vector expressing the CAR containing the LTG2323 (LP-mD1.22-L3-m36.4-CD8TM-41BB-CD3zeta-F2AF-C46-TNFRSF19TM) nucleic acid sequence (SEQ ID NO: 105) and the encoded amino acid sequence (SEQ ID NO: 106).

FIG. 2T depicts a lentiviral vector expressing the CAR containing the LTG2329 (LP-C46-L3-mD1.22-CD8TM-41BB-CD3zeta-F2AF-LP2-m36.4-TNFRSF19TM-CD3zeta2) nucleic acid sequence (SEQ ID NO: 107) and the encoded amino acid sequence (SEQ ID NO: 108).

FIG. 2U depicts a lentiviral vector expressing the CAR containing the LTG2330 (LP-C46-L5-mD1.22-CD8TM-41BB-CD3zeta-F2AF-LP2-m36.4-TNFRSF19TM-CD3zeta2) nucleic acid sequence (SEQ ID NO: 109) and the encoded amino acid sequence (SEQ ID NO: 110).

FIG. 2V depicts a lentiviral vector expressing the CAR containing the LTG2331 (LP-C46-L3-mD1.22-CD8TM-41BB-CD3zeta-F2AF-m36.4-TNFRSF19TM) nucleic acid sequence (SEQ ID NO: 113) and the encoded amino acid sequence (SEQ ID NO: 114).

FIG. 2W depicts a lentiviral vector expressing the CAR containing the LTG2332 (LP-C46-L5-mD1.22-CD8TM-41BB-CD3zeta-F2AF-m36.4-TNFRSF19TM) nucleic acid sequence (SEQ ID NO: 117) and the encoded amino acid sequence (SEQ ID NO: 118).

FIG. 2X depicts a lentiviral vector expressing the CAR containing the LTG2334 (LP-mD1.22-L5-m36.4-CD8TM-41BB-CD3zeta-F2AF-C46-TNFRSF19TM) nucleic acid sequence (SEQ ID NO: 121) and the encoded amino acid sequence (SEQ ID NO: 122).

FIG. 3A shows expression of anti-HIV CARs containing either the mD1.22 domain or C46 peptide on the surface of LV transduced human T cells. The mD1.22-CAR is detected by staining with anti-CD8 antibody (y-axis) and anti-CD4 antibody (recognizes the mD1.22 domain, x-axis left panel) or the C46-CAR is detected by staining with the 2F5 antibody (recognizes the C46 peptide, x-axis, right panel).

Figure 3A:
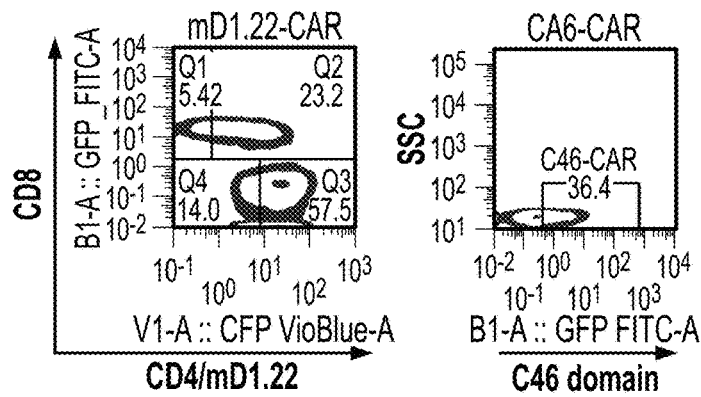
FIGS. 3A-E depict the functional characterization of monospecific anti-HIV CARs.
Figure 3B:
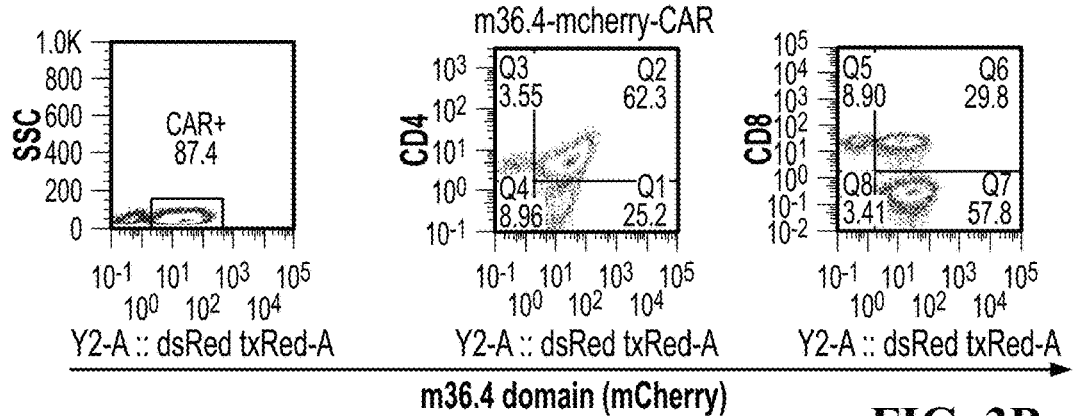

FIG. 3B depicts how m36.4 expression was detected on the surface of LV transduced primary T-cells by fusing the mCherry reporter directly upstream of the CD3 zeta signaling domain. The % of mCherry positive cells were detected in the total T-cell population (left panel), on the surface of CD4$^+$ T-cells (middle panel) and CD8$^+$ T-cells (right panel).

Figure 3C:
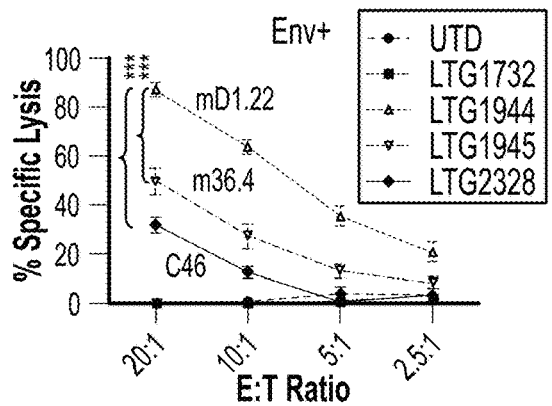

FIG. 3C demonstrates the differential cytotoxic function of monospecific CARs. Using an HIV-envelope expressing target cell line as a cytotoxicity target, untransduced T cells (UTD, no activity), T cells transduced with LTG1732 (control mCherry vector, no activity), LTG1944 (expresses the mD1.22 binder), LTG1945 (expresses the m36.4 binder), LTG2328 (expresses the C46 binder) each demonstrated cytotoxicity at the effector to target cell ratios (E:T) listed on the x-axis.

Figure 3D:
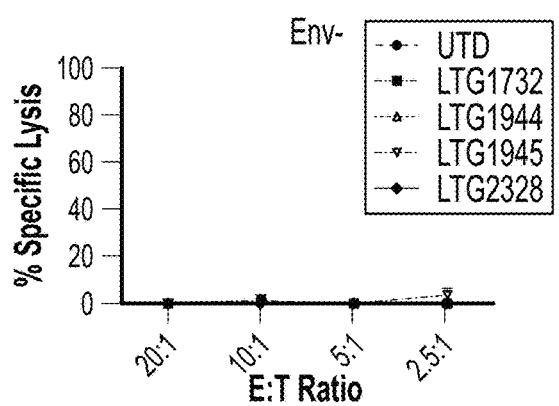

FIG. 3D demonstrates that the same transduced T cell populations does not mediate cytolytic activity against a cell line that does not express the HIV envelope protein.

Figure 3E:
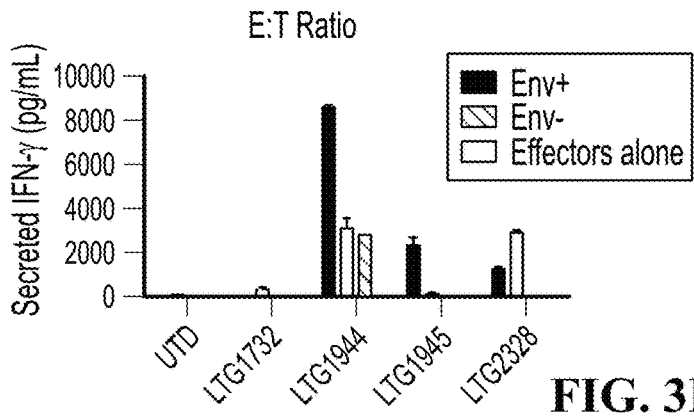

FIG. 3E demonstrates that human T cells transduced with LV expressing monospecific CARs secrete IFN-γ in the presence (solid bars) of HIV envelope-expressing cells. Background levels are seen with cells not expressing HIV envelope (checkered bars) or cultured alone (striped bars).

FIGS. 4A-E depict the expression of bispecific anti-HIV CARs on the surface of activated T-cells. Bispecific CARs are engineered in several unique configurations to determine the precise functional architecture.

Figure 4A:
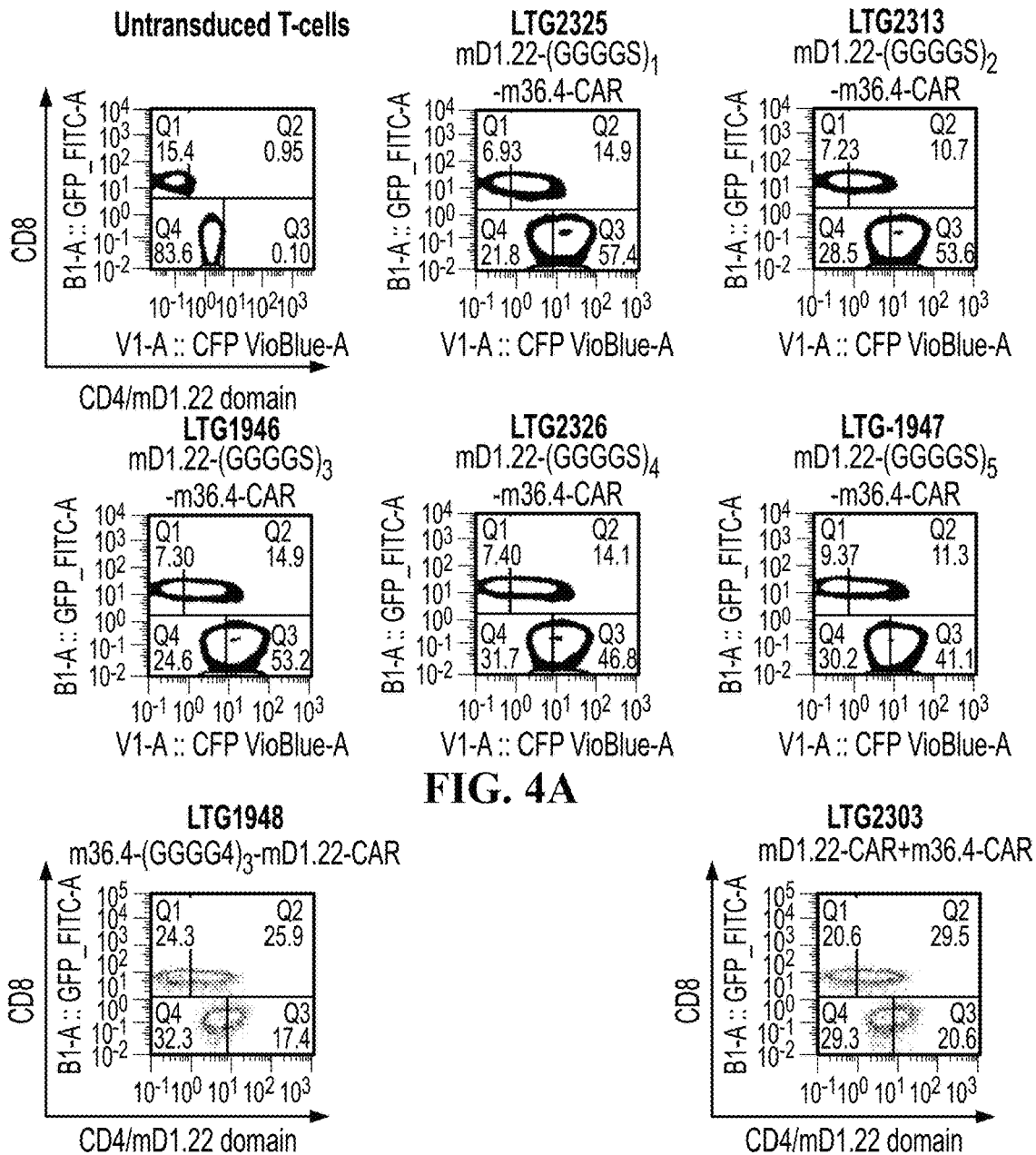

FIG. 4A depicts the bispecific anti-HIV CARs that are engineered with two anti-gp120 binders (mD1.22 and m36.4) and fused together using a flexible glycine-serine linker consisting of up to five GGGGS (G4S) motifs. The bispecific CARs are detected by flow cytometry using an antibody directed against the D1 domain of the CD4 receptor (anti-CD4 VIT4 clone, Miltenyi Biotec) which also recognizes the mD1.22 domain of the bispecific CARs.

FIG. 4B depicts the expression of a bispecific CAR engineered with the m36.4 domain presented as the first gp120 binder and then fused to the mD1.22 domain using three G4S motifs (LTG1948).

FIG. 4C depicts the expression of a bispecific CAR with mD1.22 and m36.4 domains fused to their own intracellular CD3 zeta chains via a bicistronic construct (LTG2303) incorporating the porcine teschovirus-1 derived self-cleaving P2A peptide. The expression of the LTG2303 CAR on the surface of T-cells was determined by detecting the mD1.22 domain using anti-CD4 flow cytometry.

Figure 4D:
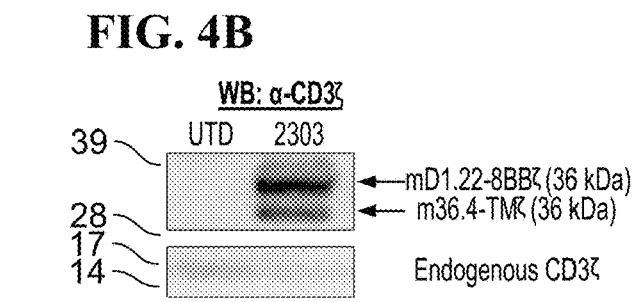

FIG. 4D depicts the western blot detection of both mD1.22-CAR and m36.4-CAR using anti-CD3 zeta staining. Both CARs are fully cleaved using the P2A self-cleaving peptide. Endogenous CD3 zeta serves as a loading control.

Figure 4E:
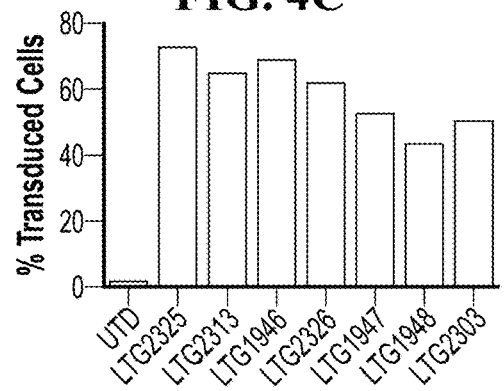

FIG. 4E depicts the graphical representation of % of CAR modified T-cells via detection of the mD1.22 by anti-CD4 flow cytometry.

Figure 5:
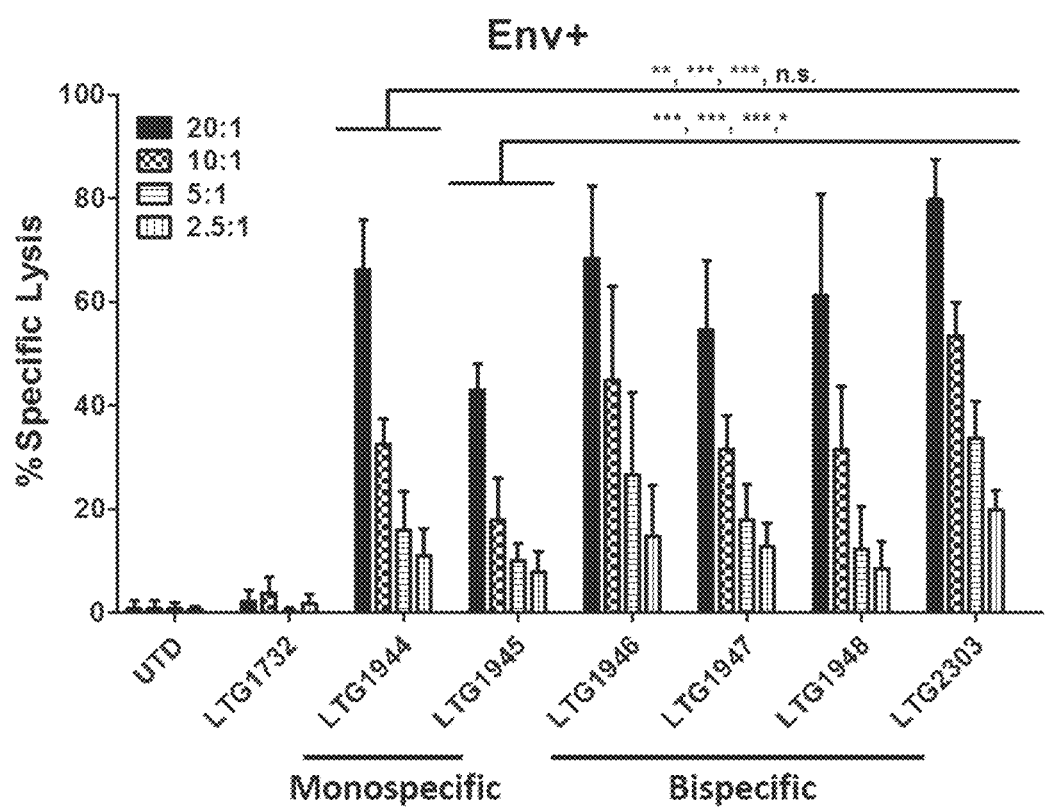

FIG. 5 depicts the potent ability of anti-HIV CARs to destroy HIV-envelope expressing 293T cells that also co-express the firefly luciferase reporter. Notably, the bispecific anti-HIV CAR configured so that each anti-HIV binder is on a single CD3 zeta chain (LTG2303) significantly killed target cells as compared to monospecific CARs, LTG1944 and LTG1945. Untransduced T-cells (no activity) and LTG1732 (T-cells transduced with the mCherry reporter, no activity) served as negative controls to monitor non-specific T-cell mediated cytotoxicity. The results shown are from three donors. Error bars represent +/−standard deviation. Statistical analysis was performed by two-way ANOVA (*P<0.0001, P<0.001, *P<0.01).

Figure 6:
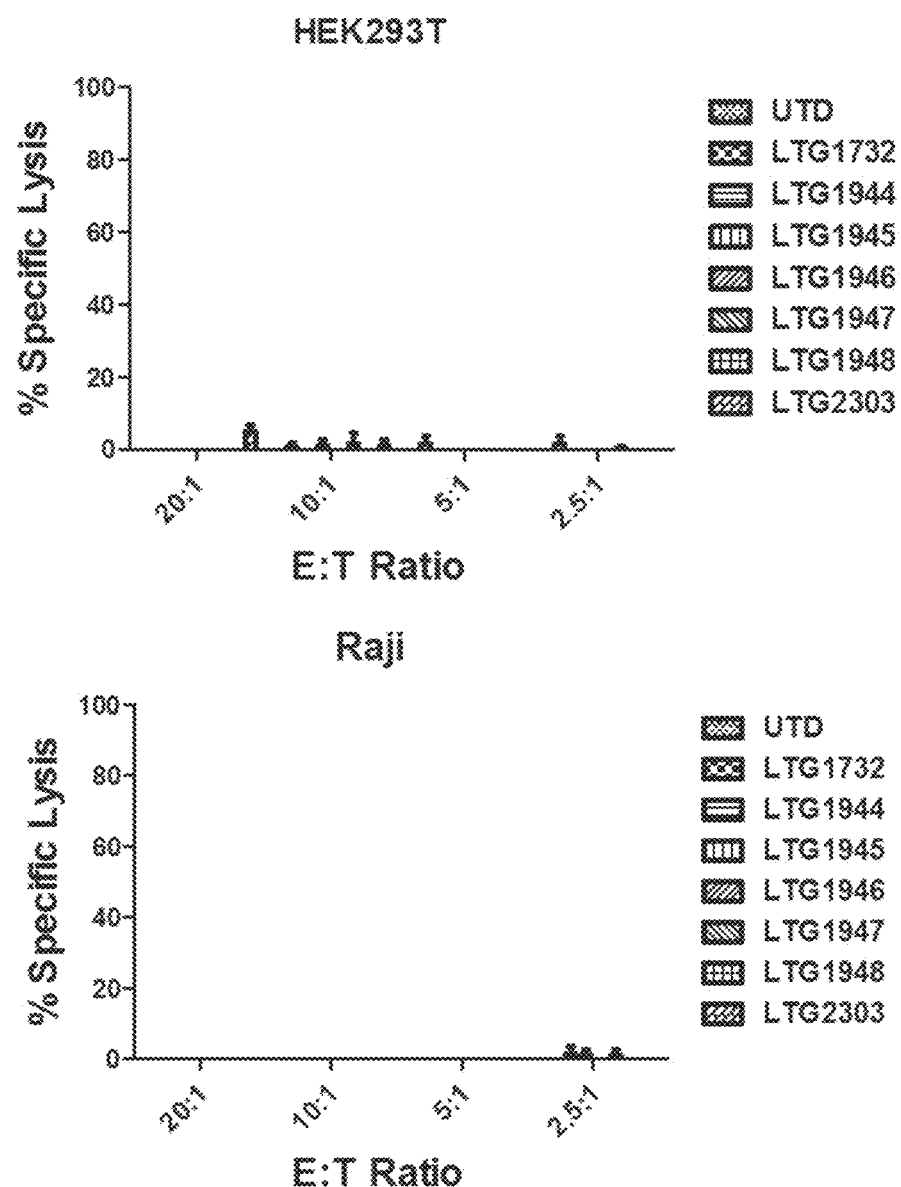

FIG. 6 depicts the exceptional specificity of anti-HIV CARs in the absence of HIV envelope expressing cell lines. Raji cells are known to express MHC class II molecules and thus may interact non-specifically with the CD4 receptor derived mD1.22 domain. As demonstrated on both cell lines, no off-target cytolysis was observed for anti-HIV CARs. Representative figure of three donors. The error bars represent +/−standard deviation.

Figure 7:
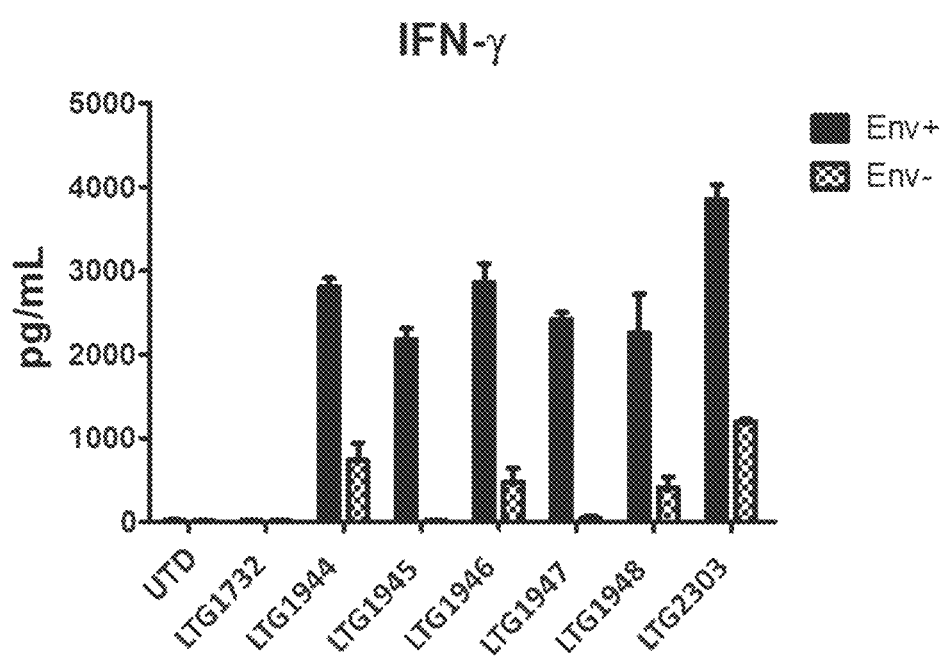

FIG. 7 shows that activation of anti-HIV CAR-T triggers IFN-gamma release. Anti-HIV CARs were co-incubated with (Env$^+$) or without (Env$^-$) envelope-expressing 293T cells that also co-express the firefly luciferase reporter. Twenty-four hours later, cell culture supernatants were collected and assayed for IFN-γ using ELISA. All anti-HIV CARs were activated in the presence of Env$^+$ cells and to a lesser extent in the presence of Env$^-$ cells. Bispecific CAR LTG2303 demonstrated enhanced IFN-gamma secretion over that of monospecific CARs, LTG1944 and LTG1945. Results shown are from two different donors. The error bars represent +/−standard deviation.

Figure 8A:
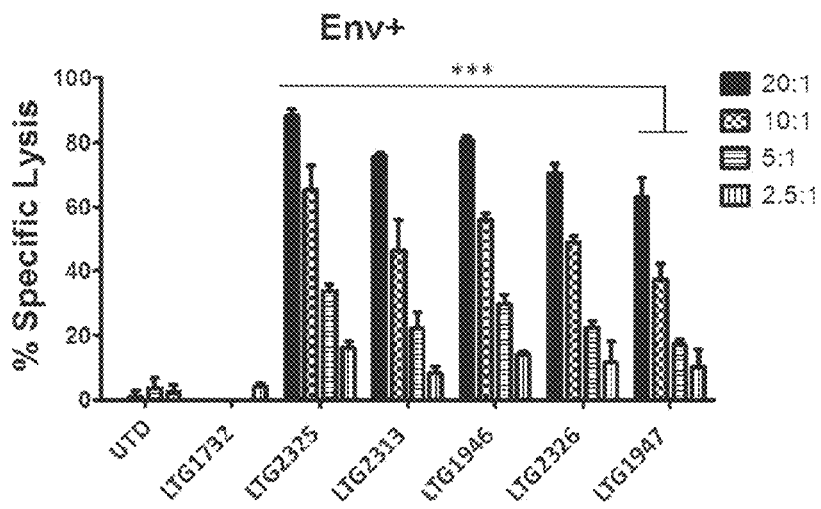
Figure 8B:
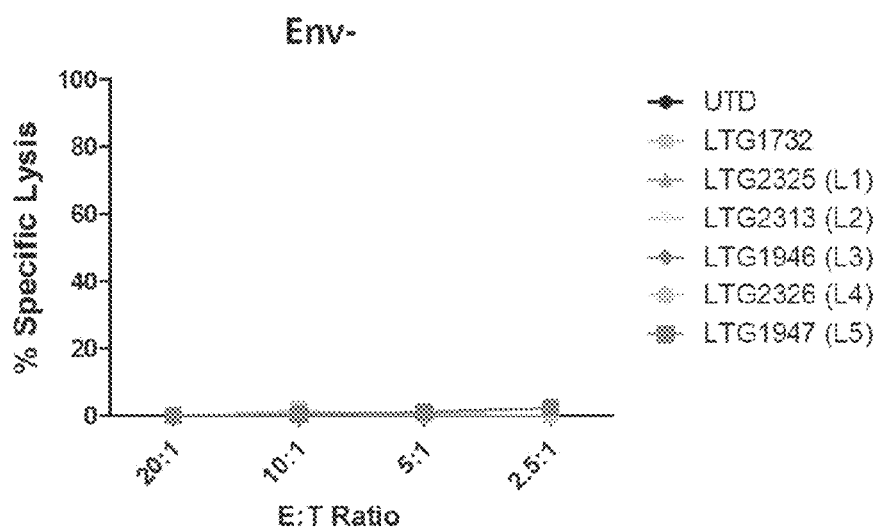

FIGS. 8A-B show that bispecific anti-HIV CAR function is governed by linker length.

FIG. 8A depicts bispecific CARs were constructed with up to five G4S motifs and their function investigated for their ability to destroy envelope-expressing target cells (Env$^+$).

FIG. 8B depicts the specificity of bispecific anti-HIV CARs in the presence of envelope-negative Raji cells (Env$^-$). The bispecific CAR with a single G4S motif was significantly more active than an anti-HIV CAR containing five G4S motifs. Statistics was performed by two-way ANOVA (***p<0.0001, LTG2325 vs. LTG1947). The error bars represent +/−standard deviation.

Figure 9:
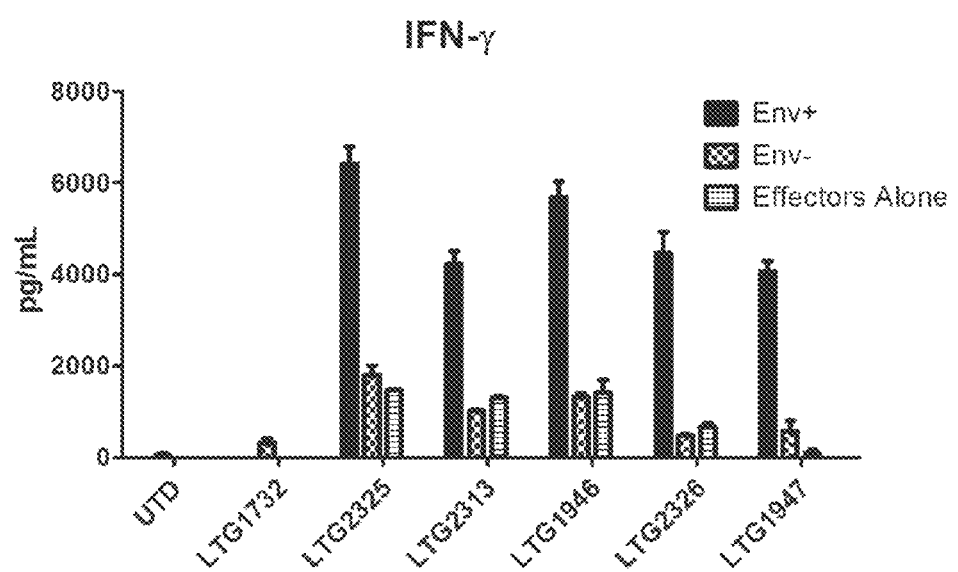

FIG. 9 shows that bispecific anti-HIV CARs engineered with increasing linker lengths are triggered to release IFN-gamma in the presence of envelope-expressing target cells (Env$^+$) and to a lesser extent in the absence of envelope-expressing cells (Env$^-$) or when effectors are cultured alone. The anti-HIV CAR with the longest linker (LTG1947) releases the lowest background level of IFN-gamma. The error bars represent +/−standard deviation.

Figure 10A:
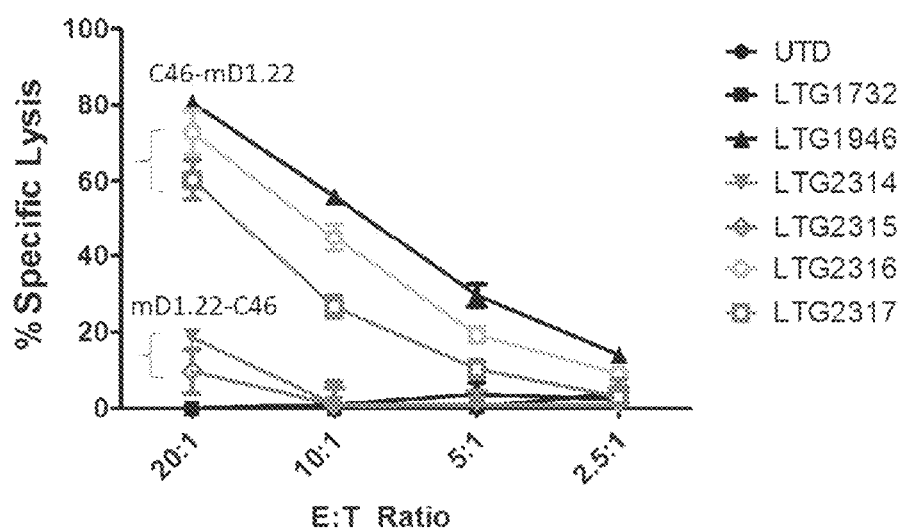
Figure 10B:
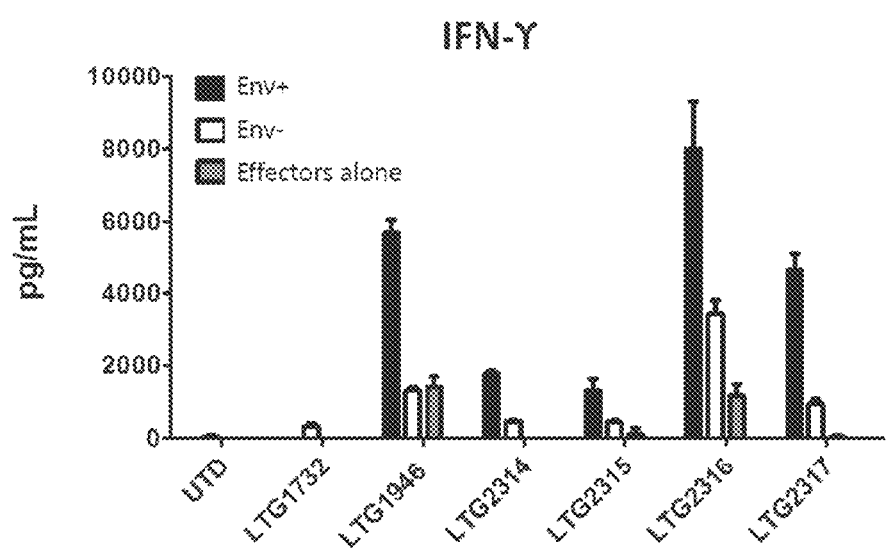

FIGS. 10A-B show that the bispecific anti-HIV CARs engineered with the mD1.22 and C46 peptide exhibit configuration-dependent activity.

FIG. 10A depicts the cytotoxic activity of C46-based bispecific CARs. The cytotoxicity of these CARs depends highly on the configuration of the bispecific gp120/gp41-binder. For example, when the C46 peptide is oriented distal to the mD1.22 domain to form CARs, LTG2316 and LTG2317, both CARs function similar to the LTG1946 CAR containing both the mD1.22 and m36.4 domains. In contrast, orienting mD1.22 distal to the C46 peptide to form CARs, LTG2314 and LTG2315, completely abolished its cytolytic function.

FIG. 10B demonstrates that C46-based bispecific CARs elaborate IFN-gamma in the presence of Env$^+$ target cells and in some instances non-specifically in its absence (Env$^-$ or effectors alone).

FIGS. 11A-F show that trispecific anti-HIV CARs robustly destroy and release cytokines in response to envelope-expressing target cells.

Figure 11A:
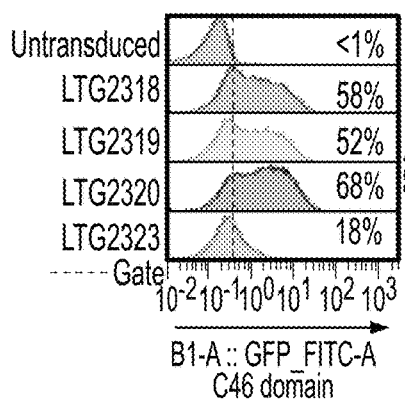

FIG. 11A depicts the expression of trispecific anti-HIV CARs on the surface of primary T-cells using a broadly-neutralizing 2F5 antibody directed against the C46 peptide. The 2F5 antibody recognizes a contiguous epitope within the C46 peptide (ELDKWA).

Figure 11B:
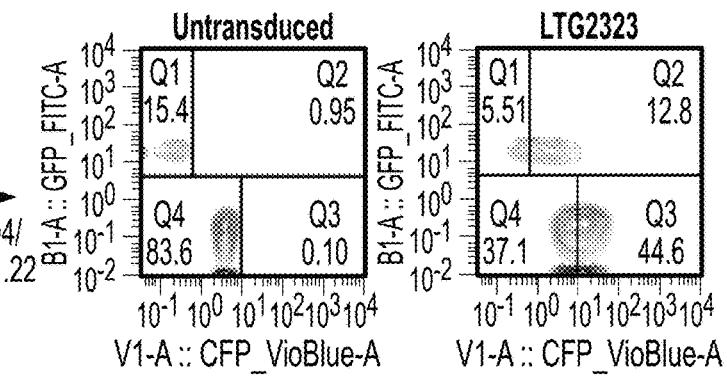

FIG. 11B depicts the detection of the mD1.22 domain found within the bispecific arm of the trispecific anti-HIV CAR, LTG2323. The mD1.22 domain was detected on the surface of T-cells using anti-CD4 (recognizes the mD1.22 domain) and anti-CD8 flow cytometry. This construct contains a bispecific CAR (LTG1946) in combination with a membrane-anchored C46 peptide presented on the surface of T-cells as a discrete entity.

Figure 11C:
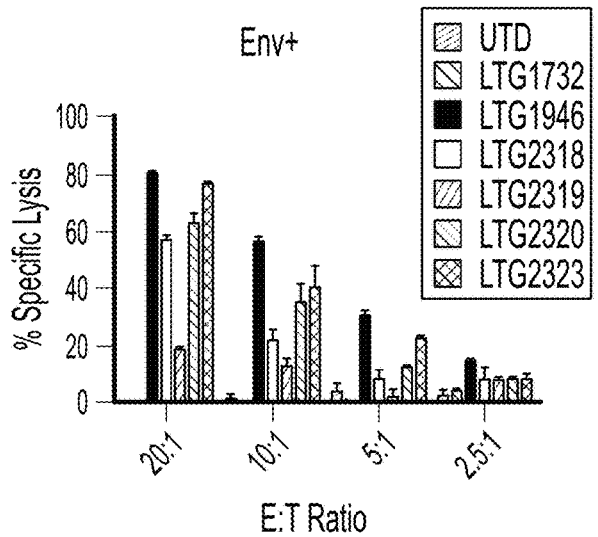

FIG. 11C depicts the robust destruction of HIV-envelope (Env+) expressing cells by all trispecific CARs.

Figure 11D:
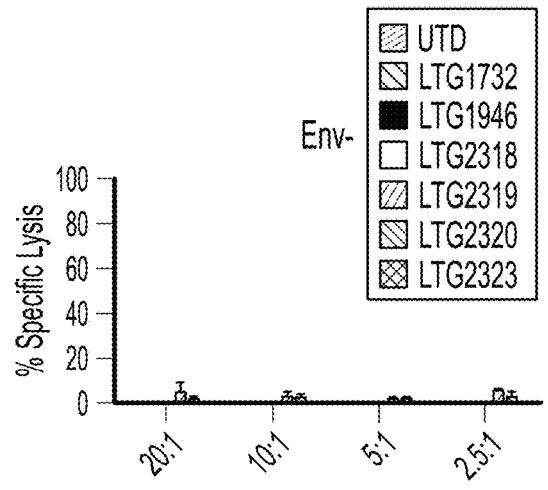

FIG. 11D depicts the specificity of the trispecific CARs in the absence of envelope expressing but MHC class II expressing Raji cells (Env−).

Figure 11E:
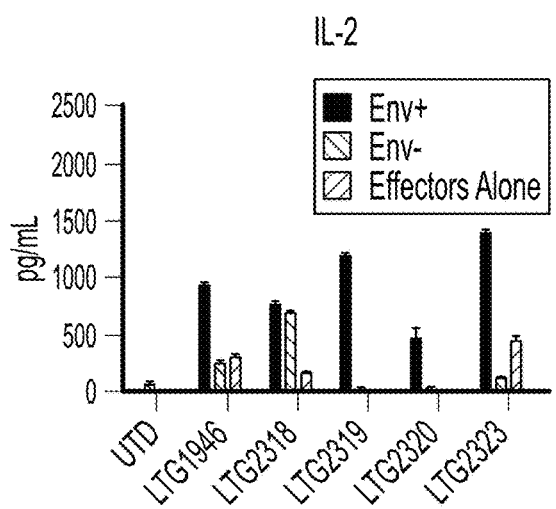

FIG. 11E depicts the release of IL-2 cytokine for all trispecific CARs as compared to the highly potent LTG1946 bispecific CAR.

Figure 11F:
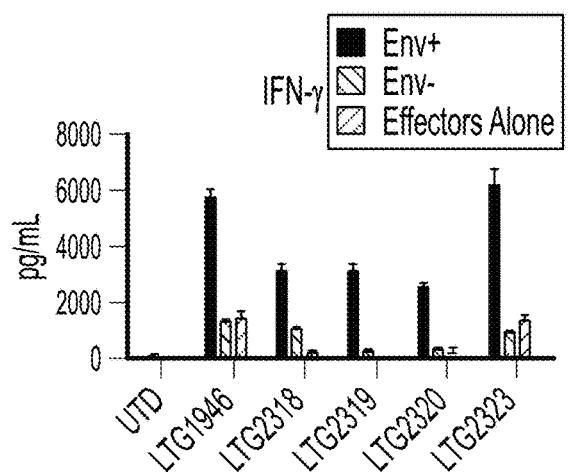

FIG. 11F depicts the release of IFN-γ cytokine for all trispecific CARs as compared to the highly potent LTG1946 bispecific CAR.

FIGS. 12A-D show a comparison of the expression and cytotoxicity exerted by the most potent trispecific and bispecific anti-HIV CARs.

Figure 12A:
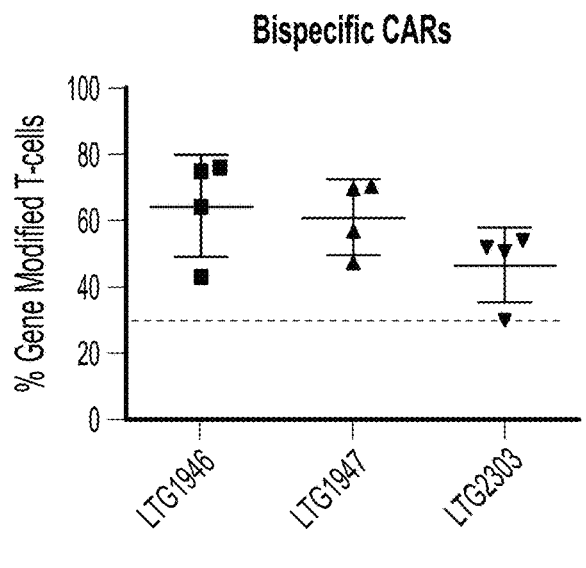

FIG. 12A depicts percentage of bispecific CAR-modified T-cells via detection of the mD1.22 domain using anti-CD4 flow cytometry.

Figure 12B:
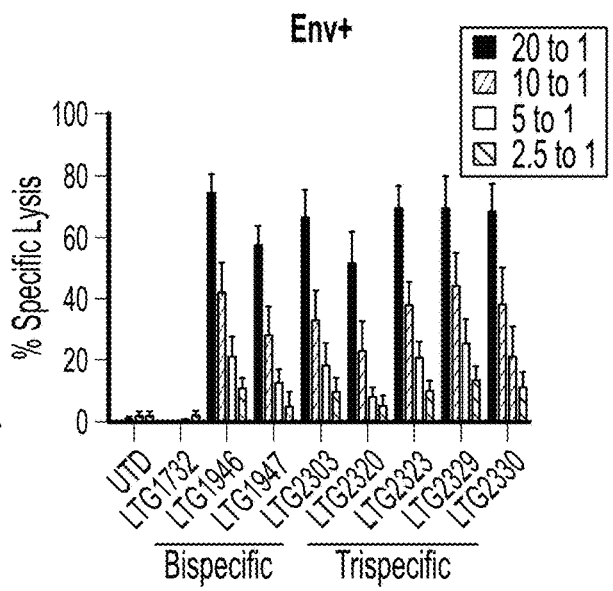

FIG. 12B depicts the cytotoxicity of trispecific anti-HIV CARs.

Figure 12C:
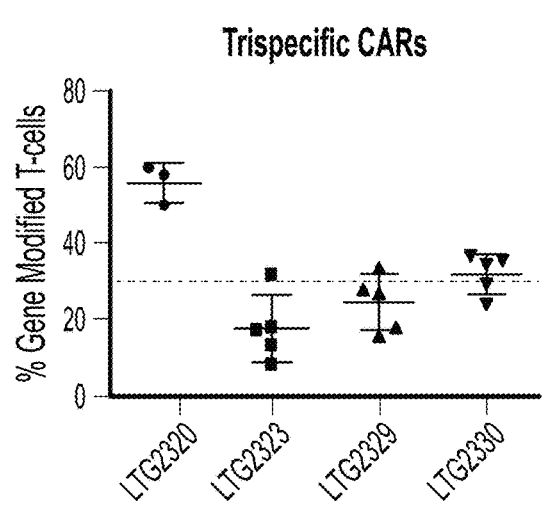

FIG. 12C depicts the percentage of trispecific CAR-modified T-cells via detection of the C46 domain using 2F5 flow cytometry. The dotted line intersecting the y-axis is set for 30% gene modification.

Figure 12D:
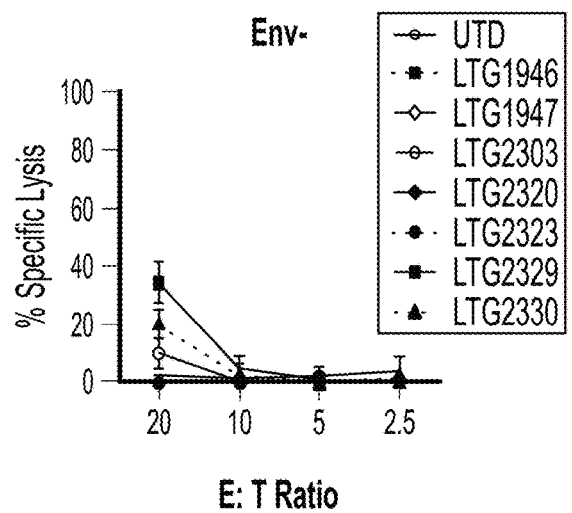

FIG. 12D depicts the specificity of trispecific anti-HIV CARs as measured by cytotoxicity on an envelope-negative cell line. Experimental data shown in this figure are of at least 3 donors (error bars=+/−S.D.).

Figure 13:
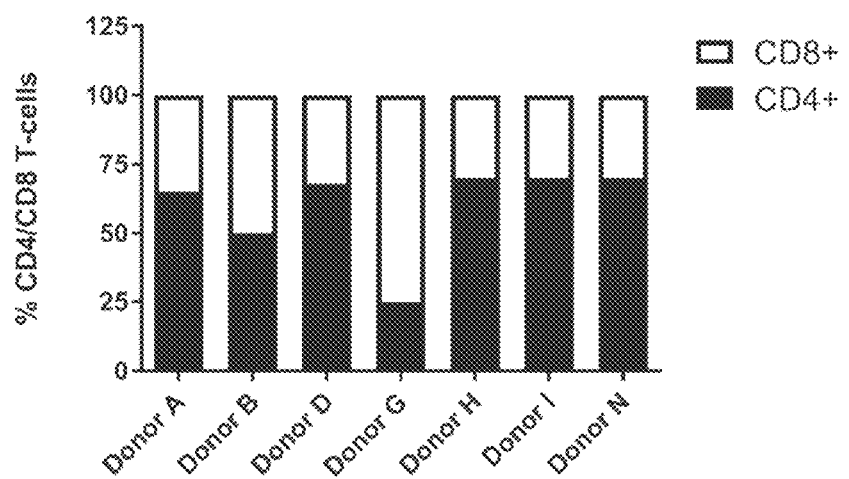

FIG. 13 shows the CD4+ and CD8+ composition of donors used in the in vitro and in vivo HIV-1 challenge studies. Donors were enriched for CD4+ and CD8+ effector T cells, activated, and expanded for up to 9 days. On day 9, the composition of donor T cells was determined by anti-CD4 and anti-CD8 flow cytometry as described in Example 1. This figure shows the percentage of CD4+ and CD8+ effectors on day 9 of culture.

FIGS. 14A-K show the in vitro killing efficacy of monospecific, bispecific, and trispecific anti-HIV CAR-T cells against PBMC infected with replication-competent, infectious molecular clones of HIV-1 encoding broad envelope (env) genes and the *Renilla luciferase* reporter (Env-IMC-LucR). The indicated anti-HIV CAR or untransduced (UTD) T cells (effectors) were co-cultured with autologous PBMC infected with the indicated Env-IMC-LucR virus (targets) one day prior to co-culture setup. Seven days later, the co-cultures were lysed and luciferase activity quantified. The bispecific and trispecific anti-HIV duoCAR-T cells eliminate PBMC infected with broad Env-IMC-LucR viruses (LTG2303, LTG2329, and LTG2330) across different donors.

Figure 14A:
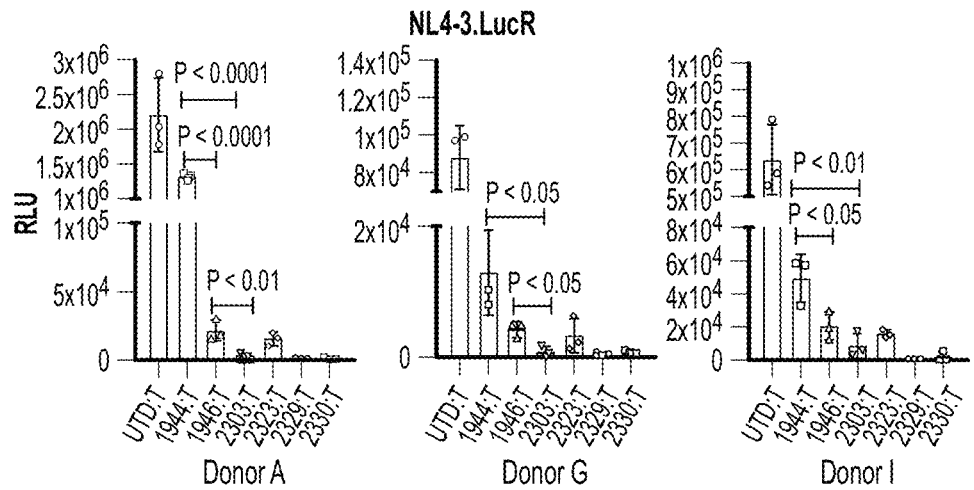

FIG. 14A shows CAR-T killing efficacy against PBMC infected with an Env-IMC-LucR virus encoding a laboratory-adapted NL4-3 env gene (clade B, X4-tropic).

Figure 14B:
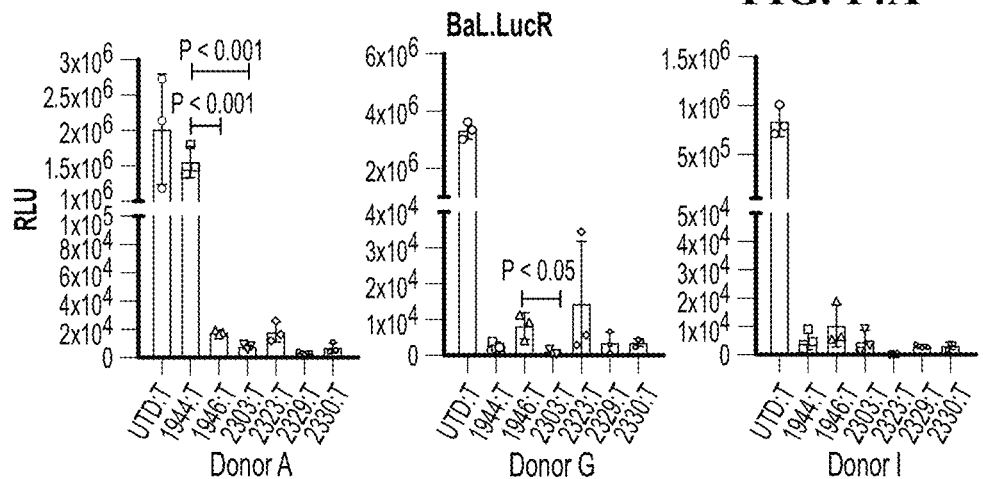

FIG. 14B shows CAR-T killing efficacy against PBMC infected with an Env-IMC-LucR virus encoding a clade B HIV-1 env gene isolated from the USA (BaL, R5-tropic).

Figure 14C:
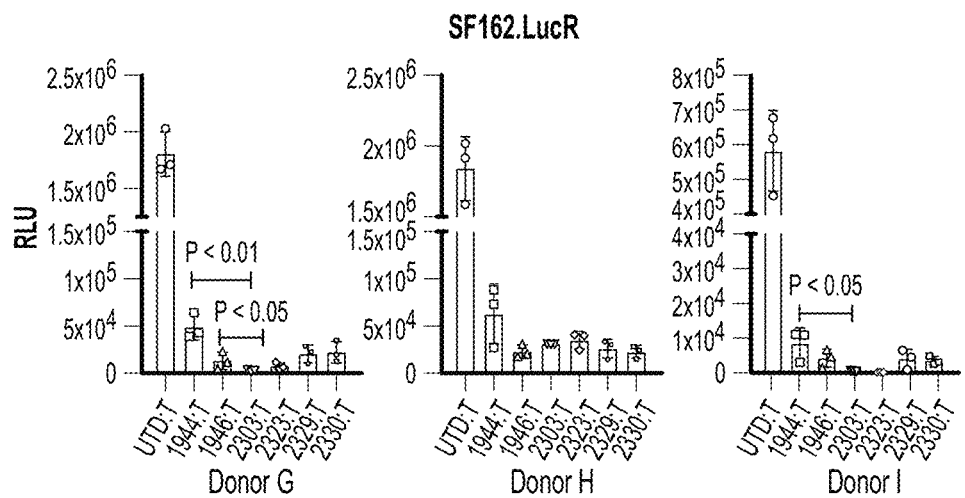

FIG. 14C shows CAR-T killing efficacy against PBMC infected with an Env-IMC-LucR virus encoding a second clade B HIV-1 env gene isolated from the USA (SF162, R5-tropic).

Figure 14D:
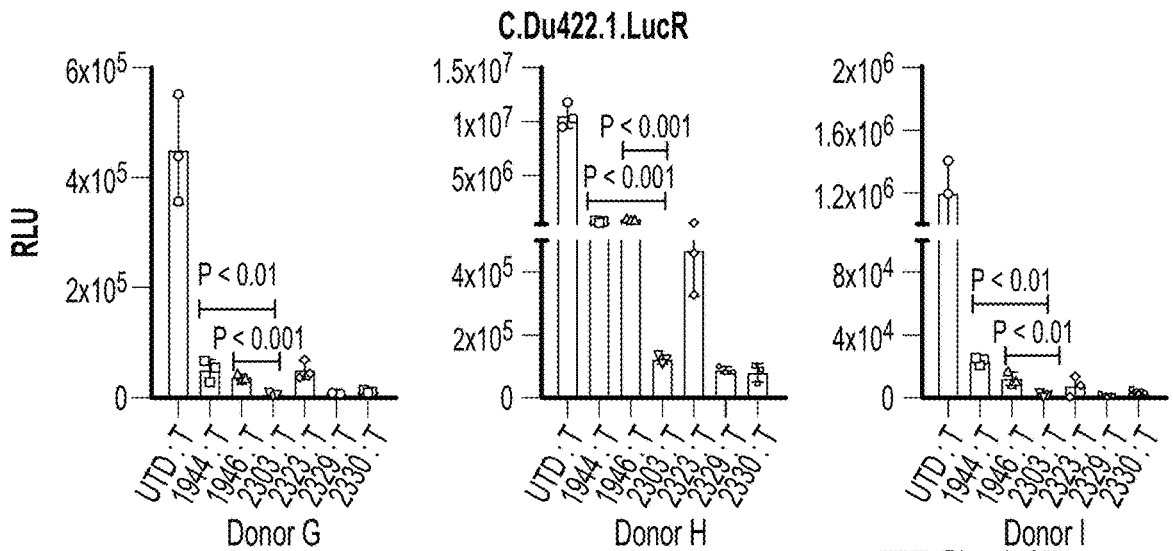

FIG. 14D shows CAR-T killing efficacy against PBMC infected with an Env-IMC-LucR virus encoding a VRC01 and 3BNC117-resistant clade C HIV-1 env gene isolated from S. Africa (C.Du422.1).

Figure 14E:
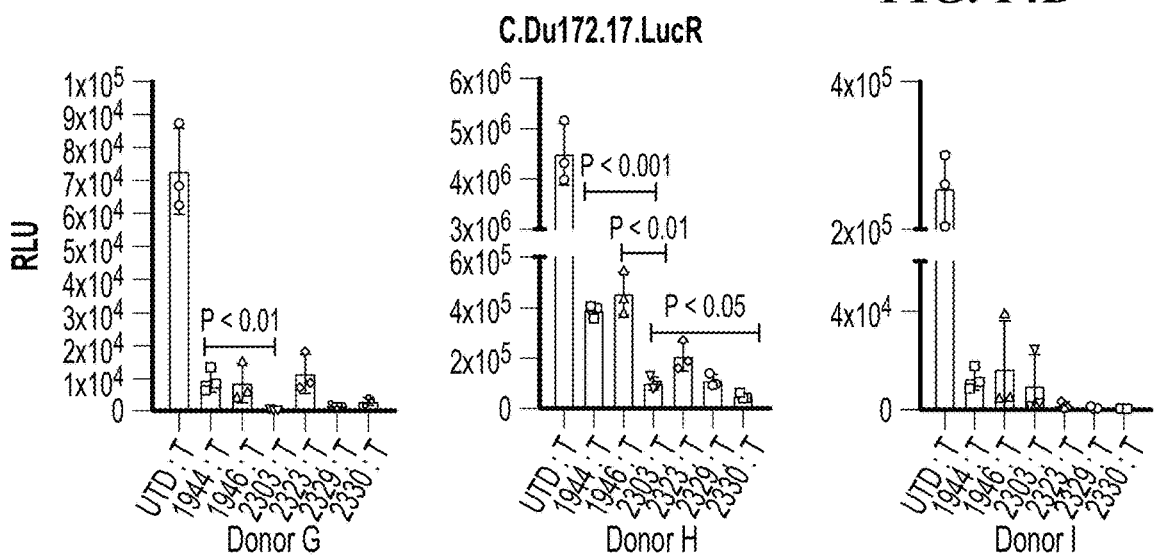

FIG. 14E shows CAR-T killing efficacy against PBMC infected with an Env-IMC-LucR virus encoding a VRC01-resistant clade C HIV-1 env gene isolated from S. Africa (C.Du172.17).

Figure 14F:
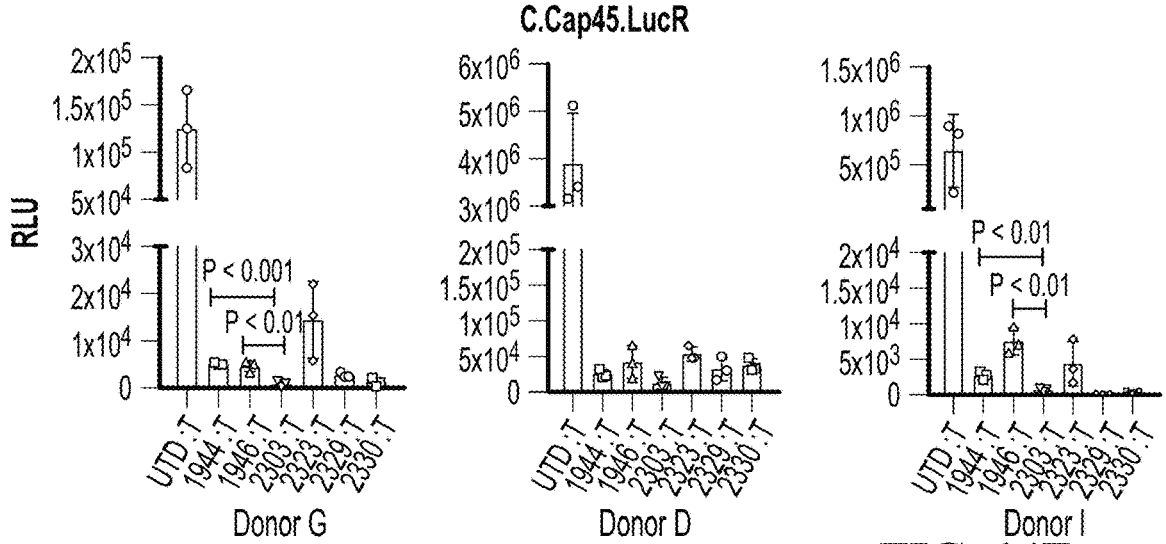

FIG. 14F shows CAR-T killing efficacy against PBMC infected with an Env-IMC-LucR virus encoding a VRC01 partially-resistant clade C HIV-1 env gene isolated from S.E. Africa (C. Cap45).

Figure 14G:
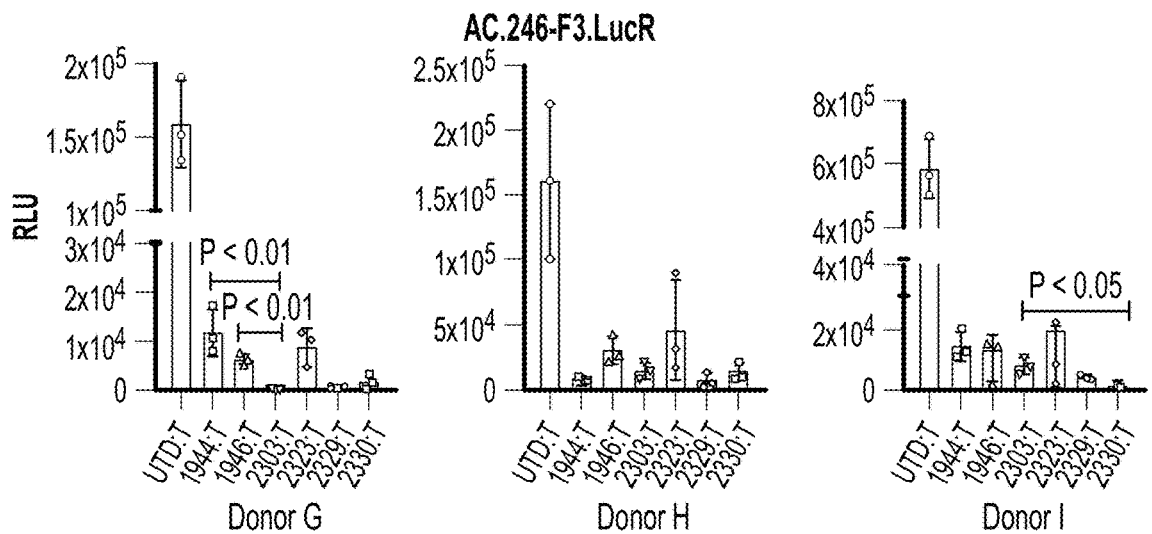

FIG. 14G shows CAR-T killing efficacy against PBMC infected with an Env-IMC-LucR virus encoding a representative clade AC HIV-1 env gene isolated from E. Africa (AC.246-F3.LucR).

Figure 14H:
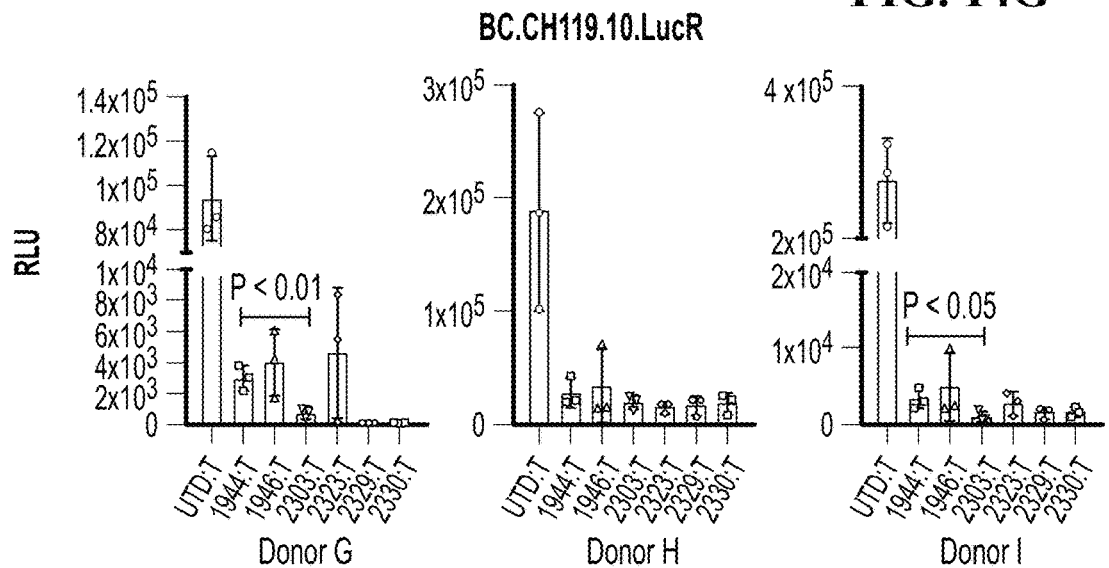

FIG. 14H shows CAR-T killing efficacy against PBMC infected with an Env-IMC-LucR encoding a representative clade BC HIV-1 env gene isolated from China (BC.CH119.10.LucR).

Figure 14I:
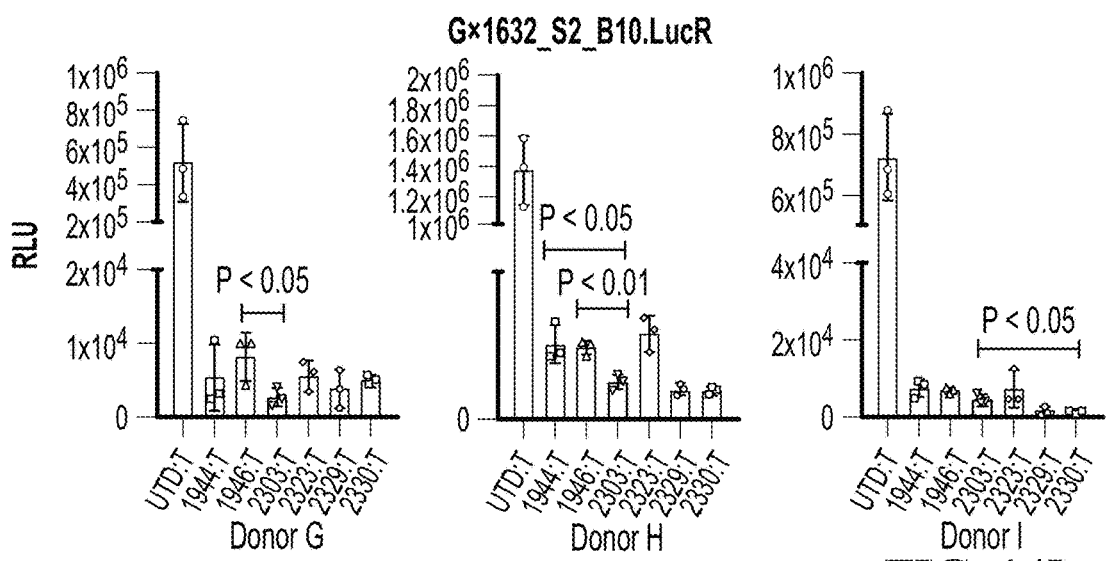

FIG. 14I shows CAR-T killing efficacy against PBMC infected with an Env-IMC-LucR virus encoding a representative clade G HIV-1 env gene isolated from Spain (GX1632_S2_B10.LucR).

FIG. 14J shows CAR-T killing efficacy against PBMC infected with an Env-IMC-LucR virus encoding a representative clade AE HIV-1 env gene found in S. China and/or Thailand (AE.CNE8.LucR).

FIG. 14K shows CAR-T killing efficacy against PBMC infected with an Env-IMC-LucR virus encoding a second representative clade AE HIV-1 env gene found in S. China and/or Thailand (AE.CNE55.LucR). The x-axis is labeled with the indicated anti-HIV CAR and "T" represents "target" or Env-IMC-LucR-infected PBMCs. Error bars represent +/−S.D. Statistical analysis was performed by multiple comparison student's t-test. Significance of findings are indicated on the graph.

FIG. 15 shows a summary of the in vitro CAR-T killing efficacy for all donors tested expressed as log inhibition of HIV-1 infection. Log inhibition is calculated relative to HIV-infected untransduced T cells after background subtraction using uninfected PBMCs. The data shows an average of at least three independent donors.

FIG. 16 shows a summary of the in vitro CAR-T killing efficacy for all donors tested expressed as % inhibition of HIV-1 infection. Percent inhibition is calculated relative to HIV-infected untransduced T cells after background subtraction using uninfected PBMCs. The data shows an average of at least three independent donors.

Figure 17A:
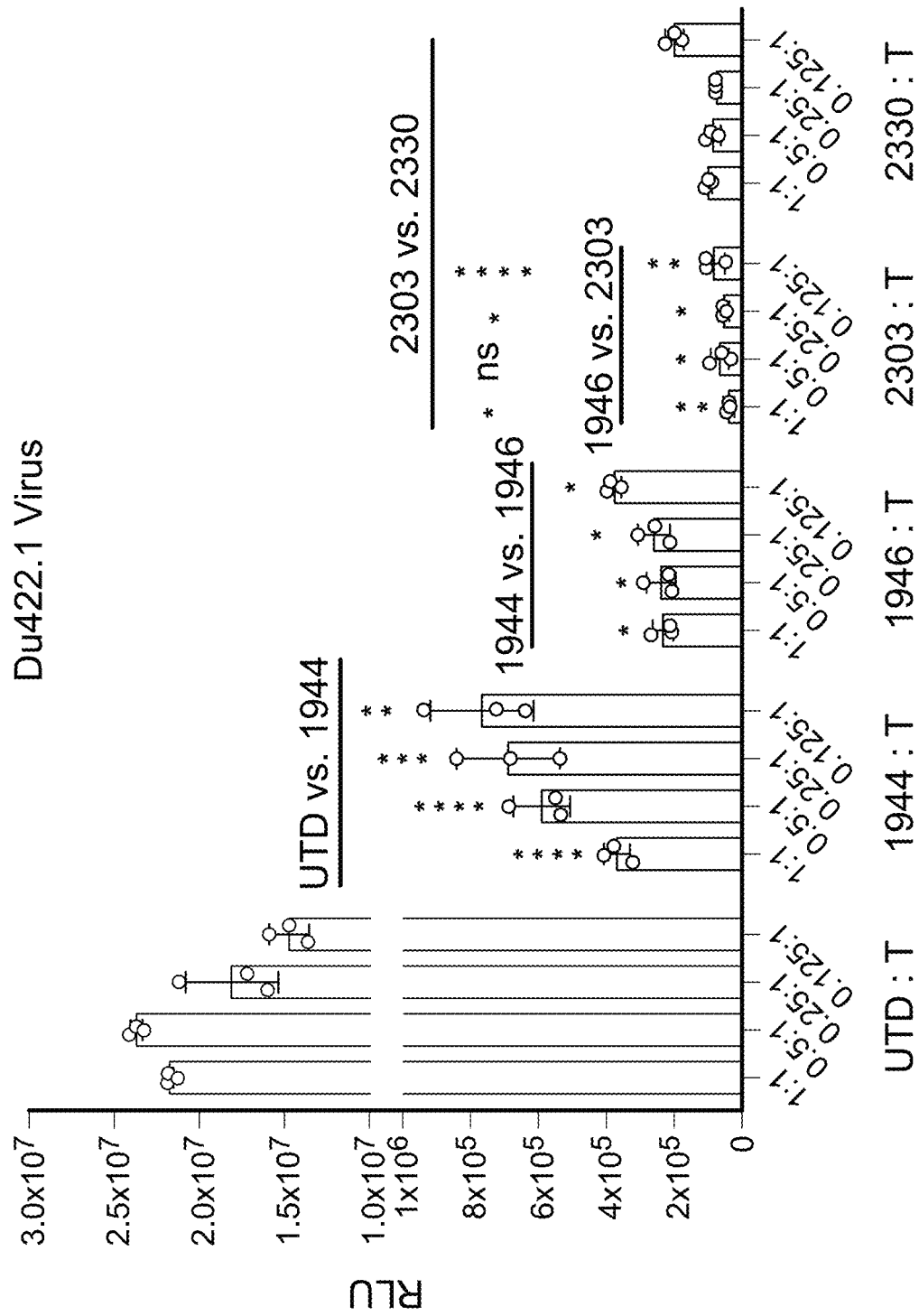
Figure 17B:
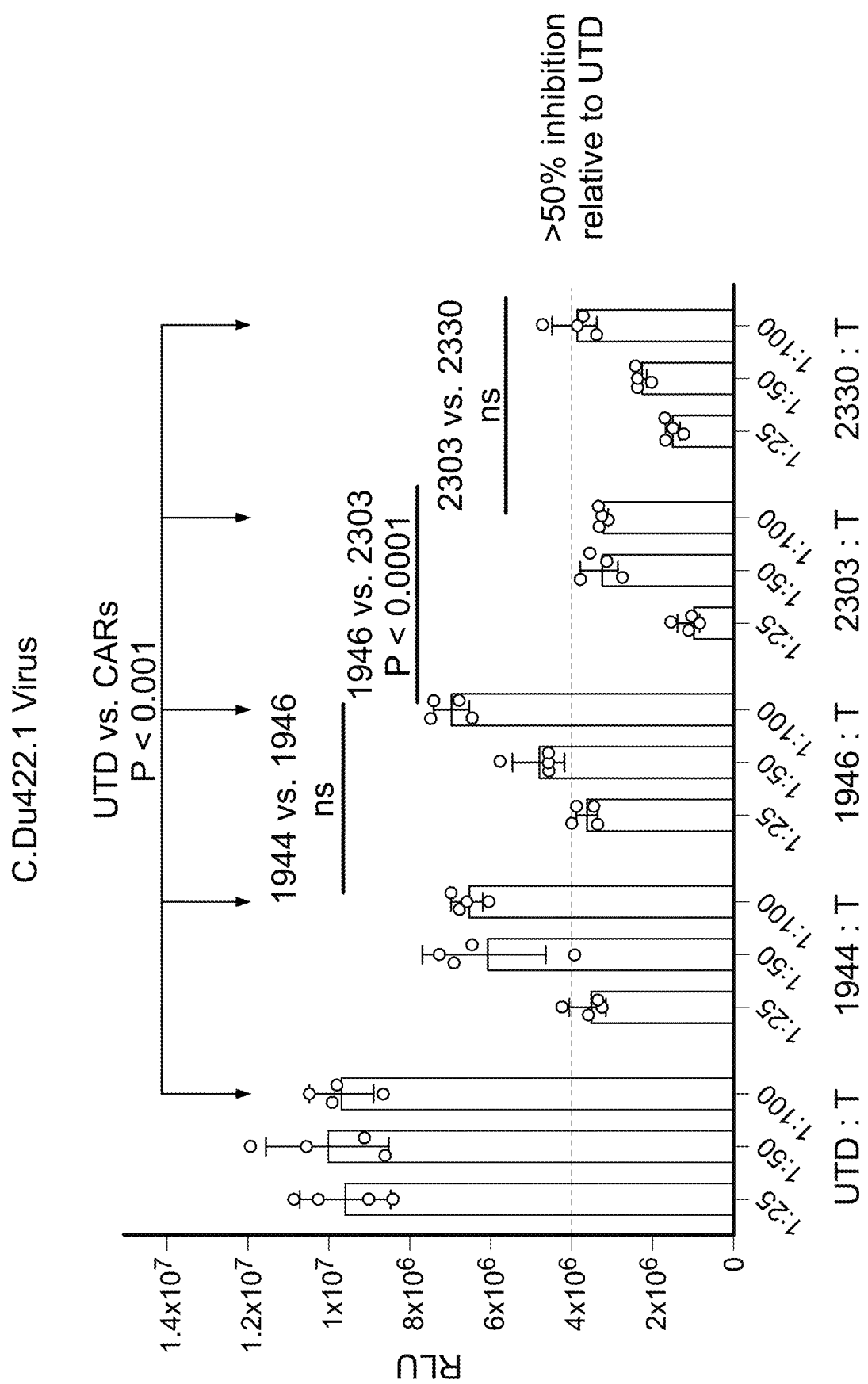

FIG. 17A-B shows that multi-specific anti-HIV duoCAR T cells exhibit superior in vitro killing efficacy at very low E:T ratios.

FIG. 17A depicts donor matched PBMC infected with Du422.1-IMC-LucR virus on Day −1 (T=targets) followed by addition of the indicated anti-HIV CAR-T cells (E=effectors) on Day 0 at different E:T ratios (1:1, 0.5:1, 0.25:1, and 0.125:1).

FIG. 17B depicts donor matched PBMC infected with Du422.1-IMC-LucR virus on Day −1 followed by addition of the indicated anti-HIV CAR-T cells on Day 0 at different E:T ratios (1:25, 1:50, and 1:100). Seven days post-addition of CAR-T cells, the co-cultures were harvested and assayed for Renilla luciferase activity. Statistical analysis was performed by multiple comparison student's t test. Statistical significance is considered P<0.05 and was determined by the Holm-Sidak method. P<0.00001**, P<0.0001*, P<0.001**, P<0.05*.

FIGS. 18A-J show broad in vitro protection of anti-HIV CAR-T cells for individual donors. For some donors, the mD1.22-CAR-T cells are more susceptible to HIV-1 infection. Conversely, the m36.4 domain protects the bispecific and trispecific CAR T cells from HIV-1 infection independent of its architecture.

Figure 18A:
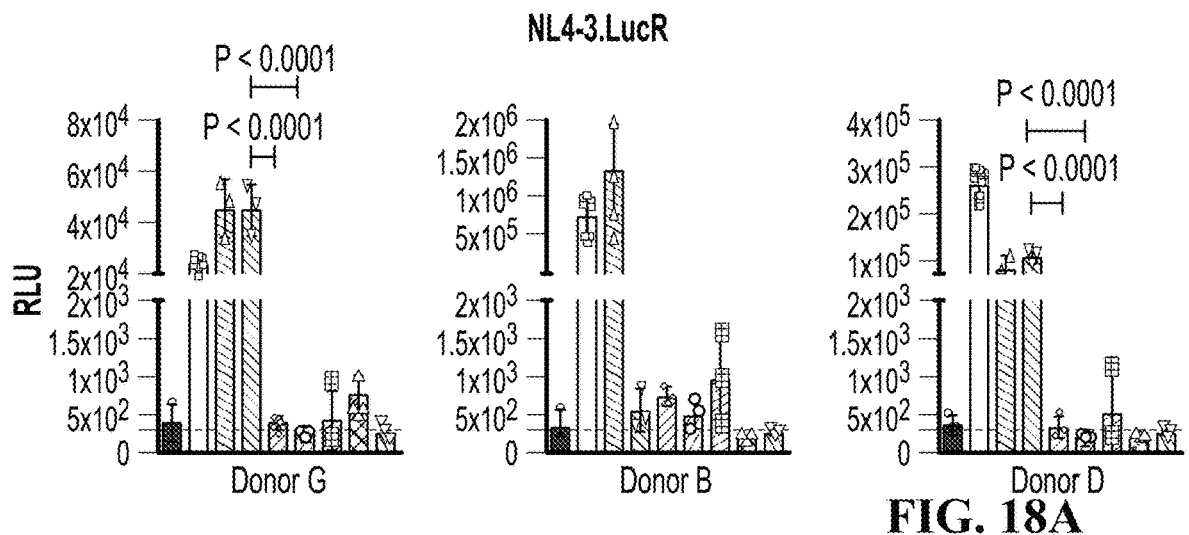

FIG. 18A shows in vitro protection of anti-HIV CAR-T cells challenged with Env-IMC-LucR virus encoding the NL4-3 env gene.

Figure 18B:
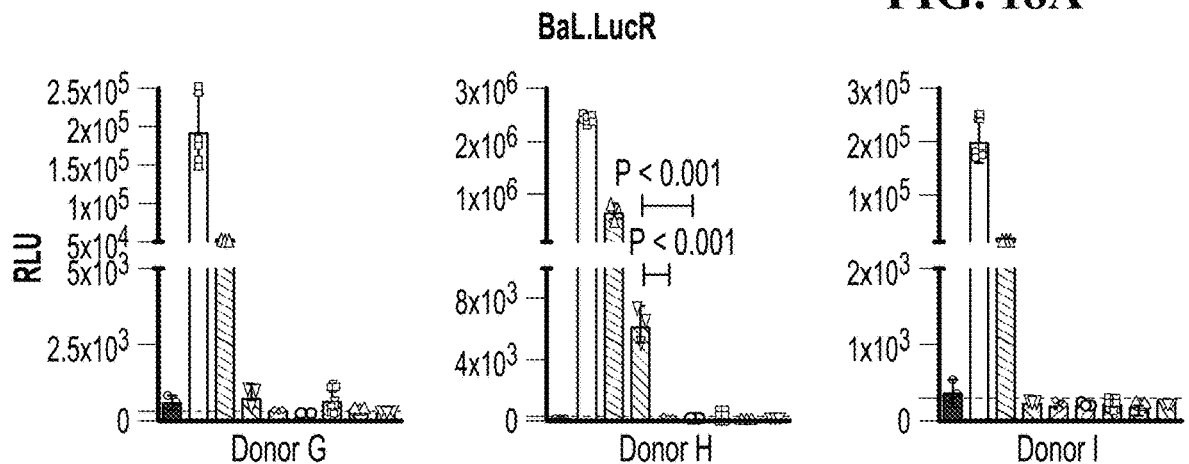

FIG. 18B shows in vitro protection of anti-HIV CAR-T cells challenged with Env-IMC-LucR virus encoding the BaL env gene.

Figure 18C:
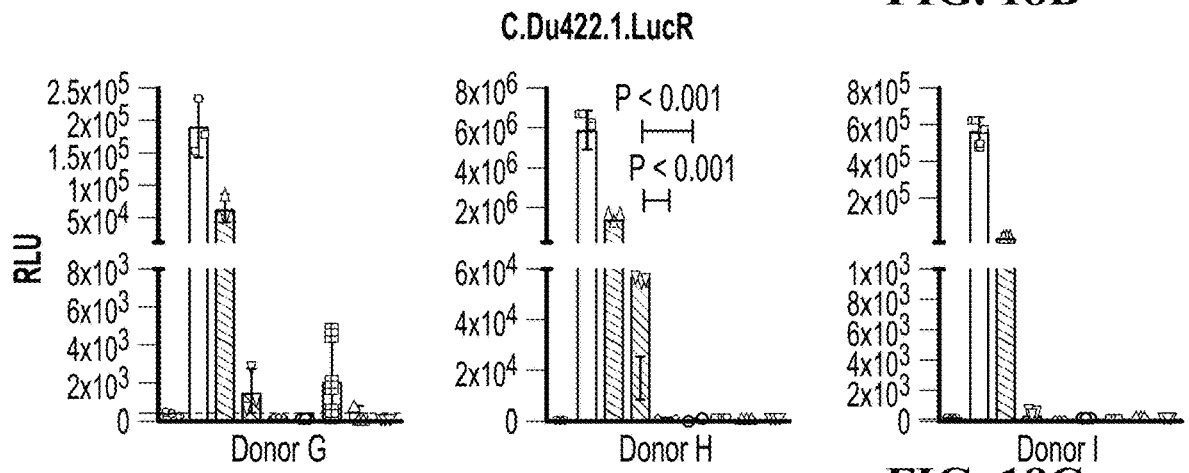

FIG. 18C shows in vitro protection of anti-HIV CAR-T cells challenged with Env-IMC-LucR virus encoding the C.Du422.1 env gene.

FIG. 18D shows in vitro protection of anti-HIV CAR-T cells challenged with Env-IMC-LucR virus encoding the C.Du172.17 env gene.

FIG. 18E shows in vitro protection of anti-HIV CAR-T cells challenged with Env-IMC-LucR virus encoding the AC.246-F3 env gene (clade AC).

FIG. 18F shows in vitro protection of anti-HIV CAR-T cells challenged with Env-IMC-LucR virus encoding a representative clade BC env gene (BC.CH119.10).

FIG. 18G shows in vitro protection of anti-HIV CAR-T cells challenged with Env-IMC-LucR virus encoding a representative clade AE env gene (AE.CNE8).

FIG. 18H shows in vitro protection of anti-HIV CAR-T cells challenged with Env-IMC-LucR virus encoding a representative clade G env gene (GX1632_S2_B10).

FIG. 18I shows in vitro protection of anti-HIV CAR-T cells challenged with Env-IMC-LucR virus encoding a second representative clade AE env gene (AE.CNE55).

Figure 18J:
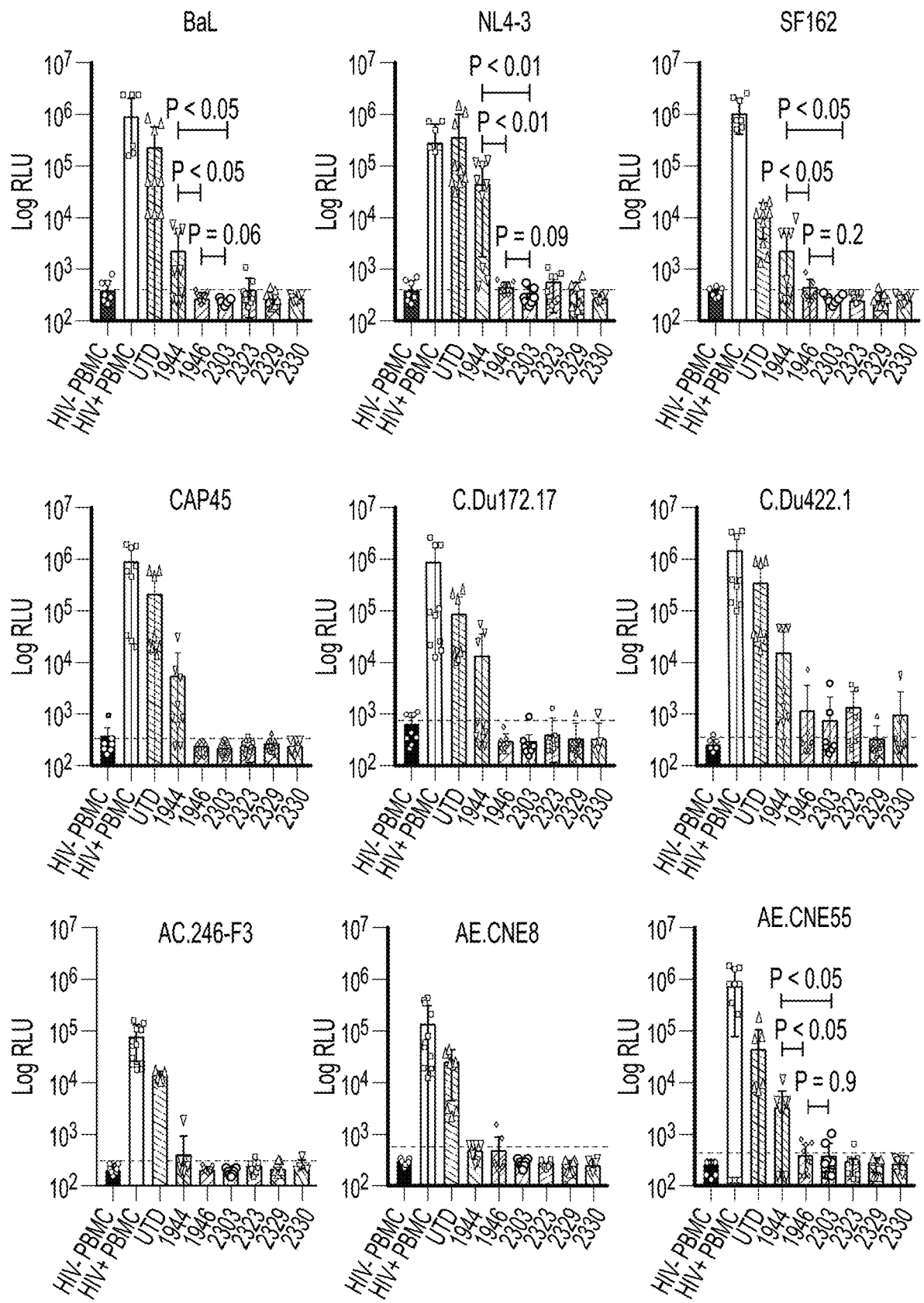

FIG. 18J shows all donors plotted together for each Env-IMC-LucR virus tested. The error bars represent +/−S.D. Statistical analysis was performed by two-way ANOVA followed by Bonferroni post-test. Significant findings are indicated on the graph.

FIGS. 19A-I shows that bispecific and trispecific anti-HIV duoCAR-T cells potently eliminate PBMC infected with bNAb-resistant virus (Du422.1-IMC-LucR) in vivo.

Figure 19A:
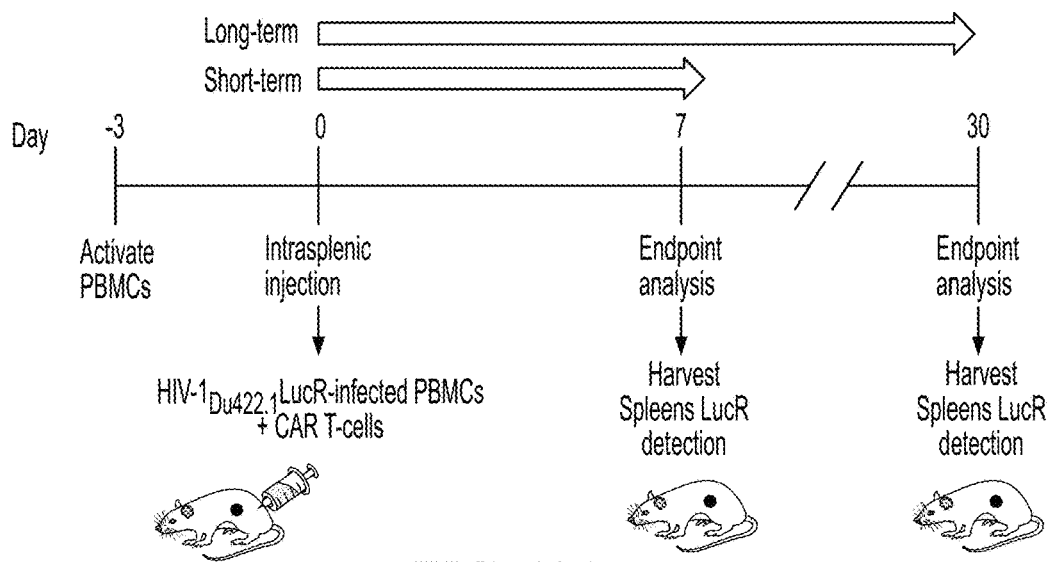

FIG. 19A depicts an illustration of the humanized intrasplenic PBMC NSG acute and chronic HIV-1 infection model (hu-spl-PBMC-NSG).

Figure 19B:
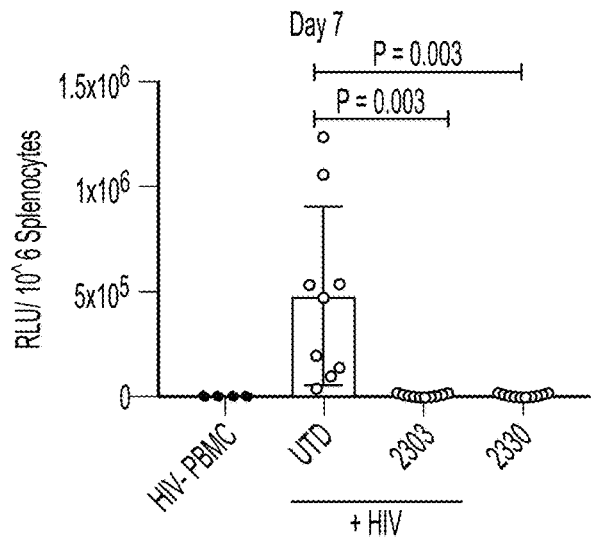

FIG. 19B depicts the in vivo killing efficacy of bispecific and trispecific anti-HIV duoCAR-T cells against PBMC infected with bNAb-resistant Du422.1-IMC-LucR virus for 7 days (acute).

Figure 19C:
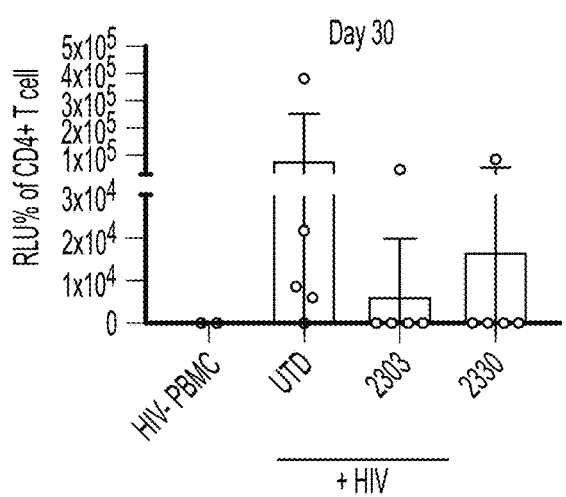

FIG. 19C depicts the in vivo killing efficacy of bispecific and trispecific anti-HIV duoCAR-T cells against PBMC infected with bNAb-resistant Du422.1-IMC-LucR virus for 30 days (chronic). Data shows luciferase activity detected in the spleens of mice at day 7 (acute) or day 30 (chronic). Day 30 luciferase activity (RLU) was normalized to % CD4$^+$ T cells to account for loss of CD4$^+$ T cells in the UTD control group due to uncontrolled HIV-1 infection.

Figure 19D:
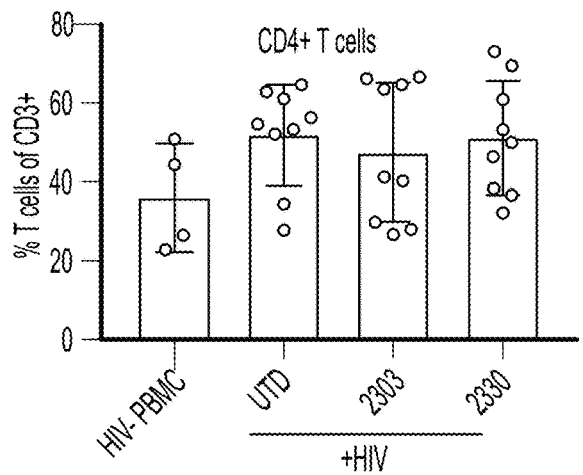

FIG. 19D depicts the % of CD4$^+$ T cells isolated from mice spleens at day 7 (acute).

Figure 19E:
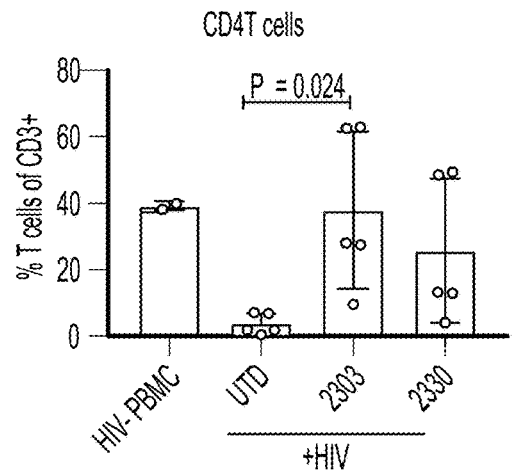

FIG. 19E depicts the % of CD4$^+$ T cells isolated from mice spleens at day 30 (chronic).

Figure 19F:
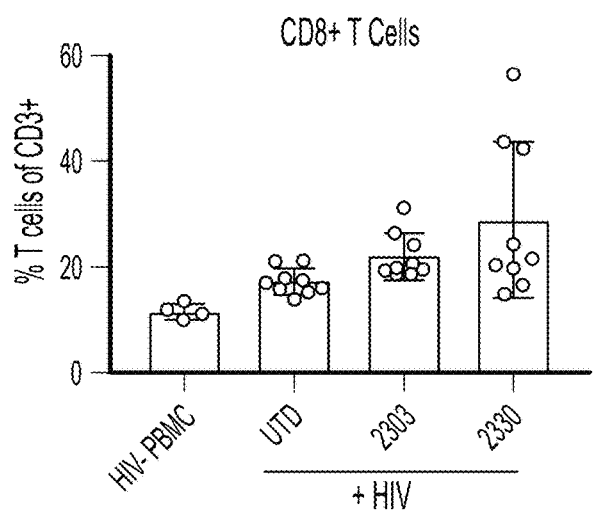

FIG. 19F depicts the % of CD8$^+$ isolated from the mice spleens during day 7 (acute).

Figure 19G:
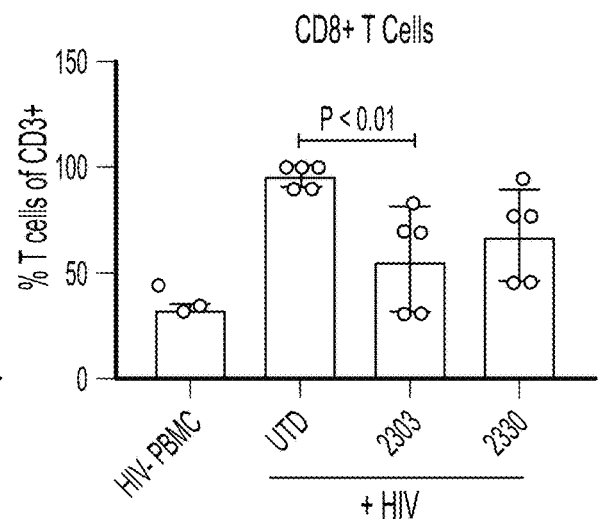

FIG. 19G depicts the % of CD8$^+$ isolated from the mice spleens during day 30 (chronic).

Figure 19H:
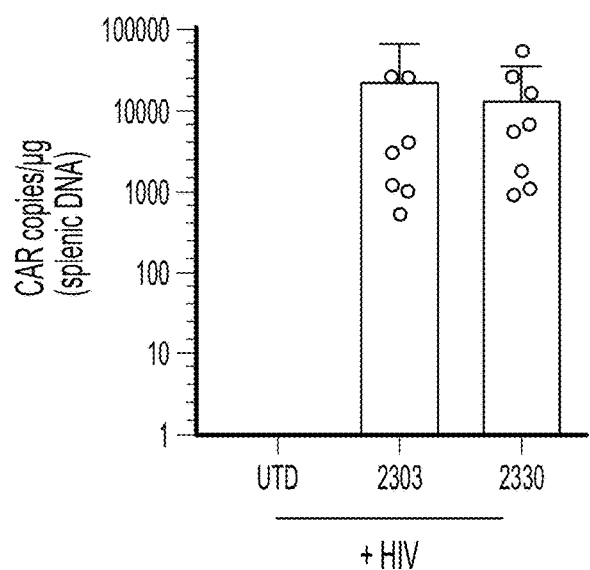

FIG. 19H depicts the CAR copies/μg of splenic DNA at day 7 (acute).

Figure 19I:
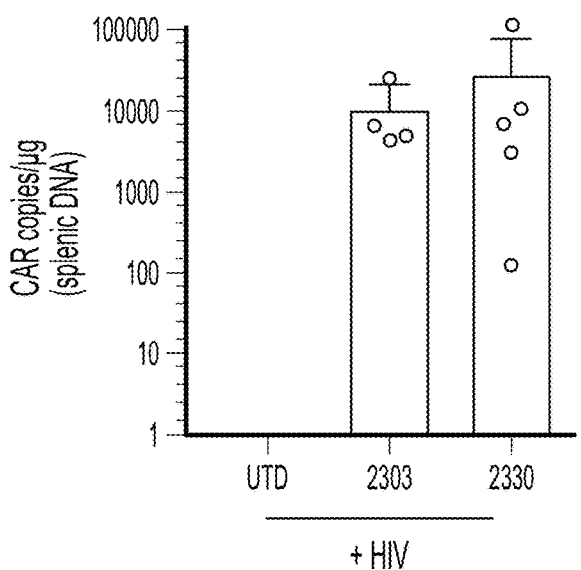

FIG. 19I depicts the CAR copies/μg of splenic DNA at day 30 (chronic). Statistical analysis was performed by one-way ANOVA followed by tukey's post-test. Significance of findings are indicated on the graph.

DETAILED DESCRIPTION

Definitions

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of .+−0.20% or in some instances .+−0.10%, or in some instances .+−0.5%, or in some instances .+−0.1%, or in some instances .+−0.0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

The present disclosure provides for HIV antibodies or fragments thereof as well as CARs having such HIV antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of CARs. The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines and has a high cytotoxic activity against a cell having, on its surface, HIV envelope antigen to which a CAR binds. The use of a human extracellular HIV antigen binding domain results in generation of a CAR that functions better in vivo, while avoiding the induction of anti-CAR immunity in the host immune response and the killing of the CAR T cell population. The CARs expressing the entirely human extracellular HIV antigen binding domains exhibit superior activities/properties including i) prevention of poor CAR T persistence and function as seen with mouse-derived binding sequences; ii) lack of regional (i.e. intrapleural) delivery of the CAR to be efficacious; and iii) ability to generate CAR T cell designs based both on binders with high and low affinity to HIV.

What follows is a detailed description of the inventive CARs including a description of their extracellular HIV antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one HIV antigen binding domain capable of binding to HIV envelope protein, at least one transmembrane domain, and at least one intracellular domain.

A chimeric antigen receptor (CAR) is an artificially constructed hybrid protein or polypeptide containing the antigen binding domains of an antibody or a receptor (e.g., single chain variable fragment (ScFv), or human CD4 which binds to the gp120 portion of HIV envelope protein) linked to T-cell signaling domains via the transmembrane domain via the linker or hinge domain. Characteristics of CARs include their ability to redirect T-cell specificity and reactivity toward a selected target in a non-Major Histocompatibility Complex (MHC)-restricted manner, and exploiting the antigen-binding properties of monoclonal antibodies or receptors. The non-MHC-restricted antigen recognition gives T cells expressing CARs the ability to recognize antigen independent of antigen processing. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a viral antigen of interest by way of engineering a desired antigen binding domain that specifically binds to an antigen on a virus infected cell. Viral antigens are proteins that are produced by virus infected cells that elicit an immune response, particularly T-cell mediated immune responses. The selection of the antigen binding domain will depend on the particular type of virus infection to be treated. Viral antigens that can serve as CAR targets include those expressed on the surface of an infected cell such as, HIV envelope protein glycoprotein (gp160, gp120/gp41), Hepatitis B Virus (HBV) surface antigen (HBsAg), Hepatitis C virus (HBV) E2 glycoprotein, Epstein-Barr envelope protein, and cytomegalovirus (CMV) glycoprotein B antigen. The viral antigens disclosed herein are merely included by way of example. The list is not intended to be exclusive and further examples will be readily apparent to those of skill in the art.

In one embodiment, the HIV envelope protein comprises one or more antigenic epitopes associated with the viral envelope protein. HIV infected cells express envelope protein that can serve as target antigen for an immune attack. In this disclosure, anti-HIV CARs have been developed that target the HIV envelope protein using a single extracellular domain to form a monospecific CAR; combination of two of these extracellular domains in different orientations and with varying linker lengths to form a bispecific CAR; or a combination of all three extracellular domains to form a trispecific CAR. The CARs are composed of three functionally distinct extracellular domains that target non-overlapping epitopes on the HIV envelope to effectively block HIV entry (mD1.22), coreceptor usage (m36.4), and viral fusion (C46). In contrast to CARs containing either a single bnAb and/or the wild-type CD4 receptor, all three extracellular domains have been precisely engineered to be compact with enhanced specificity, potency, and the ability to target newly emerging T20-resistant strains.

The mD1.22 domain is derived from the human CD4 receptor and targets a highly conserved epitope on HIV-1 gp120. In comparison to the full-length CD4 receptor, mD1.22 has been engineered to be molecularly compact, with high specificity, affinity, and potency against diverse HIV-1 clades (Chen et al., J. Virol. 2014; 88:(2) 1125-1139). The m36.4 domain is an affinity-matured, engineered human antibody domain composed of the heavy chain only (Chen et al., Antiviral Research 2010; 88:(1) 107-115). It binds to a discontinuous CD4-induced (CD4i) epitope on gp120 in the vicinity of the coreceptor binding site (Wan et al. PLOS One 2013; 8(6):e66638). When combined together, the two domains work synergistically to potently neutralize HIV-1 and inhibit viral entry (Chen et al., J. Virol. 2014; 88:(2) 1125-1139).

Targeting multiple non-overlapping epitopes is an attractive strategy to prevent viral escape. As a third layer of T-cell protection, CAR-T or T-cells themselves were engineered with the highly potent C46 fusion inhibitor. The C46 peptide belongs to a class of gp41-derived "C-peptide" fusion inhibitors that block HIV-1 infection at the level of viral fusion. It is an extended version of the FDA-approved enfuviritide or T20 and similar to T20, the C46 peptide can be used to suppress HIV variants with multidrug resistance to current cART. Notably when C-peptides are expressed on the surface of T-cells or secreted from T-cells (SAVE peptides), they potently abrogate HIV-1 fusion to the T-cell membrane (van Lunzen et al., Molecular Therapy 2007, 15: (5) 1024-1033; Kimpel et al., PLOS One 2010, 5:(8) e12357; Egerer et al., Molecular Therapy 2010, 19(7), 1236-1244). Hence, CARs engineered with these three domains are designed to potently destroy HIV-infected cells while conferring protection to the CAR T-cell.

To reduce immunogenicity, the CARs employed here are constructed of fully human sequences. This is an advantage over using mouse-based ScFv binding sequences, that are prone to induce immune response and CAR-T elimination in a human host leading to poor T-cell persistence. As described herein, CAR transduced T-cells have been generated by transduction with a lentiviral vector construct encoding the anti-HIV CAR gene. It is expected that the CAR-expressing T-cells will have long-lasting therapeutic effect in the patient. It is important to note that the therapeutic CAR-T cell product will be given once rather than through a series of recurring IV administrations.

In general, mD1.22-based CARs (containing a minimal domain human CD4 protein fragment) are highly potent and specifically destroyed 293T cells stably expressing HIV gp120 (referred to as, env$^+$ cells), which serves as a surrogate HIV-infected cell, and used to reproducibly quantify CAR-mediated cytotoxicity. Subsequently fusing the mD1.22 domain to m36.4 (an anti-HIV antibody derived binding domain) using linker domains, as in SEQ ID NOs: 24, 26, 28, 30, 32 and then joining these domains to CD8 or to TNFRSF19 transmembrane domains (TM), SEQ ID NO: 8 and SEQ ID NO: 14, by virtue of a linker domain derived from CD8, as in SEQ ID NO: 10; resulting in a CD8 linker joined to a CD8 transmembrane domain as in SEQ ID NO: 12; or CD8 linker linked to TNFRSF19TM as in SEQ ID no: 16; thus allowing for linkage to intracellular signaling domains. The intracellular signaling domains are either first generation or second generation. The second generation CARs link the 41BB (CD137) intracellular signaling domain, SEQ ID NO: 18, proximal to the transmembrane followed by CD3zeta signaling domain. The intracellular domains for CD3 zeta chain are linked directly to the transmembrane domain or in second generation constructs to the 41BB domain. In the creation of lentiviral gene vectors it is crucial to avoid sequence repetition as the vectors often edit or recombine out these sequences, and the structure of the CAR construct is then lost. Another unique characteristic of the vector family presented here is the creation of two different CD3 zeta domains. They both code for the same amino acid sequence, SEQ ID NO: 20 and SEQ ID NO: 22, yet diverge in their nucleic acid sequence, SEQ ID NO: 19 and SEQ ID NO: 21.

In some cases, a single chain forms a bispecific or trispecific CAR, that contains two or three extracellular domains linked and expressed on the same final cell surface protein. In other cases, two separate chains are expressed, being encoded in the same construct however, processed into two proteins by including a composite furin/ribosomal skip site or self-cleaving peptide, as in SEQ ID NO: 33 and SEQ ID NO: 34. The importance of a bispecific or trispecific CAR should be realized in the event that one binder is unable to recognize a HIV variant or an evolved mutation, the second and/or third domain may compensate for the loss. The effective use of these CAR constructs described herein will eliminate ART dependency and move towards a cure for HIV using CAR-T technology.

In one preferred embodiment, the target antigen is the HIV envelope protein and the infected cells and tissues associated with expression of HIV envelope that comprise and essentially define the status of being HIV infected, including infected epithelial tissues, lymphoid tissues, and lymphocytes.

In a preferred embodiment, the antigen binding domain portion of the CAR targets the extracellular HIV envelope antigen.

In one preferred embodiment, the isolated nucleic acid molecule encoding the extracellular HIV envelope antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular HIV envelope antigen binding domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 4, or an amino acid sequence with 85%, 90%, 95%, 96%, 97%, 98% or 99% identity to an amino acid sequence of SEQ ID NO: 4.

In one preferred embodiment, the isolated nucleic acid molecule encoding the extracellular HIV envelope antigen binding domain comprises a nucleotide sequence of SEQ ID NO: 5, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 6, or an amino acid sequence with 85%, 90%, 95%, 96%, 97%, 98% or 99% identity to an amino acid sequence of SEQ ID NO: 6.

In one preferred embodiment, the isolated nucleic acid molecule encoding the linked extracellular HIV envelope antigen binding domains comprises a nucleotide sequence of SEQ ID NO: 45, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 46, or an amino acid sequence with 85%, 90%, 95%, 96%, 97%, 98% or 99% identity to an amino acid sequence of SEQ ID NO: 46.

In one preferred embodiment, the isolated nucleic acid molecule encoding the linked extracellular HIV envelope antigen binding domains comprises a nucleotide sequence of SEQ ID NO: 49, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 50, or an amino acid sequence with 85%, 90%, 95%, 96%, 97%, 98% or 99% identity to an amino acid sequence of SEQ ID NO: 50.

In one preferred embodiment, the isolated nucleic acid molecule encoding the linked extracellular HIV envelope antigen binding domains comprises a nucleotide sequence of SEQ ID NO: 53, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 54, or an amino acid sequence with 85%, 90%, 95%, 96%, 97%, 98% or 99% identity to an amino acid sequence of SEQ ID NO: 54.

In one preferred embodiment, the isolated nucleic acid molecule encoding the linked extracellular HIV envelope antigen binding domains comprises a nucleotide sequence of SEQ ID NO: 57, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 58, or an amino acid sequence with 85%, 90%, 95%, 96%, 97%, 98% or 99% identity to an amino acid sequence of SEQ ID NO: 58.

In one preferred embodiment, the isolated nucleic acid molecule encoding the linked extracellular HIV envelope antigen binding domains comprises a nucleotide sequence of SEQ ID NO: 61, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 62, or an amino acid sequence with 85%, 90%, 95%, 96%, 97%, 98% or 99% identity to an amino acid sequence of SEQ ID NO: 62.

In one preferred embodiment, the isolated nucleic acid molecule encoding the linked extracellular HIV envelope antigen binding domains comprises a nucleotide sequence of SEQ ID NO: 65, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 66, or an amino acid sequence with 85%, 90%, 95%, 96%, 97%, 98% or 99% identity to an amino acid sequence of SEQ ID NO: 66.

In one preferred embodiment, the isolated nucleic acid molecule encoding the linked extracellular HIV envelope antigen binding domains comprises a nucleotide sequence of SEQ ID NO: 69, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 70, or an amino acid sequence with 85%, 90%, 95%, 96%, 97%, 98% or 99% identity to an amino acid sequence of SEQ ID NO: 70.

In one preferred embodiment, the isolated nucleic acid molecule encoding the linked extracellular HIV envelope antigen binding domains comprises a nucleotide sequence of SEQ ID NO: 75, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 76, or an amino acid sequence with 85%, 90%, 95%, 96%, 97%, 98% or 99% identity to an amino acid sequence of SEQ ID NO: 76.

In one preferred embodiment, the isolated nucleic acid molecule encoding the linked extracellular HIV envelope antigen binding domains comprises a nucleotide sequence of SEQ ID NO: 79, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 80, or an amino acid sequence with 85%, 90%, 95%, 96%, 97%, 98% or 99% identity to an amino acid sequence of SEQ ID NO: 80.

In one preferred embodiment, the isolated nucleic acid molecule encoding the linked extracellular HIV envelope antigen binding domains comprises a nucleotide sequence of SEQ ID NO: 83, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 84, or an amino acid sequence with 85%, 90%, 95%, 96%, 97%, 98% or 99% identity to an amino acid sequence of SEQ ID NO: 84.

In one preferred embodiment, the isolated nucleic acid molecule encoding the linked extracellular HIV envelope antigen binding domain comprises a nucleotide sequence of SEQ ID NO: 87, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 88, or an amino acid sequence with 85%, 90%, 95%, 96%, 97%, 98% or 99% identity to an amino acid sequence of SEQ ID NO: 88.

In one preferred embodiment, the isolated nucleic acid molecule encoding the linked extracellular HIV envelope antigen binding domains comprises a nucleotide sequence of SEQ ID NO: 91, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 92, or an amino acid sequence with 85%, 90%, 95%, 96%, 97%, 98% or 99% identity to an amino acid sequence of SEQ ID NO: 92.

In one preferred embodiment, the isolated nucleic acid molecule encoding the linked extracellular HIV envelope antigen binding domains comprises a nucleotide sequence of SEQ ID NO: 95, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 96, or an amino acid sequence with 85%, 90%, 95%, 96%, 97%, 98% or 99% identity to an amino acid sequence of SEQ ID NO: 96.

In one preferred embodiment, the isolated nucleic acid molecule encoding the linked extracellular HIV envelope antigen binding domains comprises a nucleotide sequence of SEQ ID NO: 99, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 100, or an amino acid sequence with 85%, 90%, 95%, 96%, 97%, 98% or 99% identity to an amino acid sequence of SEQ ID NO: 100.

In one preferred embodiment, the isolated nucleic acid molecule encoding the linked extracellular HIV envelope antigen binding domains comprises a nucleotide sequence of SEQ ID NO: 103, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 104, or an amino acid sequence with 85%, 90%, 95%, 96%, 97%, 98% or 99% identity to an amino acid sequence of SEQ ID NO: 104.

In one preferred embodiment, the isolated nucleic acid molecule encoding the linked extracellular HIV envelope antigen binding domains comprises a nucleotide sequence of SEQ ID NO: 111, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 112, or an amino acid sequence with 85%, 90%, 95%, 96%, 97%, 98% or 99% identity to an amino acid sequence of SEQ ID NO: 112.

In one preferred embodiment, the isolated nucleic acid molecule encoding the linked extracellular HIV envelope antigen binding domains comprises a nucleotide sequence of SEQ ID NO: 115, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 116, or an amino acid sequence with 85%, 90%, 95%, 96%, 97%, 98% or 99% identity to an amino acid sequence of SEQ ID NO: 116.

In one preferred embodiment, the isolated nucleic acid molecule encoding the linked extracellular HIV envelope antigen binding domains comprises a nucleotide sequence of SEQ ID NO: 119, or a sequence with 85%, 90%, 95%, 96%, 97%, 98% or 99% identity thereof. In one embodiment, an isolated nucleic acid molecule is provided wherein the encoded extracellular HIV antigen binding domain comprises an amino acid sequence of SEQ ID NO: 120, or an amino acid sequence with 85%, 90%, 95%, 96%, 97%, 98% or 99% identity to an amino acid sequence of SEQ ID NO: 120.

In the various embodiments of the HIV-specific CARs disclosed herein, the general scheme is set forth in FIG. 1 and includes, from the N-terminus to the C-terminus, a signal or leader peptide, anti-HIV binders, extracellular linker, CD8 transmembrane, 4-1BB, and CD3zeta. Also shown are CARs that incorporate multiple binders (bispecific, trispecific) joined by specific linkage domains.

In one embodiment, the nucleic acid sequence encoding a CAR comprises the nucleic acid sequence of SEQ ID NO: 39, and encodes the CAR comprising the amino acid sequence as set forth in SEQ ID NO: 40 [LTG1944, LP-mD1.22-CD8TM-41BB-CD3zeta amino acid sequence (as depicted in FIG. 2A)].

In one embodiment, the nucleic acid sequence encoding a CAR comprises the nucleic acid sequence of SEQ ID NO: 39, or a sequence with 85%, 90%, 95%, 96%, 97%, 98% or 99% identity thereof, and encodes the CAR comprising the amino acid sequence as set forth in SEQ ID NO: 40 or a sequence with 85%, 90%, 95%, 96%, 97%, 98% or 99% identity thereof, [LTG1944, LP-mD1.22-CD8TM-41BB-CD3zeta amino acid sequence (as depicted in FIG. 2A)].

In another embodiment, the nucleic acid sequence encoding a CAR comprises the nucleic acid sequence of SEQ ID NO: 41, and encodes the CAR comprising the amino acid sequence as set forth in SEQ ID NO: 42 [LTG1945, LP-m36.4-CD8TM-41BB-CD3zeta amino acid sequence (as depicted in FIG. 2B)].

In another embodiment, the nucleic acid sequence encoding a CAR comprises the nucleic acid sequence of SEQ ID NO: 41 or a sequence with 85%, 90%, 95%, 96%, 97%, 98% or 99% identity thereof, and encodes the CAR comprising the amino acid sequence as set forth in SEQ ID NO: 42 or a sequence with 85%, 90%, 95%, 96%, 97%, 98% or 99% identity thereof [LTG1945, LP-m36.4-CD8TM-41BB-CD3zeta amino acid sequence (as depicted in FIG. 2B)].

In another embodiment, the nucleic acid sequence encoding a CAR comprises the nucleic acid sequence of SEQ ID NO: 43, and encodes the CAR comprising the amino acid sequence as set forth in SEQ ID NO: 44 [LTG2328, LP-C46-CD8TM-41BB-CD3zeta amino acid sequence (as depicted in FIG. 2C)].

In another embodiment, the nucleic acid sequence encoding a CAR comprises the nucleic acid sequence of SEQ ID NO: 43 or a sequence with 85%, 90%, 95%, 96%, 97%, 98% or 99% identity thereof, and encodes the CAR comprising the amino acid sequence as set forth in SEQ ID NO: 44 or a sequence with 85%, 90%, 95%, 96%, 97%, 98% or 99% identity thereof [LTG2328, LP-C46-CD8TM-41BB-CD3zeta amino acid sequence (as depicted in FIG. 2C)].

In yet another embodiment, the nucleic acid sequence encoding a CAR comprises the nucleic acid sequence of SEQ ID NO: 47, and encodes the CAR comprising the amino acid sequence as set forth in SEQ ID NO: 48 [LTG2325, LP-mD1.22-L1-m36.4-CD8TM-41BB-CD3zeta amino acid sequence (as depicted in FIG. 2D)].

In yet another embodiment, the nucleic acid sequence encoding a CAR comprises the nucleic acid sequence of SEQ ID NO: 47 or a sequence with 85%, 90%, 95%, 96%, 97%, 98% or 99% identity thereof, and encodes the CAR comprising the amino acid sequence as set forth in SEQ ID NO: 48 or a sequence with 85%, 90%, 95%, 96%, 97%, 98% or 99% identity thereof [LTG2325, LP-mD1.22-L1-m36.4-CD8TM-41BB-CD3zeta amino acid sequence (as depicted in FIG. 2D)].

In yet another embodiment, the nucleic acid sequence encoding a CAR comprises the nucleic acid sequence of SEQ ID NO: 51, and encodes the CAR comprising the amino acid sequence as set forth in SEQ ID NO: 52 [LTG2313, LP-mD1.22-L2-m36.4-CD8TM-41BB-CD3zeta amino acid sequence (as depicted in FIG. 2E)].

In yet another embodiment, the nucleic acid sequence encoding a CAR comprises the nucleic acid sequence of SEQ ID NO: 51 or a sequence with 85%, 90%, 95%, 96%, 97%, 98% or 99% identity thereof, and encodes the CAR comprising the amino acid sequence as set forth in SEQ ID NO: 52 or a sequence with 85%, 90%, 95%, 96%, 97%, 98% or 99% identity thereof [LTG2313, LP-mD1.22-L2-m36.4-CD8TM-41BB-CD3zeta amino acid sequence (as depicted in FIG. 2E)].

In yet another embodiment, the nucleic acid sequence encoding a CAR comprises the nucleic acid sequence of SEQ ID NO: 55, and encodes the CAR comprising the amino acid sequence as set forth in SEQ ID NO: 56 [LTG1946, LP-mD1.22-L3-m36.4-CD8TM-41BB-CD3zeta amino acid sequence (as depicted in FIG. 2F)].

In yet another embodiment, the nucleic acid sequence encoding a CAR comprises the nucleic acid sequence of SEQ ID NO: 55 or a sequence with 85%, 90%, 95%, 96%, 97%, 98% or 99% identity thereof, and encodes the CAR comprising the amino acid sequence as set forth in SEQ ID NO: 56 or a sequence with 85%, 90%, 95%, 96%, 97%, 98% or 99% identity thereof [LTG1946, LP-mD1.22-L3-m36.4-CD8TM-41BB-CD3zeta amino acid sequence (as depicted in FIG. 2F)].

In yet another embodiment, the nucleic acid sequence encoding a CAR comprises the nucleic acid sequence of SEQ ID NO: 59, and encodes the CAR comprising the amino acid sequence as set forth in SEQ ID NO: 60 [LTG2326, LP-mD1.22-L4-m36.4-CD8TM-41BB-CD3zeta amino acid sequence (as depicted in FIG. 2G)].

In yet another embodiment, the nucleic acid sequence encoding a CAR comprises the nucleic acid sequence of SEQ ID NO: 59 or a sequence with 85%, 90%, 95%, 96%, 97%, 98% or 99% identity thereof, and encodes the CAR comprising the amino acid sequence as set forth in SEQ ID NO: 60 or a sequence with 85%, 90%, 95%, 96%, 97%, 98% or 99% identity thereof [LTG2326, LP-mD1.22-L4-m36.4-CD8TM-41BB-CD3zeta amino acid sequence (as depicted in FIG. 2G)].

In yet another embodiment, the nucleic acid sequence encoding a CAR comprises the nucleic acid sequence of SEQ ID NO: 63, and encodes the CAR comprising the amino acid sequence as set forth in SEQ ID NO: 64 [LTG1947, LP-mD1.22-L5-m36.4-CD8 TM-41BB-CD3zeta amino acid sequence (as depicted in FIG. 2H)].

In yet another embodiment, the nucleic acid sequence encoding a CAR comprises the nucleic acid sequence of SEQ ID NO: 63 or a sequence with 85%, 90%, 95%, 96%, 97%, 98% or 99% identity thereof, and encodes the CAR comprising the amino acid sequence as set forth in SEQ ID NO: 64 or a sequence with 85%, 90%, 95%, 96%, 97%, 98% or 99% identity thereof [LTG1947, LP-mD1.22-L5-m36.4-CD8TM-41BB-CD3zeta amino acid sequence (as depicted in FIG. 2H)].

In yet another embodiment, the nucleic acid sequence encoding a CAR comprises the nucleic acid sequence of SEQ ID NO: 67, and encodes the CAR comprising the amino acid sequence as set forth in SEQ ID NO: 68 [LTG1948, LP-m36.4-L3-mD1.22-CD8TM-41BB-CD3zeta amino acid sequence (as depicted in FIG. 2I)].

In yet another embodiment, the nucleic acid sequence encoding a CAR comprises the nucleic acid sequence of SEQ ID NO: 67 or a sequence with 85%, 90%, 95%, 96%, 97%, 98% or 99% identity thereof, and encodes the CAR comprising the amino acid sequence as set forth in SEQ ID NO: 68 or a sequence with 85%, 90%, 95%, 96%, 97%, 98% or 99% identity thereof [LTG1948, LP-m36.4-L3-mD1.22-CD8 TM-41BB-CD3zeta amino acid sequence (as depicted in FIG. 2I)].

In yet another embodiment, the nucleic acid sequence encoding a CAR comprises the nucleic acid sequence of SEQ ID NO: 71, and encodes the CAR comprising the amino acid sequence as set forth in SEQ ID NO: 72 [LTG2303, LP-mD1.22-CD8TM-41BB-CD3zeta-F2AF-LP2-m36.4-TNFRSF19TM-CD3zeta2 amino acid sequence (as depicted in FIG. 2J)].

In yet another embodiment, the nucleic acid sequence encoding a CAR comprises the nucleic acid sequence of SEQ ID NO: 71 or a sequence with 85%, 90%, 95%, 96%, 97%, 98% or 99% identity thereof, and encodes the CAR comprising the amino acid sequence as set forth in SEQ ID NO: 72 or a sequence with 85%, 90%, 95%, 96%, 97%, 98% or 99% identity thereof [LTG2303, LP-mD1.22-CD8TM-41BB-CD3zeta-F2AF-LP2-m36.4-TNFRSF19TM-CD3zeta2 amino acid sequence (as depicted in FIG. 2J)].

In yet another embodiment, the nucleic acid sequence encoding a CAR comprises the nucleic acid sequence of SEQ ID NO: 73, and encodes the CAR comprising the amino acid sequence as set forth in SEQ ID NO: 74 [LTG2322, LP-mD1.22-CD8TM-41BB-CD3zeta-F2AF-LP2-m36.4-TNFRSF19TM amino acid sequence (as depicted in FIG. 2K)].

In yet another embodiment, the nucleic acid sequence encoding a CAR comprises the nucleic acid sequence of SEQ ID NO: 73 or a sequence with 85%, 90%, 95%, 96%, 97%, 98% or 99% identity thereof, and encodes the CAR comprising the amino acid sequence as set forth in SEQ ID NO: 74 or a sequence with 85%, 90%, 95%, 96%, 97%, 98% or 99% identity thereof [LTG2322, LP-mD1.22-CD8 TM-41BB-CD3zeta-F2AF-LP2-m36.4-TNFRSF19TM amino acid sequence (as depicted in FIG. 2K)].

In yet another embodiment, the nucleic acid sequence encoding a CAR comprises the nucleic acid sequence of SEQ ID NO: 77, and encodes the CAR comprising the amino acid sequence as set forth in SEQ ID NO: 78 [LTG2314, LP-mD1.22-L3-C46-CD8TM-41BB-CD3zeta amino acid sequence (as depicted in FIG. 2L)].

In yet another embodiment, the nucleic acid sequence encoding a CAR comprises the nucleic acid sequence of SEQ ID NO: 77 or a sequence with 85%, 90%, 95%, 96%, 97%, 98% or 99% identity thereof, and encodes the CAR comprising the amino acid sequence as set forth in SEQ ID NO: 78 or a sequence with 85%, 90%, 95%, 96%, 97%, 98% or 99% identity thereof [LTG2314, LP-mD1.22-L3-C46-CD8TM-41BB-CD3zeta amino acid sequence (as depicted in FIG. 2L)].

In yet another embodiment, the nucleic acid sequence encoding a CAR comprises the nucleic acid sequence of SEQ ID NO: 81, and encodes the CAR comprising the amino acid sequence as set forth in SEQ ID NO: 82 [LTG2315, LP-mD1.22-L5-C46-CD8TM-41BB-CD3zeta amino acid sequence (as depicted in FIG. 2M)].

In yet another embodiment, the nucleic acid sequence encoding a CAR comprises the nucleic acid sequence of SEQ ID NO: 81 or a sequence with 85%, 90%, 95%, 96%, 97%, 98% or 99% identity thereof, and encodes the CAR comprising the amino acid sequence as set forth in SEQ ID NO: 82 or a sequence with 85%, 90%, 95%, 96%, 97%, 98% or 99% identity thereof [LTG2315, LP-mD1.22-L5-C46-CD8TM-41BB-CD3zeta amino acid sequence (as depicted in FIG. 2M)].

In yet another embodiment, the nucleic acid sequence encoding a CAR comprises the nucleic acid sequence of SEQ ID NO: 85, and encodes the CAR comprising the amino acid sequence as set forth in SEQ ID NO: 86

[LTG2316, LP-C46-L3-mD1.22-CD8TM-41BB-CD3zeta amino acid sequence (as depicted in FIG. 2N)].

In yet another embodiment, the nucleic acid sequence encoding a CAR comprises the nucleic acid sequence of SEQ ID NO: 85 or a sequence with 85%, 90%, 95%, 96%, 97%, 98% or 99% identity thereof, and encodes the CAR comprising the amino acid sequence as set forth in SEQ ID NO: 86 or a sequence with 85%, 90%, 95%, 96%, 97%, 98% or 99% identity thereof [LTG2316, LP-C46-L3-mD1.22-CD8TM-41BB-CD3zeta amino acid sequence (as depicted in FIG. 2N)].

In yet another embodiment, the nucleic acid sequence encoding a CAR comprises the nucleic acid sequence of SEQ ID NO: 89, and encodes the CAR comprising the amino acid sequence as set forth in SEQ ID NO: 90 [LTG2317, LP-C46-L5-mD1.22-CD8TM-41BB-CD3zeta amino acid sequence (as depicted in FIG. 2O)].

In yet another embodiment, the nucleic acid sequence encoding a CAR comprises the nucleic acid sequence of SEQ ID NO: 89 or a sequence with 85%, 90%, 95%, 96%, 97%, 98% or 99% identity thereof, and encodes the CAR comprising the amino acid sequence as set forth in SEQ ID NO: 90 or a sequence with 85%, 90%, 95%, 96%, 97%, 98% or 99% identity thereof [LTG2317, LP-C46-L5-mD1.22-CD8TM-41BB-CD3zeta amino acid sequence (as depicted in FIG. 2O)].

In yet another embodiment, the nucleic acid sequence encoding a CAR comprises the nucleic acid sequence of SEQ ID NO: 93, and encodes the CAR comprising the amino acid sequence as set forth in SEQ ID NO: 94 [LTG2318, LP-mD1.22-L3-m36.4-L3-C46-CD8TM-41BB-CD3zeta amino acid sequence (as depicted in FIG. 2P)].

In yet another embodiment, the nucleic acid sequence encoding a CAR comprises the nucleic acid sequence of SEQ ID NO: 93 or a sequence with 85%, 90%, 95%, 96%, 97%, 98% or 99% identity thereof, and encodes the CAR comprising the amino acid sequence as set forth in SEQ ID NO: 94 or a sequence with 85%, 90%, 95%, 96%, 97%, 98% or 99% identity thereof [LTG2318, LP-mD1.22-L3-m36.4-L3-C46-CD8TM-41BB-CD3zeta amino acid sequence (as depicted in FIG. 2P)].

In yet another embodiment, the nucleic acid sequence encoding a CAR comprises the nucleic acid sequence of SEQ ID NO: 97, and encodes the CAR comprising the amino acid sequence as set forth in SEQ ID NO: 98 [LTG2319, LP-mD1.22-L3-C46-L3-m36.4-CD8TM-41BB-CD3zeta amino acid sequence (as depicted in FIG. 2Q)].

In yet another embodiment, the nucleic acid sequence encoding a CAR comprises the nucleic acid sequence of SEQ ID NO: 97 or a sequence with 85%, 90%, 95%, 96%, 97%, 98% or 99% identity thereof, and encodes the CAR comprising the amino acid sequence as set forth in SEQ ID NO: 98 or a sequence with 85%, 90%, 95%, 96%, 97%, 98% or 99% identity thereof [LTG2319, LP-mD1.22-L3-C46-L3-m36.4-CD8TM-41BB-CD3zeta amino acid sequence (as depicted in FIG. 2Q)].

In yet another embodiment, the nucleic acid sequence encoding a CAR comprises the nucleic acid sequence of SEQ ID NO: 101, and encodes the CAR comprising the amino acid sequence as set forth in SEQ ID NO: 102 [LTG2320, LP-C46-L3-mD1.22-L3-m36.4-CD8TM-41BB-CD3zeta amino acid sequence (as depicted in FIG. 2R)].

In yet another embodiment, the nucleic acid sequence encoding a CAR comprises the nucleic acid sequence of SEQ ID NO: 101 or a sequence with 85%, 90%, 95%, 96%, 97%, 98% or 99% identity thereof, and encodes the CAR comprising the amino acid sequence as set forth in SEQ ID NO: 102 or a sequence with 85%, 90%, 95%, 96%, 97%, 98% or 99% identity thereof [LTG2320, LP-C46-L3-mD1.22-L3-m36.4-CD8TM-41BB-CD3zeta amino acid sequence (as depicted in FIG. 2R)].

In yet another embodiment, the nucleic acid sequence encoding a CAR comprises the nucleic acid sequence of SEQ ID NO: 105, and encodes the CAR comprising the amino acid sequence as set forth in SEQ ID NO: 106 [LTG2323, LP-mD1.22-L3-m36.4-CD8TM-41BB-CD3zeta-F2AF-C46-TNFRSF19TM amino acid sequence (as depicted in FIG. 2S)].

In yet another embodiment, the nucleic acid sequence encoding a CAR comprises the nucleic acid sequence of SEQ ID NO: 105 or a sequence with 85%, 90%, 95%, 96%, 97%, 98% or 99% identity thereof, and encodes the CAR comprising the amino acid sequence as set forth in SEQ ID NO: 106 or a sequence with 85%, 90%, 95%, 96%, 97%, 98% or 99% identity thereof [LTG2323, LP-mD1.22-L3-m36.4-CD8TM-41BB-CD3zeta-F2AF-C46-TNFRSF19TM amino acid sequence (as depicted in FIG. 2S)].

In yet another embodiment, the nucleic acid sequence encoding a CAR comprises the nucleic acid sequence of SEQ ID NO: 107, and encodes the CAR comprising the amino acid sequence as set forth in SEQ ID NO: 108 [LTG2329, LP-C46-L3-mD1.22-CD8TM-41BB-CD3zeta-F2AF-LP2-m36.4-TNFRSF19TM-CD3zeta2 amino acid sequence (as depicted in FIG. 2T)].

In yet another embodiment, the nucleic acid sequence encoding a CAR comprises the nucleic acid sequence of SEQ ID NO: 107 or a sequence with 85%, 90%, 95%, 96%, 97%, 98% or 99% identity thereof, and encodes the CAR comprising the amino acid sequence as set forth in SEQ ID NO: 108 or a sequence with 85%, 90%, 95%, 96%, 97%, 98% or 99% identity thereof [LTG2329, LP-C46-L3-mD1.22-CD8TM-41BB-CD3zeta-F2AF-LP2-m36.4-TNFRSF19TM-CD3zeta2 amino acid sequence (as depicted in FIG. 2T)].

In yet another embodiment, the nucleic acid sequence encoding a CAR comprises the nucleic acid sequence of SEQ ID NO: 109, and encodes the CAR comprising the amino acid sequence as set forth in SEQ ID NO: 110 [LTG2330, LP-C46-L5-mD1.22-CD8TM-41BB-CD3zeta-F2AF-LP2-m36.4-TNFRSF19TM-CD3zeta2 amino acid sequence (as depicted in FIG. 2U)].

In yet another embodiment, the nucleic acid sequence encoding a CAR comprises the nucleic acid sequence of SEQ ID NO: 109 or a sequence with 85%, 90%, 95%, 96%, 97%, 98% or 99% identity thereof, and encodes the CAR comprising the amino acid sequence as set forth in SEQ ID NO: 110 or a sequence with 85%, 90%, 95%, 96%, 97%, 98% or 99% identity thereof [LTG2330, LP-C46-L5-mD1.22-CD8TM-41BB-CD3zeta-F2AF-LP2-m36.4-TNFRSF19TM-CD3zeta2 amino acid sequence (as depicted in FIG. 2U)].

In yet another embodiment, the nucleic acid sequence encoding a CAR comprises the nucleic acid sequence of SEQ ID NO: 113, and encodes the CAR comprising the amino acid sequence as set forth in SEQ ID NO: 114 [LTG2331, LP-C46-L3-mD1.22-CD8TM-41BB-CD3zeta-F2AF-LP2-m36.4-TNFRSF19TM amino acid sequence (as depicted in FIG. 2V)].

In yet another embodiment, the nucleic acid sequence encoding a CAR comprises the nucleic acid sequence of SEQ ID NO: 113 or a sequence with 85%, 90%, 95%, 96%, 97%, 98% or 99% identity thereof, and encodes the CAR comprising the amino acid sequence as set forth in SEQ ID NO: 114 or a sequence with 85%, 90%, 95%, 96%, 97%, 98% or 99% identity thereof [LTG2331, LP-C46-L3-mD1.22-CD8TM-41BB-CD3zeta-F2AF-LP2-m36.4-TNFRSF19TM amino acid sequence (as depicted in FIG. 2V)].

In yet another embodiment, the nucleic acid sequence encoding a CAR comprises the nucleic acid sequence of SEQ ID NO: 117, and encodes the CAR comprising the amino acid sequence as set forth in SEQ ID NO: 118 [LTG2332, LP-C46-L5-mD1.22-CD8TM-41BB-CD3zeta-F2AF-LP2-m36.4-TNFRSF19TM amino acid sequence (as depicted in FIG. 2W)].

In yet another embodiment, the nucleic acid sequence encoding a CAR comprises the nucleic acid sequence of SEQ ID NO: 117 or a sequence with 85%, 90%, 95%, 96%, 97%, 98% or 99% identity thereof, and encodes the CAR comprising the amino acid sequence as set forth in SEQ ID NO: 118 or a sequence with 85%, 90%, 95%, 96%, 97%, 98% or 99% identity thereof [LTG2332, LP-C46-L5-mD1.22-CD8TM-41BB-CD3zeta-F2AF-LP2-m36.4-TNFRSF19TM amino acid sequence (as depicted in FIG. 2W)].

In yet another embodiment, the nucleic acid sequence encoding a CAR comprises the nucleic acid sequence of SEQ ID NO: 121, and encodes the CAR comprising the amino acid sequence as set forth in SEQ ID NO: 122 [LTG2334, LP-mD1.22-L5-m36.4-CD8TM-41BB-CD3zeta-F2AF-LP2-C46-TNFRSF19TM amino acid sequence (as depicted in FIG. 2X)].

In yet another embodiment, the nucleic acid sequence encoding a CAR comprises the nucleic acid sequence of SEQ ID NO: 121 or a sequence with 85%, 90%, 95%, 96%, 97%, 98% or 99% identity thereof, and encodes the CAR comprising the amino acid sequence as set forth in SEQ ID NO: 122 or a sequence with 85%, 90%, 95%, 96%, 97%, 98% or 99% identity thereof [LTG2334, LP-mD1.22-L5-m36.4-CD8TM-41BB-CD3zeta-F2AF-LP2-C46-TNFRSF19TM amino acid sequence (as depicted in FIG. 2X)].

Overall, anti-HIV CARs were highly expressed on the surface of primary T-cells (FIGS. 3A-B, 4, 11A-B, 12A, and 12C). The mD1.22-based CARs were exceptionally potent and specifically destroyed 293T cells stably expressing HIV gp120 (herein referred to as, env$^+$ cells), which serves as a surrogate to quantify CAR-mediated cytotoxicity (FIGS. 3C, 5, 8, 10, 11C, and 12B). To understand the cytotoxic contribution of each anti-HIV targeting moiety, anti-HIV CARs were engineered containing either the mD1.22 domain, m36.4 domain, or C46 peptide. These anti-HIV CARs differentially killed env cells (FIG. 3C, mD1.22>m36.4>C46, P<0.0001) with no off-target cytotoxic effect (FIG. 3D) and were triggered to produce IFN-γ in the presence of env$^+$ and to some extent in its absence (FIG. 3E).

To define the most optimal bispecific architecture, the mD1.22 domain and the m36.4 domain were fused using a series of flexible glycine-serine linkers or placed each binder on its own CD3 signaling domain. As shown in FIG. 4, all linker-specific CARs as well as other design iterations were detected on the surface of primary T-cells. Interestingly, a bispecific CAR significantly enhanced anti-HIV cytotoxic effect (FIG. 5, LTG2303 versus LTG1944 or LTG1945) while maintaining exceptional specificity (FIG. 6). Decreasing the linker length between the two domains increased CAR-mediated cytotoxicity of bispecific CARs engineered with a single CD3 while maintaining specificity (FIG. 8). However, a modest increase in tonic signaling was observed in the absence of env$^+$ target cell as measured by cytokine release assay (FIG. 9). More importantly, no off-target killing was observed in the presence of Raji cells which are known to contain MHC class II molecules that may potentially interact with the CD4-receptor derived mD1.22 domain (FIG. 6, bottom panel). Moreover, bispecific anti-HIV CARs released IFN-γ upon encountering HIV-envelope target cells and to a lesser extent in its absence (FIG. 7, 9). Taken together, a bispecific CAR serves as a potent architecture to engineer a more advanced trispecific CAR.

To build a trispecific CAR composed of mD1.22, m36.4 and the C46 peptide, additional bispecific CAR iterations were developed, in, those engineered with the mD1.22 and C46 peptide. In contrast to the bispecific CARs, replacing m36.4 with C46 severely abrogated CAR function when the C46 peptide was positioned proximal to the T-cell membrane. Only when the C46 domain was positioned distal to the mD1.22 domain, was anti-HIV CAR-mediated cytotoxicity restored (FIG. 10A). Reminiscent of the CD22 CAR previously described, binder accessibility relative to the distance from the T-cell membrane is essential for CAR function (Haso et al., Blood 2013; 121:1165-1174). As expected, abrogated CAR function as a result of mD1.22 and C46 binder configuration also led to poor levels of IFN-γ secretion (FIG. 10B). Strikingly, merely reversing the order of the domains restored high level IFN-γ secretion (LTG2316) while extending the space between the two domains led to lower tonic signaling (LTG2317). Taken together, these data clearly reveal the most optimal bispecific binder configuration for a C46-based bispecific CAR. More importantly, a set of rules that govern bispecific CAR function were identified that can be applied to rationally design a trispecific anti-HIV CAR.

Targeting multiple epitope determinants on the HIV envelope protein is an attractive strategy to engineer CARs with superior breadth, potency, and ability to prevent emergence of escape mutants. The rationale for developing a trispecific CAR is that if one binder is unable to recognize a HIV variant then the second and/or third domain would compensate for this loss of function acquired by the CAR. Thus, to improve the breadth of the most potent bispecific CAR candidates, the bispecific CAR was engineered with a third highly potent fusion inhibitor (C46 peptide) or entry inhibitor (m36.4) to form a trispecific CAR. As compared to bispecific CAR, trispecific CARs maintained their ability to potently destroy the HIV surrogate cell line and initiated a robust Th1 cytokine response (FIGS. 11C and 11E-F). Moreover, trispecific CARs exhibited exceptional specificity for their intended targets with no off-target effect on Raji cells (FIG. 11D). As shown from the data, the most optimal trispecific CAR was LTG2323 followed by LTG2320. Further evaluation of two additional trispecific CARs generated by combining the LTG2303 and LTG2316 or LTG2317 architectures again demonstrated robust killing of the surrogate HIV envelope cell line (FIG. 12B). Except for the highest E:T ratio, both LTG2329 and LTG2330 maintained their specificity (FIG. 12D). Taken together, the precise architecture of the trispecific CAR improved its anti-HIV function.

Subsequent challenge of anti-HIV CART cells with diverse and resistant HIV-1 strains further confirmed the importance of the anti-HIV CAR architecture. Starting with a CD4$^+$ enriched T cell population from multiple HIV-naïve donors (FIG. 13), CAR T cell products were generated for a select group of anti-HIV CARs. Using a modified in vitro HIV-1 Env-IMC-LucR challenge assay, the most potent anti-HIV CARs were identified as bispecific and trispecific CARs containing two CD3 chains (hereafter referred to as duoCAR). As shown in FIGS. 14-17, bispecific and trispecific duoCARs were superior to conventional anti-HIV CARs containing a single CD3 chain irrespective of its valency (LTG2303, LTG2329, and LTG2330). This is an important design feature for developing anti-HIV CARs to evade viral escape while increasing potency and breadth. It is presumed that if one domain is lost due to mutational escape, the other domain may compensate for this loss. More importantly, the anti-HIV targeting domains(s) may act independent of each other, sequentially, or simultaneously by virtue of the duoCAR architecture to attack the productive HIV-infected cell. As shown in FIG. 18, primary T cells engineered with the mD1.22-CAR were more susceptible to HIV-1 infection than bispecific or trispecific CAR-T cells (open red bar). The incorporation of the m36.4 domain, which is an entry inhibitor, was sufficient to protect CAR T cells and ablate HIV-1 infection. To further evaluate bispecific and trispecific duoCAR-T cells in vivo, a humanized NSG mouse model (hu-spl-PBMC-NSG) of acute and chronic HIV-1 infection was employed (FIG. 19A). The VRC01/3BNC117-resistant Env-IMC-LucR virus was selected to further interrogate duoCAR-T cell function. As shown in FIGS. 19B, C, bispecific and trispecific duoCARs significantly reduced HIV-1 infection as compared to the UTD-treated, HIV-infected cohort. Both bispecific and trispecific duoCARs demonstrated similar potencies (LTG2303 versus LTG2330). In the chronic HIV infection study, the $CD4^+$ T cells were significantly depleted in the spleens of mice treated with the control UTD T cells (FIG. 19E). Conversely, mice treated with the bispecific and trispecific duoCAR-T cells showed significant improvement in the % of $CD4^+$ T cells recovered from infected spleens which approached levels greater than or similar to the uninfected mice (see HIV-PBMC, FIG. 19E). Concomitant with $CD4^+$ T cell depletion during chronic HIV infection was an increase in % of $CD8^+$ T cells within the spleens of infected, UTD-treated mice with uncontrolled HIV infection (FIG. 19G). The robust control of HIV-1 infection is likely due to the in vivo persistence of the CAR-T cells within the spleens of infected mice as shown in FIGS. 19H, I. Collectively, the invention presented herein represents a powerful and universal multi-targeting HIV-1 immunotherapy with strong implication for a functional cure.

Without being intended to limit to any particular mechanism of action, it is believed that possible reasons for the enhanced therapeutic function associated with the exemplary CARs of the invention include, for example, and not by way of limitation, a) improved multi-specific targeting of non-redundant viral epitopes, b) rationale CAR design using intracellular T-cell signaling domains to leverage function of antigen binding domains, c) lateral movement within the plasma membrane allowing for more efficient signal transduction, d) superior location within plasma membrane microdomains, such as lipid rafts, and greater ability to interact with transmembrane signaling cascades associated with T cell activation, e) superior location within the plasma membrane by preferential movement away from dampening or down-modulatory interactions, such as less proximity to or interaction with phosphatases such as CD45, and f) superior assembly into T cell receptor signaling complexes (i.e. the immune synapse), or any combination thereof.

While the disclosure has been illustrated with precise combinations of three exemplary HIV envelope targeting domains (mD1.22, m36.4, and C46 peptide), other nucleotide and/or amino acid variants within these binding domains may be used to derive the HIV envelope binding domains for use in the CARs described herein.

Depending on the desired antigen to be targeted, the CAR can be additionally engineered to include the appropriate antigen binding domain that is specific to the desired antigen target.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, Epstein Barr virus (EBV), cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas,* or *Salmonella*. Particularly, there is provided a CAR capable of binding to an antigen derived from an infectious bacterium, for example, *Helicobacter pylori, Legionella pneumophilia*, a bacterial strain of Mycobacteria species. (e.g. *M. tuberculosis, M. avium, M. intracellulare, M. kansaii,* or *M. gordonea*), *Staphylococcus aureus, Neisseria gonorrhoeae, Neisseria meningitides, Listeria monocytogenes, Streptococcus pyogenes,* Group A *Streptococcus*, Group B *Streptococcus* (*Streptococcus agalactiae*), *Streptococcus pneumoniae,* or *Clostridium tetani*, or a combination thereof.

In another aspect of the present invention, there is provided a CAR in combination with advanced gene editing technologies (e.g., CRISPR/Cas9, CRISPR/Cas13, riboswitch, RNA interference, or intrabody) that excises and/or interferes with viral ribonucleic acids, integrated viral DNA (for example, HIV provirus), and/or viral proteins (e.g., viral reverse transcriptase) from host-infected cells, or in combination thereof, with advanced gene editing technologies to modulate host genetic factors implicated in the disease such as, chemokine receptor G-protein coupled receptors (e.g., CXCR4, CCR5), host susceptibility factors (e.g., LEDGF/p75), virulence factors (e.g., DC-SIGN), natural host resistance factors (e.g., Defensins), or a combination thereof, but not limited to the aforementioned combinations.

In another aspect of the present invention, there is provided a CAR in combination with a small molecule inhibitor, latency-reversing agent, anti-viral agent, anti-microbial agent, or antibody, and any derivative thereof, that potentiates and/or synergizes CAR-T function (e.g., TLR7 agonist), targets a disease-state related to CAR therapy, or a combination thereof, but not limited to the aforementioned combinations.

2. Transmembrane Domain

With respect to the transmembrane domain, the CAR comprises one or more transmembrane domains fused to the extracellular mD1.22 and m36.4 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD83, CD86, CD134, CD137, CD154, TNFRSF16, or TNFRSF19. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected or by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 7. In one embodiment, the CD8 transmembrane domain comprises the nucleic acid sequence that encodes the amino acid sequence of SEQ ID NO: 8.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 8, or a sequence with 95-99% identity to an amino acid sequence of SEQ ID NO: 8.

In some instances, the transmembrane domain of the CAR comprises the CD8.alpha.hinge domain. In one embodiment, the CD8 hinge domain comprises the nucleic acid sequence of SEQ ID NO: 9. In one embodiment, the CD8 hinge domain comprises the nucleic acid sequence that encodes the amino acid sequence of SEQ ID NO: 10. In another embodiment, the CD8 hinge domain comprises the amino acid sequence of SEQ ID NO: 10, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane TNFRSF19 domain, or a combination thereof.

In one embodiment, the encoded transmembrane TNFRSF19 domain in combination with the CD8 linker/hinge domain comprises an amino acid sequence having at least one, two or three modifications (e.g., substitutions) but not more than 20, 10 or 5 modifications (e.g., substitutions) of an amino acid sequence of SEQ ID NO: 16, or a sequence with 95-99% identity to an amino acid sequence of SEQ ID NO: 16.

3. Spacer Domain

In the CAR, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137-206 (SEQ ID NO: 10) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 36. In another embodiment, the signal peptide comprises the amino acid sequence in SEQ ID NO: 38.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3.delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 17 and the signaling domain of CD3-zeta comprises the nucleic acid sequence set forth in SEQ ID NO: 19.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 18 and the signaling domain of CD3-zeta comprises the nucleic acid sequence that encodes the amino acid sequence of SEQ ID NO: 20.

In one embodiment, the intracellular domain in the CAR is designed to comprise the codon degenerate signaling domain of CD3-zeta2, wherein the signaling domain of CD3-zeta2 comprises the nucleic acid sequence SEQ ID NO: 21 and the amino acid sequence set forth in SEQ ID NO: 22.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxyl terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" or a "CAR-T" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, $6^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," $5^{th}$ Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody or portion of a full length protein (for example, the D1 domain of the CD4 receptor) that retains the ability to specifically recognize the cognate antigen, as well as various combinations of such portions. Non-limiting examples of antigen binding fragments include protein domains, full-length proteins, Fv, Fab, Fab', Fab'-SH, F(ab')2; diabodies; nanobodies; linear antibodies; single-chain antibody molecules (e.g. ScFv); and multi-specific antibodies formed from antibody fragments or multi-specific proteins formed from more than one protein domain or fragment. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010). Multi-specific proteins and derivatives thereof include antigen binding fragments produced by fusing the fragments together in a precise configuration using the original fragments, modifications of those fragments, or those synthesized de novo using recombinant DNA technologies.

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies or antigen binding fragments can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies or multifunctional binding domains, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" or humanized derivative thereof consisting of a protein fragment is an antibody or derivative thereof which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites while a trispecific or trifunctional antibody has three different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 Al, and U.S. Pat. No. 7,338, 929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) anti-viral agents, anti-microbial agents, chemotherapeutic agents, anti-angiogenic agents, toxins, radioactive agents such as $^{125}$I, $^{32}$P, $^{14}$C, $^{3}$H and $^{35}$S and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a viral-infected cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule or detectable marker. Alternatively, the antibody or antigen binding fragment is a derivative to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolysable under acidic conditions. For example, an acid-labile linker that is hydrolysable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolysable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al., PNAS 2002, 99:7968-7973), or maytansinol and maytansinol analogues prepared synthetically according to known methods. Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λGT10, λGT11, λZapII (Stratagene), EMBL4, and λNMI 149, also can be used. Examples of plant expression vectors include pBI0l, pBI101.2, pBHOl 0.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a murine stem cell virus (MSCV) promoter, an Elongation Factor 1 alpha (EF1α) promoter, a cytomegalovirus (CMV) promoter, a SV40 promoter, or a RSV promoter. The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine deaminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human.

The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell. The host cell may be a natural killer cell (NK cell). The host cell may be a hematopoietic stem cell (HSC).

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th1 and Th2 cells, CD8$^+$ T cells (e.g., cytotoxic T cells), tumor infiltrating cells, memory T cells, memory stem cells, i.e. T$_{scm}$, naive T cells, and the like.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is purer than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing HIV/AIDS in a mammal. In this regard, an embodiment provides a method of treating or preventing HIV/AIDS in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent HIV-1 infection and/or AIDS in the mammal.

An embodiment further comprises lymphodepleting the mammal prior to administering the CARs disclosed herein. Examples of lymphodepletion include, but may not be limited to, non-myeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer associated with the HIV infection can be any cancer, including any of ALL, AML, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia (CLL), chronic myeloid cancer (CML), colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, NHL, B-chronic lymphocytic leukemia, hairy cell leukemia, Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

With respect to the methods, the HIV can be of any type (for example, HIV-1 or HIV-2), group, clade, subtype, sub-subtype, and/or circulating recombinant form (CRF), including HIV-1 groups M, N, O, and P. Within HIV-1 group M, the HIV can be of any clade, sub-subtype of a clade, and/or circulating recombinant form including but not limited to clades, A, A1, A2, A3, A4, B, C, D, F, F1, F2, G, H, J, K, and including but not limited to circulating recombinant form, CRF01 to CRF90 (see, the world wide web at hiv.lanl.gov/content/sequence/HIV/CRFs/CRFs.html).

Within HIV-2, the HIV can be of any subtype of non-recombinant or recombinant subtype including, A, B, C, D, E, F, G and HIV2_CRF01_AB).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of HIV/AIDS in a mammal.

Furthermore, the treatment or prevention provided by the method can include treatment or prevention of one or more conditions or symptoms of the disease, e.g., HIV-1 infection, being treated or prevented. Also, for purposes herein, "prevention" can encompass delaying the onset of the disease, or a symptom or condition thereof.

With respect to the methods, the treatment or prevention by the method can include or be administered in conjunction with treatment or prevention of one or more conditions or symptoms but not limited to the following found to co-exist with the disease (for example, HIV/AIDS related co-morbidities such as, Kaposi sarcoma or acute myeloid leukemia; viral co-infections such as, HIV/HBV or HIV/HCV co-infection).

With respect to the methods, the treatment or prevention by the method can be used in conjunction with an allogenic or autologous transplantation of cells of mammalian origin lacking disease-associated genetic factors (for example but not limited to, bone marrow transplantation of Δ32-CCR5 cells that are resistant to HIV-1 infection or genetically-modified CXCR4-negative T-cells).

Another embodiment provides a method of detecting the presence of infectious disease in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of infectious disease in the mammal.

The sample may be obtained by any suitable method, e.g., blood collection or biopsy. A blood collection or venipuncture is the process of intravenously collecting venous blood from an individual. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., HIV/AIDS.

With respect to an embodiment of the method of detecting the presence of an infectious disease, e.g., HIV-1 infection, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells. The contacting can take place in vitro or in vivo with respect to the mammal.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor alpha (TNF-α) or interleukin 2 (IL-2). In addition, CAR function can be evaluated by measurement of cellular cytotoxicity, as described in Zhao et al, J. Immunol, 174: 4415-4423 (2005).

Methods to assay the ability of a CAR to inhibit HIV-1 infection, but are not limited to, are in-vitro assays that measure HIV-1 viral replication. For instance, an in-vitro PBMC-based assay that uses a replication competent HIV-1 molecular clone that expresses both a heterologous HIV envelope protein and Renilla luciferase as described in Edmonds et al., Virology, 408: 1-13 (2010) can be used to monitor HIV-1 viral replication. In this assay, the level of viral infection can be monitored by measuring luciferase activity of infected PBMCs either contacted with an anti-HIV agent and/or with T-cells expressing a chimeric antigen receptor such as described herein this invention. In another assay, the level of HIV-1 infection can be assayed by determining the amount of p24 antigen present within infected cell culture supernatants using an ELISA assay. In another assay, the level of HIV-1 infection can be assayed using a qualitative or quantitative molecular-based method that detects the presence or absence of the viral nucleic acids. In another assay, the presence of infectious HIV-1 virus can be assayed by inoculating a HIV-permissive cell line and monitoring cytopathic changes indicative of viral infection in combination with other quantitative measures of HIV infection.

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of an infectious disease, e.g., HIV-1 infection, in a mammal. The infectious disease may be any of the viruses, microbes, and/or parasites described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, an anti-viral agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which an infectious disease is present or has been isolated, or a region suspected of being prone or support infectious disease development. In some embodiments, sustained intra-organ (or near-organ) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional HIV inhibitor, immunomodulatory protein, and/or a protein that enhances the function of a CAR, CAR-T cells, antibodies, antigen binding fragment, or conjugates disclosed herein to a subject. Non-limiting examples of additional therapeutic agents that can be used with the combination therapy include microtubule binding agents, DNA intercalators or cross-linkers, DNA synthesis inhibitors, DNA and RNA transcription inhibitors, reverse transcription inhibitors, viral protein inhibitors, immunomodulators, antibodies, enzymes, enzyme inhibitors, gene regulators, anti-proliferative agents, and latency reversing agents. These agents (which are administered at a therapeutically effective amount) and treatments can be used alone or in combination. For example, any suitable anti-viral or immunomodulatory agent can be administered in combination with the CARs, CAR-T cells, antibodies, antigen binding fragment, or conjugates disclosed herein. Methods and therapeutic dosages of such agents are known to those skilled in the art, and can be determined by a skilled clinician.

Additional anti-viral agents that can be combined with the CAR, CAR-T cells, antibodies, antigen binding fragment, or conjugates disclosed herein include, but are not limited to, reverse transcriptase inhibitors (for example, nucleoside reverse transcriptase inhibitors (NRTIs) such as, tenofovir, adefovir, zidovudine, didanosine, zalcitabine, stavudine, lamivudine, abacavir, emtricitabine, entecavir, and apricitabine); non-nucleoside reverse transcriptase inhibitors (NNRTIs) such as, efavirenz, nevirapine, delavirdine, rilpivirine, and etravirine; protease inhibitors (for example, ritonavir, indinavir, amprenavir, atazanavir, darunavir, tipranavir, saquinavir, nelfinavir, lopinavir, and fosamprenavir); and entry or fusion inhibitors (for example, enfuvirtide, maraviroc, gp41-derived C-peptides, and gp41-derived N-peptides); HIV integrase strand transfer inhibitors (for example, raltegravir, dolutegravir, and elvitegravir), and any combinations of these anti-viral agents. In some instances, to reverse HIV latency, a latency reversing agent can be combined with the CAR, CAR-T cells, antibodies, antigen binding fragment, or conjugates disclosed herein. Examples of such compounds include, but not limited to, PKC agonists (for example, Bryostatin, Prostratin, Ingenol B), innate immune activators (e.g., TLR7 agonist, IL-15SA), histone deacetylase inhibitors (for example, suberoylanilide hydroxamic acid (vorinostat), romidepsin, panobinostat), DNA demethylation agents, and other chromatin remodeling agents. Selection and therapeutic dosages of such agents are known to those skilled in the art, and can be determined by a skilled clinician.

Additional radiation or chemotherapeutic agents that can be combined to treat, prevent, or synergize with the method include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an CAR, CAR-T cells, antibody, or antigen binding fragment that specifically binds to one or more of the antigens disclosed herein or a conjugate thereof is administered to a subject having HIV/AIDS. After a sufficient amount of time has elapsed to allow for the administered antibody or antigen binding fragment or conjugate to form an immune complex with the antigen expressed on the respective HIV-1 infected cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-organ) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of an infectious disease, for example, and not by way of limitation, a HIV-1 infection. The compositions including a CAR, or T cell expressing a CAR, a conjugate, antibody or antigen binding fragment as disclosed herein are also of use, for example, for the detection of immune dysfunction.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30-minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the CARs, or T cells expressing a CAR, antibody or antigen binding fragment or conjugate compositions disclosed herein. Various degradable and non-degradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa. (1993)). Numerous additional systems for controlled delivery of therapeutic proteins are known (see U.S. Pat. Nos. 5,055,303; 5,188,837; 4,235, 871; 4,501,728; 4,837,028; 4,957,735; 5,019,369; 5,055, 303; 5,514,670; 5,413,797; 5,268,164; 5,004,697; 4,902, 505; 5,506,206; 5,271,961; 5,254,342 and 5,534,496).

G. Kits

In one aspect, kits employing the CARs disclosed herein are also provided. For example, kits for treating HIV/AIDS in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing HIV/AIDS or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Assembly of HIV-Specific Binders into Functional CAR Molecules

This example describes general methods for constructing monospecific, bispecific, and trispecific anti-HIV CARs containing the mD1.22, m36.4, and C46 peptide as well how to express these CARs on the surface of primary T-cells.

Materials and Methods:

Generation of Lentiviral Vector Constructs

CAR antigen-binding domain sequences were derived from published sequences (Chen et al., J. Virol. 2014; 88:(2) 1125-1139; Chen et al., Antiviral Research 2010; 88:(1) 107-115; Egerer et al., Molecular Therapy 2010; 19:(7) 1236-1244) and synthesized by ATUM (formerly known as, DNA 2.0; Newark, Calif.) or IDT Technologies (Coralville, Iowa). Synthesized gene fragments were subcloned in-frame to a MSCV promoter-based lentiviral backbone containing the CD8 linker/hinge, CD8 transmembrane domain, 41-BB, and CD3ζ signaling domain. For bicistronic bispecific and trispecific CAR constructs a cleavable furin-P2A-furin site was placed downstream of the first CAR containing a single or two-linked antigen binding domains followed by third antigen binding domain, CD8 linker/hinge, TNFRSF19 transmembrane, and with or without a CD3 signaling domain. A detailed description of the sequence and CAR structure is shown below in the Table 1. The DNA constructs were confirmed by sanger sequencing (GeneWiz, South Plainfield, N.J.). Plasmid maps were generated using Clone Manager software (Denver, Colo.).

Lentiviral Vector Production

Lentiviral vectors carrying a CAR transgene were produced by transiently transfecting 293T suspension cells using a four-plasmid system in the presence of polyethylenimine (PEI). Briefly, suspension 293T were co-transfected with the CAR transfer plasmid, VSVg envelope, gag/pol, and rev plasmids followed by addition of sodium butyrate to cultures 16 hours later. Supernatants (~400 mL) containing the lentiviral vectors were concentrated 48 hours later by overnight ultracentrifugation at 10,000×g for at least 18 hours. Pellets were resuspended in 2 mL of filtered-sterile SEC buffer containing 5.96 mM HEPES, 5% Trehalose, and 100 mM NaCl until the pellet was easy to dissolve by gentle agitation. Resuspended lentiviral particles were stored in aliquots at −80° C. until further use.

Anti-HIV CAR Detection on the Surface of Transduced Primary T-Cells

Approximately 1×106 cells were washed in MACS buffer (Phosphate-buffered saline containing 10% bovine serum albumin, pH~7.2). Vioblue-conjugated CD4 (clone VIT4) and FITC-labeled CD8 antibodies were then added to the cells following the manufacturer's instructions (Miltenyi Biotec). After a 30-minute incubation at 4° C., cells were washed twice in MACS buffer and resuspended in 0.2 mL of MACS buffer. For detection of CARs containing the C46 peptide, the recombinant human monoclonal antibody 2F5 (Polymun Scientific. Klosterneuburg, Austria) was added at a dilution of 1:1000 for 30 minutes at 4° C. followed by washing twice in MACS buffer. 2F5 recognizes the epitope ELDKWA found within the C46 peptide. Cells were then incubated with FITC-labeled F(ab')2 anti-human IgG for 30 minutes at 4° C., washed twice, and then resuspended in 0.2 mL MACS buffer. Flow cytometry was carried out using a MACS Quant VYB1 cytometer (Miltenyi Biotec) and analysis was performed using FlowJo software (Tree Star, Ashland, Oreg.).

Results:

Overall, anti-HIV CARs were highly expressed on the surface of primary T-cells ranging up to 70% gene modification using lentiviral vectors. As shown in FIGS. 3A and 3B, monospecific CARs containing either the mD1.22 domain (LTG1944), m36.4 domain (LTG1945), or C46 peptide (LTG2328) were functionally-expressed on the surface of T-cells. The m36.4 CAR was detected indirectly by fusing an intracellular mCherry reporter upstream of the CD3 signaling domain (FIG. 3B).

To define the optimal bispecific binder architecture of CARs configured with the mD1.22 and m36.4 domains, up to seven different bispecific CAR constructs were constructed. These CARs were engineered in various orientations and using different linker lengths to preserved domain modularity and functionality. As compared to untransduced T-cells, bispecific CARs containing the shortest glycine-serine linker to spatially separate the mD1.22 and m36.4 domains (LTG2325, a single G45 motif) or up to the longest linker (LTG1947, five G45 motifs) were equally expressed with similar transduction efficiencies (FIG. 4A). Reversing the orientation of the two domains to present m36.4 distal to mD1.22 (LTG1948) only slightly reduced CAR transduction efficiency (FIG. 4B). This is most likely attributed to epitope accessibility of the CD4 antibody rather than to construct design. To allow for maximal function of the two domains, a bicistronic P2A construct was generated containing two CARs, mD1.22-CAR and m36.4-CAR, to form LTG2303. The rationale for this construct is that m36.4 alone can bind to and neutralize HIV-1 strains albeit with reduced affinity in the absence of the CD4 receptor (Weizao Chen et al., Journal of Virology 2014, 88:2 1125-1139). Thus, engineering both domains as a CAR would improve CAR-mediated cytotoxicity. As shown in FIG. 4C, the mD1.22-CAR portion of the LTG2303 bicistronic construct was detected on the surface of T-cells. Further evaluation of this construct using anti-CD3 western blot revealed that both CARs were highly expressed, fully cleaved, and migrated to their predicted molecular weight (FIG. 4D). Overall, bispecific CARs were highly expressed on the surface of T-cells with similar transduction efficiencies across different constructs (FIG. 4E).

Next, trispecific CARs containing all three domains (mD1.22, m36.4, and C46 peptide) were generated using the LTG1946 and LTG2303 architectures. Specifically, trispecific CARs were engineered to generate (1) CARs that contain all three domains on a single CD3 (LTG2318, LTG2319, and LTG2320), (2) CARs that contain the LTG1946 or LTG1947 bispecific CAR in combination with the C46 peptide anchored to the T-cell membrane alone (LTG2323 and LTG2334), and lastly (3) CARs that contain the LTG2303 bispecific CAR with C46 peptide placed distal to the mD1.22 domain (LTG2329 and LTG2330). All these combinations form unique trispecific CARs to effectively interrogate trispecific CAR function.

As shown in FIG. 11A, trispecific CARs containing all three domains on a single CD3 chain were highly expressed (~50-70%) as detected by 2F5 flow cytometry (LTG2318, LTG2319, LTG2320). In contrast, detection of the membrane anchored C46 peptide in the bicistronic trispecific construct (LTG2323) was markedly reduced (FIG. 11A, 18%). However, the mD1.22-CAR portion of the LTG2323 trispecific construct was highly expressed on the surface of T-cells as compared to untransduced T-cells (FIG. 11B). Similarly, trispecific CARs LTG2329 and LTG2330 were detectable by 2F5 flow cytometry (up to 40%, FIG. 12C). Taken together, trispecific CARs are functionally-detected on the surface of T-cells.

TABLE 1

List of HIV-Targeting CAR Constructs

| LV Construct | CAR Structure |
|---|---|
| LTG1944 | LP-mD1.22-CD8TM-41BB-CD3zeta |
| LTG1945 | LP-m36.4-CD8TM-41BB-CD3zeta |
| LTG2328 | LP-C46-CD8TM-41BB-CD3zeta |
| LTG2325 | LP-mD1.22-L1-m36.4-CD8TM-41BB-CD3zeta |
| LTG2313 | LP-mD1.22-L2-m36.4-CD8TM-41BB-CD3zeta |
| LTG1946 | LP-mD1.22-L3-m36.4-CD8TM-41BB-CD3zeta |
| LTG2326 | LP-mD1.22-L4-m36.4-CD8TM-41BB-CD3zeta |
| LTG1947 | LP-mD1.22-L5-m36.4-CD8TM-41BB-CD3zeta |
| LTG1948 | LP-m36.4-L3-mD1.22-CD8TM-41BB-CD3zeta |
| LTG2303 | LP-mD1.22-CD8TM-41BB-CD3zeta-F2AF-LP2-m36.4-TNFRSF19TM-CD3zeta2 |
| LTG2322 | LP-mD1.22-CD8TM-41BB-CD3zeta-F2AF-LP2-m36.4-TNFRSF19TM |
| LTG2314 | LP-mD1.22-L3-C46-CD8TM-41BB-CD3zeta |
| LTG2315 | LP-mD1.22-L5-C46-CD8TM-41BB-CD3zeta |
| LTG2316 | LP-C46-L3-mD1.22-CD8TM-41BB-CD3zeta |
| LTG2317 | LP-C46-L5-mD1.22-CD8TM-41BB-CD3zeta |
| LTG2318 | LP-mD1.22-L3-m36.4-L3-C46-CD8TM-41BB-CD3zeta |

TABLE 1-continued

List of HIV-Targeting CAR Constructs

| LV Construct | CAR Structure |
|---|---|
| LTG2319 | LP-mD1.22-L3-C46-L3-m36.4-CD8TM-41BB-CD3zeta |
| LTG2320 | LP-C46-L3-mD1.22-L3-m36.4-CD8TM-41BB-CD3zeta |
| LTG2323 | LP-mD1.22-L3-m36.4-CD8TM-41BB-CD3zeta-F2AF-LP2-C46-TNFRSF19TM |
| LTG2329 | LP-C46-L3-mD1.22-CD8TM-41BB-CD3zeta-F2AF-LP2-m36.4-TNFRSF19TM-CD3zeta2 |
| LTG2330 | LP-C46-L5-mD1.22-CD8TM-41BB-CD3zeta-F2AF-LP2-m36.4-TNFRSF19TM-CD3zeta2 |
| LTG2331 | LP-C46-L3-mD1.22-CD8TM-41BB-CD3zeta-F2AF-LP2-m36.4-TNFRSF19TM |
| LTG2332 | LP-C46-L5-mD1.22-CD8TM-41BB-CD3zeta-F2AF-LP2-m36.4-TNFRSF19TM |
| LTG2334 | LP-mD1.22-L5-m36.4-CD8TM-41BB-CD3zeta-F2AF-LP2-C46-TNFRSF19TM |

Example 2

Novel Bispecific and Trispecific Anti-HIV CARs Potently Destroy HIV-Envelope Targets This Example describes the functional characterization of anti-HIV CARs as determined by a highly sensitive luciferase-based cytotoxicity assay. In addition, activation of T-cells is determined by quantifying cytokine secretion in the absence and presence of HIV-envelope expressing target cells.

Materials and Methods:

Cell Lines Used for Functional Characterization

The 293T cell line was engineered to stably expressing the single-chain full-length HIV envelope protein (293T-Env) and was kindly provided by Dr. Dimiter Dimitrov (NCI, Fort Detrick, Md.). Briefly, 293T-Env cells were grown in Dulbecco's modified eagle medium (DMEM) in the presence of 10% fetal bovine serum and 60 µg/ml of zeocin to maintain selection. To generate luciferase-expressing cells, 293T-Env cells were transduced with a lentiviral vector containing the firefly luciferase gene, single cell cloned, and tested for both gp120/gp41 expression on the surface of 293T cells (via 2G12, b12, and 2F5 flow cytometry) and luciferase activity. A single high-expressing HIV-1 envelope and luciferase clone was isolated and used for cytotoxicity assays described herein (293T-Env-Luc). For envelope-negative cell lines, Raji and 293T HEK cells were purchased from ATCC (Manassas, Va.) and subsequently transduced with a lentiviral vector encoding the firefly luciferase gene to generate Raji-Luc or 293T-Luc cell lines, respectively. Raji-Luc cells were maintained in RPMI media containing 10% fetal bovine serum. 293T-Luc cells were maintained in DMEM media containing 10% fetal bovine serum. Both cell lines were single-cell cloned and the absence of HIV-envelope confirmed by 2G12, b12, and 2F5 (monoclonal antibodies against HIV-1 envelope) flow cytometric analysis.

Primary T Cell Purification and Transduction

Human PBMCs from healthy donors were purified from buffy coats using ficoll-paque gradient separation combined with a leucosep tube followed by immunomagnetic bead selection of CD4$^+$ and CD8$^+$ T-cells according to manufacturer's protocol (Miltenyi Biotec, Bergisch-Gladbach, Germany). On day 0, T cells were activated with CD3/CD28 MACS® Large-scale T Cell TransAct reagent (Miltenyi Biotec) in the presence of 40 IU/mL IL-2 (Miltenyi Biotec).

On day 3, activated T-cells were transduced with lentiviral vectors encoding CAR constructs in the presence of 10 µg/m protamine sulfate (Sigma-Aldrich, St. Louis, Mo.) and 200 IU/mL IL-2. Cultures were propagated in TexMACS medium supplemented with 200 IU/ml IL-2 until harvest on day 9-10 for functional analysis.

Cytotoxicity Assay Using Luciferase Detection

Briefly, 5×10$^3$ target cells stably expressing firefly luciferase was combined with or without CAR T-cells at various effector to target ratios in a sterile 96-well plate and incubated overnight at 37° C. in the presence of 5% CO2. Twenty-four hours later, 100 µL of SteadyGlo reagent (Promega, Madison Wis.) was added to each well and incubated for 10 minutes at room temperature followed by quantification of luminescence using an Enspire plate reader (Perkin Elmer, Waltham, Mass.). The luminescence was captured as counts per second (CPS) for each experimental well containing the indicated E:T ratio (sample CPS) and target cells alone (target CPS). Percent specific lysis was calculated as: 1−(sample CPS/target CPS).

Cytokine Release Assay Using Sandwich ELISA

Supernatants from the cytotoxicity assay were collected (E:T ratio of 10:1), diluted 10-fold, and assayed for IFN-γ and IL-2 by Ready-Set-Go ELISA as per the manufacturer's instructions (eBioscience, San Diego, Calif.).

Results:

The HIV envelope protein is a heterotrimeric glycoprotein expressed on the surface of the HIV virion which is used to target and hijack T-cells. During HIV infection, the HIV envelope protein (gp120) binds to the CD4 receptor of helper T-cells leading to a conformation change in the HIV envelope protein. This change promotes its interaction with co-receptors (e.g., CCR5 or CXCR4) on the surface of T-cells in a tropic-dependent manner ultimately culminating in viral fusion and subsequent intracellular release of the HIV viral RNA to the T-cell. The viral RNA is subsequently reverse transcribed and integrated into the host genome in which it can produce more infectious virus or remain in a latent state. When T-cells are actively producing HIV virus, a portion of the HIV envelope protein (gp120/gp41) remains on the surface of those infected T-cells as a consequence of viral budding. Hence, the productive HIV-infected cell can be specifically targeted by a CAR engineered to recognize the HIV envelope glycoprotein followed by elimination of those HIV-infected cells by virtue of its design.

HIV envelope epitopes have been used as targets for passive immunotherapy with monoclonal antibodies, but without broad success (reviewed in Mascola J R, Haynes B F. *Immunological reviews*. 2013; 254(1):225-244; Jaworski J P, Vendrell A, Chiavenna S M. Frontiers in Immunology. 2016; 7:661). In the absence of ART, antibodies alone lead to rapid viral rebound and ultimately viral escape. This loss of virologic control is largely due to antibody instability and a gradual decline of antibody concentrations in the host. Hence, HIV therapies that can provide a durable response are more likely to not only control HIV in the absence of ART but possibly lead to eradication of the HIV reservoir.

With the success of the CD19 CAR, revisiting CAR-based strategies to treat and possibly cure HIV is a highly attractive approach. When combined with novel anti-HIV domains and state-of-art genome engineering tools (for example, lentiviral vectors), CARs may address the limitation of passive immunization strategies and overcome previous pitfalls in HIV CAR design. More importantly, CARs can be integrated with a new "kick and kill" paradigm that focuses on eliminating the HIV reservoir via continuous immunosurveillance and specialized drugs that reawaken the latent HIV.

Herein described are a unique collection of anti-HIV CARs that exert potent cytotoxic and cytokine functions against envelope-positive cells while maintaining exceptional specificity. As shown below in Table 1, more than 20 anti-HIV CARs were designed to fully interrogate their potency against HIV-1. These CARs were designed by uniquely combining three different HIV envelope binding sequences in a precise way to be potent and synergistic inhibitors of HIV-1 infection. Functional characterization of these binders as CARs and iterations thereof were generated by cloning into lentiviral expression vectors that contained selected structural and signaling domains under the control of a constitutively active promoter and tested in vitro for transduction efficiency, killing function, and cytokine production using a HIV-envelope cell line model. Table 1 summarizes the nomenclature used. In some experiments CAR construct LTG1732, a mCherry reporter, serves as a negative control to evaluate changes in T-cell function as a result of viral transduction.

In the early 2000s, a CD4-zeta CAR entered into clinical trials. Although these studies demonstrated a lack of efficacy, these CARs persisted for decades. Possible explanations for the lack of virologic control argue that the initial first generation CD4ζ CAR requires re-engineering using the current understanding of CARs. Hence, and similar to others in the CAR field, a CD4-CAR was designed and engineered with the second-generation structural elements described herein and compared to the more potent, specific, and compact CD4-derived mD1.22-CAR (LTG1944) disclosed herein. While the mD1.22-CAR was potent, in contrast to the CD4-CAR, the mD1.22-CAR demonstrated improved specificity elaborating a trend of lower levels of off-target cytokines (data not shown). Thus, the novel CD4-like yet improved mD1.22-CAR described supra was selected as the initial prototype for further iterative CAR design.

To fully understand the relative contribution of each binder in the context of a CAR, the m36.4-CAR (LTG1945) and C46-CAR (LTG2328) was further designed and evaluated. As shown in FIG. 3C, mD1.22-CAR (LTG1944) was the most potent followed by m36.4-CAR (LTG1945) and C46-CAR (LTG2328). All three CARs demonstrated exceptional specificity with no off target killing in the absence of HIV-envelope (FIG. 3D). Moreover, these CARs with the exception of C46-CAR were specifically triggered by HIV-envelope expressing cells to secrete IFN-γ (FIG. 3E), a marker of antigen-driven T-cell activation. Taken together, the mD1.22-CAR was the most optimal architecture for building more advanced bi- and tri-specific HIV CARs.

To engineer a bispecific HIV CAR, an iterative approach was employed to determine the best way to combine mD1.22 and m36.4 for optimal CAR function. As shown in FIG. 5, all bispecific CARs destroyed up to 80% of envelope-expressing targets (FIG. 5) and were highly specific (FIG. 6). However, T-cells engineered with both a mD1.22-CAR and a m36.4-CAR using a bicistronic P2A vector (LTG2303) were significantly more potent than cells only expressing a single CAR such as, LTG1944 or LTG1945 as measured by cytotoxicity (FIG. 5) and cytokine release (FIG. 7). Reversing the order of the two domains to place m36.4 distal to mD1.22 had no significant effect on CAR activity (LTG1948). As demonstrated in FIG. 8A, decreasing the spatial distance between the mD1.22 and m36.4 domains to a single G4S motif significantly enhanced CAR-mediated cytotoxicity (LTG2325 versus LTG1947). Moreover, these linker-specific CARs exerted no cytotoxicity on envelope-negative 293T or Raji cells (FIG. 8B). Upon further interrogation of these linker-specific CARs, all anti-HIV CARs were specifically-triggered to produce IFN-γ and in some instances increased potency was often accompanied by increased off-target IFN-γ production (FIG. 9). Overall, a series of functional assays identified LTG2303 as the most potent bispecific CAR architecture for further trispecific HIV CAR design.

A trispecific HIV CAR architecture was then designed and evaluated which started with the basic mD1.22-CAR architecture and designed several intermediate constructs to evaluate the optimal placement of a highly potent C-peptide, C46. C-peptides (for example, T20 or C46) are derived from highly conserved regions within the C-terminus heptad repeat (CHR) region of gp41. In their native state, hydrophobic interactions between C-peptides and the N-terminus heptad repeat region (NHR) are involved in viral fusion. Interestingly, several unique strategies using C-peptides as decoys have clearly demonstrated their ability to potently inhibit viral fusion leading to suppressed HIV-1 infection. For instance, a few published strategies show that anchoring the C-peptide to the T-cell membrane potently ablates HIV-1 infection (van Lunzen et al., Molecular Therapy 2007, 15:(5) 1024-1033; Kimpel et al., PLOS One 2010, 5:(8) e12357; Melikyan et al. Journal of Virology 2006, 80:(7) 3249-3258). In a second strategy, enabling T-cells to constitutively secrete a C-peptide (SAVE) also protected bystander T-cells from HIV-1 infection (Egerer et al., Molecular Therapy 2010, 19(7), 1236-1244). In 2003, Enfuviritide (T20) was approved by the FDA as a salvage therapy for treating patients with multidrug resistant HIV-1. However emerging T20 resistant mutants have led to development of improved C-peptide design.

These new C-peptides such as C46 have proven to inhibit T20 resistant HIV-1 mutants. Similar to other C-peptides, C46 targets an extended, overlapping T20 site also involved in gp41-mediated viral fusion. Moreover, improved C-peptides have been found to inhibit hard to neutralize HIV-1 strains independent of viral tropism and exhibits improved breadth alone and in combination with mD1.22-based antibodies (Yao et al., The Journal of Biological Chemistry 2012, 287:(9), 6788-6796; Qi et al., Emerging Microbes & Infections 2017, 6:(6)). Hence, it was rationalized that engineering a trispecific CAR with the C46 peptide would be an attractive strategy to protect T-cells from HIV-1 infection as well as serve to enhance breadth of CARs upon encountering highly-resistant HIV-1 viruses.

As shown in FIG. 10, C46-based CARs were configuration-dependent and functioned best when engineered with the C46 peptide oriented distal to the mD1.22 domain (LTG2316, LTG2317 versus LTG2314, LTG2315). As previously shown using m36.4-based bispecific CARs, increasing the linker length between the C46 and mD1.22 domains also led to a reduction in cytotoxicity (FIG. 10A, LTG2316 versus LTG2317). However, this slightly less active CAR (LTG2317) demonstrated improved specificity as measured by IFN-γ secretion (FIG. 10B). Furthermore, engineering the mD1.22-CAR with either the m36.4 domain (LTG1946) or the C46 peptide (LTG2316) exerted similar cytotoxic effects and released IFN-γ in the presence of envelope-expressing targets (FIGS. 10A and B). In conclusion, an iterative approach was used to determine the optimal binder architecture for bispecific HIV CARs. This approach revealed a set of rules that govern HIV CAR design and identified two highly potent CAR architectures to serve as the prototype for trispecific HIV CAR design.

Herein, trispecific anti-HIV CARs are described and characterized by their cytotoxic capabilities. Three unique trispecific CAR architectures were engineered by (1) fusing all three domains together on a single CD3 (LTG2318, LTG2319, LTG2320), or by employing the (2) bispecific CAR LTG1946 combined with a membrane-anchored C46 peptide (LTG2323, LTG2334), and lastly by employing the (3) bispecific CAR LTG2303 combined with C46 peptide placed distal to the mD1.22 domain (LTG2329, LTG2330). As described in Example 1, these trispecific CARs were expressed on the surface of primary T-cells. Functionally, trispecific CARs performed as well as bispecific CARs using the surrogate HIV-envelope expressing cell line with modest off-target killing at very high effector to target ratios. As shown in FIG. 11C, trispecific CARs engineered with all three domains on a single CD3ζchain were highly influenced by the location of the C46. For instance, placing the C46 peptide between the mD1.22 domain and m36.4 domain (LTG2319) or near the T-cell membrane (LTG2318) abrogated its cytolytic function. However, presenting the C46 domain first followed by the other two domains (LTG2320) or anchoring the C46 peptide to the T-cell membrane independent of the CAR (LTG2323) led to robust cytolytic function and similar function to bispecific CAR LTG1946 (FIG. 11C). These trispecific CARs were highly specific with no off-target killing on envelope-negative cells (FIG. 11D) and they produced cytokines in response to antigen (FIGS. 11 E-F). Among the first set of trispecific CARs, LTG2323 appeared to be the most potent.

Similarly, the third set of trispecific CARs LTG2329 and LTG2330 also demonstrated robust cytolytic effect (FIG. 12B) with some increase in non-specific killing at very high E:T ratios (FIG. 12D). This observation was only found in T-cells co-expressing two different CARs (LTG2303, LTG2329, and LTG2330). As previously observed with bispecific CARs (LTG2316 versus LTG2317), increasing the linker length also reduced off-target cytotoxicity (FIG. 12D, LTG2330 versus LTG2329). Hence, further optimization of the CAR architecture may improve CAR specificity. In conclusion, bispecific and trispecific anti-HIV CARs are highly potent and represent a novel class of therapies to treat HIV/AIDS.

Example 3

Bispecific and Trispecific Anti-HIV duoCAR-T Cells Broadly and Potently Eliminate HIV-Infected PBMC In Vitro and In Vivo This Example interrogates anti-HIV CAR-T cell killing efficacy upon in vitro and in vivo challenge with PBMC infected with different Env-IMC-LucR HIV-1 viruses as well as the susceptibility of CAR-T cells to HIV-1 infection.

Materials and Methods:

In Vitro Efficacy of Anti-HIV CARs Using Replication-Competent Env-IMC-LucR Molecular Clones to Infect Donor Matched PBMC Inhibition of HIV-1 infection was investigated using a replication-competent HIV-1 molecular clone that contains a desired heterologous HIV-1 envelope upstream of an in-frame Renilla luciferase ORF (Env-IMC-LucR). The infectious clones were generated as previously described (Edmonds et al., Virology 2010, 408: 1-13). Upon HIV-1 infection of PBMCs or $CD4^+$ T-cells, the expression of Renilla luciferase serves as a highly sensitive and quantifiable measure of HIV-1 viral replication up to several weeks post-inoculation. Briefly, autologous donor PBMCs (HIV-1 naïve) were activated using PHA (4 μg/mL) and IL-2 (100 U/mL) and cultured at 37° C. in R10 media (RPMI supplemented with 10% heat-inactivated FBS, penicillin (100 U/mL), streptomycin (10 μg/mL), glutamine (2 mM), and HEPES (10 mM)). One day later, $1 \times 10^5$ PBMCs were spinfected with $1 \times 10^5$ IU/mL (MOI=1) of the indicated Env-IMC-LucR virus in a 96 well round-bottom plate for 24 hours. The following day, $1 \times 10^5$ effector cells (anti-HIV CAR T cells) were added to the infected PBMCs and co-cultured for 7 days. For in vitro protection assays, anti-HIV CAR-T effectors were directly challenged with the indicated Env-IMC-LucR virus at a MOI=1 in the absence of PBMCs. Cell culture supernatants (60 μL) were taken from co-cultures on days 0, 3, 5, and 7 for further analysis and cultures replenished with R10 media. After 7 days, cells were pelleted and lysed with 20 μl of lysis buffer and luminescence quantified (relative light units, RLU) as per manufacturer's instructions (Promega, Madison, Wis.). Data was generated using three independent donors (error bars=standard deviation). Luciferase activity was quantified following the manufacturer's instructions. The data was presented as relative light units (RLU). For in vitro killing assays, the log inhibition of HIV-1 infection was calculated by the following formula: Log inhibition of HIV-1 infection=Log 10(CARRLU/UTDRLU). Percent HIV-1 inhibition was calculated by 1−(CARRLU/UTDRLU)× 100%. Statistical analysis was performed using a multiple analysis student t-test for in vitro killing efficacy and one-way ANOVA for in vitro protection assays.

Multi-Specific Anti-HIV duoCAR T Cells Potently Eliminate Acute and Chronically HIV-Infected PBMC within a Humanized NSG Mouse Model The in vivo efficacy of anti-HIV duoCAR-T cells was investigated using a humanized intrasplenic NOD-SCID-IL2Rγ−/− mouse model that employs human PBMC infected with an Env-IMC-LucR HIV-1 virus (hu-spl-PBMC-NSG) to establish a rapid, strong, and easily quantifiable HIV-1 infection in the spleens of mice as previously described (Bardhi et al., J Virol 2017, 91:20; Thomas et al., Methods Mol Bio 2016, 1354:221-35). Briefly, 10 million donor matched PBMCs were activated as described above and spinfected with Du422.1 at 106 IU per 107 PBMCs. HIV-infected PBMCs were co-injected intrasplenically with either untransduced T-cells (UTD), LTG2303 (bispecific duoCAR), or LTG2330 (trispecific duoCAR) containing 30-50% CAR-positive T-cells at an E:T ratio of 0.5:1 (e.g., 5 million total CAR-T cells and 10 million HIV-infected PBMC). PBMC and T cells containing CAR effector cells were mixed right before the injections. One week (acute) or one month (chronic) after infection, mice were sacrificed and spleens harvested for further analyses. The total splenocytes were separated into three groups to perform the following assays: 1) luciferase assay to measure infection, 2) flow cytometry analysis to detect $CD4^+$ and $CD8^+$ T cells, and 3) DNA extraction for precise detection of CAR-T cell persistence at the end of the experiment by qPCR. The HIV-1 infection was quantified in a portion of the splenocytes using the Renilla luciferase assay system (Promega, Madison, Wis.) as previously described Seay et al., Journal of Virology 2015.

In Vivo Persistence of CAR-T Cells Using Real-Time c-Frag qPCR

Briefly, 1 million mouse splenocytes were harvested and genomic DNA extracted by ACGT, Inc. (Germantown, Md.) using the Promega Maxwell® 16 LEV Blood DNA Kit. To determine CAR-T persistence, a unique fragment (c-frag) contained within the lentiviral vector backbone of anti-HIV CARs, but not the HIV-1 virus, was used to assess copy numbers per 50 ng of genomic DNA isolated from mouse splenocytes. The following primers and probe were used to detect c-frag: Forward primer: 5'GGAGTTGA-GACCAGTGTAGT-3' (SEQ ID NO: 123), Reverse primer: 5'-CCACTCCTGACAACTACTCT-3' (SEQ ID NO: 124), Probe: 5'-FAM-CAGTAGGTGAAGGAGTCGTAGTTG-TAMRA-3' (SEQ ID NO: 125). The following primers and probe were used to detect the polypyrimidine tract binding protein 2 (PTBP2) gene to control for PCR inhibition: Forward primer: 5'-TCTCCATTCCCTATGTTCATGC-3' (SEQ ID NO: 126), Reverse primer: 5'-GTTCCCGCAGAATGGTGAGGTG-3' (SEQ ID NO: 127), Probe: 5'-JOE-ATGTTCCTCGGACCAACTTG-BHQ-1-3' (SEQ ID NO: 128). The number of cFrag copies in splenic DNA was calculated using a standard curve consisting of known quantities of a plasmid DNA containing the c-frag genetic tag followed by normalization to input splenic DNA (0.05 µg) multiplied by the volume of sample per PCR reaction (12.5 µL).

Results:

A major challenge in the field of HIV immunotherapy is developing therapies that precisely target and control HIV to a level that prevents viral escape. Similar to combinational anti-retroviral therapies, multiple strategies to target the HIV envelope using an immunotherapy approach may enable superior control over HIV infection with the advantage of targeting the latent HIV reservoir, a problem unmet by current drug therapies. To effectively develop such an immunotherapy may require targeting multiple non-overlapping epitopes on the HIV envelope protein that are highly conserved with a propensity to reduce viral fitness upon viral escape. To this end, bispecific CARs were engineered with domains that target highly conserved regions required for key steps involved in HIV-1 viral entry (mD1.22), co-receptor usage (m36.4), and fusion (C46). The rules that govern bispecific CAR function as it relates to binder architecture enabled rationale design of a trispecific CAR. Herein describes the in vitro and in vivo efficacy of bispecific and trispecific anti-HIV CARs against genetically diverse and resistant Env-IMC-LucR HIV-1 viruses encoding env genes found globally. Further to this, the m36.4 domain and C46 peptide were also evaluated for their ability to protect anti-HIV CARs in vitro and only the most potent anti-HIV CARs evaluated for in vivo efficacy.

As shown in FIG. 13, the donors used in the HIV-1 challenge studies were enriched for CD4$^+$ T cell effectors, the major cellular target for HIV-1. As shown in FIGS. 14A-K, anti-HIV CARs exhibited exceptional potency against all Env-IMC-LucR HIV-1 viruses tested. As expected, the monospecific CAR was the least potent (LTG1944, mD1.22-CAR) followed by a bispecific CAR containing a single CD3 chain (LTG1946). For some donors and HIV-1 strains tested, the trispecific LTG2323 CAR was slightly more potent than its bispecific LTG1946 counterpart suggesting perhaps a C46-mediated effect. This enhanced anti-viral effect was observed for Env-IMC-LucR viruses encoding the env gene from SF162 (Donor I), Du172.17 (Donors H and I), and AE.CNE8 (Donor H). Conversely, LTG2323 was the least potent of the trispecific CARs. As shown in FIG. 14 for different donors, the anti-HIV bispecific (LTG2303) and trispecific CARs (LTG2329, and LTG2330) engineered with two CD3 chains (multi-specific duoCARs) were exceptionally potent and broad against PBMC infected with several Env-IMC-LucR viruses (See FIG. 15, up to 3-log suppression as compared to UTD control). Notably, bispecific and trispecific duoCAR-T cells also eliminated PBMC infected with several Env-IMC-LucR viruses encoding clade C env genes that are resistant to VRC01 and in some instances 3BNC117, two broadly neutralizing antibodies that target the CD4 binding site and are currently in clinical trials (Bar et al., N Engl J Med 2016, 375:2037-2050; Liu, Bai, Liu, Zhang, & Wang, Int Immunopharmacol 2017; 52, 44-50). As summarized in FIGS. 15 and 16, the bispecific and trispecific duoCAR-T cells were consistently the most potent CAR architecture and eliminated up to ~3 logs or ~99% of HIV-1 infection for almost all Env-IMC-LucR viruses tested, respectively. As shown in FIGS. 17A and B, further interrogation of multi-specific duoCAR T cells revealed that even at extremely low E:T ratios, for example 1:100, the multi-specific duoCAR-T cells significantly eliminated PBMC infected with 3BNC117/VRC01-resistant Du422.1-IMC-LucR virus in contrast to UTD control or conventional CAR-T cells such as, monospecific 1944 CAR or bispecific 1946 CAR.

In FIG. 18, the mD1.22-CAR T cells were apparently more susceptible to HIV-1 infection during in vitro protection assays than other CARs tested. The presence of the m36.4 domain was sufficient to confer protection of CAR T cells and ablate HIV-1 infection to levels comparable to uninfected PBMCs. No statistical difference was observed between the conventional bispecific 1946 CAR and bispecific 2303 duoCAR (BaL, P=0.06; NL4-3, P=0.09; SF162, P=0.2; AE.CNE55, P=0.9) which both contain the m36.4 domain but in different CAR architectures. This result indicates that the ability of m36.4 to protect CAR-T cells is architecture independent. Furthermore, the ability of m36.4 to fully protect CART cells and its redundancy to the C46 peptide appears to be sufficient for protection. However, it is postulated that in the event of viral escape (e.g., m36.4 mutational escape), the C46 peptide may be required for long-term anti-viral efficacy. Hence, it is unclear from these data if the C46 peptide is required in addition to the m36.4 domain. FIG. 18J shows the compiled luciferase activity data for all donors and Env-IMC-LucR viruses tested.

To evaluate the in vivo efficacy of CAR-T cells, the bispecific and trispecific duoCAR-T cells (LTG2303 and LTG2330) were tested using a humanized intrasplenic HIV infection model (hu-spl-PBMC-NSG) using the Du422.1-IMC-LucR HIV-1 virus as depicted in FIG. 19A. After seven days of HIV-1 infection, the 2303 and 2330 duoCAR-T cells potently suppressed acute HIV infection in contrast to UTD control and to levels near that of uninfected PBMCs (FIG. 19B, P=0.003). Although some non-specific activity was observed for the UTD-treated HIV-infected mice, it was not sufficient to potently eliminate HIV-1 infection as that demonstrated by duoCAR-T cells. In the month-long study, where chronic HIV infection (Du422.1-infected PBMC) persisted in NSG mice, the multi-specific duoCAR-T cells robustly eliminated HIV-infected PBMC in four out of five mice in contrast to UTD treated, HIV-infected mice (FIG. 19C). During acute HIV infection (FIG. 19D), there was no apparent loss of CD4$^+$ T cells for UTD control or CAR-treated HIV-infected mice. However, as shown in FIG. 19E, the CD4$^+$ T cells were significantly depleted in chronically-infected mice treated with the UTD control (see UTD+HIV group). Conversely, the multi-specific duoCAR-treated, HIV-infected mice had significantly higher percentages of CD4$^+$ T cell in their spleens and similar to that of uninfected mice (see group HIV-PBMC). In the HIV-infected cohort that did not control HIV infection, as expected, this group (UTD+HIV) also had significantly higher CD8$^+$ T cell percentages (P<0.01, FIG. 19G) concomitant with the loss of CD4⁺ T cells (FIG. 19E) which was not evident in the acute HIV infection study (FIGS. 19D and 19F). Lastly, the multi-specific duoCAR-T cells were durable and persisted during acute (FIG. 19H) and chronic (FIG. 19I) HIV-1 infection. Collectively, these data clearly demonstrate the superior advantage of treating HIV-1 infection with multi-specific anti-HIV CAR T cells containing the herein described novel domains and novel compositions. This data coupled with the known long-term persistence and immunosurveillance properties of CAR-T cells may represent a viable approach for controlling viral loads and eliminating HIV-infected cells in HIV positive patients in the absence of anti-retroviral therapy, with the potential to significantly delay or postpone disease progression. When combined with strategies that target the latent reservoir, anti-HIV duo-CAR-T cells could offer a path towards functionally curing HIV infection.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. An isolated nucleic acid molecule encoding a chimeric antigen receptor (CAR) comprising at least one extracellular anti-HIV antigen binding domain, wherein the isolated nucleic acid encoding the extracellular anti-HIV envelope antigen binding domain comprises a nucleic sequence comprising SEQ ID NO: 69 or SEQ ID NO: 115, at least one transmembrane domain, and at least one intracellular signaling domain.

2. A vector comprising a nucleic acid molecule of claim 1.

3. The vector of claim 2, wherein the vector is selected from the group consisting of a DNA vector, an RNA vector, a plasmid vector, a cosmid vector, a herpes virus vector, a measles virus vector, a lentivirus vector, an adenoviral vector, and a retrovirus vector.

4. A cell comprising the vector of claim 2.

5. A method of making a cell comprising transducing a T cell with a vector of claim 2.

6. A pharmaceutical composition comprising an anti-HIV effective amount of a population of human T cells, wherein the population of human T cells comprise a nucleic acid sequence that encodes a chimeric antigen receptor (CAR), wherein the CAR comprises at least one extracellular anti-HIV antigen binding domain comprising the amino acid sequence of SEQ ID NO: 70 or SEQ ID NO: 116, at least one linker domain, at least one transmembrane domain, at least one intracellular signaling domain, and wherein the population of T cells are T cells of a human subject having HIV/AIDS.

7. A method of treating HIV-related cancers or HIV/AIDS in a subject in need thereof, the method comprising administering to the subject a pharmaceutical composition comprising an anti-tumor effective amount of a population of T cells, wherein the population of T cells comprise a nucleic acid sequence that encodes a chimeric antigen receptor (CAR), wherein the CAR comprises at least one extracellular anti-HIV antigen binding domain, at least one linker or spacer domain, at least one transmembrane domain, and at least one intracellular signaling domain wherein the nucleic acid sequence encoding the extracellular anti-HIV antigen binding domain comprises a nucleic sequence comprising SEQ ID NO: 69, or a sequence with 85%, 90%, 95%, 96%, 97%, 98% or 99% identity thereof, wherein the population of T cells are T cells of the subject having HIV/AIDS.

8. The method of claim 7, wherein the at least one transmembrane domain comprises a transmembrane domain of a protein selected from the group consisting of: the alpha, the beta or the zeta chain of a T-cell receptor, CD8, CD28, CD3 epsilon, CD45, CD4, CD5, CD8, CD9, CD16, CD22, CD33, CD37, CD64, CD80, CD86, CD134, CD137 and CD154.

9. The method of claim 7, wherein the subject has a HIV-related cancer.

10. The method of claim 7, wherein the at least one extracellular anti-HIV antigen binding domain binds to a HIV-1 envelope protein.

11. The method of claim 7, wherein the at least one extracellular anti-HIV antigen binding domain, the at least one intracellular signaling domain, or both are connected to the at least one transmembrane domain by the at least one linker or spacer domain.

12. The method of claim 11, wherein the at least one linker or spacer domain is obtained from a CD8 extracellular domain and is linked to the at least one transmembrane domain.

13. The method of claim 7, wherein the at least one intracellular signaling domain further comprises a CD3 zeta intracellular domain.

14. The method of claim 7, wherein the at least one intracellular signaling domain comprises a costimulatory domain, a primary signaling domain, or any combination thereof.

15. The method of claim 7, wherein the at least one intracellular signaling domain comprises a costimulatory domain comprising a functional signaling domain of a protein selected from the group consisting of: OX40, CD70, CD27, CD28, CD5, ICAM-1, LFA-1 (CD11a/CD18), ICOS (CD278), DAP10, DAP12, and 4-1BB (CD137).

16. A method of treating HIV-related cancers or HIV/AIDS in a subject in need thereof, the method comprising administering to the subject a pharmaceutical composition comprising an anti-tumor effective amount of a population of T cells, wherein the population of T cells comprise a nucleic acid sequence that encodes a chimeric antigen receptor (CAR),
wherein the CAR comprises at least one extracellular anti-HIV antigen binding domain, at least one linker or spacer domain, at least one transmembrane domain, and at least one intracellular signaling domain wherein the nucleic acid sequence encoding the extracellular anti-HIV antigen binding domain comprises a nucleic sequence comprising SEQ ID NO: 115, or a sequence with 85%, 90%, 95%, 96%, 97%, 98% or 99% identity thereof, wherein the population of T cells are T cells of the subject having HIV/AIDS.

17. A method of treating HIV-related cancers or HIV/AIDS in a subject in need thereof, the method comprising administering to the subject a pharmaceutical composition comprising an anti-tumor effective amount of a population of T cells, wherein the population of T cells comprise a nucleic acid sequence that encodes a chimeric antigen receptor (CAR),
wherein the CAR comprises at least one extracellular anti-HIV antigen binding domain, at least one linker or spacer domain, at least one transmembrane domain, and at least one intracellular signaling domain wherein the at least one extracellular anti-HIV antigen binding domain comprises the amino acid sequence of SEQ ID NO: 70, wherein the population of T cells are T cells of the subject having HIV/AIDS.

18. A method of treating HIV-related cancers or HIV/AIDS in a subject in need thereof, the method comprising administering to the subject a pharmaceutical composition comprising an anti-tumor effective amount of a population of T cells, wherein the population of T cells comprise a nucleic acid sequence that encodes a chimeric antigen receptor (CAR),
wherein the CAR comprises at least one extracellular anti-HIV antigen binding domain, at least one linker or spacer domain, at least one transmembrane domain, and at least one intracellular signaling domain wherein the at least one extracellular anti-HIV antigen binding domain comprises the amino acid sequence of SEQ ID NO: 116, wherein the population of T cells are T cells of the subject having HIV/AIDS.

\* \* \* \* \*

```
                        SEQUENCE LISTING

<160> NUMBER OF SEQ ID NOS: 128

<210> SEQ ID NO 1
<211> LENGTH: 297
<212> TYPE: DNA
<213> ORGANISM: Artificial
<220> FEATURE:
<223> OTHER INFORMATION: HIV envelope-specific binder mD1.22

<400> SEQUENCE: 1
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggg         297

<210> SEQ ID NO 2
<211> LENGTH: 99
<212> TYPE: PRT
<213> ORGANISM: Artificial
<220> FEATURE:
<223> OTHER INFORMATION: HIV envelope-specific binder mD1.22

<400> SEQUENCE: 2

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
                20                  25                  30

Gln Ile Lys Ile Leu Gly Asn Gln Gly Ser Phe Leu Thr Lys Gly Pro
        35                  40                  45
```

```
Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Pro Glu Asp Ser Asp
 65                  70                  75                  80

Thr Tyr Ile Cys Glu Val Glu Asp Gln Lys Glu Glu Val Gln Leu Val
                 85                  90                  95

Val Val Gly

<210> SEQ ID NO 3
<211> LENGTH: 351
<212> TYPE: DNA
<213> ORGANISM: Artificial
<220> FEATURE:
<223> OTHER INFORMATION: HIV envelope-specific bind m36.4

<400> SEQUENCE: 3
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattgggaa atcaatgata gtggaaacac catttacaat      180
ccgtccctca agagtcgagt caccatctcc agagacaatt ccaagaacac actgtatctg     240
caaatgaaca ccctgagagc cgaggacaca gccatatatt actgtgcgat atatggtggt     300
aactccgggg gagagtactg ggccagggc accctggtca ccgtctcctc a               351

<210> SEQ ID NO 4
<211> LENGTH: 117
<212> TYPE: PRT
<213> ORGANISM: Artificial
<220> FEATURE:
<223> OTHER INFORMATION: HIV envelope-specific binder m36.4

<400> SEQUENCE: 4

Gln Val Gln Leu Val Gln Ser Gly Gly Gly Leu Val Gln Pro Gly Gly
  1               5                  10                  15

Ser Leu Arg Leu Ser Cys Ala Ala Ser Ala Phe Asp Phe Ser Asp Tyr
                 20                  25                  30

Glu Met Ser Trp Val Arg Glu Ala Pro Gly Lys Gly Leu Glu Trp Ile
             35                  40                  45

Gly Glu Ile Asn Asp Ser Gly Asn Thr Ile Tyr Asn Pro Ser Leu Lys
 50                  55                  60

Ser Arg Val Thr Ile Ser Arg Asp Asn Ser Lys Asn Thr Leu Tyr Leu
 65                  70                  75                  80

Gln Met Asn Thr Leu Arg Ala Glu Asp Thr Ala Ile Tyr Tyr Cys Ala
                 85                  90                  95

Ile Tyr Gly Gly Asn Ser Gly Gly Glu Tyr Trp Gly Gln Gly Thr Leu
                100                 105                 110

Val Thr Val Ser Ser
        115

<210> SEQ ID NO 5
<211> LENGTH: 138
<212> TYPE: DNA
<213> ORGANISM: Artificial
<220> FEATURE:
<223> OTHER INFORMATION: HIV envelope-specific binder C46

<400> SEQUENCE: 5
tggatggaat gggatcgcga aatcaacaac tacacctccc tgattcactc cctgattgag      60
```

```
gaatcccaga atcaacagga gaagaacgaa caagagcttc tggagctgga caaatgggcc    120
tccctgtgga actggttc                                                  138
```

```
<210> SEQ ID NO 6
<211> LENGTH: 46
<212> TYPE: PRT
<213> ORGANISM: Artificial
<220> FEATURE:
<223> OTHER INFORMATION: HIV envelope-specific binder C46

<400> SEQUENCE: 6
```

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe
        35                  40                  45

```
<210> SEQ ID NO 7
<211> LENGTH: 72
<212> TYPE: DNA
<213> ORGANISM: Artificial
<220> FEATURE:
<223> OTHER INFORMATION: CD8 transmembrane domain

<400> SEQUENCE: 7
atctacattt gggccccgct ggccggcact tgcggcgtgc tcctgctgtc gctggtcatc    60 acccttact gc                                                         72
```

```
<210> SEQ ID NO 8
<211> LENGTH: 24
<212> TYPE: PRT
<213> ORGANISM: Artificial
<220> FEATURE:
<223> OTHER INFORMATION: CD8 transmembrane domain

<400> SEQUENCE: 8
```

Ile Tyr Ile Trp Ala Pro Leu Ala Gly Thr Cys Gly Val Leu Leu Leu
1               5                   10                  15

Ser Leu Val Ile Thr Leu Tyr Cys
            20

```
<210> SEQ ID NO 9
<211> LENGTH: 135
<212> TYPE: DNA
<213> ORGANISM: Artificial
<220> FEATURE:
<223> OTHER INFORMATION: CD8 linker/hinge domain

<400> SEQUENCE: 9
actaccaccc ctgcccctcg gccgccgact ccggccccaa ccatcgcaag ccaacccctc    60
tccttgcgcc ccgaagcttg ccgccggcc gcgggtggag ccgtgcatac ccggggggctg   120 gactttgcct gcgat                                                    135
```

```
<210> SEQ ID NO 10
<211> LENGTH: 45
<212> TYPE: PRT
<213> ORGANISM: Artificial
<220> FEATURE:
<223> OTHER INFORMATION: CD8 linker/hinge domain

<400> SEQUENCE: 10
```

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 11
<211> LENGTH: 207
<212> TYPE: DNA
<213> ORGANISM: Artificial
<220> FEATURE:
<223> OTHER INFORMATION: CD8 linker/hinge/CD8 transmembrane domain

<400> SEQUENCE: 11
actaccaccc ctgcccctcg gccgccgact ccggccccaa ccatcgcaag ccaacccctc    60
tccttgcgcc ccgaagcttg ccgccggcc gcgggtggag ccgtgcatac ccggggctg    120 gactttgcct gcgatatcta catttgggcc ccgctggccg gcacttgcgg cgtgctcctg   180
ctgtcgctgg tcatcaccct ttactgc                                      207

<210> SEQ ID NO 12
<211> LENGTH: 69
<212> TYPE: PRT
<213> ORGANISM: Artificial
<220> FEATURE:
<223> OTHER INFORMATION: CD8 linker/hinge/CD8 transmembrane domain

<400> SEQUENCE: 12

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 13
<211> LENGTH: 90
<212> TYPE: DNA
<213> ORGANISM: Artificial
<220> FEATURE:
<223> OTHER INFORMATION: TNFRSF19 transmembrane

<400> SEQUENCE: 13
gataccgcac tggcggccgt gatctgtagc gccctggcca ccgtgctgct ggcgctgctc    60
atcctttgcg tgatctactg caagcggcag                                    90

<210> SEQ ID NO 14
<211> LENGTH: 30
<212> TYPE: PRT
<213> ORGANISM: Artificial
<220> FEATURE:
<223> OTHER INFORMATION: TNFRSF19 transmembrane

<400> SEQUENCE: 14

Asp Thr Ala Leu Ala Ala Val Ile Cys Ser Ala Leu Ala Thr Val Leu
1               5                   10                  15

```
Leu Ala Leu Leu Ile Leu Cys Val Ile Tyr Cys Lys Arg Gln
            20                  25                  30

<210> SEQ ID NO 15
<211> LENGTH: 207
<212> TYPE: DNA
<213> ORGANISM: Artificial
<220> FEATURE:
<223> OTHER INFORMATION: CD8 linker linked to TNFRSF19 transmembrane

<400> SEQUENCE: 15
ccggctccac gaccacccac tccagcccca acgattgcga gccaacctct cagtcttcgg      60
cccgaggctt gcaggccagc cgcaggagga gcagtgcaca cccgaggact ggatttcgat     120
accgcactgg cggccgtgat ctgtagcgcc ctggccaccg tgctgctggc gctgctcatc     180
ctttgcgtga tctactgcaa gcggcag                                          207

<210> SEQ ID NO 16
<211> LENGTH: 69
<212> TYPE: PRT
<213> ORGANISM: Artificial
<220> FEATURE:
<223> OTHER INFORMATION: CD8 linker linked to TNFRSF19 transmembrane

<400> SEQUENCE: 16

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Asp Thr Ala Leu Ala Ala Val Ile Cys
        35                  40                  45

Ser Ala Leu Ala Thr Val Leu Leu Ala Leu Leu Ile Leu Cys Val Ile
    50                  55                  60

Tyr Cys Lys Arg Gln
65

<210> SEQ ID NO 17
<211> LENGTH: 126
<212> TYPE: DNA
<213> ORGANISM: Artificial
<220> FEATURE:
<223> OTHER INFORMATION: 4-1BB signaling domain

<400> SEQUENCE: 17
aagaggggcc ggaagaagct gctttacatc ttcaagcagc cgttcatgcg gcccgtgcag      60
acgactcagg aagaggacgg atgctcgtgc agattccctg aggaggaaga ggggggatgc     120
gaactg                                                                 126

<210> SEQ ID NO 18
<211> LENGTH: 42
<212> TYPE: PRT
<213> ORGANISM: Artificial
<220> FEATURE:
<223> OTHER INFORMATION: 4-1BB signaling domain

<400> SEQUENCE: 18

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
```

<210> SEQ ID NO 19
<211> LENGTH: 336
<212> TYPE: DNA
<213> ORGANISM: Artificial
<220> FEATURE:
<223> OTHER INFORMATION: CD3 zeta signaling domain

<400> SEQUENCE: 19

```
cgcgtcaagt tctcacggtc cgccgacgcc cccgcatatc aacagggcca gaatcagctc    60
tacaacgagc tgaacctggg aaggagagag gagtacgacg tgctggacaa gcgacgcgga   120
cgcgacccgg agatggggggg gaaaccacgg cggaaaaacc ctcaggaagg actgtacaac   180
gaactccaga agacaagat ggcggaagcc tactcagaaa tcgggatgaa gggagagcgg   240
aggaggggaa agggtcacga cgggctgtac cagggactga gcaccgccac taaggatacc   300
tacgatgcct tgcatatgca agcactccca ccccgg                             336
```

<210> SEQ ID NO 20
<211> LENGTH: 112
<212> TYPE: PRT
<213> ORGANISM: Artificial
<220> FEATURE:
<223> OTHER INFORMATION: CD3 zeta signaling domain

<400> SEQUENCE: 20

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 21
<211> LENGTH: 339
<212> TYPE: DNA
<213> ORGANISM: Artificial
<220> FEATURE:
<223> OTHER INFORMATION: CD3 zeta2 signaling domain

<400> SEQUENCE: 21

```
cgggttaaat tctcccgcag cgcagacgca cccgcctacc agcaaggaca gaatcagctc    60
tacaacgaac tgaaccttgg taggagagaa gaatatgatg ttctcgacaa gcgcagaggg   120
agagatccag agatgggtgg gaagccgcaa cgccggaaaa acccacaaga gggactgtac   180
aatgaattgc agaaagataa gatggccgag gcttactcag aaatcggaat gaagggggag   240
cggcggaggg gcaagggaca tgatggtctc taccaagggc tttcaaccgc tactaaggac   300
acttatgacg cactccacat gcaggcgctg cctccgcga                          339
```

<210> SEQ ID NO 22

```
<211> LENGTH: 112
<212> TYPE: PRT
<213> ORGANISM: Artificial
<220> FEATURE:
<223> OTHER INFORMATION: CD3 zeta2 signaling domain

<400> SEQUENCE: 22

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 23
<211> LENGTH: 15
<212> TYPE: DNA
<213> ORGANISM: Artificial
<220> FEATURE:
<223> OTHER INFORMATION: Linker domain L1

<400> SEQUENCE: 23
ggcggaggcg ggtca                                                        15

<210> SEQ ID NO 24
<211> LENGTH: 5
<212> TYPE: PRT
<213> ORGANISM: Artificial
<220> FEATURE:
<223> OTHER INFORMATION: Linker domain L1

<400> SEQUENCE: 24

Gly Gly Gly Gly Ser
1               5

<210> SEQ ID NO 25
<211> LENGTH: 30
<212> TYPE: DNA
<213> ORGANISM: Artificial
<220> FEATURE:
<223> OTHER INFORMATION: Linker domain L2

<400> SEQUENCE: 25
ggcggaggcg ggtcaggtgg cggtggtagt                                        30

<210> SEQ ID NO 26
<211> LENGTH: 10
<212> TYPE: PRT
<213> ORGANISM: Artificial
<220> FEATURE:
<223> OTHER INFORMATION: Linker domain L2

<400> SEQUENCE: 26

Gly Gly Gly Gly Ser Gly Gly Gly Gly Ser
1               5                   10
```

```
<210> SEQ ID NO 27
<211> LENGTH: 45
<212> TYPE: DNA
<213> ORGANISM: Artificial
<220> FEATURE:
<223> OTHER INFORMATION: Linker domain L3

<400> SEQUENCE: 27
ggaggtggcg gttcaggcgg aggggggagt ggaggtgggg gaagc            45

<210> SEQ ID NO 28
<211> LENGTH: 15
<212> TYPE: PRT
<213> ORGANISM: Artificial
<220> FEATURE:
<223> OTHER INFORMATION: Linker domain L3

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 60
<212> TYPE: DNA
<213> ORGANISM: Artificial
<220> FEATURE:
<223> OTHER INFORMATION: Linker domain L4

<400> SEQUENCE: 29
ggcggaggcg ggtcaggtgg cggtggtagt ggcggtggcg gttcaggcgg tggtgggagt    60

<210> SEQ ID NO 30
<211> LENGTH: 20
<212> TYPE: PRT
<213> ORGANISM: Artificial
<220> FEATURE:
<223> OTHER INFORMATION: Linker domain L4

<400> SEQUENCE: 30

Gly Gly Gly Gly Ser Gly Gly Gly Gly Ser Gly Gly Gly Gly Ser Gly
1               5                   10                  15

Gly Gly Gly Ser
            20

<210> SEQ ID NO 31
<211> LENGTH: 75
<212> TYPE: DNA
<213> ORGANISM: Artificial
<220> FEATURE:
<223> OTHER INFORMATION: Linker domain L5

<400> SEQUENCE: 31
ggcggaggcg ggtcaggtgg cggtggtagt ggcggtggcg gttcaggcgg tggtgggagt    60
gggggaggag gcagc                                                    75

<210> SEQ ID NO 32
<211> LENGTH: 25
<212> TYPE: PRT
<213> ORGANISM: Artificial
<220> FEATURE:
<223> OTHER INFORMATION: Linker domain L5

<400> SEQUENCE: 32

Gly Gly Gly Gly Ser Gly Gly Gly Gly Ser Gly Gly Gly Gly Ser Gly
1               5                   10                  15
```

Gly Gly Gly Ser Gly Gly Gly Gly Ser
            20                  25

<210> SEQ ID NO 33
<211> LENGTH: 93
<212> TYPE: DNA
<213> ORGANISM: Artificial
<220> FEATURE:
<223> OTHER INFORMATION: Linker and cleavage site domain Furin-2A-Furin

<400> SEQUENCE: 33
cgcgcgaaac gcagcggcag cggcgcgacc aactttagcc tgctgaaaca ggcgggcgat    60
gtggaagaaa acccgggccc gcgagcaaag agg                                93

<210> SEQ ID NO 34
<211> LENGTH: 31
<212> TYPE: PRT
<213> ORGANISM: Artificial
<220> FEATURE:
<223> OTHER INFORMATION: Linker and cleavage site domain Furin-2A-Furin

<400> SEQUENCE: 34

Arg Ala Lys Arg Ser Gly Ser Gly Ala Thr Asn Phe Ser Leu Leu Lys
1               5                  10                  15

Gln Ala Gly Asp Val Glu Glu Asn Pro Gly Pro Arg Ala Lys Arg
            20                  25                  30

<210> SEQ ID NO 35
<211> LENGTH: 72
<212> TYPE: DNA
<213> ORGANISM: Artificial
<220> FEATURE:
<223> OTHER INFORMATION: Leader peptide LP derived from GMCSFR

<400> SEQUENCE: 35
atgcttctcc tggtcacctc cctgctcctc tgcgaactgc ctcaccctgc cttccttctg    60
attcctgaca cc                                                       72

<210> SEQ ID NO 36
<211> LENGTH: 24
<212> TYPE: PRT
<213> ORGANISM: Artificial
<220> FEATURE:
<223> OTHER INFORMATION: Leader peptide LP derived from GMCSFR

<400> SEQUENCE: 36

Met Leu Leu Leu Val Thr Ser Leu Leu Leu Cys Glu Leu Pro His Pro
1               5                  10                  15

Ala Phe Leu Leu Ile Pro Asp Thr
            20

<210> SEQ ID NO 37
<211> LENGTH: 81
<212> TYPE: DNA
<213> ORGANISM: Artificial
<220> FEATURE:
<223> OTHER INFORMATION: Leader peptide LP2 derived from CD59

<400> SEQUENCE: 37
atgggaattc aggggggttc cgtgctcttt ggcttgctcc tggtcctggc agtgttttgt    60
cactcgggac acagcctgca g                                             81

```
<210> SEQ ID NO 38
<211> LENGTH: 27
<212> TYPE: PRT
<213> ORGANISM: Artificial
<220> FEATURE:
<223> OTHER INFORMATION: Leader peptide LP2 derived from CD59

<400> SEQUENCE: 38

Met Gly Ile Gln Gly Gly Ser Val Leu Phe Gly Leu Leu Leu Val Leu
1               5                   10                  15

Ala Val Phe Cys His Ser Gly His Ser Leu Gln
            20                  25

<210> SEQ ID NO 39
<211> LENGTH: 1050
<212> TYPE: DNA
<213> ORGANISM: Artificial
<220> FEATURE:
<223> OTHER INFORMATION: Anti-HIV CAR LTG1944

<400> SEQUENCE: 39
atgcttctcc tggtcacctc cctgctcctc tgcgaactgc ctcaccctgc cttccttctg      60
attcctgaca ccaagaaagt cgtgtacgga agaagggag acactgtgga gctgacctgt     120
accgcaagcc agaagaagaa catccagttc cactggaaga actccaacca aatcaagatc     180
ctggggaacc agggttcctt cctgactaag ggaccctcaa agctgaacga ccgcgtggat     240
agcagacgct ccctgtggga ccaggaaac ttcccgctta tcattaagaa cctcaaacct     300
gaggactcgg atacctacat ctgcgaagtg gaggaccaga aggaggaggt gcagctggtg     360
gtggtggggg cggccgcaac taccaccct gccctcggc cgccgactcc ggccccaacc     420
atcgcaagcc aaccctctc cttgcgcccc gaagcttgcc gccggccgc gggtggagcc     480 gtgcataccc gggggctgga cttttgcctgc gatatctaca tttgggcccc gctggccggc     540
acttgcggcg tgctcctgct gtcgctggtc atcacccttt actgcaagag gggccggaag     600
aagctgcttt acatcttcaa gcagccgttc atgcggcccg tgcagacgac tcaggaagag     660
gacggatgct cgtgcagatt ccctgaggag aagagggg gatgcgaact gcgcgtcaag     720
ttctcacggt ccgccgacgc ccccgcatat caacagggcc agaatcagct ctacaacgag     780
ctgaacctgg aaggagaga ggagtacgac gtgctggaca gcgacgcgg acgcgacccg     840 gagatggggg ggaaaccacg gcggaaaaac cctcaggaag actgtacaa cgaactccag     900 aaagacaaga tggcggaagc ctactcagaa atcgggatga agggagagcg gaggagggga     960
aagggtcacg acgggctgta ccagggactg agcaccgcca ctaaggatac ctacgatgcc    1020
ttgcatatgc aagcactccc accccggtag                                    1050

<210> SEQ ID NO 40
<211> LENGTH: 349
<212> TYPE: PRT
<213> ORGANISM: Artificial
<220> FEATURE:
<223> OTHER INFORMATION: Anti-HIV CAR LTG1944

<400> SEQUENCE: 40

Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45
```

```
Gln Phe His Trp Lys Asn Ser Asn Gln Ile Lys Ile Leu Gly Asn Gln
         50                  55                  60

Gly Ser Phe Leu Thr Lys Gly Pro Ser Lys Leu Asn Asp Arg Val Asp
 65                  70                  75                  80

Ser Arg Arg Ser Leu Trp Asp Gln Gly Asn Phe Pro Leu Ile Ile Lys
                 85                  90                  95

Asn Leu Lys Pro Glu Asp Ser Asp Thr Tyr Ile Cys Glu Val Glu Asp
             100                 105                 110

Gln Lys Glu Glu Val Gln Leu Val Val Gly Ala Ala Ala Thr Thr
         115                 120                 125

Thr Pro Ala Pro Arg Pro Pro Thr Pro Ala Pro Thr Ile Ala Ser Gln
         130                 135                 140

Pro Leu Ser Leu Arg Pro Glu Ala Cys Arg Pro Ala Ala Gly Gly Ala
145                 150                 155                 160

Val His Thr Arg Gly Leu Asp Phe Ala Cys Asp Ile Tyr Ile Trp Ala
                 165                 170                 175

Pro Leu Ala Gly Thr Cys Gly Val Leu Leu Leu Ser Leu Val Ile Thr
             180                 185                 190

Leu Tyr Cys Lys Arg Gly Arg Lys Lys Leu Leu Tyr Ile Phe Lys Gln
         195                 200                 205

Pro Phe Met Arg Pro Val Gln Thr Thr Gln Glu Glu Asp Gly Cys Ser
         210                 215                 220

Cys Arg Phe Pro Glu Glu Glu Glu Gly Gly Cys Glu Leu Arg Val Lys
225                 230                 235                 240

Phe Ser Arg Ser Ala Asp Ala Pro Ala Tyr Gln Gln Gly Gln Asn Gln
                 245                 250                 255

Leu Tyr Asn Glu Leu Asn Leu Gly Arg Arg Glu Glu Tyr Asp Val Leu
             260                 265                 270

Asp Lys Arg Arg Gly Arg Asp Pro Glu Met Gly Gly Lys Pro Arg Arg
         275                 280                 285

Lys Asn Pro Gln Glu Gly Leu Tyr Asn Glu Leu Gln Lys Asp Lys Met
     290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                 325                 330                 335

Thr Tyr Asp Ala Leu His Met Gln Ala Leu Pro Pro Arg
                 340                 345

<210> SEQ ID NO 41
<211> LENGTH: 1104
<212> TYPE: DNA
<213> ORGANISM: Artificial
<220> FEATURE:
<223> OTHER INFORMATION: Anti-HIV CAR LTG1945

<400> SEQUENCE: 41
atgcttctcc tggtcaccct cctgctcctc tgcgaactgc ctcaccctgc cttccttctg      60
attcctgaca cccaggtgca gctggtgcag tctgggggag gcttggtaca gcctggaggg     120
tccctgagac tctcctgtgc agcctctgct ttcgatttct ctgattatga aatgagctgg     180
gtccgcgagg ctccagggaa ggggctggag tggattgggg aaatcaatga tagtggaaac     240
accatttaca atcgtcccct caagagtcga gtcaccatct ccagagacaa ttccaagaac     300
acactgtatc tgcaaatgaa caccctgaga gccgaggaca cagccatata ttactgtgcg     360
```

```
atatatggtg gtaactccgg gggagagtac tggggccagg gcaccctggt caccgtctcc      420
tcagcggccg caactaccac ccctgccccc cggccgccga ctccggcccc aaccatcgca      480
agccaacccc tctccttgcg ccccgaagct tgccgcccgg ccgcgggtgg agccgtgcat      540
acccgggggc tggactttgc ctgcgatatc tacatttggg ccccgctggc cggcacttgc      600
ggcgtgctcc tgctgtcgct ggtcatcacc ctttactgca agaggggccg gaagaagctg      660
ctttacatct tcaagcagcc gttcatgcgg cccgtgcaga cgactcagga agaggacgga      720
tgctcgtgca gattccctga ggaggaagag gggggatgcg aactgcgcgt caagttctca      780
cggtccgccg acgcccccgc atatcaacag ggccagaatc agctctacaa cgagctgaac      840
ctgggaagga gagaggagta cgacgtgctg acaagcgac gcggacgcga cccggagatg       900 gggggggaaac cacggcggaa aaaccctcag gaaggactgt acaacgaact ccagaaagac      960
aagatggcgg aagcctactc agaaatcggg atgaagggag agcggaggag gggaaagggt     1020
cacgacgggc tgtaccaggg actgagcacc gccactaagg atacctacga tgccttgcat     1080
atgcaagcac tcccaccccg gtag                                              1104
```

<210> SEQ ID NO 42
<211> LENGTH: 367
<212> TYPE: PRT
<213> ORGANISM: Artificial
<220> FEATURE:
<223> OTHER INFORMATION: Anti-HIV CAR LTG1945

<400> SEQUENCE: 42

```
Met Leu Leu Leu Val Thr Ser Leu Leu Leu Cys Glu Leu Pro His Pro
1               5                  10                  15

Ala Phe Leu Leu Ile Pro Asp Thr Gln Val Gln Leu Val Gln Ser Gly
            20                  25                  30

Gly Gly Leu Val Gln Pro Gly Gly Ser Leu Arg Leu Ser Cys Ala Ala
        35                  40                  45

Ser Ala Phe Asp Phe Ser Asp Tyr Glu Met Ser Trp Val Arg Glu Ala
    50                  55                  60

Pro Gly Lys Gly Leu Glu Trp Ile Gly Glu Ile Asn Asp Ser Gly Asn
65                  70                  75                  80

Thr Ile Tyr Asn Pro Ser Leu Lys Ser Arg Val Thr Ile Ser Arg Asp
                85                  90                  95

Asn Ser Lys Asn Thr Leu Tyr Leu Gln Met Asn Thr Leu Arg Ala Glu
            100                 105                 110

Asp Thr Ala Ile Tyr Tyr Cys Ala Ile Tyr Gly Gly Asn Ser Gly Gly
        115                 120                 125

Glu Tyr Trp Gly Gln Gly Thr Leu Val Thr Val Ser Ser Ala Ala Ala
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220
```

-continued

```
Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
            245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320

Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
            355                 360                 365
```

<210> SEQ ID NO 43
<211> LENGTH: 891
<212> TYPE: DNA
<213> ORGANISM: Artificial
<220> FEATURE:
<223> OTHER INFORMATION: Anti-HIV CAR LTG2328

<400> SEQUENCE: 43

```
atgcttctcc tggtcacctc cctgctcctc tgcgaactgc ctcaccctgc cttccttctg      60
attcctgaca cctggatgga atgggatcgc gaaatcaaca actacaccct cctgattcac     120
tccctgattg aggaatccca gaatcaacag agagaagaacg aacaagagct tctggagctg     180
gacaaatggg cctccctgtg gaactggttc gcggccgcaa ctaccacccc tgcccctcgg     240
ccgccgactc cggccccaac catcgcaagc caaccctct ccttgcgccc cgaagcttgc      300
cgccgggccg cgggtggagc cgtgcatacc cggggggctgg actttgcctg cgatatctac     360
atttgggccc cgctggccgg cacttgcggc gtgctcctgc tgtcgctggt catcaccctt     420
tactgcaaga ggggccggaa gaagctgctt tacatcttca gcagccgtt catgcggccc     480
gtgcagacga ctcaggaaga ggacggatgc tcgtgcagat ccctgagga ggaagagggg     540
ggatgcgaac tgcgcgtcaa gttctcacgg tccgccgacg cccccgcata tcaacagggc     600
cagaatcagc tctacaacga gctgaacctg gaaggagag aggagtacga cgtgctggac     660
aagcgacgcg gacgcgaccc ggagatgggg gggaaaccac ggcggaaaaa ccctcaggaa     720
ggactgtaca cgaactcca gaaagacaag atggcggaag cctactcaga aatcgggatg     780
aagggagagc ggaggagggg aaagggtcac gacgggctgt accagggact gagcaccgcc     840
actaaggata cctacgatgc cttgcatatg caagcactcc caccccggta g              891
```

<210> SEQ ID NO 44
<211> LENGTH: 296
<212> TYPE: PRT
<213> ORGANISM: Artificial
<220> FEATURE:
<223> OTHER INFORMATION: Anti-HIV CAR LTG2328

<400> SEQUENCE: 44

```
Met Leu Leu Leu Val Thr Ser Leu Leu Leu Cys Glu Leu Pro His Pro
1               5                   10                  15
```

Ala Phe Leu Leu Ile Pro Asp Thr Trp Met Glu Trp Asp Arg Glu Ile
            20                  25                  30

Asn Asn Tyr Thr Ser Leu Ile His Ser Leu Ile Glu Glu Ser Gln Asn
            35                  40                  45

Gln Gln Glu Lys Asn Glu Gln Glu Leu Leu Glu Leu Asp Lys Trp Ala
50                  55                  60

Ser Leu Trp Asn Trp Phe Ala Ala Thr Thr Thr Pro Ala Pro Arg
65                  70                  75                  80

Pro Pro Thr Pro Ala Pro Thr Ile Ala Ser Gln Pro Leu Ser Leu Arg
                85                  90                  95

Pro Glu Ala Cys Arg Pro Ala Ala Gly Gly Ala Val His Thr Arg Gly
            100                 105                 110

Leu Asp Phe Ala Cys Asp Ile Tyr Ile Trp Ala Pro Leu Ala Gly Thr
            115                 120                 125

Cys Gly Val Leu Leu Leu Ser Leu Val Ile Thr Leu Tyr Cys Lys Arg
        130                 135                 140

Gly Arg Lys Lys Leu Leu Tyr Ile Phe Lys Gln Pro Phe Met Arg Pro
145                 150                 155                 160

Val Gln Thr Thr Gln Glu Glu Asp Gly Cys Ser Cys Arg Phe Pro Glu
                165                 170                 175

Glu Glu Glu Gly Gly Cys Glu Leu Arg Val Lys Phe Ser Arg Ser Ala
            180                 185                 190

Asp Ala Pro Ala Tyr Gln Gln Gly Gln Asn Gln Leu Tyr Asn Glu Leu
            195                 200                 205

Asn Leu Gly Arg Arg Glu Glu Tyr Asp Val Leu Asp Lys Arg Arg Gly
        210                 215                 220

Arg Asp Pro Glu Met Gly Gly Lys Pro Arg Arg Lys Asn Pro Gln Glu
225                 230                 235                 240

Gly Leu Tyr Asn Glu Leu Gln Lys Asp Lys Met Ala Glu Ala Tyr Ser
                245                 250                 255

Glu Ile Gly Met Lys Gly Glu Arg Arg Arg Gly Lys Gly His Asp Gly
            260                 265                 270

Leu Tyr Gln Gly Leu Ser Thr Ala Thr Lys Asp Thr Tyr Asp Ala Leu
        275                 280                 285

His Met Gln Ala Leu Pro Pro Arg
    290                 295

<210> SEQ ID NO 45
<211> LENGTH: 663
<212> TYPE: DNA
<213> ORGANISM: Artificial
<220> FEATURE:
<223> OTHER INFORMATION: Anti-HIV binders contained in LTG2325

<400> SEQUENCE: 45
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggcggc     300
ggaggcgggt cacaggtgca gctggtgcag tctggggagg cttggtaca gcctggaggg     360 tccctgagac tctcctgtgc agcctctgct ttcgatttct ctgattatga aatgagctgg     420

```
gtccgcgagg ctccagggaa ggggctggag tggattgggg aaatcaatga tagtggaaac    480
accatttaca atccgtccct caagagtcga gtcaccatct ccagagacaa ttccaagaac    540
acactgtatc tgcaaatgaa caccctgaga gccgaggaca cagccatata ttactgtgcg    600
atatatggtg gtaactccgg gggagagtac tggggccagg caccctggt caccgtctcc     660 tca                                                                   663
```

<210> SEQ ID NO 46
<211> LENGTH: 221
<212> TYPE: PRT
<213> ORGANISM: Artificial
<220> FEATURE:
<223> OTHER INFORMATION: Anti-HIV binders contained in LTG2325

<400> SEQUENCE: 46

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gln Val Gln Leu Val Gln Ser Gly
            100                 105                 110

Gly Gly Leu Val Gln Pro Gly Gly Ser Leu Arg Leu Ser Cys Ala Ala
        115                 120                 125

Ser Ala Phe Asp Phe Ser Asp Tyr Glu Met Ser Trp Val Arg Glu Ala
    130                 135                 140

Pro Gly Lys Gly Leu Glu Trp Ile Gly Glu Ile Asn Asp Ser Gly Asn
145                 150                 155                 160

Thr Ile Tyr Asn Pro Ser Leu Lys Ser Arg Val Thr Ile Ser Arg Asp
                165                 170                 175

Asn Ser Lys Asn Thr Leu Tyr Leu Gln Met Asn Thr Leu Arg Ala Glu
            180                 185                 190

Asp Thr Ala Ile Tyr Tyr Cys Ala Ile Tyr Gly Gly Asn Ser Gly Gly
        195                 200                 205

Glu Tyr Trp Gly Gln Gly Thr Leu Val Thr Val Ser Ser
    210                 215                 220
```

<210> SEQ ID NO 47
<211> LENGTH: 1416
<212> TYPE: DNA
<213> ORGANISM: Artificial
<220> FEATURE:
<223> OTHER INFORMATION: Anti-HIV CAR LTG2325

<400> SEQUENCE: 47

```
atgcttctcc tggtcacctc cctgctcctc tgcgaactgc ctcaccctgc cttccttctg    60
attcctgaca ccaagaaagt cgtgtacgga aagaagggag acactgtgga gctgacctgt   120
accgcaagcc agaagaagaa catccagttc cactggaaga actccaacca aatcaagatc   180
ctggggaacc agggttcctt cctgactaag ggaccctcaa agctgaacga ccgcgtggat   240
```

```
agcagacgct ccctgtggga ccagggaaac ttcccgctta tcattaagaa cctcaaacct    300
gaggactcgg atacctacat ctgcgaagtg gaggaccaga aggaggaggt gcagctggtg    360
gtggtgggcg gcggaggcgg gtcacaggtg cagctggtgc agtctggggg aggcttggta    420
cagcctggag ggtccctgag actctcctgt gcagcctctg ctttcgattt ctctgattat    480
gaaatgagct gggtccgcga ggctccaggg aaggggctgg agtggattgg ggaaatcaat    540
gatagtggaa acaccattta caatccgtcc ctcaagagtc gagtcaccat ctccagagac    600
aattccaaga acacactgta tctgcaaatg aacaccctga gagccgagga cacagccata    660
tattactgtg cgatatatgg tggtaactcc gggggagagt actggggcca gggcaccctg    720
gtcaccgtct cctcagcggc cgcaactacc acccctgccc ctcggccgcc gactccggcc    780
ccaaccatcg caagccaacc cctctccttg cgccccgaag cttgccgccc ggccgcgggt    840
ggagccgtgc atacccgggg gctggacttt gcctgcgata tctacatttg gccccgctg     900 gccggcactt gcggcgtgct cctgctgtcg ctggtcatca cccttactg caagaggggc     960 cggaagaagc tgctttacat cttcaagcag ccgttcatgc ggcccgtgca gacgactcag   1020
gaagaggacg gatgctcgtg cagattccct gaggaggaag aggggggatg cgaactgcgc   1080
gtcaagttct cacggtccgc cgacgccccc gcatatcaac agggccagaa tcagctctac   1140
aacgagctga acctgggaag agagaggag tacgacgtgc tggacaagcg acgcggacgc     1200
gacccggaga tggggggaa accacggcgg aaaaaccctc aggaaggact gtacaacgaa     1260
ctccagaaag acaagatggc ggaagcctac tcagaaatcg ggatgaaggg agagcggagg   1320
aggggaaagg gtcacgacgg gctgtaccag ggactgagca ccgccactaa ggatacctac   1380
gatgccttgc atatgcaagc actcccaccc cggtag                             1416
```

<210> SEQ ID NO 48
<211> LENGTH: 471
<212> TYPE: PRT
<213> ORGANISM: Artificial
<220> FEATURE:
<223> OTHER INFORMATION: Anti-HIV CAR LTG2325

<400> SEQUENCE: 48

```
Met Leu Leu Leu Val Thr Ser Leu Leu Cys Glu Leu Pro His Pro
1               5                   10                  15

Ala Phe Leu Leu Ile Pro Asp Thr Lys Lys Val Val Tyr Gly Lys Lys
                20                  25                  30

Gly Asp Thr Val Glu Leu Thr Cys Thr Ala Ser Gln Lys Lys Asn Ile
            35                  40                  45

Gln Phe His Trp Lys Asn Ser Asn Gln Ile Lys Ile Leu Gly Asn Gln
        50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
                100                 105                 110

Gln Lys Glu Glu Val Gln Leu Val Val Gly Gly Gly Gly Ser
            115                 120                 125

Gln Val Gln Leu Val Gln Ser Gly Gly Gly Leu Val Gln Pro Gly Gly
        130                 135                 140

Ser Leu Arg Leu Ser Cys Ala Ala Ser Ala Phe Asp Phe Ser Asp Tyr
```

```
            145                 150                 155                 160
        Glu Met Ser Trp Val Arg Glu Ala Pro Gly Lys Gly Leu Glu Trp Ile
                            165                 170                 175
        Gly Glu Ile Asn Asp Ser Gly Asn Thr Ile Tyr Asn Pro Ser Leu Lys
                            180                 185                 190
        Ser Arg Val Thr Ile Ser Arg Asp Asn Ser Lys Asn Thr Leu Tyr Leu
                            195                 200                 205
        Gln Met Asn Thr Leu Arg Ala Glu Asp Thr Ala Ile Tyr Tyr Cys Ala
                    210                 215                 220
        Ile Tyr Gly Gly Asn Ser Gly Gly Tyr Trp Gly Gln Gly Thr Leu
        225                 230                 235                 240
        Val Thr Val Ser Ser Ala Ala Thr Thr Pro Ala Pro Arg Pro
                            245                 250                 255
        Pro Thr Pro Ala Pro Thr Ile Ala Ser Gln Pro Leu Ser Leu Arg Pro
                    260                 265                 270
        Glu Ala Cys Arg Pro Ala Ala Gly Gly Ala Val His Thr Arg Gly Leu
                    275                 280                 285
        Asp Phe Ala Cys Asp Ile Tyr Ile Trp Ala Pro Leu Ala Gly Thr Cys
                290                 295                 300
        Gly Val Leu Leu Leu Ser Leu Val Ile Thr Leu Tyr Cys Lys Arg Gly
        305                 310                 315                 320
        Arg Lys Lys Leu Leu Tyr Ile Phe Lys Gln Pro Phe Met Arg Pro Val
                            325                 330                 335
        Gln Thr Thr Gln Glu Glu Asp Gly Cys Ser Cys Arg Phe Pro Glu Glu
                    340                 345                 350
        Glu Glu Gly Gly Cys Glu Leu Arg Val Lys Phe Ser Arg Ser Ala Asp
                    355                 360                 365
        Ala Pro Ala Tyr Gln Gln Gly Gln Asn Gln Leu Tyr Asn Glu Leu Asn
                    370                 375                 380
        Leu Gly Arg Arg Glu Glu Tyr Asp Val Leu Asp Lys Arg Arg Gly Arg
        385                 390                 395                 400
        Asp Pro Glu Met Gly Gly Lys Pro Arg Arg Lys Asn Pro Gln Glu Gly
                            405                 410                 415
        Leu Tyr Asn Glu Leu Gln Lys Asp Lys Met Ala Glu Ala Tyr Ser Glu
                    420                 425                 430
        Ile Gly Met Lys Gly Glu Arg Arg Arg Gly Lys Gly His Asp Gly Leu
                    435                 440                 445
        Tyr Gln Gly Leu Ser Thr Ala Thr Lys Asp Thr Tyr Asp Ala Leu His
            450                 455                 460
        Met Gln Ala Leu Pro Pro Arg
        465                 470

<210> SEQ ID NO 49
<211> LENGTH: 678
<212> TYPE: DNA
<213> ORGANISM: Artificial
<220> FEATURE:
<223> OTHER INFORMATION: Anti-HIV binders contained in CAR LTG2313

<400> SEQUENCE: 49
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
```

```
acctacatct gcgaagtgga ggaccagaag gaggaggtgc agctggtggt ggtgggcgga      300
ggtggcggtt caggcggagg ggggagtcag gtgcagctgg tgcagtctgg gggaggcttg      360
gtacagcctg gagggtccct gagactctcc tgtgcagcct ctgctttcga tttctctgat      420
tatgaaatga gctgggtccg cgaggctcca gggaaggggc tggagtggat tggggaaatc      480
aatgatagtg aaacaccat ttacaatccg tccctcaaga gtcgagtcac catctccaga       540
gacaattcca agaacacact gtatctgcaa atgaacaccc tgagagccga ggacacagcc      600
atatattact gtgcgatata tggtggtaac tccggggag agtactgggg ccagggcacc       660
ctggtcaccg tctcctca                                                    678
```

<210> SEQ ID NO 50
<211> LENGTH: 226
<212> TYPE: PRT
<213> ORGANISM: Artificial
<220> FEATURE:
<223> OTHER INFORMATION: Anti-HIV binders contained in CAR LTG2313

<400> SEQUENCE: 50

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Gly Ser Gln Val Gln
            100                 105                 110

Leu Val Gln Ser Gly Gly Gly Leu Val Gln Pro Gly Gly Ser Leu Arg
        115                 120                 125

Leu Ser Cys Ala Ala Ser Ala Phe Asp Phe Ser Asp Tyr Glu Met Ser
    130                 135                 140

Trp Val Arg Glu Ala Pro Gly Lys Gly Leu Glu Trp Ile Gly Glu Ile
145                 150                 155                 160

Asn Asp Ser Gly Asn Thr Ile Tyr Asn Pro Ser Leu Lys Ser Arg Val
                165                 170                 175

Thr Ile Ser Arg Asp Asn Ser Lys Asn Thr Leu Tyr Leu Gln Met Asn
            180                 185                 190

Thr Leu Arg Ala Glu Asp Thr Ala Ile Tyr Tyr Cys Ala Ile Tyr Gly
        195                 200                 205

Gly Asn Ser Gly Gly Glu Tyr Trp Gly Gln Gly Thr Leu Val Thr Val
    210                 215                 220

Ser Ser
225
```

<210> SEQ ID NO 51
<211> LENGTH: 1431
<212> TYPE: DNA
<213> ORGANISM: Artificial
<220> FEATURE:
<223> OTHER INFORMATION: Anti-HIV CAR LTG2313

<400> SEQUENCE: 51

```
atgcttctcc tggtcaccct cctgctcctc tgcgaactgc ctcaccctgc cttccttctg      60
attcctgaca ccaagaaagt cgtgtacgga agaagggag acactgtgga gctgacctgt     120
accgcaagcc agaagaagaa catccagttc cactggaaga actccaacca aatcaagatc    180
ctggggaacc agggttcctt cctgactaag ggaccctcaa agctgaacga ccgcgtggat    240
agcagacgct ccctgtggga ccagggaaac ttcccgctta tcattaagaa cctcaaacct    300
gaggactcgg atacctacat ctgcgaagtg gaggaccaga aggaggaggt gcagctggtg    360
gtggtgggcg gaggtggcgg ttcaggcgga ggggggagtc aggtgcagct ggtgcagtct    420
ggggaggct tggtacagcc tggagggtcc ctgagactct cctgtgcagc ctctgctttc    480
gatttctctg attatgaaat gagctgggtc cgcgaggctc agggaaggg gctggagtgg    540
attggggaaa tcaatgatag tggaaacacc atttacaatc cgtccctcaa gagtcgagtc    600
accatctcca gagacaattc caagaacaca ctgtatctgc aaatgaacac cctgagagcc    660
gaggacacag ccatatatta ctgtgcgata tatggtggta actccggggg agagtactgg    720
ggccagggca ccctggtcac cgtctcctca gcggccgcaa ctaccacccc tgcccctcgg    780
ccgccgactc cggccccaac catcgcaagc caacccctct ccttgcgccc cgaagcttgc    840
cgccggccg cgggtggagc cgtgcatacc cgggggctgg actttgcctg cgatatctac    900
atttgggccc cgctggccgg cacttgcggc gtgctcctgc tgtcgctggt catcacccct    960
tactgcaaga gggccggaa gaagctgctt tacatcttca gcagccgtt catgcggccc   1020
gtgcagacga ctcaggaaga ggacggatgc tcgtgcagat ccctgaagga ggaagagggg   1080
ggatgcgaac tgcgcgtcaa gttctcacgg tccgccgacg ccccgcata tcaacagggc   1140
cagaatcagc tctacaacga gctgaacctg gaaggagag aggagtacga cgtgctggac   1200
aagcgacgcg gacgcgaccc ggagatgggg gggaaaccac ggcggaaaaa ccctcaggaa   1260
ggactgtaca cgaactcca gaaagacaag atggcggaag cctactcaga aatcgggatg   1320
aaggagagc ggaggagggg aaagggtcac gacgggctgt accagggact gagcaccgcc   1380
actaaggata cctacgatgc cttgcatatg caagcactcc caccccggta g           1431
```

<210> SEQ ID NO 52
<211> LENGTH: 476
<212> TYPE: PRT
<213> ORGANISM: Artificial
<220> FEATURE:
<223> OTHER INFORMATION: Anti-HIV CAR LTG2313

<400> SEQUENCE: 52

```
Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95
```

Asn Leu Lys Pro Glu Asp Ser Asp Thr Tyr Ile Cys Glu Val Glu Asp
                100                 105                 110

Gln Lys Glu Glu Val Gln Leu Val Val Gly Gly Gly Gly Ser
        115                 120                 125

Gly Gly Gly Gly Ser Gln Val Gln Leu Val Gln Ser Gly Gly Gly Leu
        130                 135                 140

Val Gln Pro Gly Gly Ser Leu Arg Leu Ser Cys Ala Ala Ser Ala Phe
145                 150                 155                 160

Asp Phe Ser Asp Tyr Glu Met Ser Trp Val Arg Glu Ala Pro Gly Lys
                165                 170                 175

Gly Leu Glu Trp Ile Gly Glu Ile Asn Asp Ser Gly Asn Thr Ile Tyr
            180                 185                 190

Asn Pro Ser Leu Lys Ser Arg Val Thr Ile Ser Arg Asp Asn Ser Lys
            195                 200                 205

Asn Thr Leu Tyr Leu Gln Met Asn Thr Leu Arg Ala Glu Asp Thr Ala
210                 215                 220

Ile Tyr Tyr Cys Ala Ile Tyr Gly Gly Asn Ser Gly Gly Glu Tyr Trp
225                 230                 235                 240

Gly Gln Gly Thr Leu Val Thr Val Ser Ser Ala Ala Thr Thr Thr
                245                 250                 255

Pro Ala Pro Arg Pro Pro Thr Pro Ala Pro Thr Ile Ala Ser Gln Pro
                260                 265                 270

Leu Ser Leu Arg Pro Glu Ala Cys Arg Pro Ala Ala Gly Gly Ala Val
                275                 280                 285

His Thr Arg Gly Leu Asp Phe Ala Cys Asp Ile Tyr Ile Trp Ala Pro
            290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Asp Gly Cys Ser Cys
                340                 345                 350

Arg Phe Pro Glu Glu Glu Glu Gly Gly Cys Glu Leu Arg Val Lys Phe
                355                 360                 365

Ser Arg Ser Ala Asp Ala Pro Ala Tyr Gln Gln Gly Gln Asn Gln Leu
370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
                420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 53
<211> LENGTH: 693
<212> TYPE: DNA
<213> ORGANISM: Artificial
<220> FEATURE:
<223> OTHER INFORMATION: Anti-HIV binders contained in LTG1946

<400> SEQUENCE: 53

```
aagaaagtcg tgtacggaaa gaagggagac actgtggagc tgacctgtac cgcaagccag    60
aagaagaaca tccagttcca ctggaagaac tccaaccaaa tcaagatcct ggggaaccag   120
ggttccttcc tgactaaggg accctcaaag ctgaacgacc gcgtggatag cagacgctcc   180
ctgtgggacc agggaaactt cccgcttatc attaagaacc tcaaacctga ggactcggat   240
acctacatct gcgaagtgga ggaccagaag gaggaggtgc agctggtggt ggtgggcgga   300
ggtggcggtt caggcggagg ggggagtgga ggtgggggaa gccaggtgca gctggtgcag   360
tctggggag gcttggtaca gcctggaggg tccctgagac tctcctgtgc agcctctgct   420
ttcgatttct ctgattatga aatgagctgg gtccgcgagg ctccagggaa ggggctggag   480
tggattgggg aaatcaatga tagtggaaac accatttaca atccgtccct caagagtcga   540
gtcaccatct ccagagacaa ttccaagaac acactgtatc tgcaaatgaa caccctgaga   600
gccgaggaca cagccatata ttactgtgcg atatatggtg gtaactccgg gggagagtac   660
tggggccagg gcaccctggt caccgtctcc tca                                693
```

<210> SEQ ID NO 54
<211> LENGTH: 231
<212> TYPE: PRT
<213> ORGANISM: Artificial
<220> FEATURE:
<223> OTHER INFORMATION: Anti-HIV binders contained in LTG1946

<400> SEQUENCE: 54

```
Lys Lys Val Val Tyr Gly Lys Lys Gly Asp Thr Val Glu Leu Thr Cys
  1               5                  10                  15
Thr Ala Ser Gln Lys Lys Asn Ile Gln Phe His Trp Lys Asn Ser Asn
             20                  25                  30
Gln Ile Lys Ile Leu Gly Asn Gln Gly Ser Phe Leu Thr Lys Gly Pro
         35                  40                  45
Ser Lys Leu Asn Asp Arg Val Asp Ser Arg Arg Ser Leu Trp Asp Gln
     50                  55                  60
Gly Asn Phe Pro Leu Ile Ile Lys Asn Leu Lys Pro Glu Asp Ser Asp
 65                  70                  75                  80
Thr Tyr Ile Cys Glu Val Glu Asp Gln Lys Glu Glu Val Gln Leu Val
                 85                  90                  95
Val Val Gly Gly Gly Gly Ser Gly Gly Gly Ser Gly Gly
            100                 105                 110
Gly Ser Gln Val Gln Leu Val Gln Ser Gly Gly Leu Val Gln Pro
            115                 120                 125
Gly Gly Ser Leu Arg Leu Ser Cys Ala Ala Ser Ala Phe Asp Phe Ser
        130                 135                 140
Asp Tyr Glu Met Ser Trp Val Arg Glu Ala Pro Gly Lys Gly Leu Glu
145                 150                 155                 160
Trp Ile Gly Glu Ile Asn Asp Ser Gly Asn Thr Ile Tyr Asn Pro Ser
                165                 170                 175
Leu Lys Ser Arg Val Thr Ile Ser Arg Asp Asn Ser Lys Asn Thr Leu
            180                 185                 190
Tyr Leu Gln Met Asn Thr Leu Arg Ala Glu Asp Thr Ala Ile Tyr Tyr
        195                 200                 205
Cys Ala Ile Tyr Gly Gly Asn Ser Gly Gly Glu Tyr Trp Gly Gln Gly
    210                 215                 220
```

Thr Leu Val Thr Val Ser Ser
225                 230

<210> SEQ ID NO 55
<211> LENGTH: 1446
<212> TYPE: DNA
<213> ORGANISM: Artificial
<220> FEATURE:
<223> OTHER INFORMATION: Anti-HIV CAR LTG1946

<400> SEQUENCE: 55

```
atgcttctcc tggtcacctc cctgctcctc tgcgaactgc ctcaccctgc cttccttctg      60
attcctgaca ccaagaaagt cgtgtacgga agaagggag  acactgtgga gctgacctgt    120
accgcaagcc agaagaagaa catccagttc cactggaaga actccaacca aatcaagatc    180
ctggggaacc agggttcctt cctgactaag ggaccctcaa agctgaacga ccgcgtggat    240
agcagacgct ccctgtggga ccagggaaac ttcccgctta tcattaagaa cctcaaacct    300
gaggactcgg atacctacat ctgcgaagtg gaggaccaga aggaggaggt gcagctggtg    360
gtggtgggcg gagtggcgg ttcaggcgga ggggggagtg gaggtggggg aagccaggtg     420
cagctggtgc agtctggggg aggcttggta cagcctggag ggtccctgag actctcctgt    480
gcagcctctg ctttcgattt ctctgattat gaaatgagct gggtccgcga ggctccaggg    540
aaggggctgg agtggattgg gaaaatcaat gatagtggaa acaccattta caatccgtcc    600
ctcaagagtc gagtcaccat ctccagagac aattccaaga cacactgta  tctgcaaatg    660
aacaccctga gaccgagga cacagccata tattactgtg cgatatatgg tggtaactcc    720
ggggggagt actggggcca gggcaccctg gtcaccgtct cctcagcggc cgcaactacc    780
accccgtccc ctcggccgcc gactccggcc ccaaccatcg caagccaacc cctctccttg    840
cgccccgaag cttgccgccc ggccgcgggt ggagccgtgc atacccgggg gctggacttt    900
gcctgcgata tctacatttg gccccgctg ccggcactt  gcggcgtgct  cctgctgtcg    960
ctggtcatca ccctttactg caagaggggc cggaagaagc tgctttacat cttcaagcag   1020
ccgttcatgc ggcccgtgca gacgactcag gaagaggacg gatgctcgtg cagattccct   1080
gaggaggaag aggggggatg cgaactgcgc gtcaagttct cacggtccgc cgacgccccc   1140
gcatatcaac agggccagaa tcagctctac aacgagctga acctgggaag gagagaggag   1200
tacgacgtgc tggacaagcg acgcggacgc gacccggaga tggggggaa  accacggcgg    1260
aaaaaccctc aggaaggact gtacaacgaa ctccagaaag acaagatggc ggaagcctac   1320
tcagaaatcg ggatgaaggg agagcggagg aggggaagg  gtcacgacgg gctgtaccag   1380
ggactgagca ccgccactaa ggatacctac gatgccttgc atatgcaagc actcccaccc   1440
cggtag                                                              1446
```

<210> SEQ ID NO 56
<211> LENGTH: 481
<212> TYPE: PRT
<213> ORGANISM: Artificial
<220> FEATURE:
<223> OTHER INFORMATION: Anti-HIV CAR LTG1946

<400> SEQUENCE: 56

Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

-continued

```
Gly Asp Thr Val Glu Leu Thr Cys Thr Ala Ser Gln Lys Lys Asn Ile
         35                  40                  45

Gln Phe His Trp Lys Asn Ser Asn Gln Ile Lys Ile Leu Gly Asn Gln
 50                  55                  60

Gly Ser Phe Leu Thr Lys Gly Pro Ser Lys Leu Asn Asp Arg Val Asp
 65                  70                  75                  80

Ser Arg Arg Ser Leu Trp Asp Gln Gly Asn Phe Pro Leu Ile Ile Lys
                 85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Val Gly Gly Gly Gly Gly Ser
        115                 120                 125

Gly Gly Gly Gly Ser Gly Gly Gly Ser Gln Val Gln Leu Val Gln
        130                 135                 140

Ser Gly Gly Gly Leu Val Gln Pro Gly Gly Ser Leu Arg Leu Ser Cys
145                 150                 155                 160

Ala Ala Ser Ala Phe Asp Phe Ser Asp Tyr Glu Met Ser Trp Val Arg
                165                 170                 175

Glu Ala Pro Gly Lys Gly Leu Glu Trp Ile Gly Glu Ile Asn Asp Ser
            180                 185                 190

Gly Asn Thr Ile Tyr Asn Pro Ser Leu Lys Ser Arg Val Thr Ile Ser
        195                 200                 205

Arg Asp Asn Ser Lys Asn Thr Leu Tyr Leu Gln Met Asn Thr Leu Arg
    210                 215                 220

Ala Glu Asp Thr Ala Ile Tyr Tyr Cys Ala Ile Tyr Gly Gly Asn Ser
225                 230                 235                 240

Gly Gly Glu Tyr Trp Gly Gln Gly Thr Leu Val Thr Val Ser Ser Ala
                245                 250                 255

Ala Ala Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
```

-continued

```
                450                 455                 460
Ala Thr Lys Asp Thr Tyr Asp Ala Leu His Met Gln Ala Leu Pro Pro
465                 470                 475                 480

Arg

<210> SEQ ID NO 57
<211> LENGTH: 708
<212> TYPE: DNA
<213> ORGANISM: Artificial
<220> FEATURE:
<223> OTHER INFORMATION: Anti-HIV binders contained in LTG2326

<400> SEQUENCE: 57
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggcggc     300
ggaggcgggt caggtggcgg tggtagtggc ggtggcggtt caggcggtgg tgggagtcag     360
gtgcagctgg tgcagtctgg gggaggcttg gtacagcctg agggtccct gagactctcc      420 tgtgcagcct ctgctttcga tttctctgat tatgaaatga gctgggtccg cgaggctcca     480 gggaagggc tggagtggat tggggaaatc aatgatagtg aaacaccat ttacaatccg       540 tccctcaaga gtcgagtcac catctccaga gacaattcca agaacacact gtatctgcaa     600
atgaacaccc tgagagccga ggacacagcc atatattact gtgcgatata tggtggtaac     660
tccgggggag agtactgggg ccagggcacc ctggtcaccg tctcctca                  708

<210> SEQ ID NO 58
<211> LENGTH: 236
<212> TYPE: PRT
<213> ORGANISM: Artificial
<220> FEATURE:
<223> OTHER INFORMATION: Anti-HIV binders contained in LTG2326

<400> SEQUENCE: 58

Lys Lys Val Val Tyr Gly Lys Lys Gly Asp Thr Val Glu Leu Thr Cys
1               5                  10                  15

Thr Ala Ser Gln Lys Lys Asn Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Val Asp Ser Arg Arg Ser Leu Trp Asp Gln
        50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110

Gly Ser Gly Gly Gly Gly Ser Gln Val Gln Leu Val Gln Ser Gly Gly
        115                 120                 125

Gly Leu Val Gln Pro Gly Gly Ser Leu Arg Leu Ser Cys Ala Ala Ser
    130                 135                 140

Ala Phe Asp Phe Ser Asp Tyr Glu Met Ser Trp Val Arg Glu Ala Pro
```

```
                145                 150                 155                 160
Gly Lys Gly Leu Glu Trp Ile Gly Glu Ile Asn Asp Ser Gly Asn Thr
                    165                 170                 175

Ile Tyr Asn Pro Ser Leu Lys Ser Arg Val Thr Ile Ser Arg Asp Asn
                180                 185                 190

Ser Lys Asn Thr Leu Tyr Leu Gln Met Asn Thr Leu Arg Ala Glu Asp
            195                 200                 205

Thr Ala Ile Tyr Tyr Cys Ala Ile Tyr Gly Gly Asn Ser Gly Gly Glu
        210                 215                 220

Tyr Trp Gly Gln Gly Thr Leu Val Thr Val Ser Ser
225                 230                 235

<210> SEQ ID NO 59
<211> LENGTH: 1461
<212> TYPE: DNA
<213> ORGANISM: Artificial
<220> FEATURE:
<223> OTHER INFORMATION: Anti-HIV CAR LTG2326

<400> SEQUENCE: 59
```

| | | | | |
|---|---|---|---|---|
| atgcttctcc | tggtcacctc | cctgctcctc | tgcgaactgc | ctcaccctgc cttccttctg | 60 |
| attcctgaca | ccaagaaagt | cgtgtacgga | agaagggag | acactgtgga gctgacctgt | 120 |
| accgcaagcc | agaagaagaa | catccagttc | cactggaaga | actccaacca atcaagatc | 180 |
| ctggggaacc | agggttcctt | cctgactaag | ggaccctcaa | agctgaacga ccgcgtggat | 240 |
| agcagacgct | ccctgtggga | ccagggaaac | ttcccgctta | tcattaagaa cctcaaacct | 300 |
| gaggactcgg | atacctacat | ctgcgaagtg | gaggaccaga | aggaggaggt gcagctggtg | 360 |
| gtggtgggcg | gcggaggcgg | gtcaggtggc | ggtggtagtg | gcggtggcgg ttcaggcggt | 420 |
| ggtgggagtc | aggtgcagct | ggtgcagtct | ggggaggct | tggtacagcc tggagggtcc | 480 |
| ctgagactct | cctgtgcagc | ctctgctttc | gatttctctg | attatgaaat gagctgggtc | 540 |
| cgcgaggctc | cagggaaggg | gctggagtgg | attgggaaa | tcaatgatag tggaaacacc | 600 |
| atttacaatc | cgtccctcaa | gagtcgagtc | accatctcca | gagacaattc caagaacaca | 660 |
| ctgtatctgc | aaatgaacac | cctgagagcc | gaggacacag | ccatatatta ctgtgcgata | 720 |
| tatggtggta | actccggggg | agagtactgg | ggccagggca | ccctggtcac cgtctcctca | 780 |
| gcggccgcaa | ctaccacccc | tgcccctcgg | ccgccgactc | cggccccaac catcgcaagc | 840 |
| caaccctct | ccttgcgccc | cgaagcttgc | cgcccggccg | cgggtggagc cgtgcatacc | 900 |
| cgggggctgg | actttgcctg | cgatatctac | atttgggccc | cgctggccgg cacttgcggc | 960 |
| gtgctcctgc | tgtcgctggt | catcacccct | tactgcaaga | ggggccggaa gaagctgctt | 1020 |
| tacatcttca | agcagccgtt | catgcggccc | gtgcagacga | ctcaggaaga ggacggatgc | 1080 |
| tcgtgcagat | tccctgagga | ggaagagggg | ggatgcgaac | tgcgcgtcaa gttctcacgg | 1140 |
| tccgccgacg | cccccgcata | tcaacagggc | cagaatcagc | tctacaacga gctgaacctg | 1200 |
| ggaaggagag | aggagtacga | cgtgctggac | aagcgacgcg | gacgcgaccc ggagatgggg | 1260 |
| gggaaaccac | ggcggaaaaa | ccctcaggaa | ggactgtaca | acgaactcca gaaagacaag | 1320 |
| atggcggaag | cctactcaga | aatcgggatg | aaggagagc | ggaggagggg aaagggtcac | 1380 |
| gacgggctgt | accagggact | gagcaccgcc | actaaggata | cctacgatgc cttgcatatg | 1440 |
| caagcactcc | caccccggta | g | | | 1461 |

```
<210> SEQ ID NO 60
```

<211> LENGTH: 486
<212> TYPE: PRT
<213> ORGANISM: Artificial
<220> FEATURE:
<223> OTHER INFORMATION: Anti-HIV CAR LTG2326

<400> SEQUENCE: 60

```
Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Gly Gly Gly Gly Gly Gly Ser
        115                 120                 125

Gly Gly Gly Gly Ser Gly Gly Gly Ser Gly Gly Gly Ser Gln
    130                 135                 140

Val Gln Leu Val Gln Ser Gly Gly Gly Leu Val Gln Pro Gly Gly Ser
145                 150                 155                 160

Leu Arg Leu Ser Cys Ala Ala Ser Ala Phe Asp Phe Ser Asp Tyr Glu
                165                 170                 175

Met Ser Trp Val Arg Glu Ala Pro Gly Lys Gly Leu Glu Trp Ile Gly
            180                 185                 190

Glu Ile Asn Asp Ser Gly Asn Thr Ile Tyr Asn Pro Ser Leu Lys Ser
        195                 200                 205

Arg Val Thr Ile Ser Arg Asp Asn Ser Lys Asn Thr Leu Tyr Leu Gln
    210                 215                 220

Met Asn Thr Leu Arg Ala Glu Asp Thr Ala Ile Tyr Tyr Cys Ala Ile
225                 230                 235                 240

Tyr Gly Gly Asn Ser Gly Gly Glu Tyr Trp Gly Gln Gly Thr Leu Val
                245                 250                 255

Thr Val Ser Ser Ala Ala Ala Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380
```

```
Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
        420                 425                 430

Tyr Asn Glu Leu Gln Lys Asp Lys Met Ala Glu Ala Tyr Ser Glu Ile
    435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
            485
```

<210> SEQ ID NO 61
<211> LENGTH: 723
<212> TYPE: DNA
<213> ORGANISM: Artificial
<220> FEATURE:
<223> OTHER INFORMATION: Linked Anti-HIV binder contained in LTG1947

<400> SEQUENCE: 61

```
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggcggc     300
ggaggcgggt caggtggcgg tggtagtggc ggtggcggtt caggcggtgg tgggagtggg     360
ggaggaggca gccaggtgca gctggtgcag tctggggggag gcttggtaca gcctggaggg     420
tccctgagac tctcctgtgc agcctctgct ttcgatttct ctgattatga aatgagctgg     480
gtccgcgagg ctccagggaa ggggctggag tggattgggg aaatcaatga tagtggaaac     540
accatttaca atccgtccct caagagtcga gtcaccatct ccagagacaa ttccaagaac     600
acactgtatc tgcaaatgaa caccctgaga gccgaggaca cagccatata ttactgtgcg     660
atatatggtg gtaactccgg gggagagtac tggggccagg gcaccctggt caccgtctcc     720
tca                                                                   723
```

<210> SEQ ID NO 62
<211> LENGTH: 241
<212> TYPE: PRT
<213> ORGANISM: Artificial
<220> FEATURE:
<223> OTHER INFORMATION: Linked Anti-HIV binder contained in LTG1947

<400> SEQUENCE: 62

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60
```

Gly Asn Phe Pro Leu Ile Ile Lys Asn Leu Lys Pro Glu Asp Ser Asp
65                  70                  75                  80

Thr Tyr Ile Cys Glu Val Asp Gln Lys Glu Val Gln Leu Val
            85                  90                  95

Val Val Gly Gly Gly Gly Ser Gly Gly Gly Ser Gly Gly Gly
            100                 105                 110

Gly Ser Gly Gly Gly Gly Ser Gly Gly Gly Ser Gln Val Gln Leu
            115                 120                 125

Val Gln Ser Gly Gly Gly Leu Val Gln Pro Gly Gly Ser Leu Arg Leu
    130                 135                 140

Ser Cys Ala Ala Ser Ala Phe Asp Phe Ser Asp Tyr Glu Met Ser Trp
145                 150                 155                 160

Val Arg Glu Ala Pro Gly Lys Gly Leu Glu Trp Ile Gly Glu Ile Asn
                165                 170                 175

Asp Ser Gly Asn Thr Ile Tyr Asn Pro Ser Leu Lys Ser Arg Val Thr
            180                 185                 190

Ile Ser Arg Asp Asn Ser Lys Asn Thr Leu Tyr Leu Gln Met Asn Thr
        195                 200                 205

Leu Arg Ala Glu Asp Thr Ala Ile Tyr Tyr Cys Ala Ile Tyr Gly Gly
    210                 215                 220

Asn Ser Gly Gly Glu Tyr Trp Gly Gln Gly Thr Leu Val Thr Val Ser
225                 230                 235                 240

Ser

<210> SEQ ID NO 63
<211> LENGTH: 1476
<212> TYPE: DNA
<213> ORGANISM: Artificial
<220> FEATURE:
<223> OTHER INFORMATION: Anti-HIV CAR LTG1947

<400> SEQUENCE: 63
atgcttctcc tggtcacctc cctgctcctc tgcgaactgc ctcaccctgc cttccttctg    60
attcctgaca ccaagaaagt cgtgtacgga agaagggag acactgtgga gctgacctgt   120
accgcaagcc agaagaagaa catccagttc cactggaaga actccaacca aatcaagatc   180
ctggggaacc agggttcctt cctgactaag ggaccctcaa agctgaacga ccgcgtggat   240
agcagacgct ccctgtggga ccagggaaac ttcccgctta tcattaagaa cctcaaacct   300
gaggactcgg ataccacat ctgcgaagtg gaggaccaga aggaggaggt gcagctggtg   360
gtggtgggcg gcggaggcgg gtcaggtggc ggtggtagtg gcggtggcgg ttcaggcggt   420
ggtgggagtg ggggaggagg cagccaggtg cagctggtgc agtctggggg aggcttggta   480
cagcctggag gctccctgag actctcctgt gcagcctctg ctttcgattt ctctgattat   540
gaaatgagct gggtccgcga ggctccaggg aaggggctgg agtggattgg ggaaatcaat   600
gatagtggaa acaccattta caatccgtcc ctcaagagtc gagtcaccat ctccagagac   660
aattccaaga acacactgta tctgcaaatg aacaccctga gagccgagga cacagccata   720
tattactgtg cgatatatgg tggtaactcc gggggagagt actggggcca gggcaccctg   780
gtcaccgtct cctcagcggc cgcaactacc acccctgccc ctcggccgcc gactccggcc   840
ccaaccatcg caagccaacc cctctccttg cgccccgaag cttgccgccc ggccgcgggt   900
ggagccgtgc atacccgggg gctggacttt gcctgcgata tctacatttg ggcccccgctg   960
gccggcactt gcggcgtgct cctgctgtcg ctggtcatca ccctttactg caagagggc  1020

```
cggaagaagc tgctttacat cttcaagcag ccgttcatgc ggcccgtgca gacgactcag    1080
gaagaggacg gatgctcgtg cagattccct gaggaggaag aggggggatg cgaactgcgc    1140
gtcaagttct cacggtccgc cgacgccccc gcatatcaac agggccagaa tcagctctac    1200
aacgagctga actgggaag gagagaggag tacgacgtgc tggacaagcg acgcggacgc    1260
gacccggaga tgggggggaa accacggcgg aaaaaccctc aggaaggact gtacaacgaa    1320
ctccagaaag acaagatggc ggaagcctac tcagaaatcg ggatgaaggg agagcggagg    1380
aggggaaagg gtcacgacgg gctgtaccag ggactgagca ccgccactaa ggatacctac    1440
gatgccttgc atatgcaagc actcccaccc cggtag                              1476
```

<210> SEQ ID NO 64
<211> LENGTH: 491
<212> TYPE: PRT
<213> ORGANISM: Artificial
<220> FEATURE:
<223> OTHER INFORMATION: Anti-HIV CAR LTG1947

<400> SEQUENCE: 64

```
Met Leu Leu Leu Val Thr Ser Leu Leu Cys Glu Leu Pro His Pro
1               5                   10                  15

Ala Phe Leu Leu Ile Pro Asp Thr Lys Lys Val Tyr Gly Lys Lys
                20                  25                  30

Gly Asp Thr Val Glu Leu Thr Cys Thr Ala Ser Gln Lys Asn Ile
            35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
                100                 105                 110

Gln Lys Glu Glu Val Gln Leu Val Val Val Gly Gly Gly Gly Ser
            115                 120                 125

Gly Gly Gly Gly Ser Gly Gly Gly Ser Gly Gly Gly Ser Gly
        130                 135                 140

Gly Gly Gly Ser Gln Val Gln Leu Val Gln Ser Gly Gly Gly Leu Val
145                 150                 155                 160

Gln Pro Gly Gly Ser Leu Arg Leu Ser Cys Ala Ala Ser Ala Phe Asp
                165                 170                 175

Phe Ser Asp Tyr Glu Met Ser Trp Val Arg Glu Ala Pro Gly Lys Gly
                180                 185                 190

Leu Glu Trp Ile Gly Glu Ile Asn Asp Ser Gly Asn Thr Ile Tyr Asn
            195                 200                 205

Pro Ser Leu Lys Ser Arg Val Thr Ile Ser Arg Asp Asn Ser Lys Asn
        210                 215                 220

Thr Leu Tyr Leu Gln Met Asn Thr Leu Arg Ala Glu Asp Thr Ala Ile
225                 230                 235                 240

Tyr Tyr Cys Ala Ile Tyr Gly Gly Asn Ser Gly Gly Glu Tyr Trp Gly
                245                 250                 255

Gln Gly Thr Leu Val Thr Val Ser Ser Ala Ala Ala Thr Thr Thr Pro
            260                 265                 270

Ala Pro Arg Pro Pro Thr Pro Ala Pro Thr Ile Ala Ser Gln Pro Leu
```

```
                   275                 280                 285
Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 65
<211> LENGTH: 693
<212> TYPE: DNA
<213> ORGANISM: Artificial
<220> FEATURE:
<223> OTHER INFORMATION: Linked anti-HIV binders contained in LTG1948

<400> SEQUENCE: 65
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattgggaa  atcaatgata gtggaaacac catttacaat     180
ccgtccctca gagtcgagt  caccatctcc agagacaatt ccaagaacac actgtatctg     240
caaatgaaca ccctgagagc cgaggacaca gccatatatt actgtgcgat atatggtggt     300
aactccgggg gagagtactg gggccagggc accctggtca ccgtctcctc aggaggtggc     360
ggttcaggcg aggggggag  tggaggtggg ggaagcaaga aagtcgtgta cggaaagaag     420
ggagacactg tggagctgac ctgtaccgca agccagaaga gaacatcca  gttccactgg     480 aagaactcca accaaatcaa gatcctgggg aaccagggtt ccttcctgac taagggaccc     540
tcaaagctga cgaccgcgt  ggatagcaga cgctccctgt gggaccaggg aaacttcccg     600
cttatcatta gaacctcaa  acctgaggac tcggatacct acatctgcga agtggaggac     660
cagaaggagg aggtgcagct ggtggtggtg ggc                                  693

<210> SEQ ID NO 66
<211> LENGTH: 231
<212> TYPE: PRT
```

<213> ORGANISM: Artificial
<220> FEATURE:
<223> OTHER INFORMATION: Linked anti-HIV binders contained in LTG1948

<400> SEQUENCE: 66

```
Gln Val Gln Leu Val Gln Ser Gly Gly Gly Leu Val Gln Pro Gly Gly
1               5                   10                  15
Ser Leu Arg Leu Ser Cys Ala Ala Ser Ala Phe Asp Phe Ser Asp Tyr
            20                  25                  30
Glu Met Ser Trp Val Arg Gln Ala Pro Gly Lys Gly Leu Glu Trp Ile
        35                  40                  45
Gly Glu Ile Asn Asp Ser Gly Asn Thr Ile Tyr Asn Pro Ser Leu Lys
    50                  55                  60
Ser Arg Val Thr Ile Ser Arg Asp Asn Ser Lys Asn Thr Leu Tyr Leu
65                  70                  75                  80
Gln Met Asn Thr Leu Arg Ala Glu Asp Thr Ala Ile Tyr Tyr Cys Ala
                85                  90                  95
Ile Tyr Gly Gly Asn Ser Gly Gly Glu Tyr Trp Gly Gln Gly Thr Leu
            100                 105                 110
Val Thr Val Ser Ser Gly Gly Gly Gly Ser Gly Gly Gly Gly Ser Gly
        115                 120                 125
Gly Gly Ser Lys Lys Val Val Tyr Gly Lys Lys Gly Asp Thr Val
    130                 135                 140
Glu Leu Thr Cys Thr Ala Ser Gln Lys Lys Asn Ile Gln Phe His Trp
145                 150                 155                 160
Lys Asn Ser Asn Gln Ile Lys Ile Leu Gly Asn Gln Gly Ser Phe Leu
                165                 170                 175
Thr Lys Gly Pro Ser Lys Leu Asn Asp Arg Val Asp Ser Arg Arg Ser
            180                 185                 190
Leu Trp Asp Gln Gly Asn Phe Pro Leu Ile Ile Lys Asn Leu Lys Pro
        195                 200                 205
Glu Asp Ser Asp Thr Tyr Ile Cys Glu Val Glu Asp Gln Lys Glu Glu
    210                 215                 220
Val Gln Leu Val Val Val Gly
225                 230
```

<210> SEQ ID NO 67
<211> LENGTH: 1446
<212> TYPE: DNA
<213> ORGANISM: Artificial
<220> FEATURE:
<223> OTHER INFORMATION: Anti-HIV CAR LTG1948

<400> SEQUENCE: 67

```
atgcttctcc tggtcacctc cctgctcctc tgcgaactgc ctcaccctgc cttccttctg     60
attcctgaca cccaggtgca gctggtgcag tctgggggag gcttggtaca gcctggaggg    120
tccctgagac tctcctgtgc agcctctgct ttcgatttct ctgattatga aatgagctgg    180
gtccgcgagg ctccagggaa ggggctggag tggattgggg aaatcaatga tagtggaaac    240
accatttaca atccgtccct caagagtcga gtcaccatct ccagagacaa ttccaagaac    300
acactgtatc tgcaaatgaa cacccctgaga gccgaggaca cagccatata ttactgtgcg    360
atatatggtg gtaactccgg gggagagtac tggggccagg gcaccctggt caccgtctcc    420
tcaggaggtg gcggttcagg cggagggggg agtggaggtg ggggaagcaa gaaagtcgtg    480
tacggaaaga agggagacac tgtggagctg acctgtaccg caagccagaa gaagaacatc    540
```

-continued

```
cagttccact ggaagaactc caaccaaatc aagatcctgg ggaaccaggg ttccttcctg    600
actaagggac cctcaaagct gaacgaccgc gtggatagca gacgctccct gtgggaccag    660
ggaaacttcc cgcttatcat taagaacctc aaacctgagg actcggatac ctacatctgc    720
gaagtggagg accagaagga ggaggtgcag ctggtggtgg tgggcgcggc cgcaactacc    780 accctgccc ctcggccgcc gactccggcc ccaaccatcg caagccaacc cctctccttg    840
cgccccgaag cttgccgccc ggcgcgggt ggagccgtgc atacccgggg gctggacttt    900
gcctgcgata tctacatttg gccccgctg gccggcactt gcggcgtgct cctgctgtcg    960
ctggtcatca ccctttactg caagaggggc cggaagaagc tgctttacat cttcaagcag   1020
ccgttcatgc ggcccgtgca gacgactcag gaagaggacg gatgctcgtg cagattccct   1080
gaggaggaag aggggggatg cgaactcgcg gtcaagttct cacggtccgc cgacgccccc   1140
gcatatcaac agggccagaa tcagctctac aacgagctga acctgggaag agagaggag   1200 tacgacgtgc tggacaagcg acgcggacgc gacccggaga tgggggggaa accacggcgg   1260
aaaaaccctc aggaaggact gtacaacgaa ctccagaaag acaagatggc ggaagcctac   1320
tcagaaatcg ggatgaaggg agagcggagg aggggaaagg gtcacgacgg gctgtaccag   1380
ggactgagca ccgccactaa ggatacctac gatgccttgc atatgcaagc actcccaccc   1440
cggtag                                                              1446
```

<210> SEQ ID NO 68
<211> LENGTH: 481
<212> TYPE: PRT
<213> ORGANISM: Artificial
<220> FEATURE:
<223> OTHER INFORMATION: Linked anti-HIV binders contained in LTG1948 Anti-HIV CAR LTG1948

<400> SEQUENCE: 68

```
Met Leu Leu Leu Val Thr Ser Leu Leu Cys Glu Leu Pro His Pro
1               5                   10                  15

Ala Phe Leu Leu Ile Pro Asp Thr Gln Val Gln Leu Val Gln Ser Gly
                20                  25                  30

Gly Gly Leu Val Gln Pro Gly Gly Ser Leu Arg Leu Ser Cys Ala Ala
            35                  40                  45

Ser Ala Phe Asp Phe Ser Asp Tyr Glu Met Ser Trp Val Arg Glu Ala
        50                  55                  60

Pro Gly Lys Gly Leu Glu Trp Ile Gly Glu Ile Asn Asp Ser Gly Asn
65                  70                  75                  80

Thr Ile Tyr Asn Pro Ser Leu Lys Ser Arg Val Thr Ile Ser Arg Asp
                85                  90                  95

Asn Ser Lys Asn Thr Leu Tyr Leu Gln Met Asn Thr Leu Arg Ala Glu
            100                 105                 110

Asp Thr Ala Ile Tyr Tyr Cys Ala Ile Tyr Gly Gly Asn Ser Gly Gly
        115                 120                 125

Glu Tyr Trp Gly Gln Gly Thr Leu Val Thr Val Ser Gly Gly Gly
    130                 135                 140

Gly Ser Gly Gly Gly Gly Ser Gly Gly Gly Gly Ser Lys Lys Val Val
145                 150                 155                 160

Tyr Gly Lys Lys Gly Asp Thr Val Glu Leu Thr Cys Thr Ala Ser Gln
                165                 170                 175

Lys Lys Asn Ile Gln Phe His Trp Lys Asn Ser Asn Gln Ile Lys Ile
            180                 185                 190
```

Leu Gly Asn Gln Gly Ser Phe Leu Thr Lys Gly Pro Ser Lys Leu Asn
            195                 200                 205

Asp Arg Val Asp Ser Arg Ser Leu Trp Asp Gln Gly Asn Phe Pro
210                 215                 220

Leu Ile Ile Lys Asn Leu Lys Pro Glu Asp Ser Asp Thr Tyr Ile Cys
225                 230                 235                 240

Glu Val Glu Asp Gln Lys Glu Val Gln Leu Val Val Gly Ala
            245                 250                 255

Ala Ala Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
            275                 280                 285

Ala Gly Gly Ala Val His Thr Arg Gly Leu Asp Phe Ala Cys Asp Ile
290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
            325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
            355                 360                 365

Leu Arg Val Lys Phe Ser Arg Ser Ala Asp Ala Pro Ala Tyr Gln Gln
            370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
            405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
450                 455                 460

Ala Thr Lys Asp Thr Tyr Asp Ala Leu His Met Gln Ala Leu Pro Pro
465                 470                 475                 480

Arg

<210> SEQ ID NO 69
<211> LENGTH: 648
<212> TYPE: DNA
<213> ORGANISM: Artificial
<220> FEATURE:
<223> OTHER INFORMATION: Anti-HIV binders contained in LTG2303 and
      LTG2322

<400> SEQUENCE: 69
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggcag     300 gtgcagctgg tgcagtctgg gggaggcttg gtacagcctg agggtccct gagactctcc     360

```
tgtgcagcct ctgctttcga tttctctgat tatgaaatga gctgggtccg cgaggctcca      420
gggaaggggc tggagtggat tgggaaatc aatgatagtg aaacaccat ttacaatccg        480 tccctcaaga gtcgagtcac catctccaga gacaattcca agaacacact gtatctgcaa      540
atgaacaccc tgagagccga ggacacagcc atatattact gtgcgatata tggtggtaac     600 tccggggggag agtactgggg ccagggcacc ctggtcaccg tctcctca                 648
```

<210> SEQ ID NO 70
<211> LENGTH: 216
<212> TYPE: PRT
<213> ORGANISM: Artificial
<220> FEATURE:
<223> OTHER INFORMATION: Anti-HIV binders contained in LTG2303 and
      LTG2322

<400> SEQUENCE: 70

```
Lys Lys Val Val Tyr Gly Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gln Val Gln Leu Val Gln Ser Gly Gly Gly Leu Val Gln
            100                 105                 110

Pro Gly Gly Ser Leu Arg Leu Ser Cys Ala Ala Ser Ala Phe Asp Phe
        115                 120                 125

Ser Asp Tyr Glu Met Ser Trp Val Arg Glu Ala Pro Gly Lys Gly Leu
    130                 135                 140

Glu Trp Ile Gly Glu Ile Asn Asp Ser Gly Asn Thr Ile Tyr Asn Pro
145                 150                 155                 160

Ser Leu Lys Ser Arg Val Thr Ile Ser Arg Asp Asn Ser Lys Asn Thr
                165                 170                 175

Leu Tyr Leu Gln Met Asn Thr Leu Arg Ala Glu Asp Thr Ala Ile Tyr
            180                 185                 190

Tyr Cys Ala Ile Tyr Gly Gly Asn Ser Gly Gly Glu Tyr Trp Gly Gln
        195                 200                 205

Gly Thr Leu Val Thr Val Ser Ser
    210                 215
```

<210> SEQ ID NO 71
<211> LENGTH: 2121
<212> TYPE: DNA
<213> ORGANISM: Artificial
<220> FEATURE:
<223> OTHER INFORMATION: Anti-HIV CAR LTG2303

<400> SEQUENCE: 71

```
atgcttctcc tggtcacctc cctgctcctc tgcgaactgc ctcaccctgc cttccttctg      60
attcctgaca ccaagaaagt cgtgtacgga agaagggag acactgtgga gctgacctgt      120
accgcaagcc agaagaagaa catccagttc cactggaaga actccaacca aatcaagatc     180
```

```
ctggggaacc agggttcctt cctgactaag ggaccctcaa agctgaacga ccgcgtggat    240
agcagacgct ccctgtggga ccagggaaac ttcccgctta tcattaagaa cctcaaacct    300
gaggactcgg atacctacat ctgcgaagtg gaggaccaga aggaggaggt gcagctggtg    360
gtggtggggg cggccgcaac taccacccct gcccctcggc cgccgactcc ggccccaacc    420
atcgcaagcc aaccctctc cttgcgcccc gaagcttgcc gccggccgc gggtggagcc    480
gtgcataccc gggggctgga cttttgcctgc gatatctaca tttgggcccc gctggccggc    540
acttgcggcg tgctcctgct gtcgctggtc atccccttt actgcaagag gggccggaag    600
aagctgcttt acatcttcaa gcagccgttc atgcggcccg tgcagacgac tcaggaagag    660
gacggatgct cgtgcagatt ccctgaggag gaagaggggg gatgcgaact gcgcgtcaag    720
ttctcacggt ccgccgacgc ccccgcatat caacagggcc agaatcagct ctacaacgag    780
ctgaacctgg gaaggagaga ggagtacgac gtgctggaca gcgacgcgg acgcgacccg    840
gagatggggg ggaaaccacg gcggaaaaac cctcaggaag gactgtacaa cgaactccag    900
aaagacaaga tggcggaagc ctactcagaa atcgggatga agggagagcg gaggagggga    960
aagggtcacg acgggctgta ccagggactg agcaccgcca ctaaggatac ctacgatgcc    1020
ttgcatatgc aagcactccc acccggcgc gcgaaacgca gcggcagcgg cgcgaccaac    1080
tttagcctgc tgaaacaggc gggcgatgtg aagaaaaacc cgggcccgcg agcaaagagg    1140
atgggaattc agggggttc cgtgctcttt ggcttgctcc tggtcctggc agtgttttgt    1200
cactcgggac acagcctgca gcaggtgcag ctggtgcagt ctgggggagg cttggtacag    1260
cctggagggt ccctgagact ctcctgtgca gcctctgctt tcgatttctc tgattatgaa    1320
atgagctggg tccgcgaggc tccagggaag gggctggagt ggattgggga aatcaatgat    1380
agtgaaaca ccatttacaa tccgtccctc aagagtcgag tcaccatctc cagagacaat    1440
tccaagaaca cactgtatct gcaaatgaac accctgagag ccgaggacac agccatatat    1500
tactgtgcga tatatggtgg taactccggg ggagagtact ggggccaggg caccctggtc    1560
accgtctcct caccggctcc acgaccaccc actccagccc caacgattgc gagccaacct    1620
ctcagtcttc ggcccgaggc ttgcaggcca gccgcaggag gagcagtgca cacccgagga    1680
ctggatttcg ataccgcact ggcggccgtg atctgtagcg ccctggccac cgtgctgctg    1740
gcgctgctca tcctttgcgt gatctactgc aagcggcagc gggttaaatt ctcccgcagc    1800
gcagacgcac ccgcctacca gcaaggacag aatcagctct acaacgaact gaaccttggt    1860
aggagagaag aatatgatgt tctcgacaag cgcagaggga gagatccaga gatgggtggg    1920
aagccgcaac gccggaaaaa cccacaagag ggactgtaca atgaattgca gaaagataag    1980
atggccgagg cttactcaga aatcggaatg aaggggagc ggcggagggg caagggacat    2040
gatggtctct accaagggct ttcaaccgct actaaggaca cttatgacgc actccacatg    2100
caggcgctgc ctccgcgata a                                             2121
```

<210> SEQ ID NO 72
<211> LENGTH: 706
<212> TYPE: PRT
<213> ORGANISM: Artificial
<220> FEATURE:
<223> OTHER INFORMATION: Anti-HIV CAR LTG2303

<400> SEQUENCE: 72

Met Leu Leu Leu Val Thr Ser Leu Leu Leu Cys Glu Leu Pro His Pro
 1               5                  10                  15

```
Ala Phe Leu Leu Ile Pro Asp Thr Lys Lys Val Val Tyr Gly Lys Lys
                20                  25                  30

Gly Asp Thr Val Glu Leu Thr Cys Thr Ala Ser Gln Lys Lys Asn Ile
            35                  40                  45

Gln Phe His Trp Lys Asn Ser Asn Gln Ile Lys Ile Leu Gly Asn Gln
        50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Val Gly Ala Ala Ala Thr Thr
        115                 120                 125

Thr Pro Ala Pro Arg Pro Pro Thr Pro Ala Pro Thr Ile Ala Ser Gln
130                 135                 140

Pro Leu Ser Leu Arg Pro Glu Ala Cys Arg Pro Ala Ala Gly Gly Ala
145                 150                 155                 160

Val His Thr Arg Gly Leu Asp Phe Ala Cys Asp Ile Tyr Ile Trp Ala
                165                 170                 175

Pro Leu Ala Gly Thr Cys Gly Val Leu Leu Leu Ser Leu Val Ile Thr
            180                 185                 190

Leu Tyr Cys Lys Arg Gly Arg Lys Leu Leu Tyr Ile Phe Lys Gln
        195                 200                 205

Pro Phe Met Arg Pro Val Gln Thr Thr Gln Glu Glu Asp Gly Cys Ser
210                 215                 220

Cys Arg Phe Pro Glu Glu Glu Glu Gly Gly Cys Glu Leu Arg Val Lys
225                 230                 235                 240

Phe Ser Arg Ser Ala Asp Ala Pro Ala Tyr Gln Gln Gly Gln Asn Gln
                245                 250                 255

Leu Tyr Asn Glu Leu Asn Leu Gly Arg Arg Glu Glu Tyr Asp Val Leu
            260                 265                 270

Asp Lys Arg Arg Gly Arg Asp Pro Glu Met Gly Gly Lys Pro Arg Arg
        275                 280                 285

Lys Asn Pro Gln Glu Gly Leu Tyr Asn Glu Leu Gln Lys Asp Lys Met
290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg Arg Ala Lys
            340                 345                 350

Arg Ser Gly Ser Gly Ala Thr Asn Phe Ser Leu Leu Lys Gln Ala Gly
        355                 360                 365

Asp Val Glu Glu Asn Pro Gly Pro Arg Ala Lys Arg Met Gly Ile Gln
370                 375                 380

Gly Gly Ser Val Leu Phe Gly Leu Leu Leu Val Leu Ala Val Phe Cys
385                 390                 395                 400

His Ser Gly His Ser Leu Gln Gln Val Gln Leu Val Gln Ser Gly Gly
                405                 410                 415

Gly Leu Val Gln Pro Gly Gly Ser Leu Arg Leu Ser Cys Ala Ala Ser
            420                 425                 430

Ala Phe Asp Phe Ser Asp Tyr Glu Met Ser Trp Val Arg Glu Ala Pro
```

```
            435                 440                 445
Gly Lys Gly Leu Glu Trp Ile Gly Glu Ile Asn Asp Ser Gly Asn Thr
    450                 455                 460

Ile Tyr Asn Pro Ser Leu Lys Ser Arg Val Thr Ile Ser Arg Asp Asn
465                 470                 475                 480

Ser Lys Asn Thr Leu Tyr Leu Gln Met Asn Thr Leu Arg Ala Glu Asp
                485                 490                 495

Thr Ala Ile Tyr Tyr Cys Ala Ile Tyr Gly Gly Asn Ser Gly Gly Glu
            500                 505                 510

Tyr Trp Gly Gln Gly Thr Leu Val Thr Val Ser Ser Pro Ala Pro Arg
        515                 520                 525

Pro Pro Thr Pro Ala Pro Thr Ile Ala Ser Gln Pro Leu Ser Leu Arg
    530                 535                 540

Pro Glu Ala Cys Arg Pro Ala Ala Gly Gly Ala Val His Thr Arg Gly
545                 550                 555                 560

Leu Asp Phe Asp Thr Ala Leu Ala Ala Val Ile Cys Ser Ala Leu Ala
                565                 570                 575

Thr Val Leu Leu Ala Leu Leu Ile Leu Cys Val Ile Tyr Cys Lys Arg
            580                 585                 590

Gln Arg Val Lys Phe Ser Arg Ser Ala Asp Ala Pro Ala Tyr Gln Gln
        595                 600                 605

Gly Gln Asn Gln Leu Tyr Asn Glu Leu Asn Leu Gly Arg Arg Glu Glu
    610                 615                 620

Tyr Asp Val Leu Asp Lys Arg Gly Arg Asp Pro Glu Met Gly Gly
625                 630                 635                 640

Lys Pro Gln Arg Arg Lys Asn Pro Gln Glu Gly Leu Tyr Asn Glu Leu
                645                 650                 655

Gln Lys Asp Lys Met Ala Glu Ala Tyr Ser Glu Ile Gly Met Lys Gly
            660                 665                 670

Glu Arg Arg Arg Gly Lys Gly His Asp Gly Leu Tyr Gln Gly Leu Ser
        675                 680                 685

Thr Ala Thr Lys Asp Thr Tyr Asp Ala Leu His Met Gln Ala Leu Pro
    690                 695                 700

Pro Arg
705

<210> SEQ ID NO 73
<211> LENGTH: 1782
<212> TYPE: DNA
<213> ORGANISM: Artificial
<220> FEATURE:
<223> OTHER INFORMATION: Anti-HIV CAR LTG2322

<400> SEQUENCE: 73
atgcttctcc tggtcacctc cctgctcctc tgcgaactgc ctcaccctgc cttccttctg      60
attcctgaca ccaagaaagt cgtgtacgga agaagggag acactgtgga gctgacctgt     120
accgcaagcc agaagaagaa catccagttc cactggaaga actccaacca aatcaagatc     180
ctggggaacc agggttcctt cctgactaag ggaccctcaa agctgaacga ccgcgtggat     240
agcagacgct cccgtgtggga ccagggaaac ttccgcgctta tcattaagaa cctcaaacct     300
gaggactcgg atacctacat ctgcgaagtg gaggaccaga aggaggaggt gcagctggtg     360
gtggtggggg cggccgcaac taccacccct gccctcggc cgccgactcc ggccccaacc     420
atcgcaagcc aacccctctc cttgcgcccc gaagcttgcc gccggccgc gggtggagcc     480
```

-continued

```
gtgcatacccc gggggctgga cttttgcctgc gatatctaca tttgggcccc gctggccggc     540
acttgcggcg tgctcctgct gtcgctggtc atcaccctttt actgcaagag gggccggaag     600
aagctgcttt acatcttcaa gcagccgttc atgcggcccg tgcagacgac tcaggaagag     660
gacggatgct cgtgcagatt ccctgaggag gaagaggggg gatgcgaact gcgcgtcaag     720
ttctcacggt ccgccgacgc ccccgcatat caacagggcc agaatcagct ctacaacgag     780
ctgaacctgg aaggagaga ggagtacgac gtgctggaca gcgacgcgg acgcgacccg      840
gagatggggg ggaaaccacg gcggaaaaac cctcaggaag gactgtacaa cgaactccag     900
aaagacaaga tggcggaagc ctactcagaa atcgggatga agggagagcg gaggaggggga    960
aagggtcacg acgggctgta ccagggactg agcaccgcca ctaaggatac ctacgatgcc    1020
ttgcatatgc aagcactccc acccggcgc gcgaaacgca gcggcagcgg cgcgaccaac    1080
tttagcctgc tgaaacaggc gggcgatgtg aagaaaacc cgggcccgcg agcaaagagg    1140
atgggaattc agggggggttc cgtgctcttt ggcttgctcc tggtcctggc agtgtttttgt   1200
cactcgggac acagcctgca gcaggtgcag ctggtgcagt ctggggggagg cttggtacag    1260
cctggagggt ccctgagact ctcctgtgca gcctctgctt tcgatttctc tgattatgaa    1320
atgagctggg tccgcgaggc tccagggaag gggctggagt ggattgggga aatcaatgat   1380
agtggaaaca ccatttacaa tccgtccctc aagagtcgag tcaccatctc cagagacaat    1440
tccaagaaca cactgtatct gcaaatgaac accctgagac cgaggacac agccatatat    1500
tactgtgcga tatatggtgg taactccggg ggagagtact ggggccaggg caccctggtc    1560
accgtctcct caccggctcc acgaccaccc actccagccc caacgattgc gagccaacct    1620
ctcagtcttc ggcccgaggc ttgcaggcca gccgcaggag gagcagtgca cacccgagga    1680
ctggatttcg ataccgcact ggcggccgtg atctgtagcg ccctggccac cgtgctgctg    1740
gcgctgctca tcctttgcgt gatctactgc aagcggcagt ag                       1782
```

<210> SEQ ID NO 74
<211> LENGTH: 593
<212> TYPE: PRT
<213> ORGANISM: Artificial
<220> FEATURE:
<223> OTHER INFORMATION: Anti-HIV CAR LTG2322

<400> SEQUENCE: 74

```
Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Gly Ala Ala Ala Thr Thr
        115                 120                 125

Thr Pro Ala Pro Arg Pro Pro Thr Pro Ala Pro Thr Ile Ala Ser Gln
```

```
            130                 135                 140
Pro Leu Ser Leu Arg Pro Glu Ala Cys Arg Pro Ala Ala Gly Gly Ala
145                 150                 155                 160

Val His Thr Arg Gly Leu Asp Phe Ala Cys Asp Ile Tyr Ile Trp Ala
                165                 170                 175

Pro Leu Ala Gly Thr Cys Gly Val Leu Leu Leu Ser Leu Val Ile Thr
                180                 185                 190

Leu Tyr Cys Lys Arg Gly Arg Lys Leu Leu Tyr Ile Phe Lys Gln
            195                 200                 205

Pro Phe Met Arg Pro Val Gln Thr Thr Gln Glu Glu Asp Gly Cys Ser
210                 215                 220

Cys Arg Phe Pro Glu Glu Glu Gly Gly Cys Glu Leu Arg Val Lys
225                 230                 235                 240

Phe Ser Arg Ser Ala Asp Ala Pro Ala Tyr Gln Gln Gly Gln Asn Gln
                245                 250                 255

Leu Tyr Asn Glu Leu Asn Leu Gly Arg Arg Glu Glu Tyr Asp Val Leu
                260                 265                 270

Asp Lys Arg Arg Gly Arg Asp Pro Glu Met Gly Gly Lys Pro Arg Arg
            275                 280                 285

Lys Asn Pro Gln Glu Gly Leu Tyr Asn Glu Leu Gln Lys Asp Lys Met
            290                 295                 300

Ala Glu Ala Tyr Ser Glu Ile Gly Met Lys Gly Glu Arg Arg Arg Gly
305                 310                 315                 320

Lys Gly His Asp Gly Leu Tyr Gln Gly Leu Ser Thr Ala Thr Lys Asp
                325                 330                 335

Thr Tyr Asp Ala Leu His Met Gln Ala Leu Pro Pro Arg Arg Ala Lys
                340                 345                 350

Arg Ser Gly Ser Gly Ala Thr Asn Phe Ser Leu Leu Lys Gln Ala Gly
            355                 360                 365

Asp Val Glu Glu Asn Pro Gly Pro Arg Ala Lys Arg Met Gly Ile Gln
370                 375                 380

Gly Gly Ser Val Leu Phe Gly Leu Leu Leu Val Leu Ala Val Phe Cys
385                 390                 395                 400

His Ser Gly His Ser Leu Gln Gln Val Gln Leu Val Gln Ser Gly Gly
                405                 410                 415

Gly Leu Val Gln Pro Gly Gly Ser Leu Arg Leu Ser Cys Ala Ala Ser
            420                 425                 430

Ala Phe Asp Phe Ser Asp Tyr Glu Met Ser Trp Val Arg Glu Ala Pro
            435                 440                 445

Gly Lys Gly Leu Glu Trp Ile Gly Glu Ile Asn Asp Ser Gly Asn Thr
450                 455                 460

Ile Tyr Asn Pro Ser Leu Lys Ser Arg Val Thr Ile Ser Arg Asp Asn
465                 470                 475                 480

Ser Lys Asn Thr Leu Tyr Leu Gln Met Asn Thr Leu Arg Ala Glu Asp
                485                 490                 495

Thr Ala Ile Tyr Tyr Cys Ala Ile Tyr Gly Gly Asn Ser Gly Gly Glu
                500                 505                 510

Tyr Trp Gly Gln Gly Thr Leu Val Thr Val Ser Ser Pro Ala Pro Arg
            515                 520                 525

Pro Pro Thr Pro Ala Pro Thr Ile Ala Ser Gln Pro Leu Ser Leu Arg
530                 535                 540

Pro Glu Ala Cys Arg Pro Ala Ala Gly Gly Ala Val His Thr Arg Gly
545                 550                 555                 560
```

```
Leu Asp Phe Asp Thr Ala Leu Ala Ala Val Ile Cys Ser Ala Leu Ala
                565                 570                 575

Thr Val Leu Leu Ala Leu Leu Ile Leu Cys Val Ile Tyr Cys Lys Arg
            580                 585                 590

Gln

<210> SEQ ID NO 75
<211> LENGTH: 480
<212> TYPE: DNA
<213> ORGANISM: Artificial
<220> FEATURE:
<223> OTHER INFORMATION: Linked anti-HIV binders in LTG2314

<400> SEQUENCE: 75
aagaaagtcg tgtacggaaa gaagggagac actgtggagc tgacctgtac cgcaagccag     60
aagaagaaca tccagttcca ctggaagaac tccaaccaaa tcaagatcct ggggaaccag    120
ggttccttcc tgactaaggg accctcaaag ctgaacgacc gcgtggatag cagacgctcc    180
ctgtgggacc agggaaactt cccgcttatc attaagaacc tcaaacctga ggactcggat    240
acctacatct gcgaagtgga ggaccagaag gaggaggtgc agctggtggt ggtgggcgga    300
ggtggcggtt caggcggagg ggggagtgga ggtgggggaa gctggatgga atgggatcgc    360
gaaatcaaca actacacctc cctgattcac tccctgattg aggaatccca gaatcaacag    420
gagaagaacg aacaagagct tctggagctg gacaaatggg cctccctgtg gaactggttc    480

<210> SEQ ID NO 76
<211> LENGTH: 160
<212> TYPE: PRT
<213> ORGANISM: Artificial
<220> FEATURE:
<223> OTHER INFORMATION: Linked anti-HIV binders in LTG2314

<400> SEQUENCE: 76

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly
            100                 105                 110

Gly Ser Trp Met Glu Trp Asp Arg Glu Ile Asn Asn Tyr Thr Ser Leu
        115                 120                 125

Ile His Ser Leu Ile Glu Glu Ser Gln Asn Gln Gln Glu Lys Asn Glu
    130                 135                 140

Gln Glu Leu Leu Glu Leu Asp Lys Trp Ala Ser Leu Trp Asn Trp Phe
145                 150                 155                 160

<210> SEQ ID NO 77
<211> LENGTH: 1233
<212> TYPE: DNA
```

<213> ORGANISM: Artificial
<220> FEATURE:
<223> OTHER INFORMATION: Anti-HIV CAR LTG2314

<400> SEQUENCE: 77

```
atgcttctcc tggtcacctc cctgctcctc tgcgaactgc ctcaccctgc cttccttctg      60
attcctgaca ccaagaaagt cgtgtacgga aagaagggag acactgtgga gctgacctgt     120
accgcaagcc agaagaagaa catccagttc cactggaaga actccaacca aatcaagatc     180
ctggggaacc agggttcctt cctgactaag ggaccctcaa agctgaacga ccgcgtggat     240
agcagacgct ccctgtggga ccagggaaac ttcccgctta tcattaagaa cctcaaacct     300
gaggactcgg atacctacat ctgcgaagtg gaggaccaga aggaggaggt gcagctggtg     360
gtggtgggcg gaggtggcgg ttcaggcgga ggggggagtg gaggtggggg aagctggatg     420
gaatgggatc gcgaaatcaa caactacacc tccctgattc actccctgat tgaggaatcc     480
cagaatcaac aggagaagaa cgaacaagag cttctggagc tggacaaatg ggcctccctg     540
tggaactggt tcgcggccgc aactaccacc cctgcccctc ggccgccgac tccggcccca     600
accatcgcaa gccaaccccT ctccttgcgc cccgaagctt gccgcccggc cgcgggtgga     660
gccgtgcata cccgggggct ggactttgcc tgcgatatct acatttgggc cccgctggcc     720
ggcacttgcg gcgtgctcct gctgtcgctg gtcatcaccc tttactgcaa gaggggccgg     780
aagaagctgc tttacatctt caagcagccg ttcatgcggc ccgtgcagac gactcaggaa     840
gaggacggat gctcgtgcag attccctgag gaggaagagg ggggatgcga actgcgcgtc     900
aagttctcac ggtccgccga cgcccccgca tatcaacagg ccagaatca gctctacaac     960
gagctgaacc tgggaaggag agaggagtac gacgtgctgg acaagcgacg cggacgcgac    1020
ccggagatgg gggggaaacc acggcggaaa aaccctcagg aaggactgta caacgaactc    1080
cagaaagaca agatggcgga agcctactca gaaatcggga tgaagggaga gcggaggagg    1140
ggaaagggtc acgacgggct gtaccaggga ctgagcaccg ccactaagga tacctacgat    1200
gccttgcata tgcaagcact cccaccccgg tag                                 1233
```

<210> SEQ ID NO 78
<211> LENGTH: 410
<212> TYPE: PRT
<213> ORGANISM: Artificial
<220> FEATURE:
<223> OTHER INFORMATION: Anti-HIV CAR LTG2314

<400> SEQUENCE: 78

```
Met Leu Leu Leu Val Thr Ser Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110
```

```
Gln Lys Glu Glu Val Gln Leu Val Val Gly Gly Gly Gly Ser
            115                 120                 125
Gly Gly Gly Gly Ser Gly Gly Gly Ser Trp Met Glu Trp Asp Arg
        130                 135                 140
Glu Ile Asn Asn Tyr Thr Ser Leu Ile His Ser Leu Ile Glu Glu Ser
145                 150                 155                 160
Gln Asn Gln Gln Glu Lys Asn Glu Gln Glu Leu Leu Glu Leu Asp Lys
                165                 170                 175
Trp Ala Ser Leu Trp Asn Trp Phe Ala Ala Thr Thr Thr Pro Ala
            180                 185                 190
Pro Arg Pro Pro Thr Pro Ala Pro Thr Ile Ala Ser Gln Pro Leu Ser
        195                 200                 205
Leu Arg Pro Glu Ala Cys Arg Pro Ala Ala Gly Gly Ala Val His Thr
210                 215                 220
Arg Gly Leu Asp Phe Ala Cys Asp Ile Tyr Ile Trp Ala Pro Leu Ala
225                 230                 235                 240
Gly Thr Cys Gly Val Leu Leu Leu Ser Leu Val Ile Thr Leu Tyr Cys
            245                 250                 255
Lys Arg Gly Arg Lys Lys Leu Leu Tyr Ile Phe Lys Gln Pro Phe Met
        260                 265                 270
Arg Pro Val Gln Thr Thr Gln Glu Glu Asp Gly Cys Ser Cys Arg Phe
    275                 280                 285
Pro Glu Glu Glu Glu Gly Gly Cys Glu Leu Arg Val Lys Phe Ser Arg
        290                 295                 300
Ser Ala Asp Ala Pro Ala Tyr Gln Gln Gly Gln Asn Gln Leu Tyr Asn
305                 310                 315                 320
Glu Leu Asn Leu Gly Arg Arg Glu Glu Tyr Asp Val Leu Asp Lys Arg
                325                 330                 335
Arg Gly Arg Asp Pro Glu Met Gly Gly Lys Pro Arg Arg Lys Asn Pro
            340                 345                 350
Gln Glu Gly Leu Tyr Asn Glu Leu Gln Lys Asp Lys Met Ala Glu Ala
        355                 360                 365
Tyr Ser Glu Ile Gly Met Lys Gly Glu Arg Arg Gly Lys Gly His
    370                 375                 380
Asp Gly Leu Tyr Gln Gly Leu Ser Thr Ala Thr Lys Asp Thr Tyr Asp
385                 390                 395                 400
Ala Leu His Met Gln Ala Leu Pro Pro Arg
                405                 410

<210> SEQ ID NO 79
<211> LENGTH: 510
<212> TYPE: DNA
<213> ORGANISM: Artificial
<220> FEATURE:
<223> OTHER INFORMATION: Linked anti-HIV binders in LTG2315

<400> SEQUENCE: 79
aagaaagtcg tgtacggaaa gaagggagac actgtggagc tgacctgtac cgcaagccag     60
aagaagaaca tccagttcca ctggaagaac tccaaccaaa tcaagatcct ggggaaccag    120
ggttccttcc tgactaaggg accctcaaag ctgaacgacc gcgtggatag cagacgctcc    180
ctgtgggacc agggaaactt cccgcttatc attaagaacc tcaaacctga ggactcggat    240
acctacatct gcgaagtgga ggaccagaag gaggaggtgc agctggtggt ggtgggcggc    300
ggaggcgggt caggtggcgg tggtagtggc ggtggcggtt caggcggtgg tgggagtggg    360
```

```
ggaggaggca gctggatgga atgggatcgc gaaatcaaca actacacctc cctgattcac    420
tccctgattg aggaatccca gaatcaacag gagaagaacg aacaagagct tctggagctg    480
gacaaatggg cctccctgtg gaactggttc                                     510
```

<210> SEQ ID NO 80
<211> LENGTH: 170
<212> TYPE: PRT
<213> ORGANISM: Artificial
<220> FEATURE:
<223> OTHER INFORMATION: Linked anti-HIV binders in LTG2315

<400> SEQUENCE: 80

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly
                100                 105                 110

Gly Ser Gly Gly Gly Gly Ser Gly Gly Gly Ser Trp Met Glu Trp
            115                 120                 125

Asp Arg Glu Ile Asn Asn Tyr Thr Ser Leu Ile His Ser Leu Ile Glu
    130                 135                 140

Glu Ser Gln Asn Gln Gln Glu Lys Asn Glu Gln Glu Leu Leu Glu Leu
145                 150                 155                 160

Asp Lys Trp Ala Ser Leu Trp Asn Trp Phe
                165                 170
```

<210> SEQ ID NO 81
<211> LENGTH: 1263
<212> TYPE: DNA
<213> ORGANISM: Artificial
<220> FEATURE:
<223> OTHER INFORMATION: Anti-HIV CAR LTG2315

<400> SEQUENCE: 81

```
atgcttctcc tggtcacctc cctgctcctc tgcgaactgc ctcaccctgc cttccttctg     60
attcctgaca ccaagaaagt cgtgtacgga aagaagggag acactgtgga gctgacctgt    120
accgcaagcc agaagaagaa catccagttc cactggaaga actccaacca aatcaagatc    180
ctggggaacc agggttcctt cctgactaag ggaccctcaa agctgaacga ccgcgtggat    240
agcagacgct ccctgtggga ccagggaaac ttcccgctta tcattaagaa cctcaaacct    300
gaggactcgg ataccttcat ctgcgaagtg gaggaccaga aggaggaggt gcagctggtg    360
gtggtgggcg gcggaggcgg gtcaggtggc ggtggtagtg gcggtggcgg ttcaggcggt    420
ggtgggagtg ggggaggagg cagctggatg gaatgggatc gcgaaatcaa caactacacc    480
tccctgattc actccctgat tgaggaatcc cagaatcaac aggagaagaa cgaacaagag    540
cttctggagc tggacaaatg ggcctccctg tggaactggt tcgcggccgc aactaccacc    600
```

-continued

```
cctgccccte ggccgccgac tccggcccca accatcgcaa gccaacccct ctccttgcgc    660
cccgaagctt gccgcccggc cgcgggtgga gccgtgcata cccgggggct ggactttgcc    720
tgcgatatct acatttgggc cccgctggcc ggcacttgcg gcgtgctcct gctgtcgctg    780
gtcatcaccc tttactgcaa gagggaccgg aagaagctgc tttacatctt caagcagccg    840
ttcatgcggc ccgtgcagac gactcaggaa gaggacggat gctcgtgcag attccctgag    900
gaggaagagg ggggatgcga actgcgcgtc aagttctcac ggtccgccga cgcccccgca    960
tatcaacagg gccagaatca gctctacaac gagctgaacc tgggaaggag agaggagtac   1020
gacgtgctgg acaagcgacg cggacgcgac ccggagatgg ggggaaaacc acggcggaaa   1080
aaccctcagg aaggactgta caacgaactc cagaaagaca agatggcgga agcctactca   1140
gaaatcggga tgaagggaga gcggaggagg ggaaagggtc acgacgggct gtaccaggga   1200
ctgagcaccg ccactaagga tacctacgat gccttgcata tgcaagcact cccaccccgg   1260
tag                                                                1263
```

<210> SEQ ID NO 82
<211> LENGTH: 420
<212> TYPE: PRT
<213> ORGANISM: Artificial
<220> FEATURE:
<223> OTHER INFORMATION: Anti-HIV CAR LTG2315

<400> SEQUENCE: 82

```
Met Leu Leu Leu Val Thr Ser Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Val Gly Gly Gly Gly Ser
        115                 120                 125

Gly Gly Gly Gly Ser Gly Gly Gly Ser Gly Gly Gly Ser Gly
        130                 135                 140

Gly Gly Gly Ser Trp Met Glu Trp Asp Arg Glu Ile Asn Asn Tyr Thr
145                 150                 155                 160

Ser Leu Ile His Ser Leu Ile Glu Glu Ser Gln Asn Gln Gln Glu Lys
                165                 170                 175

Asn Glu Gln Glu Leu Leu Glu Leu Asp Lys Trp Ala Ser Leu Trp Asn
            180                 185                 190

Trp Phe Ala Ala Thr Thr Thr Pro Ala Pro Arg Pro Pro Thr Pro
        195                 200                 205

Ala Pro Thr Ile Ala Ser Gln Pro Leu Ser Leu Arg Pro Glu Ala Cys
    210                 215                 220

Arg Pro Ala Ala Gly Gly Ala Val His Thr Arg Gly Leu Asp Phe Ala
225                 230                 235                 240
```

```
Cys Asp Ile Tyr Ile Trp Ala Pro Leu Ala Gly Thr Cys Gly Val Leu
            245                 250                 255

Leu Leu Ser Leu Val Ile Thr Leu Tyr Cys Lys Arg Gly Arg Lys Lys
        260                 265                 270

Leu Leu Tyr Ile Phe Lys Gln Pro Phe Met Arg Pro Val Gln Thr Thr
            275                 280                 285

Gln Glu Glu Asp Gly Cys Ser Cys Arg Phe Pro Glu Glu Glu Glu Gly
        290                 295                 300

Gly Cys Glu Leu Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
        355                 360                 365

Glu Leu Gln Lys Asp Lys Met Ala Glu Ala Tyr Ser Glu Ile Gly Met
    370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 83
<211> LENGTH: 480
<212> TYPE: DNA
<213> ORGANISM: Artificial
<220> FEATURE:
<223> OTHER INFORMATION: Linked anti-HIV binders in LTG2316

<400> SEQUENCE: 83
tggatggaat gggatcgcga aatcaacaac tacacctccc tgattcactc cctgattgag      60
gaatcccaga tcaacagga gaagaacgaa caagagcttc tggagctgga caaatgggcc     120
tccctgtgga actggttcgg cggagggggg agtggaggtg gcggttcagg aggtggggga     180
agcaagaaag tcgtgtacgg aaagaaggga gacactgtgg agctgacctg taccgcaagc     240
cagaagaaga acatccagtt ccactggaag aactccaacc aaatcaagat cctggggaac     300
cagggttcct tcctgactaa ggaccctca aagctgaacg accgcgtgga tagcagacgc     360
tccctgtggg accagggaaa cttcccgctt atcattaaga acctcaaacc tgaggactcg     420
gatacctaca tctgcgaagt ggaggaccag aaggaggagg tgcagctggt ggtggtgggc     480

<210> SEQ ID NO 84
<211> LENGTH: 160
<212> TYPE: PRT
<213> ORGANISM: Artificial
<220> FEATURE:
<223> OTHER INFORMATION: Linked anti-HIV binders in LTG2316

<400> SEQUENCE: 84

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
                20                  25                  30

Leu Leu Glu Leu Asp Lys Trp Ala Ser Leu Trp Asn Trp Phe Gly Gly
```

```
                      35                  40                  45
Gly Gly Ser Gly Gly Gly Ser Gly Gly Gly Ser Lys Lys Val
         50                  55                  60
Val Tyr Gly Lys Lys Gly Asp Thr Val Glu Leu Thr Cys Thr Ala Ser
 65                  70                  75                  80
Gln Lys Lys Asn Ile Gln Phe His Trp Lys Asn Ser Asn Gln Ile Lys
                 85                  90                  95
Ile Leu Gly Asn Gln Gly Ser Phe Leu Thr Lys Gly Pro Ser Lys Leu
            100                 105                 110
Asn Asp Arg Val Asp Ser Arg Arg Ser Leu Trp Asp Gln Gly Asn Phe
        115                 120                 125
Pro Leu Ile Ile Lys Asn Leu Lys Pro Glu Asp Ser Asp Thr Tyr Ile
        130                 135                 140
Cys Glu Val Glu Asp Gln Lys Glu Glu Val Gln Leu Val Val Val Gly
145                 150                 155                 160
```

<210> SEQ ID NO 85
<211> LENGTH: 1233
<212> TYPE: DNA
<213> ORGANISM: Artificial
<220> FEATURE:
<223> OTHER INFORMATION: Anti-HIV CAR LTG2316

<400> SEQUENCE: 85

| | | |
|---|---|---|
| atgcttctcc tggtcaccct cctgctcctc tgcgaactgc tcaccctgc cttccttctg | 60 |
| attcctgaca cctggatgga atgggatcgc gaaatcaaca actacacctc cctgattcac | 120 |
| tccctgattg aggaatccca gaatcaacag gagaagaacg aacaagagct tctggagctg | 180 |
| gacaaatggg cctccctgtg gaactggttc ggcggagggg ggagtggagg tggcggttca | 240 |
| ggaggtgggg gaagcaagaa agtcgtgtac ggaaagaagg gagacactgt ggagctgacc | 300 |
| tgtaccgcaa gccagaagaa gaacatccag ttccactgga gaactccaa ccaaatcaag | 360 |
| atcctgggga accagggttc cttcctgact aagggaccct caaagctgaa cgaccgcgtg | 420 |
| gatagcagac gctccctgtg ggaccaggga acttcccgc ttatcattaa gaaccctcaaa | 480 |
| cctgaggact cggataccta catctgcgaa gtggaggacc agaaggagga ggtgcagctg | 540 |
| gtggtggtgg gcgcggccgc aactaccacc cctgcccctc ggccgccgac tccggcccca | 600 |
| accatcgcaa gccaaccct ctccttgcgc cccgaagctt gccgcccggc cgcgggtgga | 660 |
| gccgtgcata cccgggggct ggactttgcc tgcgatatct acatttgggc cccgctggcc | 720 |
| ggcacttgcg gcgtgctcct gctgtcgctg gtcatcaccc tttactgcaa gaggggccgg | 780 |
| aagaagctgc tttacatctt caagcagccg ttcatgcggc ccgtgcagac gactcaggaa | 840 |
| gaggacggat gctcgtgcag attccctgag gaggaagagg ggggatgcga actgcgcgtc | 900 |
| aagttctcac ggtccgccga cgcccccgca tatcaacagg ccagaatca gctctacaac | 960 |
| gagctgaacc tggaaggag agaggagtac gacgtgctgg acaagcgacg cggacgcgac | 1020 |
| ccggagatgg gggggaaacc acggcggaaa aaccctcagg aaggactgta caacgaactc | 1080 |
| cagaaagaca gatggcggga agcctactca gaaatcggga tgaagggaga gcggaggagg | 1140 |
| ggaaagggtc acgacgggct gtaccaggga ctgagcaccg ccactaagga tacctacgat | 1200 |
| gccttgcata tgcaagcact cccaccccgg tag | 1233 |

<210> SEQ ID NO 86
<211> LENGTH: 410
<212> TYPE: PRT

<213> ORGANISM: Artificial
<220> FEATURE:
<223> OTHER INFORMATION: Anti-HIV CAR LTG2316

<400> SEQUENCE: 86

```
Met Leu Leu Leu Val Thr Ser Leu Leu Leu Cys Glu Leu Pro His Pro
1               5                   10                  15

Ala Phe Leu Leu Ile Pro Asp Thr Trp Met Glu Trp Asp Arg Glu Ile
            20                  25                  30

Asn Asn Tyr Thr Ser Leu Ile His Ser Leu Ile Glu Ser Gln Asn
                35                  40                  45

Gln Gln Glu Lys Asn Glu Gln Glu Leu Leu Glu Leu Asp Lys Trp Ala
    50                  55                  60

Ser Leu Trp Asn Trp Phe Gly Gly Gly Ser Gly Gly Gly Gly Ser
65                  70                  75                  80

Gly Gly Gly Gly Ser Lys Lys Val Val Tyr Gly Lys Lys Gly Asp Thr
                85                  90                  95

Val Glu Leu Thr Cys Thr Ala Ser Gln Lys Lys Asn Ile Gln Phe His
            100                 105                 110

Trp Lys Asn Ser Asn Gln Ile Lys Ile Leu Gly Asn Gln Gly Ser Phe
        115                 120                 125

Leu Thr Lys Gly Pro Ser Lys Leu Asn Asp Arg Val Asp Ser Arg Arg
    130                 135                 140

Ser Leu Trp Asp Gln Gly Asn Phe Pro Leu Ile Ile Lys Asn Leu Lys
145                 150                 155                 160

Pro Glu Asp Ser Asp Thr Tyr Ile Cys Glu Val Glu Asp Gln Lys Glu
                165                 170                 175

Glu Val Gln Leu Val Val Val Gly Ala Ala Ala Thr Thr Thr Pro Ala
            180                 185                 190

Pro Arg Pro Pro Thr Pro Ala Pro Thr Ile Ala Ser Gln Pro Leu Ser
        195                 200                 205

Leu Arg Pro Glu Ala Cys Arg Pro Ala Ala Gly Gly Ala Val His Thr
    210                 215                 220

Arg Gly Leu Asp Phe Ala Cys Asp Ile Tyr Ile Trp Ala Pro Leu Ala
225                 230                 235                 240

Gly Thr Cys Gly Val Leu Leu Leu Ser Leu Val Ile Thr Leu Tyr Cys
                245                 250                 255

Lys Arg Gly Arg Lys Lys Leu Leu Tyr Ile Phe Lys Gln Pro Phe Met
            260                 265                 270

Arg Pro Val Gln Thr Thr Gln Glu Glu Asp Gly Cys Ser Cys Arg Phe
        275                 280                 285

Pro Glu Glu Glu Glu Gly Gly Cys Glu Leu Arg Val Lys Phe Ser Arg
    290                 295                 300

Ser Ala Asp Ala Pro Ala Tyr Gln Gln Gly Gln Asn Gln Leu Tyr Asn
305                 310                 315                 320

Glu Leu Asn Leu Gly Arg Arg Glu Glu Tyr Asp Val Leu Asp Lys Arg
                325                 330                 335

Arg Gly Arg Asp Pro Glu Met Gly Gly Lys Pro Arg Arg Lys Asn Pro
            340                 345                 350

Gln Glu Gly Leu Tyr Asn Glu Leu Gln Lys Asp Lys Met Ala Glu Ala
        355                 360                 365

Tyr Ser Glu Ile Gly Met Lys Gly Glu Arg Arg Arg Gly Lys Gly His
    370                 375                 380

Asp Gly Leu Tyr Gln Gly Leu Ser Thr Ala Thr Lys Asp Thr Tyr Asp
```

```
                385                 390                 395                 400
Ala Leu His Met Gln Ala Leu Pro Pro Arg
                405                 410

<210> SEQ ID NO 87
<211> LENGTH: 510
<212> TYPE: DNA
<213> ORGANISM: Artificial
<220> FEATURE:
<223> OTHER INFORMATION: Linked anti-HIV binders in LTG2317

<400> SEQUENCE: 87
tggatggaat gggatcgcga aatcaacaac tacacctccc tgattcactc cctgattgag        60
gaatcccaga atcaacagga agaacgaa caagagcttc tggagctgga caaatgggcc        120
tccctgtgga actggttcgg cggagggggg agtggaggtg gcggttcagg aggtggggga       180
agcggtggcg gtggtagtgg cggtggcggt tcaaagaaag tcgtgtacgg aaagaaggga       240
gacactgtgg agctgacctg taccgcaagc cagaagaaga acatccagtt ccactggaag       300
aactccaacc aaatcaagat cctggggaac cagggttcct tcctgactaa ggaccctca        360 aagctgaacg accgcgtgga tagcagacgc tccctgtggg accagggaaa cttcccgctt       420
atcattaaga acctcaaacc tgaggactcg gataacctaca tctgcgaagt ggaggaccag      480
aaggaggagg tgcagctggt ggtggtgggc                                        510
```

```
<210> SEQ ID NO 88
<211> LENGTH: 170
<212> TYPE: PRT
<213> ORGANISM: Artificial
<220> FEATURE:
<223> OTHER INFORMATION: Linked anti-HIV binders in LTG2317

<400> SEQUENCE: 88

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe Gly Gly
        35                  40                  45

Gly Gly Ser Gly Gly Gly Ser Gly Gly Gly Ser Gly Gly Gly
    50                  55                  60

Gly Ser Gly Gly Gly Ser Lys Lys Val Val Tyr Gly Lys Lys Gly
65                  70                  75                  80

Asp Thr Val Glu Leu Thr Cys Thr Ala Ser Gln Lys Lys Asn Ile Gln
                85                  90                  95

Phe His Trp Lys Asn Ser Asn Gln Ile Lys Ile Leu Gly Asn Gln Gly
            100                 105                 110

Ser Phe Leu Thr Lys Gly Pro Ser Lys Leu Asn Asp Arg Val Asp Ser
        115                 120                 125

Arg Arg Ser Leu Trp Asp Gln Gly Asn Phe Pro Leu Ile Ile Lys Asn
    130                 135                 140

Leu Lys Pro Glu Asp Ser Asp Thr Tyr Ile Cys Glu Val Glu Asp Gln
145                 150                 155                 160

Lys Glu Glu Val Gln Leu Val Val Val Gly
                165                 170

<210> SEQ ID NO 89
<211> LENGTH: 1263
```

<212> TYPE: DNA
<213> ORGANISM: Artificial
<220> FEATURE:
<223> OTHER INFORMATION: Anti-HIV CAR LTG2317

<400> SEQUENCE: 89

```
atgcttctcc tggtcaccct cctgctcctc tgcgaactgc ctcaccctgc cttccttctg      60
attcctgaca cctggatgga atgggatcgc gaaatcaaca actacacctc cctgattcac     120
tccctgattg aggaatccca gaatcaacag gagaagaacg aacaagagct tctggagctg     180
gacaaatggg cctccctgtg gaactggttc ggcggagggg ggagtggagg tggcggttca     240
ggaggtgggg gaagcggtgg cggtggtagt ggcggtggcg gttcaaagaa agtcgtgtac     300
ggaaagaagg gagacactgt ggagctgacc tgtaccgcaa gccagaagaa gaacatccag     360
ttccactgga gaactccaa ccaaatcaag atcctgggga accagggttc cttcctgact      420
aagggacccct caaagctgaa cgaccgcgtg gatagcagac gctccctgtg ggaccaggga     480
aacttcccgc ttatcattaa gaacctcaaa cctgaggact cggataccta catctgcgaa     540
gtggaggacc agaaggagga ggtgcagctg gtggtggtgg gcgcggccgc aactaccacc     600
cctgcccctc ggccgccgac tccggcccca accatcgcaa gccaaccccct ctccttgcgc    660
cccgaagctt gccgcccggc cgcgggtgga gccgtgcata ccggggggct ggactttgcc     720
tgcgatatct acatttgggc cccgctggcc ggcacttgcg gcgtgctcct gctgtcgctg     780
gtcatcaccc tttactgcaa gaggggccgg aagaagctgc tttacatctt caagcagccg     840
ttcatgcggc ccgtgcagac gactcaggaa gaggacggat gctcgtgcag attccctgag     900
gaggaagagg ggggatgcga actgcgcgtc aagttctcac ggtccgccga cgcccccgca     960
tatcaacagg gccagaatca gctctacaac gagctgaacc tgggaaggag agaggagtac    1020
gacgtgctgg acaagcgacg cggacgcgac ccggagatgg gggggaaacc acggcggaaa    1080
aaccctcagg aaggactgta caacgaactc cagaaagaca agatggcgga agcctactca    1140
gaaatcggga tgaagggaga gcggaggagg ggaaagggtc acgacgggct gtaccaggga    1200
ctgagcaccg ccactaagga tacctacgat gccttgcata tgcaagcact cccaccccgg    1260
tag                                                                  1263
```

<210> SEQ ID NO 90
<211> LENGTH: 420
<212> TYPE: PRT
<213> ORGANISM: Artificial
<220> FEATURE:
<223> OTHER INFORMATION: Anti-HIV CAR LTG2317

<400> SEQUENCE: 90

```
Met Leu Leu Leu Val Thr Ser Leu Leu Leu Cys Glu Leu Pro His Pro
1               5                   10                  15

Ala Phe Leu Leu Ile Pro Asp Thr Trp Met Glu Trp Asp Arg Glu Ile
                20                  25                  30

Asn Asn Tyr Thr Ser Leu Ile His Ser Leu Ile Glu Glu Ser Gln Asn
            35                  40                  45

Gln Gln Glu Lys Asn Glu Gln Glu Leu Leu Glu Leu Asp Lys Trp Ala
        50                  55                  60

Ser Leu Trp Asn Trp Phe Gly Gly Gly Gly Ser Gly Gly Gly Gly Ser
65                  70                  75                  80

Gly Gly Gly Gly Ser Gly Gly Gly Gly Ser Gly Gly Gly Gly Ser Lys
                85                  90                  95
```

```
Lys Val Val Tyr Gly Lys Gly Asp Thr Val Glu Leu Thr Cys Thr
                100                 105                 110
Ala Ser Gln Lys Lys Asn Ile Gln Phe His Trp Lys Asn Ser Asn Gln
        115                 120                 125
Ile Lys Ile Leu Gly Asn Gln Gly Ser Phe Leu Thr Lys Gly Pro Ser
130                 135                 140
Lys Leu Asn Asp Arg Val Asp Ser Arg Arg Ser Leu Trp Asp Gln Gly
145                 150                 155                 160
Asn Phe Pro Leu Ile Ile Lys Asn Leu Lys Pro Glu Asp Ser Asp Thr
                165                 170                 175
Tyr Ile Cys Glu Val Glu Asp Gln Lys Glu Glu Val Gln Leu Val Val
                180                 185                 190
Val Gly Ala Ala Thr Thr Thr Pro Ala Pro Arg Pro Pro Thr Pro
            195                 200                 205
Ala Pro Thr Ile Ala Ser Gln Pro Leu Ser Leu Arg Pro Glu Ala Cys
        210                 215                 220
Arg Pro Ala Ala Gly Gly Ala Val His Thr Arg Gly Leu Asp Phe Ala
225                 230                 235                 240
Cys Asp Ile Tyr Ile Trp Ala Pro Leu Ala Gly Thr Cys Gly Val Leu
                245                 250                 255
Leu Leu Ser Leu Val Ile Thr Leu Tyr Cys Lys Arg Gly Arg Lys Lys
                260                 265                 270
Leu Leu Tyr Ile Phe Lys Gln Pro Phe Met Arg Pro Val Gln Thr Thr
            275                 280                 285
Gln Glu Glu Asp Gly Cys Ser Cys Arg Phe Pro Glu Glu Glu Glu Gly
        290                 295                 300
Gly Cys Glu Leu Arg Val Lys Phe Ser Arg Ser Ala Asp Ala Pro Ala
305                 310                 315                 320
Tyr Gln Gln Gly Gln Asn Gln Leu Tyr Asn Glu Leu Asn Leu Gly Arg
                325                 330                 335
Arg Glu Glu Tyr Asp Val Leu Asp Lys Arg Arg Gly Arg Asp Pro Glu
                340                 345                 350
Met Gly Gly Lys Pro Arg Arg Lys Asn Pro Gln Glu Gly Leu Tyr Asn
            355                 360                 365
Glu Leu Gln Lys Asp Lys Met Ala Glu Ala Tyr Ser Glu Ile Gly Met
        370                 375                 380
Lys Gly Glu Arg Arg Arg Gly Lys Gly His Asp Gly Leu Tyr Gln Gly
385                 390                 395                 400
Leu Ser Thr Ala Thr Lys Asp Thr Tyr Asp Ala Leu His Met Gln Ala
                405                 410                 415
Leu Pro Pro Arg
            420

<210> SEQ ID NO 91
<211> LENGTH: 876
<212> TYPE: DNA
<213> ORGANISM: Artificial
<220> FEATURE:
<223> OTHER INFORMATION: Linked anti-HIV binders in LTG2318

<400> SEQUENCE: 91
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
```

```
ctgtgggacc agggaaactt cccgcttatc attaagaacc tcaaacctga ggactcggat    240
acctacatct gcgaagtgga ggaccagaag gaggaggtgc agctggtggt ggtgggcgga    300
ggtggcggtt caggcggagg ggggagtgga ggtgggggaa gccaggtgca gctggtgcag    360 tctggggggag gcttggtaca gcctggaggg tccctgagac tctcctgtgc agcctctgct    420
ttcgatttct ctgattatga aatgagctgg gtccgcgagg ctccagggaa ggggctggag    480
tggattgggg aaatcaatga tagtggaaac accatttaca atccgtccct caagagtcga    540
gtcaccatct ccagagacaa ttccaagaac acactgtatc tgcaaatgaa caccctgaga    600
gccgaggaca cagccatata ttactgtgcg atatatggtg gtaactccgg gggagagtac    660
tggggccagg gcaccctggt caccgtctcc tcaggtggag ggggctctgg cggtggaggg    720
tccgggggag gtggctcgtg gatggaatgg gatcgcgaaa tcaacaacta cacctcccctg   780 attcactccc tgattgagga atcccagaat caacaggaga gaacgaaca agagcttctg     840 gagctggaca atgggcctc cctgtggaac tggttc                              876
```

<210> SEQ ID NO 92
<211> LENGTH: 292
<212> TYPE: PRT
<213> ORGANISM: Artificial
<220> FEATURE:
<223> OTHER INFORMATION: Linked anti-HIV binders in LTG2318

<400> SEQUENCE: 92

```
Lys Lys Val Val Tyr Gly Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Gly Ser Gly Gly Gly
            100                 105                 110

Gly Ser Gln Val Gln Leu Val Gln Ser Gly Gly Gly Leu Val Gln Pro
        115                 120                 125

Gly Gly Ser Leu Arg Leu Ser Cys Ala Ala Ser Ala Phe Asp Phe Ser
    130                 135                 140

Asp Tyr Glu Met Ser Trp Val Arg Glu Ala Pro Gly Lys Gly Leu Glu
145                 150                 155                 160

Trp Ile Gly Glu Ile Asn Asp Ser Gly Asn Thr Ile Tyr Asn Pro Ser
                165                 170                 175

Leu Lys Ser Arg Val Thr Ile Ser Arg Asp Asn Ser Lys Asn Thr Leu
            180                 185                 190

Tyr Leu Gln Met Asn Thr Leu Arg Ala Glu Asp Thr Ala Ile Tyr Tyr
        195                 200                 205

Cys Ala Ile Tyr Gly Gly Asn Ser Gly Gly Glu Tyr Trp Gly Gln Gly
    210                 215                 220

Thr Leu Val Thr Val Ser Ser Gly Gly Gly Gly Ser Gly Gly Gly Gly
225                 230                 235                 240
```

```
Ser Gly Gly Gly Gly Ser Trp Met Glu Trp Asp Arg Glu Ile Asn Asn
            245                 250                 255

Tyr Thr Ser Leu Ile His Ser Leu Ile Glu Glu Ser Gln Asn Gln Gln
        260                 265                 270

Glu Lys Asn Glu Gln Glu Leu Leu Glu Leu Asp Lys Trp Ala Ser Leu
    275                 280                 285

Trp Asn Trp Phe
    290

<210> SEQ ID NO 93
<211> LENGTH: 1629
<212> TYPE: DNA
<213> ORGANISM: Artificial
<220> FEATURE:
<223> OTHER INFORMATION: Anti-HIV CAR LTG2318

<400> SEQUENCE: 93
```

| | | | | |
|---|---|---|---|---|
| atgcttctcc | tggtcacctc | cctgctcctc | tgcgaactgc | ctcaccctgc | cttccttctg | 60 |
| attcctgaca | ccaagaaagt | cgtgtacgga | aagaagggag | acactgtgga | gctgacctgt | 120 |
| accgcaagcc | agaagaagaa | catccagttc | cactggaaga | actccaacca | aatcaagatc | 180 |
| ctggggaacc | agggttcctt | cctgactaag | ggaccctcaa | agctgaacga | ccgcgtggat | 240 |
| agcagacgct | ccctgtggga | ccagggaaac | ttcccgctta | tcattaagaa | cctcaaacct | 300 |
| gaggactcgg | atacctacat | ctgcgaagtg | gaggaccaga | aggaggaggt | gcagctggtg | 360 |
| gtggtgggcg | gaggtggcgg | ttcaggcgga | ggggggagtg | gaggtggggg | aagccaggtg | 420 |
| cagctggtgc | agtctggggg | aggcttggta | cagcctggag | ggtccctgag | actctcctgt | 480 |
| gcagcctctg | ctttcgattt | ctctgattat | gaaatgagct | gggtccgcga | ggctccaggg | 540 |
| aaggggctgg | agtggattgg | ggaaatcaat | gatagtggaa | acaccattta | caatccgtcc | 600 |
| ctcaagagtc | gagtcaccat | ctccagagac | aattccaaga | cacactgta | tctgcaaatg | 660 |
| aacaccctga | gaccgagga | cacagccata | tattactgtg | cgatatatgg | tggtaactcc | 720 |
| gggggagagt | actggggcca | gggcaccctg | gtcaccgtct | cctcaggtgg | aggggctct | 780 |
| ggcggtggag | ggtccggggg | aggtggctcg | tggatggaat | gggatcgcga | aatcaacaac | 840 |
| tacacctccc | tgattcactc | cctgattgag | gaatcccaga | atcaacagga | agaacgaa | 900 |
| caagagcttc | tggagctgga | caaatgggcc | tccctgtgga | actggttcgc | ggccgcaact | 960 |
| accaccctg | ccctcggcc | gccgactccg | gccccaacca | tcgcaagcca | acccctctcc | 1020 |
| ttgcgcccg | aagcttgccg | cccggccgcg | ggtggagccg | tgcatacccg | ggggctggac | 1080 |
| tttgcctgcg | atatctacat | ttgggccccg | ctggccggca | cttgcggcgt | gctcctgctg | 1140 |
| tcgctggtca | tcacccttta | ctgcaagagg | ggccggaaga | agctgcttta | catcttcaag | 1200 |
| cagccgttca | tgcggcccgt | gcagacgact | caggaagagg | acggatgctc | gtgcagattc | 1260 |
| cctgaggagg | aagagggggg | atgcgaactg | cgcgtcaagt | tctcacggtc | cgccgacgcc | 1320 |
| cccgcatatc | aacagggcca | gaatcagctc | tacaacgagc | tgaacctggg | aaggagagag | 1380 |
| gagtacgacg | tgctggacaa | gcgacgcgga | cgcgacccgg | agatgggggg | gaaaccacgg | 1440 |
| cggaaaaacc | ctcaggaagg | actgtacaac | gaactccaga | aagacaagat | ggcggaagcc | 1500 |
| tactcagaaa | tcgggatgaa | gggagagcgg | aggaggggaa | agggtcacga | cgggctgtac | 1560 |
| cagggactga | gcaccgccac | taaggatacc | tacgatgcct | tgcatatgca | agcactccca | 1620 |
| ccccggtag | | | | | 1629 |

<210> SEQ ID NO 94
<211> LENGTH: 542
<212> TYPE: PRT
<213> ORGANISM: Artificial
<220> FEATURE:
<223> OTHER INFORMATION: Anti-HIV CAR LTG2318

<400> SEQUENCE: 94

```
Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
                20                  25                  30

Gly Asp Thr Val Glu Leu Thr Cys Thr Ala Ser Gln Lys Lys Asn Ile
            35                  40                  45

Gln Phe His Trp Lys Asn Ser Asn Gln Ile Lys Ile Leu Gly Asn Gln
        50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Gly Gly Gly Gly Ser
        115                 120                 125

Gly Gly Gly Gly Ser Gly Gly Gly Ser Gln Val Gln Leu Val Gln
    130                 135                 140

Ser Gly Gly Gly Leu Val Gln Pro Gly Gly Ser Leu Arg Leu Ser Cys
145                 150                 155                 160

Ala Ala Ser Ala Phe Asp Phe Ser Asp Tyr Glu Met Ser Trp Val Arg
                165                 170                 175

Glu Ala Pro Gly Lys Gly Leu Glu Trp Ile Gly Glu Ile Asn Asp Ser
            180                 185                 190

Gly Asn Thr Ile Tyr Asn Pro Ser Leu Lys Ser Arg Val Thr Ile Ser
        195                 200                 205

Arg Asp Asn Ser Lys Asn Thr Leu Tyr Leu Gln Met Asn Thr Leu Arg
    210                 215                 220

Ala Glu Asp Thr Ala Ile Tyr Tyr Cys Ala Ile Tyr Gly Gly Asn Ser
225                 230                 235                 240

Gly Gly Glu Tyr Trp Gly Gln Gly Thr Leu Val Thr Val Ser Ser Gly
                245                 250                 255

Gly Gly Gly Ser Gly Gly Gly Ser Gly Gly Gly Ser Trp Met
            260                 265                 270

Glu Trp Asp Arg Glu Ile Asn Asn Tyr Thr Ser Leu Ile His Ser Leu
        275                 280                 285

Ile Glu Glu Ser Gln Asn Gln Gln Glu Lys Asn Glu Gln Glu Leu Leu
    290                 295                 300

Glu Leu Asp Lys Trp Ala Ser Leu Trp Asn Trp Phe Ala Ala Ala Thr
305                 310                 315                 320

Thr Thr Pro Ala Pro Arg Pro Pro Thr Pro Ala Pro Thr Ile Ala Ser
                325                 330                 335

Gln Pro Leu Ser Leu Arg Pro Glu Ala Cys Arg Pro Ala Ala Gly Gly
            340                 345                 350

Ala Val His Thr Arg Gly Leu Asp Phe Ala Cys Asp Ile Tyr Ile Trp
        355                 360                 365

Ala Pro Leu Ala Gly Thr Cys Gly Val Leu Leu Leu Ser Leu Val Ile
```

```
                370                 375                 380
Thr Leu Tyr Cys Lys Arg Gly Arg Lys Leu Leu Tyr Ile Phe Lys
385                 390                 395                 400

Gln Pro Phe Met Arg Pro Val Gln Thr Thr Gln Glu Asp Gly Cys
                405                 410                 415

Ser Cys Arg Phe Pro Glu Glu Glu Gly Gly Cys Glu Leu Arg Val
                420                 425                 430

Lys Phe Ser Arg Ser Ala Asp Ala Pro Ala Tyr Gln Gln Gly Gln Asn
                435                 440                 445

Gln Leu Tyr Asn Glu Leu Asn Leu Gly Arg Arg Glu Glu Tyr Asp Val
450                 455                 460

Leu Asp Lys Arg Arg Gly Arg Asp Pro Glu Met Gly Gly Lys Pro Arg
465                 470                 475                 480

Arg Lys Asn Pro Gln Glu Gly Leu Tyr Asn Glu Leu Gln Lys Asp Lys
                485                 490                 495

Met Ala Glu Ala Tyr Ser Glu Ile Gly Met Lys Gly Glu Arg Arg Arg
                500                 505                 510

Gly Lys Gly His Asp Gly Leu Tyr Gln Gly Leu Ser Thr Ala Thr Lys
                515                 520                 525

Asp Thr Tyr Asp Ala Leu His Met Gln Ala Leu Pro Pro Arg
                530                 535                 540

<210> SEQ ID NO 95
<211> LENGTH: 876
<212> TYPE: DNA
<213> ORGANISM: Artificial
<220> FEATURE:
<223> OTHER INFORMATION: Linked anti-HIV binders in LTG2319

<400> SEQUENCE: 95
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggcgga     300
ggtggcggtt caggcggagg ggggagtgga ggtggggggaa gctggatgga atgggatcgc     360
gaaatcaaca actacaccctc cctgattcac tccctgattg aggaatccca gaatcaacag     420
gagaagaacg aacaagagct tctggagctg acaaatgggc cctccctgtg gaactggttc     480
ggtggagggg gctctggcgg tggagggtcc gggggaggtg gctcgcaggt gcagctggtg     540
cagtctgggg gaggcttggt acagcctgga gggtccctga ctctcctg tgcagcctct     600 gctttcgatt tctctgatta tgaaatgagc tgggtccgcg aggctccagg gaagggctg     660 gagtggattg ggaaatcaa tgatagtgga aacaccattt acaatccgtc cctcaagagt     720
cgagtcacca tctccagaga caattccaag aacacactgt atctgcaaat gaacaccctg     780
agagccgagg acacagccat atattactgt gcgatatatg gtggtaactc cggggagag    840 tactggggcc agggcaccct ggtcaccgtc tcctca                             876

<210> SEQ ID NO 96
<211> LENGTH: 292
<212> TYPE: PRT
<213> ORGANISM: Artificial
<220> FEATURE:
<223> OTHER INFORMATION: Linked anti-HIV binders in LTG2319
```

<400> SEQUENCE: 96

```
Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
            100                 105                 110

Gly Ser Trp Met Glu Trp Asp Arg Glu Ile Asn Asn Tyr Thr Ser Leu
            115                 120                 125

Ile His Ser Leu Ile Glu Glu Ser Gln Asn Gln Gln Glu Lys Asn Glu
130                 135                 140

Gln Glu Leu Leu Glu Leu Asp Lys Trp Ala Ser Leu Trp Asn Trp Phe
145                 150                 155                 160

Gly Gly Gly Gly Ser Gly Gly Gly Ser Gly Gly Gly Gly Ser Gln
                165                 170                 175

Val Gln Leu Val Gln Ser Gly Gly Leu Val Gln Pro Gly Gly Ser
            180                 185                 190

Leu Arg Leu Ser Cys Ala Ala Ser Ala Phe Asp Phe Ser Asp Tyr Glu
            195                 200                 205

Met Ser Trp Val Arg Glu Ala Pro Gly Lys Gly Leu Glu Trp Ile Gly
210                 215                 220

Glu Ile Asn Asp Ser Gly Asn Thr Ile Tyr Asn Pro Ser Leu Lys Ser
225                 230                 235                 240

Arg Val Thr Ile Ser Arg Asp Asn Ser Lys Asn Thr Leu Tyr Leu Gln
            245                 250                 255

Met Asn Thr Leu Arg Ala Glu Asp Thr Ala Ile Tyr Tyr Cys Ala Ile
            260                 265                 270

Tyr Gly Gly Asn Ser Gly Gly Glu Tyr Trp Gly Gln Gly Thr Leu Val
            275                 280                 285

Thr Val Ser Ser
    290
```

<210> SEQ ID NO 97
<211> LENGTH: 1629
<212> TYPE: DNA
<213> ORGANISM: Artificial
<220> FEATURE:
<223> OTHER INFORMATION: Anti-HIV CAR LTG2319

<400> SEQUENCE: 97

```
atgcttctcc tggtcacctc cctgctcctc tgcgaactgc ctcaccctgc cttccttctg    60
attcctgaca ccaagaaagt cgtgtacgga aagaagggag acactgtgga gctgacctgt   120
accgcaagcc agaagaagaa catccagttc cactggaaga ctccaaccaa atcaagatc   180
ctggggaaca agggttcctt cctgactaag ggaccctcaa agctgaacga ccgcgtggat   240
agcagacgct ccctgtggga ccagggaaac ttcccgctta tcattaagaa cctcaaacct   300
```

```
gaggactcgg atacctacat ctgcgaagtg gaggaccaga aggaggaggt gcagctggtg    360
gtggtgggcg gaggtggcgg ttcaggcgga ggggggagtg gaggtgggg aagctggatg    420 gaatgggatc gcgaaatcaa caactacacc tccctgattc actccctgat tgaggaatcc    480
cagaatcaac aggagaagaa cgaacaagag cttctggagc tggacaaatg ggcctccctg    540
tggaactggt cggtggaggg ggctctggc ggtggagggt ccggggagg tggctcgcag      600 gtgcagctgg tgcagtctgg gggaggcttg gtacagcctg agggtccct gagactctcc    660 tgtgcagcct ctgctttcga tttctctgat tatgaaatga gctgggtccg cgaggctcca    720 gggaagggc tggagtggat tgggaaatc aatgatagtg gaaacaccat ttacaatccg      780
tccctcaaga gtcgagtcac catctccaga gacaattcca agaacacact gtatctgcaa    840
atgaacaccc tgagagccga ggacacagcc atatattact gtgcgatata tggtggtaac    900
tccgggggag agtactgggg ccagggcacc ctggtcaccg tctcctcagc ggccgcaact    960 accaccctg cccctcggcc gccgactccg gccccaacca tcgcaagcca accctctcc     1020 ttgcgcccg aagcttgccg cccggccgcg ggtggagccg tgcatacccg ggggctggac    1080
tttgcctgcg atatctacat ttgggccccg ctggccggca cttgcggcgt gctcctgctg    1140
tcgctggtca tcacccttta ctgcaagagg ggccggaaga agctgctta catcttcaag     1200 cagccgttca tgcggcccgt gcagacgact caggaagagg acggatgctc gtgcagattc    1260
cctgaggagg aagaggggg atgcgaactg cgcgtcaagt tctcacggtc cgccgacgcc    1320
cccgcatatc aacagggcca gaatcagctc tacaacgagc tgaacctggg aaggagagag    1380
gagtacgacg tgctggacaa gcgacgcgga cgcgacccgg agatgggggg gaaaccacgg    1440
cggaaaaacc ctcaggaagg actgtacaac gaactccaga agacaagat ggcggaagcc     1500 tactcagaaa tcgggatgaa gggagagcgg aggagggaa agggtcacga cgggctgtac    1560
cagggactga gcaccgccac taaggatacc tacgatgcct tgcatatgca agcactccca    1620
ccccggtag                                                           1629
```

<210> SEQ ID NO 98
<211> LENGTH: 542
<212> TYPE: PRT
<213> ORGANISM: Artificial
<220> FEATURE:
<223> OTHER INFORMATION: Anti-HIV CAR LTG2319

<400> SEQUENCE: 98

```
Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
        35                  40                  45

Gln Phe His Trp Lys Asn Ser Asn Gln Ile Lys Ile Leu Gly Asn Gln
    50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Val Gly Gly Gly Gly Ser
```

-continued

```
            115                 120                 125
Gly Gly Gly Gly Ser Gly Gly Gly Ser Trp Met Glu Trp Asp Arg
        130                 135                 140
Glu Ile Asn Asn Tyr Thr Ser Leu Ile His Ser Leu Ile Glu Glu Ser
145                 150                 155                 160
Gln Asn Gln Gln Glu Lys Asn Glu Gln Glu Leu Leu Glu Leu Asp Lys
                165                 170                 175
Trp Ala Ser Leu Trp Asn Trp Phe Gly Gly Gly Ser Gly Gly Gly
            180                 185                 190
Gly Ser Gly Gly Gly Gly Ser Gln Val Gln Leu Val Gln Ser Gly Gly
        195                 200                 205
Gly Leu Val Gln Pro Gly Gly Ser Leu Arg Leu Ser Cys Ala Ala Ser
        210                 215                 220
Ala Phe Asp Phe Ser Asp Tyr Glu Met Ser Trp Val Arg Glu Ala Pro
225                 230                 235                 240
Gly Lys Gly Leu Glu Trp Ile Gly Glu Ile Asn Asp Ser Gly Asn Thr
                245                 250                 255
Ile Tyr Asn Pro Ser Leu Lys Ser Arg Val Thr Ile Ser Arg Asp Asn
                260                 265                 270
Ser Lys Asn Thr Leu Tyr Leu Gln Met Asn Thr Leu Arg Ala Glu Asp
        275                 280                 285
Thr Ala Ile Tyr Tyr Cys Ala Ile Tyr Gly Gly Asn Ser Gly Gly Glu
        290                 295                 300
Tyr Trp Gly Gln Gly Thr Leu Val Thr Val Ser Ser Ala Ala Ala Thr
305                 310                 315                 320
Thr Thr Pro Ala Pro Arg Pro Pro Thr Pro Ala Pro Thr Ile Ala Ser
                325                 330                 335
Gln Pro Leu Ser Leu Arg Pro Glu Ala Cys Arg Pro Ala Ala Gly Gly
        340                 345                 350
Ala Val His Thr Arg Gly Leu Asp Phe Ala Cys Asp Ile Tyr Ile Trp
        355                 360                 365
Ala Pro Leu Ala Gly Thr Cys Gly Val Leu Leu Leu Ser Leu Val Ile
        370                 375                 380
Thr Leu Tyr Cys Lys Arg Gly Arg Lys Lys Leu Leu Tyr Ile Phe Lys
385                 390                 395                 400
Gln Pro Phe Met Arg Pro Val Gln Thr Thr Gln Glu Glu Asp Gly Cys
                405                 410                 415
Ser Cys Arg Phe Pro Glu Glu Glu Glu Gly Gly Cys Glu Leu Arg Val
                420                 425                 430
Lys Phe Ser Arg Ser Ala Asp Ala Pro Ala Tyr Gln Gln Gly Gln Asn
        435                 440                 445
Gln Leu Tyr Asn Glu Leu Asn Leu Gly Arg Arg Glu Glu Tyr Asp Val
        450                 455                 460
Leu Asp Lys Arg Arg Gly Arg Asp Pro Glu Met Gly Gly Lys Pro Arg
465                 470                 475                 480
Arg Lys Asn Pro Gln Glu Gly Leu Tyr Asn Glu Leu Gln Lys Asp Lys
                485                 490                 495
Met Ala Glu Ala Tyr Ser Glu Ile Gly Met Lys Gly Glu Arg Arg Arg
            500                 505                 510
Gly Lys Gly His Asp Gly Leu Tyr Gln Gly Leu Ser Thr Ala Thr Lys
        515                 520                 525
Asp Thr Tyr Asp Ala Leu His Met Gln Ala Leu Pro Pro Arg
        530                 535                 540
```

<210> SEQ ID NO 99
<211> LENGTH: 876
<212> TYPE: DNA
<213> ORGANISM: Artificial
<220> FEATURE:
<223> OTHER INFORMATION: Linked anti-HIV binders in LTG2320

<400> SEQUENCE: 99

```
tggatggaat gggatcgcga aatcaacaac tacacctccc tgattcactc cctgattgag     60
gaatcccaga atcaacagga gaagaacgaa caagagcttc tggagctgga caaatgggcc    120
tccctgtgga actggttcgg tggagggggc tctggcggtg agggtccgg  ggaggtggc     180
tcgaagaaag tcgtgtacgg aaagaaggga gacactgtgg agctgacctg taccgcaagc    240
cagaagaaga acatccagtt ccactggaag aactccaacc aaatcaagat cctggggaac    300
cagggttcct tcctgactaa ggaccctca aagctgaacg accgcgtgga tagcagacgc     360
tccctgtggg accagggaaa cttcccgctt atcattaaga acctcaaacc tgaggactcg    420
gataccctaca tctgcgaagt ggaggaccag aaggaggagg tgcagctggt ggtggtgggc    480
ggaggtggcg gttcaggcgg aggggggagt ggaggtgggg gaagccaggt gcagctggtg    540
cagtctgggg gaggcttggt acagcctgga gggtccctga ctctcctg tgcagcctct      600
gctttcgatt tctctgatta tgaaatgagc tgggtccgcg aggctccagg gaaggggctg    660
gagtggattg gggaaatcaa tgatagtgga aacaccattt acaatccgtc cctcaagagt    720
cgagtcacca tctccagaga caattccaag aacacactgt atctgcaaat gaacaccctg    780
agagccgagg acacagccat atattactgt gcgatatatg gtggtaactc cggggagag    840
tactggggcc agggcaccct ggtcaccgtc tcctca                              876
```

<210> SEQ ID NO 100
<211> LENGTH: 292
<212> TYPE: PRT
<213> ORGANISM: Artificial
<220> FEATURE:
<223> OTHER INFORMATION: Linked anti-HIV binders in LTG2320

<400> SEQUENCE: 100

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
                20                  25                  30

Leu Leu Glu Leu Asp Lys Trp Ala Ser Leu Trp Asn Trp Phe Gly Gly
            35                  40                  45

Gly Gly Ser Gly Gly Gly Gly Ser Gly Gly Gly Gly Ser Lys Lys Val
        50                  55                  60

Val Tyr Gly Lys Lys Gly Asp Thr Val Glu Leu Thr Cys Thr Ala Ser
65                  70                  75                  80

Gln Lys Lys Asn Ile Gln Phe His Trp Lys Asn Ser Asn Gln Ile Lys
                85                  90                  95

Ile Leu Gly Asn Gln Gly Ser Phe Leu Thr Lys Gly Pro Ser Lys Leu
            100                 105                 110

Asn Asp Arg Val Asp Ser Arg Arg Ser Leu Trp Asp Gln Gly Asn Phe
        115                 120                 125

Pro Leu Ile Ile Lys Asn Leu Lys Pro Glu Asp Ser Asp Thr Tyr Ile
    130                 135                 140

Cys Glu Val Glu Asp Gln Lys Glu Glu Val Gln Leu Val Val Val Gly

```
                145                 150                 155                 160
Gly Gly Gly Gly Ser Gly Gly Gly Ser Gly Gly Gly Ser Gln
                    165                 170                 175

Val Gln Leu Val Gln Ser Gly Gly Leu Val Gln Pro Gly Gly Ser
                180                 185                 190

Leu Arg Leu Ser Cys Ala Ala Ser Ala Phe Asp Phe Ser Asp Tyr Glu
            195                 200                 205

Met Ser Trp Val Arg Glu Ala Pro Gly Lys Gly Leu Glu Trp Ile Gly
        210                 215                 220

Glu Ile Asn Asp Ser Gly Asn Thr Ile Tyr Asn Pro Ser Leu Lys Ser
225                 230                 235                 240

Arg Val Thr Ile Ser Arg Asp Asn Ser Lys Asn Thr Leu Tyr Leu Gln
                245                 250                 255

Met Asn Thr Leu Arg Ala Glu Asp Thr Ala Ile Tyr Tyr Cys Ala Ile
                260                 265                 270

Tyr Gly Gly Asn Ser Gly Gly Glu Tyr Trp Gly Gln Gly Thr Leu Val
            275                 280                 285

Thr Val Ser Ser
    290

<210> SEQ ID NO 101
<211> LENGTH: 1629
<212> TYPE: DNA
<213> ORGANISM: Artificial
<220> FEATURE:
<223> OTHER INFORMATION: Anti-HIV CAR LTG2320

<400> SEQUENCE: 101
atgcttctcc tggtcacctc cctgctcctc tgcgaactgc ctcaccctgc cttccttctg     60
attcctgaca cctggatgga atgggatcgc gaaatcaaca actacacctc cctgattcac    120
tccctgattg aggaatccca gaatcaacag gagaagaacg aacaagagct tctggagctg    180
gacaaatggg cctccctgtg gaactggttc ggtggagggg gctctggcgg tggagggtcc    240 ggggggaggtg gctcgaagaa agtcgtgtac ggaaagaagg gagacactgt ggagctgacc    300
tgtaccgcaa gccagaagaa gaacatccag ttccactgga gaactccaa ccaaatcaag    360 atcctgggga accaggggttc cttcctgact aagggaccct caaagctgaa cgaccgcgtg    420
gatagcagac gctccctgtg ggaccaggga acttcccgc ttatcattaa gaaccctcaaa    480 cctgaggact cggataccta catctgcgaa gtggaggacc agaaggagga ggtgcagctg    540
gtggtggtgg gcggaggtgg cggttcaggc ggagggggga gtggaggtgg gggaagccag    600
gtgcagctgg tgcagtctgg gggaggcttg gtacagcctg gagggtccct gagactctcc    660
tgtgcagcct ctgctttcga tttctctgat tatgaaatga gctgggtccg cgaggctcca    720
gggaaggggc tggagtggat tggggaaatc aatgatagtg gaaacaccat ttacaatccg    780
tccctcaaga gtcgagtcac catctccaga gacaattcca gaacacact gtatctgcaa    840 atgaacaccc tgagagccga ggacacagcc atatattact gtgcgatata tggtggtaac    900
tccgggggag agtactgggg ccagggcacc ctggtcaccg tctcctcagc ggccgcaact    960 accaccctg cccctcggcc gccgactccg gccccaacca tcgcaagcca accctctcc    1020 ttgcgccccg aagcttgccg cccggccgcg ggtggagccg tgcataccg ggggctggac    1080 tttgcctgcg atatctacat ttgggccccg ctggccggca cttgcggcgt gctcctgctg    1140
tcgctggtca tcaccctta ctgcaagagg ggccggaaga agctgcttta catcttcaag    1200
```

-continued

```
cagccgttca tgcggcccgt gcagacgact caggaagagg acggatgctc gtgcagattc    1260
cctgaggagg aagaggggggg atgcgaactg cgcgtcaagt tctcacggtc cgccgacgcc    1320
cccgcatatc aacagggcca gaatcagctc tacaacgagc tgaacctggg aaggagagag    1380
gagtacgacg tgctggacaa gcgacgcgga cgcgacccgg agatgggggg gaaaccacgg    1440
cggaaaaacc ctcaggaagg actgtacaac gaactccaga agacaagat ggcggaagcc     1500 tactcagaaa tcgggatgaa gggagagcgg aggaggggaa agggtcacga cgggctgtac    1560
cagggactga gcaccgccac taaggatacc tacgatgcct tgcatatgca agcactccca    1620
ccccggtag                                                              1629
```

<210> SEQ ID NO 102
<211> LENGTH: 542
<212> TYPE: PRT
<213> ORGANISM: Artificial
<220> FEATURE:
<223> OTHER INFORMATION: Anti-HIV CAR LTG2320

<400> SEQUENCE: 102

```
Met Leu Leu Leu Val Thr Ser Leu Leu Leu Cys Glu Leu Pro His Pro
1               5                   10                  15

Ala Phe Leu Leu Ile Pro Asp Thr Trp Met Glu Trp Asp Arg Glu Ile
            20                  25                  30

Asn Asn Tyr Thr Ser Leu Ile His Ser Leu Ile Glu Glu Ser Gln Asn
        35                  40                  45

Gln Gln Glu Lys Asn Glu Gln Glu Leu Leu Glu Leu Asp Lys Trp Ala
    50                  55                  60

Ser Leu Trp Asn Trp Phe Gly Gly Gly Ser Gly Gly Gly Gly Ser
65                  70                  75                  80

Gly Gly Gly Gly Ser Lys Lys Val Val Tyr Gly Lys Lys Gly Asp Thr
                85                  90                  95

Val Glu Leu Thr Cys Thr Ala Ser Gln Lys Lys Asn Ile Gln Phe His
            100                 105                 110

Trp Lys Asn Ser Asn Gln Ile Lys Ile Leu Gly Asn Gln Gly Ser Phe
        115                 120                 125

Leu Thr Lys Gly Pro Ser Lys Leu Asn Asp Arg Val Asp Ser Arg Arg
    130                 135                 140

Ser Leu Trp Asp Gln Gly Asn Phe Pro Leu Ile Ile Lys Asn Leu Lys
145                 150                 155                 160

Pro Glu Asp Ser Asp Thr Tyr Ile Cys Glu Val Glu Asp Gln Lys Glu
                165                 170                 175

Glu Val Gln Leu Val Val Val Gly Gly Gly Gly Ser Gly Gly Gly
            180                 185                 190

Gly Ser Gly Gly Gly Gly Ser Gln Val Gln Leu Val Gln Ser Gly Gly
        195                 200                 205

Gly Leu Val Gln Pro Gly Gly Ser Leu Arg Leu Ser Cys Ala Ala Ser
    210                 215                 220

Ala Phe Asp Phe Ser Asp Tyr Glu Met Ser Trp Val Arg Glu Ala Pro
225                 230                 235                 240

Gly Lys Gly Leu Glu Trp Ile Gly Glu Ile Asn Asp Ser Gly Asn Thr
                245                 250                 255

Ile Tyr Asn Pro Ser Leu Lys Ser Arg Val Thr Ile Ser Arg Asp Asn
            260                 265                 270

Ser Lys Asn Thr Leu Tyr Leu Gln Met Asn Thr Leu Arg Ala Glu Asp
        275                 280                 285
```

Thr Ala Ile Tyr Tyr Cys Ala Ile Tyr Gly Gly Asn Ser Gly Gly Glu
    290                 295                 300

Tyr Trp Gly Gln Gly Thr Leu Val Thr Val Ser Ser Ala Ala Ala Thr
305                 310                 315                 320

Thr Thr Pro Ala Pro Arg Pro Pro Thr Pro Ala Pro Thr Ile Ala Ser
            325                 330                 335

Gln Pro Leu Ser Leu Arg Pro Glu Ala Cys Arg Pro Ala Ala Gly Gly
            340                 345                 350

Ala Val His Thr Arg Gly Leu Asp Phe Ala Cys Asp Ile Tyr Ile Trp
        355                 360                 365

Ala Pro Leu Ala Gly Thr Cys Gly Val Leu Leu Leu Ser Leu Val Ile
        370                 375                 380

Thr Leu Tyr Cys Lys Arg Gly Arg Lys Lys Leu Leu Tyr Ile Phe Lys
385                 390                 395                 400

Gln Pro Phe Met Arg Pro Val Gln Thr Thr Gln Glu Glu Asp Gly Cys
            405                 410                 415

Ser Cys Arg Phe Pro Glu Glu Glu Gly Gly Cys Glu Leu Arg Val
            420                 425                 430

Lys Phe Ser Arg Ser Ala Asp Ala Pro Ala Tyr Gln Gln Gly Gln Asn
        435                 440                 445

Gln Leu Tyr Asn Glu Leu Asn Leu Gly Arg Arg Glu Glu Tyr Asp Val
    450                 455                 460

Leu Asp Lys Arg Arg Gly Arg Asp Pro Glu Met Gly Gly Lys Pro Arg
465                 470                 475                 480

Arg Lys Asn Pro Gln Glu Gly Leu Tyr Asn Glu Leu Gln Lys Asp Lys
            485                 490                 495

Met Ala Glu Ala Tyr Ser Glu Ile Gly Met Lys Gly Glu Arg Arg Arg
            500                 505                 510

Gly Lys Gly His Asp Gly Leu Tyr Gln Gly Leu Ser Thr Ala Thr Lys
        515                 520                 525

Asp Thr Tyr Asp Ala Leu His Met Gln Ala Leu Pro Pro Arg
    530                 535                 540

<210> SEQ ID NO 103
<211> LENGTH: 831
<212> TYPE: DNA
<213> ORGANISM: Artificial
<220> FEATURE:
<223> OTHER INFORMATION: Anti-HIV binders contained in LTG2323

<400> SEQUENCE: 103
aagaaagtcg tgtacggaaa gaagggagac actgtggagc tgacctgtac cgcaagccag     60
aagaagaaca tccagttcca ctggaagaac tccaaccaaa tcaagatcct ggggaaccag    120
ggttccttcc tgactaaggg accctcaaag ctgaacgacc gcgtggatag cagacgctcc    180
ctgtgggacc agggaaactt cccgcttatc attaagaacc tcaaacctga ggactcggat    240
acctacatct gcgaagtgga ggaccagaag gaggaggtgc agctggtggt ggtgggggga    300
ggtggcggtt caggcggagg ggggagtgga ggtgggggaa gccaggtgca gctggtgcag    360 tctggggag gcttggtaca gcctggaggg tccctgagac tctcctgtgc agcctctgct    420
ttcgatttct ctgattatga aatgagctgg gtccgcgagg ctccagggaa ggggctggag    480
tggattgggg aaatcaatga tagtggaaac accatttaca atccgtccct caagagtcga    540
gtcaccatct ccagagacaa ttccaagaac acactgtatc tgcaaatgaa caccctgaga    600

```
gccgaggaca cagccatata ttactgtgcg atatatggtg gtaactccgg gggagagtac      660
tggggccagg gcaccctggt caccgtctcc tcatggatgg aatgggatcg cgaaatcaac      720
aactacacct ccctgattca ctccctgatt gaggaatccc agaatcaaca ggagaagaac      780
gaacaagagc ttctggagct ggacaaatgg gcctccctgt ggaactggtt c               831
```

```
<210> SEQ ID NO 104
<211> LENGTH: 277
<212> TYPE: PRT
<213> ORGANISM: Artificial
<220> FEATURE:
<223> OTHER INFORMATION: Anti-HIV binders contained in LTG2323

<400> SEQUENCE: 104
```

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
50                  55                  60

Gly Asn Phe Pro Leu Ile Ile Lys Asn Leu Lys Pro Glu Asp Ser Asp
65                  70                  75                  80

Thr Tyr Ile Cys Glu Val Asp Gln Lys Glu Val Gln Leu Val
                85                  90                  95

Val Val Gly Gly Gly Gly Ser Gly Gly Gly Ser Gly Gly Gly
            100                 105                 110

Gly Ser Gln Val Gln Leu Val Gln Ser Gly Gly Gly Leu Val Gln Pro
        115                 120                 125

Gly Gly Ser Leu Arg Leu Ser Cys Ala Ala Ser Ala Phe Asp Phe Ser
130                 135                 140

Asp Tyr Glu Met Ser Trp Val Arg Glu Ala Pro Gly Lys Gly Leu Glu
145                 150                 155                 160

Trp Ile Gly Glu Ile Asn Asp Ser Gly Asn Thr Ile Tyr Asn Pro Ser
                165                 170                 175

Leu Lys Ser Arg Val Thr Ile Ser Arg Asp Asn Ser Lys Asn Thr Leu
            180                 185                 190

Tyr Leu Gln Met Asn Thr Leu Arg Ala Glu Asp Thr Ala Ile Tyr Tyr
        195                 200                 205

Cys Ala Ile Tyr Gly Gly Asn Ser Gly Gly Glu Tyr Trp Gly Gln Gly
210                 215                 220

Thr Leu Val Thr Val Ser Ser Trp Met Glu Trp Asp Arg Glu Ile Asn
225                 230                 235                 240

Asn Tyr Thr Ser Leu Ile His Ser Leu Ile Glu Glu Ser Gln Asn Gln
                245                 250                 255

Gln Glu Lys Asn Glu Gln Glu Leu Leu Glu Leu Asp Lys Trp Ala Ser
            260                 265                 270

Leu Trp Asn Trp Phe
        275

```
<210> SEQ ID NO 105
<211> LENGTH: 1965
<212> TYPE: DNA
<213> ORGANISM: Artificial
<220> FEATURE:
<223> OTHER INFORMATION: Anti-HIV CAR LTG2323
```

<400> SEQUENCE: 105

```
atgcttctcc tggtcaccct cctgctcctc tgcgaactgc ctcaccctgc cttccttctg      60
attcctgaca ccaagaaagt cgtgtacgga agaagggag acactgtgga gctgacctgt      120
accgcaagcc agaagaagaa catccagttc cactggaaga actccaacca aatcaagatc     180
ctggggaacc agggttcctt cctgactaag ggaccctcaa agctgaacga ccgcgtggat     240
agcagacgct ccctgtggga ccagggaaac ttcccgctta tcattaagaa cctcaaacct    300
gaggactcgg atacctacat ctgcgaagtg gaggaccaga aggaggaggt gcagctggtg    360
gtggtggggg gaggtggcgg ttcaggcgga gggggagtg gaggtggggg aagccaggtg     420
cagctggtgc agtctggggg aggcttggta cagcctggag ggtccctgag actctcctgt    480
gcagcctctg ctttcgattt ctctgattat gaaatgagct gggtccgcga ggctccaggg    540
aaggggctgg agtggattgg ggaaatcaat gatagtggaa acaccattta caatccgtcc    600
ctcaagagtc gagtcaccat ctccagagac aattccaaga acacactgta tctgcaaatg   660
aacaccctga gagccgagga cacagccata tattactgtg cgatatatgg tggtaactcc    720
gggggagagt actggggcca gggcaccctg gtcaccgtct cctcagcggc cgcaactacc   780
acccctgccc ctcggccgcc gactccggcc ccaaccatcg caagccaacc cctctccttg    840
cgccccgaag cttgccgccc ggccgcgggt ggagccgtgc ataccgggg gctggacttt     900
gcctgcgata tctacatttg gccccgctg gccggcactt gcggcgtgct cctgctgtcg     960
ctggtcatca cccttactg caagagggg cggaagaagc tgctttacat cttcaagcag    1020
ccgttcatgc ggcccgtgca gacgactcag gaagaggacg gatgctcgtg cagattccct    1080
gaggaggaag aggggggatg cgaactgcgc gtcaagttct cacggtccgc cgacgccccc    1140
gcatatcaac agggccagaa tcagctctac aacgagctga acctgggaag agagaggag    1200
tacgacgtgc tggacaagcg acgcggacgc gacccggaga tggggggaa ccacggcgg      1260
aaaaaccctc aggaaggact gtacaacgaa ctccagaaag acaagatggc ggaagcctac   1320
tcagaaatcg ggatgaaggg agagcggagg aggggaaagg gtcacgacgg gctgtaccag    1380
ggactgagca ccgccactaa ggatacctac gatgccttgc atatgcaagc actcccaccc    1440
cggcgcgcga aacgcagcgg cagcggcgcg accaactttta gcctgctgaa acaggcgggc    1500
gatgtggaag aaaacccggg cccgcgagca agaggatgg gaattcaggg gggttccgtg    1560
ctctttggct tgctcctggt cctggcagtg ttttgtcact cgggacacag cctgcagtgg   1620
atggaatggg atcgcgaaat caacaactac acctccctga ttcactccct gattgaggaa   1680
tcccagaatc aacaggagaa gaacgaacaa gagcttctgg agctggacaa atgggcctcc   1740
ctgtggaact ggttcccggc tccacgacca cccactccag ccccaacgat tgcgagccaa    1800
cctctcagtc ttcggcccga ggcttgcagg ccagccgcag gaggagcagt gcacacccga    1860
ggactggatt tcgataccgc actggcggcc gtgatctgta cgccctggc caccgtgctg    1920
ctggcgctgc tcatcctttg cgtgatctac tgcaagcggc agtag                     1965
```

<210> SEQ ID NO 106
<211> LENGTH: 654
<212> TYPE: PRT
<213> ORGANISM: Artificial
<220> FEATURE:
<223> OTHER INFORMATION: Anti-HIV CAR LTG2323

<400> SEQUENCE: 106

-continued

```
Met Leu Leu Leu Val Thr Ser Leu Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
            35                  40                  45

Gln Phe His Trp Lys Asn Ser Asn Gln Ile Lys Ile Leu Gly Asn Gln
        50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Gly Gly Gly Gly Ser
        115                 120                 125

Gly Gly Gly Gly Ser Gly Gly Gly Ser Gln Val Gln Leu Val Gln
    130                 135                 140

Ser Gly Gly Gly Leu Val Gln Pro Gly Gly Ser Leu Arg Leu Ser Cys
145                 150                 155                 160

Ala Ala Ser Ala Phe Asp Phe Ser Asp Tyr Glu Met Ser Trp Val Arg
            165                 170                 175

Glu Ala Pro Gly Lys Gly Leu Glu Trp Ile Gly Glu Ile Asn Asp Ser
            180                 185                 190

Gly Asn Thr Ile Tyr Asn Pro Ser Leu Lys Ser Arg Val Thr Ile Ser
        195                 200                 205

Arg Asp Asn Ser Lys Asn Thr Leu Tyr Leu Gln Met Asn Thr Leu Arg
210                 215                 220

Ala Glu Asp Thr Ala Ile Tyr Tyr Cys Ala Ile Tyr Gly Gly Asn Ser
225                 230                 235                 240

Gly Gly Glu Tyr Trp Gly Gln Gly Thr Leu Val Thr Val Ser Ser Ala
            245                 250                 255

Ala Ala Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
        290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Lys Arg Gly Arg Lys Lys Leu Leu Tyr
            325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
            355                 360                 365

Leu Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
            405                 410                 415

Lys Pro Arg Arg Lys Asn Pro Gln Glu Gly Leu Tyr Asn Glu Leu Gln
```

| | | | | | | | | | | | |
|---|---|---|---|---|---|---|---|---|---|---|---|
| Lys | Asp | Lys | Met | Ala | Glu | Ala | Tyr | Ser | Glu | Ile | Gly | Met | Lys | Gly | Glu |
| | | | 435 | | | | 440 | | | | 445 | | | | |
| Arg | Arg | Arg | Gly | Lys | Gly | His | Asp | Gly | Leu | Tyr | Gln | Gly | Leu | Ser | Thr |
| 450 | | | | | 455 | | | | | 460 | | | | | |
| Ala | Thr | Lys | Asp | Thr | Tyr | Asp | Ala | Leu | His | Met | Gln | Ala | Leu | Pro | Pro |
| 465 | | | | 470 | | | | | 475 | | | | | | 480 |
| Arg | Arg | Ala | Lys | Arg | Ser | Gly | Ser | Gly | Ala | Thr | Asn | Phe | Ser | Leu | Leu |
| | | | | 485 | | | | | 490 | | | | | 495 | |
| Lys | Gln | Ala | Gly | Asp | Val | Glu | Glu | Asn | Pro | Gly | Pro | Arg | Ala | Lys | Arg |
| | | | 500 | | | | | 505 | | | | | 510 | | |
| Met | Gly | Ile | Gln | Gly | Gly | Ser | Val | Leu | Phe | Gly | Leu | Leu | Leu | Val | Leu |
| | | | 515 | | | | | 520 | | | | | 525 | | |
| Ala | Val | Phe | Cys | His | Ser | Gly | His | Ser | Leu | Gln | Trp | Met | Glu | Trp | Asp |
| | | | 530 | | | | | 535 | | | | | 540 | | |
| Arg | Glu | Ile | Asn | Asn | Tyr | Thr | Ser | Leu | Ile | His | Ser | Leu | Ile | Glu | Glu |
| 545 | | | | | 550 | | | | | 555 | | | | | 560 |
| Ser | Gln | Asn | Gln | Gln | Glu | Lys | Asn | Glu | Gln | Glu | Leu | Leu | Glu | Leu | Asp |
| | | | | 565 | | | | | 570 | | | | | 575 | |
| Lys | Trp | Ala | Ser | Leu | Trp | Asn | Trp | Phe | Pro | Ala | Pro | Arg | Pro | Pro | Thr |
| | | | | 580 | | | | | 585 | | | | | 590 | |
| Pro | Ala | Pro | Thr | Ile | Ala | Ser | Gln | Pro | Leu | Ser | Leu | Arg | Pro | Glu | Ala |
| | | | 595 | | | | | 600 | | | | | 605 | | |
| Cys | Arg | Pro | Ala | Ala | Gly | Gly | Ala | Val | His | Thr | Arg | Gly | Leu | Asp | Phe |
| | | 610 | | | | | 615 | | | | | 620 | | | |
| Asp | Thr | Ala | Leu | Ala | Ala | Val | Ile | Cys | Ser | Ala | Leu | Ala | Thr | Val | Leu |
| 625 | | | | | 630 | | | | | 635 | | | | | 640 |
| Leu | Ala | Leu | Leu | Ile | Leu | Cys | Val | Ile | Tyr | Cys | Lys | Arg | Gln | | |
| | | | | 645 | | | | | 650 | | | | | | |

<210> SEQ ID NO 107
<211> LENGTH: 2304
<212> TYPE: DNA
<213> ORGANISM: Artificial
<220> FEATURE:
<223> OTHER INFORMATION: Anti-HIV CAR LTG2329

<400> SEQUENCE: 107

```
atgcttctcc tggtcacctc cctgctcctc tgcgaactgc ctcaccctgc cttccttctg    60
attcctgaca cctggatgga atgggatcgc gaaatcaaca actacacctc cctgattcac   120
tccctgattg aggaatccca gaatcaacag agaagaacg aacaagagct tctggagctg   180
gacaaatggg cctccctgtg gaactggttc ggcggagggg ggagtggagg tggcggttca   240
ggaggtgggg gaagcaagaa agtcgtgtac ggaaagaagg gagacactgt ggagctgacc   300
tgtaccgcaa gccagaagaa gaacatccag ttccactgga gaactccaa ccaaatcaag   360
atcctgggga accagggttc cttcctgact aagggaccct caaagctgaa cgaccgcgtg   420
gatagcagac gctccctgtg ggaccaggga aacttcccgc ttatcattaa gaacctcaaa   480
cctgaggact cggatacctta catctgcgaa gtggaggacc agaaggagga ggtgcagctg   540
gtggtggtgg gcgcggccgc aactaccacc cctgcccctc ggccgccgac tccggcccca   600
accatcgcaa gccaacccct ctccttgcgc ccgaagcttg ccgcccggc cgcgggtgga   660
gccgtgcata cccgggggct ggactttgcc tgcgatatct acatttgggc cccgctggcc   720
ggcacttgcg gcgtgctcct gctgtcgctg gtcatcaccc tttactgcaa gaggggccgg   780
```

-continued

```
aagaagctgc tttacatctt caagcagccg ttcatgcggc ccgtgcagac gactcaggaa    840
gaggacggat gctcgtgcag attccctgag gaggaagagg ggggatgcga actgcgcgtc    900
aagttctcac ggtccgccga cgcccccgca tatcaacagg ccagaatca gctctacaac     960 gagctgaacc tgggaaggag agaggagtac gacgtgctgg acaagcgacg cggacgcgac   1020
ccggagatgg ggggaaaacc acggcggaaa aaccctcagg aaggactgta caacgaactc   1080
cagaaagaca gatggcggaa agcctactca gaaatcggga tgaagggaga gcggaggagg   1140
ggaaagggtc acgacgggct gtaccaggga ctgagcaccg ccactaagga tacctacgat   1200
gccttgcata tgcaagcact cccaccccgg cgcgcgaaac gcagcggcag cggcgcgacc   1260
aactttagcc tgctgaaaca ggcgggcgat gtggaagaaa acccgggccc gcgagcaaag   1320
aggatgggaa ttcagggggg ttccgtgctc tttggcttgc tcctggtcct ggcagtgttt   1380
tgtcactcgg gacacagcct gcagcaggtg cagctggtgc agtctggggg aggcttggta   1440
cagcctggag ggtccctgag actctcctgt gcagcctctg ctttcgattt ctctgattat   1500
gaaatgagct gggtccgcga ggctccaggg aaggggctgg agtggattgg ggaaatcaat   1560
gatagtggaa acaccattta caatccgtcc ctcaagagtc gagtcaccat ctccagagac   1620
aattccaaga acacactgta tctgcaaatg aacaccctga gagccgagga cacagccata   1680
tattactgtg cgatatatgg tggtaactcc ggggagagt actggggcca gggcaccctg   1740
gtcaccgtct cctcaccggc tccacgacca cccactccag ccccaacgat tgcgagccaa   1800
cctctcagtc ttcggcccga ggcttgcagg ccagccgcag gaggagcagt gcacacccga   1860
ggactggatt tcgataccgc actggcggcc gtgatctgta gcgccctggc caccgtgctg   1920
ctggcgctgc tcatcctttg cgtgatctac tgcaagcggc agcgggttaa attctcccgc   1980
agcgcagacg caccgccta ccagcaagga cagaatcagc tctacaacga actgaacctt   2040
ggtaggagag aagaatatga tgttctcgac aagcgcagag ggagagatcc agagatgggt   2100
gggaagccgc aacgccggaa aaacccacaa gagggactgt acaatgaatt gcagaaagat   2160
aagatggccg aggcttactc agaaatcgga atgaagggg agcggcggag gggcaaggga   2220
catgatggtc tctaccaagg gctttcaacc gctactaagg acacttatga cgcactccac   2280
atgcaggcgc tgcctccgcg ataa                                          2304
```

<210> SEQ ID NO 108
<211> LENGTH: 767
<212> TYPE: PRT
<213> ORGANISM: Artificial
<220> FEATURE:
<223> OTHER INFORMATION: Anti-HIV CAR LTG2329

<400> SEQUENCE: 108

```
Met Leu Leu Leu Val Thr Ser Leu Leu Cys Glu Leu Pro His Pro
1               5                   10                  15

Ala Phe Leu Leu Ile Pro Asp Thr Trp Met Glu Trp Asp Arg Glu Ile
            20                  25                  30

Asn Asn Tyr Thr Ser Leu Ile His Ser Leu Ile Glu Glu Ser Gln Asn
        35                  40                  45

Gln Gln Glu Lys Asn Glu Gln Glu Leu Leu Glu Leu Asp Lys Trp Ala
    50                  55                  60

Ser Leu Trp Asn Trp Phe Gly Gly Gly Ser Gly Gly Gly Gly Ser
65                  70                  75                  80

Gly Gly Gly Gly Ser Lys Lys Val Val Tyr Gly Lys Lys Gly Asp Thr
```

```
            85                  90                  95
Val Glu Leu Thr Cys Thr Ala Ser Gln Lys Asn Ile Gln Phe His
            100                 105                 110

Trp Lys Asn Ser Asn Gln Ile Lys Ile Leu Gly Asn Gln Gly Ser Phe
            115                 120                 125

Leu Thr Lys Gly Pro Ser Lys Leu Asn Asp Arg Val Asp Ser Arg Arg
130             135                 140

Ser Leu Trp Asp Gln Gly Asn Phe Pro Leu Ile Ile Lys Asn Leu Lys
145             150                 155                 160

Pro Glu Asp Ser Asp Thr Tyr Ile Cys Glu Val Glu Asp Gln Lys Glu
                165                 170                 175

Glu Val Gln Leu Val Val Gly Ala Ala Thr Thr Pro Ala
            180                 185                 190

Pro Arg Pro Thr Pro Ala Pro Thr Ile Ala Ser Gln Pro Leu Ser
            195                 200                 205

Leu Arg Pro Glu Ala Cys Arg Pro Ala Ala Gly Gly Ala Val His Thr
            210                 215                 220

Arg Gly Leu Asp Phe Ala Cys Asp Ile Tyr Ile Trp Ala Pro Leu Ala
225             230                 235                 240

Gly Thr Cys Gly Val Leu Leu Leu Ser Leu Val Ile Thr Leu Tyr Cys
                245                 250                 255

Lys Arg Gly Arg Lys Lys Leu Leu Tyr Ile Phe Lys Gln Pro Phe Met
                260                 265                 270

Arg Pro Val Gln Thr Thr Gln Glu Glu Asp Gly Cys Ser Cys Arg Phe
            275                 280                 285

Pro Glu Glu Glu Glu Gly Gly Cys Glu Leu Arg Val Lys Phe Ser Arg
            290                 295                 300

Ser Ala Asp Ala Pro Ala Tyr Gln Gln Gly Gln Asn Gln Leu Tyr Asn
305             310                 315                 320

Glu Leu Asn Leu Gly Arg Arg Glu Glu Tyr Asp Val Leu Asp Lys Arg
                325                 330                 335

Arg Gly Arg Asp Pro Glu Met Gly Gly Lys Pro Arg Arg Lys Asn Pro
            340                 345                 350

Gln Glu Gly Leu Tyr Asn Glu Leu Gln Lys Asp Lys Met Ala Glu Ala
                355                 360                 365

Tyr Ser Glu Ile Gly Met Lys Gly Glu Arg Arg Arg Gly Lys Gly His
            370                 375                 380

Asp Gly Leu Tyr Gln Gly Leu Ser Thr Ala Thr Lys Asp Thr Tyr Asp
385             390                 395                 400

Ala Leu His Met Gln Ala Leu Pro Pro Arg Arg Ala Lys Arg Ser Gly
                405                 410                 415

Ser Gly Ala Thr Asn Phe Ser Leu Leu Lys Gln Ala Gly Asp Val Glu
            420                 425                 430

Glu Asn Pro Gly Pro Arg Ala Lys Arg Met Gly Ile Gln Gly Gly Ser
            435                 440                 445

Val Leu Phe Gly Leu Leu Leu Val Leu Ala Val Phe Cys His Ser Gly
            450                 455                 460

His Ser Leu Gln Gln Val Gln Leu Val Gln Ser Gly Gly Gly Leu Val
465             470                 475                 480

Gln Pro Gly Gly Ser Leu Arg Leu Ser Cys Ala Ala Ser Ala Phe Asp
            485                 490                 495

Phe Ser Asp Tyr Glu Met Ser Trp Val Arg Glu Ala Pro Gly Lys Gly
            500                 505                 510
```

Leu Glu Trp Ile Gly Glu Ile Asn Asp Ser Gly Asn Thr Ile Tyr Asn
            515                 520                 525

Pro Ser Leu Lys Ser Arg Val Thr Ile Ser Arg Asp Asn Ser Lys Asn
        530                 535                 540

Thr Leu Tyr Leu Gln Met Asn Thr Leu Arg Ala Glu Asp Thr Ala Ile
545                 550                 555                 560

Tyr Tyr Cys Ala Ile Tyr Gly Gly Asn Ser Gly Gly Glu Tyr Trp Gly
                565                 570                 575

Gln Gly Thr Leu Val Thr Val Ser Ser Pro Ala Pro Arg Pro Pro Thr
            580                 585                 590

Pro Ala Pro Thr Ile Ala Ser Gln Pro Leu Ser Leu Arg Pro Glu Ala
            595                 600                 605

Cys Arg Pro Ala Ala Gly Gly Ala Val His Thr Arg Gly Leu Asp Phe
        610                 615                 620

Asp Thr Ala Leu Ala Ala Val Ile Cys Ser Ala Leu Ala Thr Val Leu
625                 630                 635                 640

Leu Ala Leu Leu Ile Leu Cys Val Ile Tyr Cys Lys Arg Gln Arg Val
                645                 650                 655

Lys Phe Ser Arg Ser Ala Asp Ala Pro Ala Tyr Gln Gln Gly Gln Asn
            660                 665                 670

Gln Leu Tyr Asn Glu Leu Asn Leu Gly Arg Arg Glu Glu Tyr Asp Val
            675                 680                 685

Leu Asp Lys Arg Arg Gly Arg Asp Pro Glu Met Gly Gly Lys Pro Gln
        690                 695                 700

Arg Arg Lys Asn Pro Gln Glu Gly Leu Tyr Asn Glu Leu Gln Lys Asp
705                 710                 715                 720

Lys Met Ala Glu Ala Tyr Ser Glu Ile Gly Met Lys Gly Glu Arg Arg
                725                 730                 735

Arg Gly Lys Gly His Asp Gly Leu Tyr Gln Gly Leu Ser Thr Ala Thr
            740                 745                 750

Lys Asp Thr Tyr Asp Ala Leu His Met Gln Ala Leu Pro Pro Arg
        755                 760                 765

<210> SEQ ID NO 109
<211> LENGTH: 2334
<212> TYPE: DNA
<213> ORGANISM: Artificial
<220> FEATURE:
<223> OTHER INFORMATION: Anti-HIV CAR LTG2330

<400> SEQUENCE: 109

```
atgcttctcc tggtcacctc cctgctcctc tgcgaactgc ctcaccctgc cttccttctg      60
attcctgaca cctggatgga atgggatcgc gaaatcaaca actacacctc cctgattcac     120
tccctgattg aggaatccca gaatcaacag agaagaacg aacaagagct tctggagctg      180
gacaaatggg cctccctgtg aactggttc ggcggagggg ggagtggagg tggcggttca      240
ggaggtgggg aagcggtgg cggtggtagt ggcggtggcg gttcaaagaa agtcgtgtac      300
ggaaagaagg gagacactgt ggagctgacc tgtaccgcaa gccagaagaa gaacatccag      360
ttccactgga gaactccaa ccaaatcaag atcctgggga ccagggttc cttcctgact      420
aagggaccct caaagctgaa cgaccgcgtg atagcagac gctccctgtg ggaccaggga      480
aacttcccgc ttatcattaa gaaccctcaaa cctgaggact cggatcccta catctgcgaa      540
gtggaggacc agaaggagga ggtgcagctg gtggtggtgg gcgcggccgc aactaccacc      600
```

-continued

```
cctgcccctc ggccgccgac tccggcccca accatcgcaa gccaacccct ctccttgcgc    660
cccgaagctt gccgcccggc cgcgggtgga gccgtgcata cccggggggct ggactttgcc    720
tgcgatatct acatttgggc cccgctggcc ggcacttgcg gcgtgctcct gctgtcgctg    780
gtcatcaccc tttactgcaa gaggggccgg aagaagctgc tttacatctt caagcagccg    840
ttcatgcggc ccgtgcagac gactcaggaa gaggacggat gctcgtgcag attccctgag    900
gaggaagagg ggggatgcga actgcgcgtc aagttctcac ggtccgccga cgcccccgca    960
tatcaacagg gccagaatca gctctacaac gagctgaacc tgggaaggag agaggagtac   1020
gacgtgctgg acaagcgacg cggacgcgac ccggagatgg ggggaaaacc acggcggaaa   1080
aaccctcagg aaggactgta caacgaactc cagaaagaca agatggcgga agcctactca   1140
gaaatcggga tgaagggaga gcggaggagg ggaaagggtc acgacgggct gtaccaggga   1200
ctgagcaccg ccactaagga tacctacgat gccttgcata tgcaagcact cccaccccgg   1260
cgcgcgaaac gcagcggcag cggcgcgacc aactttagcc tgctgaaaca ggcgggcgat   1320
gtggaagaaa acccgggccc gcgagcaaag aggatgggaa ttcaggggg ttccgtgctc     1380
tttggcttgc tcctggtcct ggcagtgttt tgtcactcgg gacacagcct gcagcaggtg   1440
cagctggtgc agtctggggg aggcttggta cagcctggag ggtccctgag actctcctgt   1500
gcagcctctg ctttcgattt ctctgattat gaaatgagct gggtccgcga ggctccaggg   1560
aaggggctgg agtggattgg gaaatcaat gatagtggaa acaccattta caatccgtcc    1620
ctcaagagtc gagtcaccat ctccagagac aattccaaga acacactgta tctgcaaatg   1680
aacaccctga gagccgagga cacagccata tattactgtg cgatatatgg tggtaactcc   1740
ggggagagt actggggcca gggcacccctg gtcaccgtct cctcaccggc tccacgacca    1800
cccactccag ccccaacgat tgcgagccaa cctctcagtc ttcggcccga ggcttgcagg   1860
ccagccgcag gaggagcagt gcacacccga ggactggatt tcgataccgc actggcggcc   1920
gtgatctgta gcgccctggc caccgtgctg ctggcgctgc tcatcctttg cgtgatctac   1980
tgcaagcggc agcgggttaa attctcccgc agcgcagacg caccgcccta ccagcaagga   2040
cagaatcagc tctacaacga actgaacctt ggtaggagaa gaatatga tgttctcgac     2100
aagcgcagag ggagagatcc agagatgggt gggaagccgc aacgccggaa aaacccacaa   2160
gagggactgt acaatgaatt gcagaaagat aagatggccg aggcttactc agaaatcgga   2220
atgaagggg agcggcggag gggcaaggga catgatggtc tctaccaagg gctttcaacc    2280
gctactaagg acacttatga cgcactccac atgcaggcgc tgcctccgcg ataa         2334
```

<210> SEQ ID NO 110
<211> LENGTH: 777
<212> TYPE: PRT
<213> ORGANISM: Artificial
<220> FEATURE:
<223> OTHER INFORMATION: Anti-HIV CAR LTG2330

<400> SEQUENCE: 110

```
Met Leu Leu Leu Val Thr Ser Leu Leu Leu Cys Glu Leu Pro His Pro
1               5                   10                  15

Ala Phe Leu Leu Ile Pro Asp Thr Trp Met Glu Trp Asp Arg Glu Ile
            20                  25                  30

Asn Asn Tyr Thr Ser Leu Ile His Ser Leu Ile Glu Glu Ser Gln Asn
        35                  40                  45

Gln Gln Glu Lys Asn Glu Gln Glu Leu Leu Glu Leu Asp Lys Trp Ala
    50                  55                  60
```

-continued

Ser Leu Trp Asn Trp Phe Gly Gly Gly Ser Gly Gly Gly Ser
65                  70                  75                  80

Gly Gly Gly Gly Ser Gly Gly Gly Ser Gly Gly Gly Ser Lys
                85                  90                  95

Lys Val Val Tyr Gly Lys Lys Gly Asp Thr Val Glu Leu Thr Cys Thr
                100                 105                 110

Ala Ser Gln Lys Lys Asn Ile Gln Phe His Trp Lys Asn Ser Asn Gln
            115                 120                 125

Ile Lys Ile Leu Gly Asn Gln Gly Ser Phe Leu Thr Lys Gly Pro Ser
            130                 135                 140

Lys Leu Asn Asp Arg Val Asp Ser Arg Arg Ser Leu Trp Asp Gln Gly
145                 150                 155                 160

Asn Phe Pro Leu Ile Ile Lys Asn Leu Lys Pro Glu Asp Ser Asp Thr
                165                 170                 175

Tyr Ile Cys Glu Val Glu Asp Gln Lys Glu Glu Val Gln Leu Val Val
            180                 185                 190

Val Gly Ala Ala Ala Thr Thr Thr Pro Ala Pro Arg Pro Pro Thr Pro
            195                 200                 205

Ala Pro Thr Ile Ala Ser Gln Pro Leu Ser Leu Arg Pro Glu Ala Cys
210                 215                 220

Arg Pro Ala Ala Gly Gly Ala Val His Thr Arg Gly Leu Asp Phe Ala
225                 230                 235                 240

Cys Asp Ile Tyr Ile Trp Ala Pro Leu Ala Gly Thr Cys Gly Val Leu
                245                 250                 255

Leu Leu Ser Leu Val Ile Thr Leu Tyr Cys Lys Arg Gly Arg Lys Lys
            260                 265                 270

Leu Leu Tyr Ile Phe Lys Gln Pro Phe Met Arg Pro Val Gln Thr Thr
            275                 280                 285

Gln Glu Glu Asp Gly Cys Ser Cys Arg Phe Pro Glu Glu Glu Glu Gly
            290                 295                 300

Gly Cys Glu Leu Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
            355                 360                 365

Glu Leu Gln Lys Asp Lys Met Ala Glu Ala Tyr Ser Glu Ile Gly Met
370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
            405                 410                 415

Leu Pro Pro Arg Arg Ala Lys Arg Ser Gly Ser Gly Ala Thr Asn Phe
            420                 425                 430

Ser Leu Leu Lys Gln Ala Gly Asp Val Glu Glu Asn Pro Gly Pro Arg
            435                 440                 445

Ala Lys Arg Met Gly Ile Gln Gly Gly Ser Val Leu Phe Gly Leu Leu
            450                 455                 460

Leu Val Leu Ala Val Phe Cys His Ser Gly His Ser Leu Gln Gln Val
465                 470                 475                 480

Gln Leu Val Gln Ser Gly Gly Gly Leu Val Gln Pro Gly Gly Ser Leu
            485                 490                 495

Arg Leu Ser Cys Ala Ala Ser Ala Phe Asp Phe Ser Asp Tyr Glu Met
        500                 505                 510

Ser Trp Val Arg Glu Ala Pro Gly Lys Gly Leu Glu Trp Ile Gly Glu
    515                 520                 525

Ile Asn Asp Ser Gly Asn Thr Ile Tyr Asn Pro Ser Leu Lys Ser Arg
530                 535                 540

Val Thr Ile Ser Arg Asp Asn Ser Lys Asn Thr Leu Tyr Leu Gln Met
545                 550                 555                 560

Asn Thr Leu Arg Ala Glu Asp Thr Ala Ile Tyr Tyr Cys Ala Ile Tyr
                565                 570                 575

Gly Gly Asn Ser Gly Gly Glu Tyr Trp Gly Gln Gly Thr Leu Val Thr
            580                 585                 590

Val Ser Ser Pro Ala Pro Arg Pro Pro Thr Pro Ala Pro Thr Ile Ala
        595                 600                 605

Ser Gln Pro Leu Ser Leu Arg Pro Glu Ala Cys Arg Pro Ala Ala Gly
    610                 615                 620

Gly Ala Val His Thr Arg Gly Leu Asp Phe Asp Thr Ala Leu Ala Ala
625                 630                 635                 640

Val Ile Cys Ser Ala Leu Ala Thr Val Leu Leu Ala Leu Leu Ile Leu
                645                 650                 655

Cys Val Ile Tyr Cys Lys Arg Gln Arg Val Lys Phe Ser Arg Ser Ala
            660                 665                 670

Asp Ala Pro Ala Tyr Gln Gln Gly Gln Asn Gln Leu Tyr Asn Glu Leu
        675                 680                 685

Asn Leu Gly Arg Arg Glu Glu Tyr Asp Val Leu Asp Lys Arg Arg Gly
    690                 695                 700

Arg Asp Pro Glu Met Gly Gly Lys Pro Gln Arg Arg Lys Asn Pro Gln
705                 710                 715                 720

Glu Gly Leu Tyr Asn Glu Leu Gln Lys Asp Lys Met Ala Glu Ala Tyr
                725                 730                 735

Ser Glu Ile Gly Met Lys Gly Glu Arg Arg Arg Gly Lys Gly His Asp
            740                 745                 750

Gly Leu Tyr Gln Gly Leu Ser Thr Ala Thr Lys Asp Thr Tyr Asp Ala
        755                 760                 765

Leu His Met Gln Ala Leu Pro Pro Arg
    770                 775

<210> SEQ ID NO 111
<211> LENGTH: 831
<212> TYPE: DNA
<213> ORGANISM: Artificial
<220> FEATURE:
<223> OTHER INFORMATION: Anti-HIV binders contained in LTG2329 and
    LTG2331

<400> SEQUENCE: 111
tggatggaat gggatcgcga atcaacaac tacacctccc tgattcactc cctgattgag      60
gaatcccaga tcaacagga gaagaacgaa caagagcttc tggagctgga caaatgggcc     120
tccctgtgga actggttcgg cggagggggg agtggaggtg gcggttcagg aggtggggga     180
agcaagaaag tcgtgtacgg aaagaaggga gacactgtgg agctgacctg taccgcaagc     240
cagaagaaga acatccagtt ccactggaag aactccaacc aaatcaagat cctgggaaac     300
cagggttcct tcctgactaa ggacccctca aagctgaacg accgcgtgga tagcagacgc     360

```
tccctgtggg accagggaaa cttcccgctt atcattaaga acctcaaacc tgaggactcg    420
gatacctaca tctgcgaagt ggaggaccag aaggaggagg tgcagctggt ggtggtgggc    480
caggtgcagc tggtgcagtc tggggggaggc ttggtacagc ctggagggtc cctgagactc    540
tcctgtgcag cctctgcttt cgatttctct gattatgaaa tgagctgggt ccgcgaggct    600
ccagggaagg ggctggagtg gattgggaa atcaatgata gtggaaacac catttacaat    660
ccgtccctca agagtcgagt caccatctcc agagacaatt ccaagaacac actgtatctg    720
caaatgaaca ccctgagagc cgaggacaca gccatatatt actgtgcgat atatggtggt    780
aactccgggg gagagtactg gggccagggc accctggtca ccgtctcctc a            831
```

<210> SEQ ID NO 112
<211> LENGTH: 277
<212> TYPE: PRT
<213> ORGANISM: Artificial
<220> FEATURE:
<223> OTHER INFORMATION: Anti-HIV binders contained in LTG2329 and LTG2331

<400> SEQUENCE: 112

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe Gly Gly
        35                  40                  45

Gly Gly Ser Gly Gly Gly Gly Ser Gly Gly Gly Gly Ser Lys Lys Val
    50                  55                  60

Val Tyr Gly Lys Lys Gly Asp Thr Val Glu Leu Thr Cys Thr Ala Ser
65                  70                  75                  80

Gln Lys Lys Asn Ile Gln Phe His Trp Lys Asn Ser Asn Gln Ile Lys
                85                  90                  95

Ile Leu Gly Asn Gln Gly Ser Phe Leu Thr Lys Gly Pro Ser Lys Leu
            100                 105                 110

Asn Asp Arg Val Asp Ser Arg Ser Leu Trp Asp Gln Gly Asn Phe
        115                 120                 125

Pro Leu Ile Ile Lys Asn Leu Lys Pro Glu Asp Ser Asp Thr Tyr Ile
    130                 135                 140

Cys Glu Val Glu Asp Gln Lys Glu Glu Val Gln Leu Val Val Val Gly
145                 150                 155                 160

Gln Val Gln Leu Val Gln Ser Gly Gly Gly Leu Val Gln Pro Gly Gly
                165                 170                 175

Ser Leu Arg Leu Ser Cys Ala Ala Ser Ala Phe Asp Phe Ser Asp Tyr
            180                 185                 190

Glu Met Ser Trp Val Arg Glu Ala Pro Gly Lys Gly Leu Glu Trp Ile
        195                 200                 205

Gly Glu Ile Asn Asp Ser Gly Asn Thr Ile Tyr Asn Pro Ser Leu Lys
    210                 215                 220

Ser Arg Val Thr Ile Ser Arg Asp Asn Ser Lys Asn Thr Leu Tyr Leu
225                 230                 235                 240

Gln Met Asn Thr Leu Arg Ala Glu Asp Thr Ala Ile Tyr Tyr Cys Ala
                245                 250                 255

Ile Tyr Gly Gly Asn Ser Gly Gly Glu Tyr Trp Gly Gln Gly Thr Leu
            260                 265                 270

Val Thr Val Ser Ser
          275

<210> SEQ ID NO 113
<211> LENGTH: 1965
<212> TYPE: DNA
<213> ORGANISM: Artificial
<220> FEATURE:
<223> OTHER INFORMATION: Anti-HIV CAR LTG2331

<400> SEQUENCE: 113

```
atgcttctcc tggtcacctc cctgctcctc tgcgaactgc tcaccctgc cttccttctg      60
attcctgaca cctggatgga atgggatcgc gaaatcaaca actacaccct cctgattcac     120
tccctgattg aggaatccca gaatcaacag gagaagaacg aacaagagct tctggagctg     180
gacaaatggg cctccctgtg gaactggttc ggcggagggg ggagtggagg tggcggttca     240
ggaggtgggg gaagcaagaa agtcgtgtac ggaaagaagg agacactgt ggagctgacc      300
tgtaccgcaa gccagaagaa gaacatccag ttccactgga agaactccaa ccaaatcaag     360
atcctgggga accagggttc cttcctgact aagggaccct caaagctgaa cgaccgcgtg     420
gatagcagac gctccctgtg ggaccaggga aacttcccgc ttatcattaa gaaccctcaaa    480
cctgaggact cggataccta catctgcgaa gtggaggacc agaaggagga ggtgcagctg     540
gtggtggtgg gcgcggccgc aactaccacc cctgcccctc ggccgccgac tccgccccca    600
accatcgcaa gccaacccct ctccttgcgc cccgaagctt gccgcccggc cgcgggtgga     660
gccgtgcata cccgggggct ggactttgcc tgcgatatct acatttgggc cccgctggcc     720
ggcacttgcg gcgtgctcct gctgtcgctg gtcatcaccc tttactgcaa gaggggccgg     780
aagaagctgc tttacatctt caagcagccg ttcatgcggc ccgtgcagac gactcaggaa     840
gaggacggat gctcgtgcag attccctgag gaggaagagg ggggatgcga actgcgcgtc     900
aagttctcac ggtccgccga cgcccccgca tatcaacagg gccagaatca gctctacaac     960
gagctgaacc tgggaaggag agaggagtac gacgtgctgg acaagcgacg cggacgcgac    1020
ccggagatgg gggggaaacc acggcggaaa aaccctcagg aaggactgta caacgaactc    1080
cagaaagaca agatggcgga agcctactca gaaatcggga tgaagggaga gcggaggagg    1140
ggaaagggtc acgacgggct gtaccaggga ctgagcaccg ccactaagga tacctacgat    1200
gccttgcata tgcaagcact cccacccccgg cgcgcgaaac gcagcggcag cggcgcgacc   1260
aactttagcc tgctgaaaca ggcgggcgat gtggaagaaa acccgggccc gcgagcaaag    1320
aggatgggaa ttcagggggg ttccgtgctc tttggcttgc tcctggtcct ggcagtgttt    1380
tgtcactcgg acacagcct gcagcaggtg cagctggtgc agtctggggg aggcttggta    1440
cagcctggag ggtccctgag actctcctgt gcagcctctg ctttcgattt ctctgattat    1500
gaaatgagct gggtccgcga ggctccaggg aaggggctgg agtggattgg ggaaatcaat    1560
gatagtggaa acaccattta caatccgtcc ctcaagagtc gagtcaccat ctccagagac    1620
aattccaaga acacactgta tctgcaaatg aacaccctga gagccgagga cacagccata    1680
tattactgtg cgatatatgg tggtaactcc gggggagagt actggggcca gggcaccctg    1740
gtcaccgtct cctcaccggc tccacgacca cccactccag ccccaacgat gcgagccaa    1800
cctctcagtc ttcggcccga ggcttgcagg ccagccgcag gaggagcagt gcacaccga    1860
ggactggatt tcgataccgc actggcggcc gtgatctgta cgccctggc accgtgctg    1920
ctggcgctgc tcatcctttg cgtgatctac tgcaagcggc agtag              1965
```

```
<210> SEQ ID NO 114
<211> LENGTH: 654
<212> TYPE: PRT
<213> ORGANISM: Artificial
<220> FEATURE:
<223> OTHER INFORMATION: Anti-HIV CAR LTG2331

<400> SEQUENCE: 114

Met Leu Leu Leu Val Thr Ser Leu Leu Cys Glu Leu Pro His Pro
1               5                   10                  15

Ala Phe Leu Leu Ile Pro Asp Thr Trp Met Glu Trp Asp Arg Glu Ile
                20                  25                  30

Asn Asn Tyr Thr Ser Leu Ile His Ser Leu Ile Glu Glu Ser Gln Asn
            35                  40                  45

Gln Gln Glu Lys Asn Glu Gln Glu Leu Leu Glu Leu Asp Lys Trp Ala
        50                  55                  60

Ser Leu Trp Asn Trp Phe Gly Gly Gly Ser Gly Gly Gly Gly Ser
65                  70                  75                  80

Gly Gly Gly Gly Ser Lys Lys Val Val Tyr Gly Lys Lys Gly Asp Thr
                85                  90                  95

Val Glu Leu Thr Cys Thr Ala Ser Gln Lys Lys Asn Ile Gln Phe His
                100                 105                 110

Trp Lys Asn Ser Asn Gln Ile Lys Ile Leu Gly Asn Gln Gly Ser Phe
            115                 120                 125

Leu Thr Lys Gly Pro Ser Lys Leu Asn Asp Arg Val Asp Ser Arg Arg
        130                 135                 140

Ser Leu Trp Asp Gln Gly Asn Phe Pro Leu Ile Ile Lys Asn Leu Lys
145                 150                 155                 160

Pro Glu Asp Ser Asp Thr Tyr Ile Cys Glu Val Glu Asp Gln Lys Glu
                165                 170                 175

Glu Val Gln Leu Val Val Val Gly Ala Ala Ala Thr Thr Thr Pro Ala
                180                 185                 190

Pro Arg Pro Pro Thr Pro Ala Pro Thr Ile Ala Ser Gln Pro Leu Ser
            195                 200                 205

Leu Arg Pro Glu Ala Cys Arg Pro Ala Ala Gly Gly Ala Val His Thr
        210                 215                 220

Arg Gly Leu Asp Phe Ala Cys Asp Ile Tyr Ile Trp Ala Pro Leu Ala
225                 230                 235                 240

Gly Thr Cys Gly Val Leu Leu Leu Ser Leu Val Ile Thr Leu Tyr Cys
                245                 250                 255

Lys Arg Gly Arg Lys Lys Leu Leu Tyr Ile Phe Lys Gln Pro Phe Met
                260                 265                 270

Arg Pro Val Gln Thr Thr Gln Glu Glu Asp Gly Cys Ser Cys Arg Phe
            275                 280                 285

Pro Glu Glu Glu Glu Gly Gly Cys Glu Leu Arg Val Lys Phe Ser Arg
        290                 295                 300

Ser Ala Asp Ala Pro Ala Tyr Gln Gln Gly Gln Asn Gln Leu Tyr Asn
305                 310                 315                 320

Glu Leu Asn Leu Gly Arg Arg Glu Glu Tyr Asp Val Leu Asp Lys Arg
                325                 330                 335

Arg Gly Arg Asp Pro Glu Met Gly Gly Lys Pro Arg Arg Lys Asn Pro
                340                 345                 350

Gln Glu Gly Leu Tyr Asn Glu Leu Gln Lys Asp Lys Met Ala Glu Ala
            355                 360                 365
```

-continued

```
Tyr Ser Glu Ile Gly Met Lys Gly Glu Arg Arg Gly Lys Gly His
    370                 375                 380

Asp Gly Leu Tyr Gln Gly Leu Ser Thr Ala Thr Lys Asp Thr Tyr Asp
385                 390                 395                 400

Ala Leu His Met Gln Ala Leu Pro Pro Arg Ala Lys Arg Ser Gly
                405                 410                 415

Ser Gly Ala Thr Asn Phe Ser Leu Leu Lys Gln Ala Gly Asp Val Glu
                420                 425                 430

Glu Asn Pro Gly Pro Arg Ala Lys Arg Met Gly Ile Gln Gly Gly Ser
                435                 440                 445

Val Leu Phe Gly Leu Leu Leu Val Leu Ala Val Phe Cys His Ser Gly
    450                 455                 460

His Ser Leu Gln Gln Val Gln Leu Val Gln Ser Gly Gly Gly Leu Val
465                 470                 475                 480

Gln Pro Gly Gly Ser Leu Arg Leu Ser Cys Ala Ala Ser Ala Phe Asp
                485                 490                 495

Phe Ser Asp Tyr Glu Met Ser Trp Val Arg Glu Ala Pro Gly Lys Gly
                500                 505                 510

Leu Glu Trp Ile Gly Glu Ile Asn Asp Ser Gly Asn Thr Ile Tyr Asn
    515                 520                 525

Pro Ser Leu Lys Ser Arg Val Thr Ile Ser Arg Asp Asn Ser Lys Asn
    530                 535                 540

Thr Leu Tyr Leu Gln Met Asn Thr Leu Arg Ala Glu Asp Thr Ala Ile
545                 550                 555                 560

Tyr Tyr Cys Ala Ile Tyr Gly Gly Asn Ser Gly Gly Glu Tyr Trp Gly
                565                 570                 575

Gln Gly Thr Leu Val Thr Val Ser Ser Pro Ala Pro Arg Pro Pro Thr
                580                 585                 590

Pro Ala Pro Thr Ile Ala Ser Gln Pro Leu Ser Leu Arg Pro Glu Ala
            595                 600                 605

Cys Arg Pro Ala Ala Gly Gly Ala Val His Thr Arg Gly Leu Asp Phe
    610                 615                 620

Asp Thr Ala Leu Ala Ala Val Ile Cys Ser Ala Leu Ala Thr Val Leu
625                 630                 635                 640

Leu Ala Leu Leu Ile Leu Cys Val Ile Tyr Cys Lys Arg Gln
                645                 650
```

<210> SEQ ID NO 115
<211> LENGTH: 861
<212> TYPE: DNA
<213> ORGANISM: Artificial
<220> FEATURE:
<223> OTHER INFORMATION: Anti-HIV binders contained in LTG2330 and LTG2332

<400> SEQUENCE: 115

```
tggatggaat gggatcgcga aatcaacaac tacacctccc tgattcactc cctgattgag     60
gaatcccaga atcaacagga gaagaacgaa caagagcttc tggagctgga caaatgggcc    120
tccctgtgga actggttcgg cggagggggg agtggaggtg gcggttcagg aggtggggga    180
agcggtggcg gtggtagtgg cggtggcggt tcaaagaaag tcgtgtacgg aaagaaggga    240
gacactgtgg agctgacctg taccgcaagc cagaagaaga acatccagtt ccactggaag    300
aactccaacc aaatcaagat cctggggaac cagggttcct tcctgactaa ggaccctca    360 aagctgaacg accgcgtgga tagcagacgc tccctgtggg accagggaaa cttcccgctt    420
```

```
atcattaaga acctcaaacc tgaggactcg gataccatca tctgcgaagt ggaggaccag    480
aaggaggagg tgcagctggt ggtggtgggc caggtgcagc tggtgcagtc tgggggaggc    540
ttggtacagc ctggagggtc cctgagactc tcctgtgcag cctctgcttt cgatttctct    600
gattatgaaa tgagctgggt ccgcgaggct ccagggaagg gcctggagtg gattggggaa    660
atcaatgata gtggaaacac catttacaat ccgtccctca gagtcgagt caccatctcc      720 agagacaatt ccaagaacac actgtatctg caaatgaaca ccctgagagc cgaggacaca    780
gccatatatt actgtgcgat atatggtggt aactccgggg agagtactg gggccagggc     840 accctggtca ccgtctcctc a                                                861
```

<210> SEQ ID NO 116
<211> LENGTH: 287
<212> TYPE: PRT
<213> ORGANISM: Artificial
<220> FEATURE:
<223> OTHER INFORMATION: Anti-HIV binders contained in LTG2330 and LTG2332

<400> SEQUENCE: 116

```
Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu Asp Lys Trp Ala Ser Leu Trp Asn Trp Phe Gly Gly
        35                  40                  45

Gly Gly Ser Gly Gly Gly Ser Gly Gly Gly Ser Gly Gly Gly
    50                  55                  60

Gly Ser Gly Gly Gly Gly Ser Lys Lys Val Val Tyr Gly Lys Gly
65                  70                  75                  80

Asp Thr Val Glu Leu Thr Cys Thr Ala Ser Gln Lys Lys Asn Ile Gln
                85                  90                  95

Phe His Trp Lys Asn Ser Asn Gln Ile Lys Ile Leu Gly Asn Gln Gly
            100                 105                 110

Ser Phe Leu Thr Lys Gly Pro Ser Lys Leu Asn Asp Arg Val Asp Ser
        115                 120                 125

Arg Arg Ser Leu Trp Asp Gln Gly Asn Phe Pro Leu Ile Ile Lys Asn
    130                 135                 140

Leu Lys Pro Glu Asp Ser Asp Thr Tyr Ile Cys Glu Val Glu Asp Gln
145                 150                 155                 160

Lys Glu Glu Val Gln Leu Val Val Val Gly Gln Val Gln Leu Val Gln
                165                 170                 175

Ser Gly Gly Gly Leu Val Gln Pro Gly Gly Ser Leu Arg Leu Ser Cys
            180                 185                 190

Ala Ala Ser Ala Phe Asp Phe Ser Asp Tyr Glu Met Ser Trp Val Arg
        195                 200                 205

Glu Ala Pro Gly Lys Gly Leu Glu Trp Ile Gly Glu Ile Asn Asp Ser
    210                 215                 220

Gly Asn Thr Ile Tyr Asn Pro Ser Leu Lys Ser Arg Val Thr Ile Ser
225                 230                 235                 240

Arg Asp Asn Ser Lys Asn Thr Leu Tyr Leu Gln Met Asn Thr Leu Arg
                245                 250                 255

Ala Glu Asp Thr Ala Ile Tyr Tyr Cys Ala Ile Tyr Gly Gly Asn Ser
            260                 265                 270

Gly Gly Glu Tyr Trp Gly Gln Gly Thr Leu Val Thr Val Ser Ser
```

<210> SEQ ID NO 117
<211> LENGTH: 1995
<212> TYPE: DNA
<213> ORGANISM: Artificial
<220> FEATURE:
<223> OTHER INFORMATION: Anti-HIV CAR LTG2332

<400> SEQUENCE: 117

```
atgcttctcc tggtcacctc cctgctcctc tgcgaactgc ctcaccctgc cttccttctg      60
attcctgaca cctggatgga atgggatcgc gaaatcaaca actacacctc cctgattcac     120
tccctgattg aggaatccca gaatcaacag agagaagaacg aacaagagct tctggagctg     180
gacaaatggg cctccctgtg aactggttc ggcggagggg ggagtggagg tggcggttca     240
ggaggtgggg gaagcggtgg cggtggtagt ggcggtggcg gttcaaagaa agtcgtgtac     300
ggaaagaagg gagacactgt ggagctgacc tgtaccgcaa gccagaagaa gaacatccag     360
ttccactgga agaactccaa ccaaatcaag atcctgggga accaggggttc cttcctgact     420
aagggaccct caaagctgaa cgaccgcgtg gatagcagac gctccctgtg ggaccaggga     480
aacttcccgc ttatcattaa gaacctcaaa cctgaggact cggataccta catctgcgaa     540
gtggaggacc agaaggagga ggtgcagctg gtggtggtgg gcgcggccgc aactaccacc     600
cctgcccctc ggccgccgac tccggcccca accatcgcaa gccaacccct ctccttgcgc     660
cccgaagctt gccgcccggc cgcgggtgga gccgtgcata cccgggggct ggactttgcc     720
tgcgatatct acatttgggc cccgctgccc ggcacttgcg gcgtgctcct gctgtcgctg     780
gtcatcaccc tttactgcaa gaggggccgg aagaagctgc tttacatctt caagcagccg     840
ttcatgcggc ccgtgcagac gactcaggaa gaggacggat gctcgtgcag attccctgag     900
gaggaagagg gggatgcgga actgcgcgtc aagttctcac ggtccgccga cgcccccgca     960
tatcaacagg gccagaatca gctctacaac gagctgaacc tgggaaggag agaggagtac    1020
gacgtgctgg acaagcgacg cggacgcgac ccggagatgg ggggaaaacc acggcggaaa    1080
aaccctcagg aaggactgta caacgaactc cagaaagaca gatggcggaa agcctactca    1140
gaaatcggga tgaagggaga gcggaggagg ggaaagggtc acgacgggct gtaccaggga    1200
ctgagcaccg ccactaagga tacctacgat gccttgcata tgcaagcact cccaccccgg    1260
cgcgcgaaac gcagcggcag cggcgcgacc aactttagcc tgctgaaaca ggcgggcgat    1320
gtggaagaaa acccgggccc gcgagcaaag aggatgggaa ttcagggggg ttccgtgctc    1380
tttggcttgc tcctggtcct ggcagtgttt tgtcactcgg acacagcct gcagcaggtg    1440
cagctggtgc agtctggggg aggcttggta cagcctggag gtccctgag actctcctgt    1500
gcagcctctg ctttcgattt ctctgattat gaaatgagct gggtccgcga ggctccaggg    1560
aaggggctgg agtggattgg ggaaatcaat gatagtggaa acaccattta caatccgtcc    1620
ctcaagagtc gagtcaccat ctccagagac aattccaaga cacactgta tctgcaaatg    1680
aacacccctga gagccgagga cacagccata tattactgtg cgatatatgg tggtaactcc    1740
gggggagagt actggggcca gggcaccctg gtcaccgtct cctcaccggc tccacgacca    1800
cccactccag ccccaacgat tgcgagccaa cctctcagtc ttcggcccga ggcttgcagg    1860
ccagccgcag gaggagcagt gcacacccga ggactggatt tcgataccgc actggcggcc    1920
gtgatcgtta gcgccctggc caccgtgctg ctggcgctgc tcatccttg cgtgatctac    1980
tgcaagcggc agtag                                                    1995
```

<210> SEQ ID NO 118
<211> LENGTH: 664
<212> TYPE: PRT
<213> ORGANISM: Artificial
<220> FEATURE:
<223> OTHER INFORMATION: Anti-HIV CAR LTG2332

<400> SEQUENCE: 118

| | | | | | | | | | | | | | | | |
|---|---|---|---|---|---|---|---|---|---|---|---|---|---|---|---|
| Met | Leu | Leu | Leu | Val | Thr | Ser | Leu | Leu | Cys | Glu | Leu | Pro | His | Pro | |
| 1 | | | | 5 | | | | | 10 | | | | | 15 | |
| Ala | Phe | Leu | Leu | Ile | Pro | Asp | Thr | Trp | Met | Glu | Trp | Asp | Arg | Glu | Ile |
| | | | 20 | | | | | 25 | | | | | 30 | | |
| Asn | Asn | Tyr | Thr | Ser | Leu | Ile | His | Ser | Leu | Ile | Glu | Glu | Ser | Gln | Asn |
| | | | 35 | | | | | 40 | | | | | 45 | | |
| Gln | Gln | Glu | Lys | Asn | Glu | Gln | Glu | Leu | Leu | Glu | Leu | Asp | Lys | Trp | Ala |
| | | 50 | | | | | 55 | | | | | 60 | | | |
| Ser | Leu | Trp | Asn | Trp | Phe | Gly | Gly | Gly | Ser | Gly | Gly | Gly | Gly | Ser | |
| 65 | | | | | 70 | | | | | 75 | | | | | 80 |
| Gly | Gly | Gly | Gly | Ser | Gly | Gly | Gly | Ser | Gly | Gly | Gly | Gly | Ser | Lys | |
| | | | | 85 | | | | | 90 | | | | | 95 | |
| Lys | Val | Val | Tyr | Gly | Lys | Lys | Gly | Asp | Thr | Val | Glu | Leu | Thr | Cys | Thr |
| | | | 100 | | | | | 105 | | | | | 110 | | |
| Ala | Ser | Gln | Lys | Lys | Asn | Ile | Gln | Phe | His | Trp | Lys | Asn | Ser | Asn | Gln |
| | | | 115 | | | | | 120 | | | | | 125 | | |
| Ile | Lys | Ile | Leu | Gly | Asn | Gln | Gly | Ser | Phe | Leu | Thr | Lys | Gly | Pro | Ser |
| | | 130 | | | | | 135 | | | | | 140 | | | |
| Lys | Leu | Asn | Asp | Arg | Val | Asp | Ser | Arg | Arg | Ser | Leu | Trp | Asp | Gln | Gly |
| 145 | | | | | 150 | | | | | 155 | | | | | 160 |
| Asn | Phe | Pro | Leu | Ile | Ile | Lys | Asn | Leu | Lys | Pro | Glu | Asp | Ser | Asp | Thr |
| | | | | 165 | | | | | 170 | | | | | 175 | |
| Tyr | Ile | Cys | Glu | Val | Glu | Asp | Gln | Lys | Glu | Glu | Val | Gln | Leu | Val | Val |
| | | | 180 | | | | | 185 | | | | | 190 | | |
| Val | Gly | Ala | Ala | Ala | Thr | Thr | Thr | Pro | Ala | Pro | Arg | Pro | Pro | Thr | Pro |
| | | 195 | | | | | 200 | | | | | 205 | | | |
| Ala | Pro | Thr | Ile | Ala | Ser | Gln | Pro | Leu | Ser | Leu | Arg | Pro | Glu | Ala | Cys |
| | | 210 | | | | | 215 | | | | | 220 | | | |
| Arg | Pro | Ala | Ala | Gly | Gly | Ala | Val | His | Thr | Arg | Gly | Leu | Asp | Phe | Ala |
| 225 | | | | | 230 | | | | | 235 | | | | | 240 |
| Cys | Asp | Ile | Tyr | Ile | Trp | Ala | Pro | Leu | Ala | Gly | Thr | Cys | Gly | Val | Leu |
| | | | | 245 | | | | | 250 | | | | | 255 | |
| Leu | Leu | Ser | Leu | Val | Ile | Thr | Leu | Tyr | Cys | Lys | Arg | Gly | Arg | Lys | Lys |
| | | | 260 | | | | | 265 | | | | | 270 | | |
| Leu | Leu | Tyr | Ile | Phe | Lys | Gln | Pro | Phe | Met | Arg | Pro | Val | Gln | Thr | Thr |
| | | | 275 | | | | | 280 | | | | | 285 | | |
| Gln | Glu | Glu | Asp | Gly | Cys | Ser | Cys | Arg | Phe | Pro | Glu | Glu | Glu | Glu | Gly |
| | | 290 | | | | | 295 | | | | | 300 | | | |
| Gly | Cys | Glu | Leu | Arg | Val | Lys | Phe | Ser | Arg | Ser | Ala | Asp | Ala | Pro | Ala |
| 305 | | | | | 310 | | | | | 315 | | | | | 320 |
| Tyr | Gln | Gln | Gly | Gln | Asn | Gln | Leu | Tyr | Asn | Glu | Leu | Asn | Leu | Gly | Arg |
| | | | | 325 | | | | | 330 | | | | | 335 | |
| Arg | Glu | Glu | Tyr | Asp | Val | Leu | Asp | Lys | Arg | Arg | Gly | Arg | Asp | Pro | Glu |
| | | | 340 | | | | | 345 | | | | | 350 | | |
| Met | Gly | Gly | Lys | Pro | Arg | Arg | Lys | Asn | Pro | Gln | Glu | Gly | Leu | Tyr | Asn |
| | | | 355 | | | | | 360 | | | | | 365 | | |

| Glu | Leu | Gln | Lys | Asp | Lys | Met | Ala | Glu | Ala | Tyr | Ser | Glu | Ile | Gly | Met |
|---|---|---|---|---|---|---|---|---|---|---|---|---|---|---|---|
| | 370 | | | | 375 | | | | 380 | | | | | | |

Lys Gly Glu Arg Arg Arg Gly Lys Gly His Asp Gly Leu Tyr Gln Gly
385                     390                     395                     400

Leu Ser Thr Ala Thr Lys Asp Thr Tyr Asp Ala Leu His Met Gln Ala
                405                     410                     415

Leu Pro Pro Arg Arg Ala Lys Arg Ser Gly Ser Gly Ala Thr Asn Phe
            420                     425                     430

Ser Leu Leu Lys Gln Ala Gly Asp Val Glu Glu Asn Pro Gly Pro Arg
        435                     440                     445

Ala Lys Arg Met Gly Ile Gln Gly Gly Ser Val Leu Phe Gly Leu Leu
    450                     455                     460

Leu Val Leu Ala Val Phe Cys His Ser Gly His Ser Leu Gln Gln Val
465                     470                     475                     480

Gln Leu Val Gln Ser Gly Gly Gly Leu Val Gln Pro Gly Gly Ser Leu
                485                     490                     495

Arg Leu Ser Cys Ala Ala Ser Ala Phe Asp Phe Ser Asp Tyr Glu Met
            500                     505                     510

Ser Trp Val Arg Glu Ala Pro Gly Lys Gly Leu Glu Trp Ile Gly Glu
        515                     520                     525

Ile Asn Asp Ser Gly Asn Thr Ile Tyr Asn Pro Ser Leu Lys Ser Arg
    530                     535                     540

Val Thr Ile Ser Arg Asp Asn Ser Lys Asn Thr Leu Tyr Leu Gln Met
545                     550                     555                     560

Asn Thr Leu Arg Ala Glu Asp Thr Ala Ile Tyr Tyr Cys Ala Ile Tyr
                565                     570                     575

Gly Gly Asn Ser Gly Gly Glu Tyr Trp Gly Gln Gly Thr Leu Val Thr
            580                     585                     590

Val Ser Ser Pro Ala Pro Arg Pro Pro Thr Pro Ala Pro Thr Ile Ala
        595                     600                     605

Ser Gln Pro Leu Ser Leu Arg Pro Glu Ala Cys Arg Pro Ala Ala Gly
    610                     615                     620

Gly Ala Val His Thr Arg Gly Leu Asp Phe Asp Thr Ala Leu Ala Ala
625                     630                     635                     640

Val Ile Cys Ser Ala Leu Ala Thr Val Leu Leu Ala Leu Leu Ile Leu
                645                     650                     655

Cys Val Ile Tyr Cys Lys Arg Gln
            660

<210> SEQ ID NO 119
<211> LENGTH: 861
<212> TYPE: DNA
<213> ORGANISM: Artificial
<220> FEATURE:
<223> OTHER INFORMATION: Anti-HIV binders contained in LTG2334

<400> SEQUENCE: 119
aagaaagtcg tgtacggaaa gaagggagac actgtggagc tgacctgtac cgcaagccag      60
aagaagaaca tccagttcca ctggaagaac tccaaccaaa tcaagatcct ggggaaccag     120
ggttccttcc tgactaaggg accctcaaag ctgaacgacc gcgtggatag cagacgctcc     180
ctgtgggacc agggaaactt cccgcttatc attaagaacc tcaaacctga ggactcggat     240
acctacatct gcgaagtgga ggaccagaag gaggaggtgc agctggtggt ggtgggcggc     300
ggaggcgggt caggtggcgg tggtagtggc ggtggcggtt caggcggtgg tgggagtggg     360

```
ggaggaggca gccaggtgca gctggtgcag tctgggggag gcttggtaca gcctggaggg    420
tccctgagac tctcctgtgc agcctctgct ttcgatttct ctgattatga aatgagctgg    480
gtccgcgagg ctccagggaa ggggctggag tggattgggg aaatcaatga tagtggaaac    540
accatttaca atccgtccct caagagtcga gtcaccatct ccagagacaa ttccaagaac    600
acactgtatc tgcaaatgaa caccctgaga gccgaggaca cagccatata ttactgtgcg    660
atatatggtg gtaactccgg gggagagtac tggggccagg gcaccctggt caccgtctcc    720
tcatggatgg aatgggatcg cgaaatcaac aactacacct ccctgattca ctccctgatt    780
gaggaatccc agaatcaaca ggagaagaac gaacaagagc ttctggagct ggacaaatgg    840
gcctccctgt ggaactggtt c                                              861
```

<210> SEQ ID NO 120
<211> LENGTH: 287
<212> TYPE: PRT
<213> ORGANISM: Artificial
<220> FEATURE:
<223> OTHER INFORMATION: Anti-HIV binders contained in LTG2334

<400> SEQUENCE: 120

```
Lys Lys Val Val Tyr Gly Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Gly Gly Ser Gly Gly Gly
                100                 105                 110

Gly Ser Gly Gly Gly Ser Gly Gly Gly Ser Gln Val Gln Leu
            115                 120                 125

Val Gln Ser Gly Gly Gly Leu Val Gln Pro Gly Gly Ser Leu Arg Leu
    130                 135                 140

Ser Cys Ala Ala Ser Ala Phe Asp Phe Ser Asp Tyr Glu Met Ser Trp
145                 150                 155                 160

Val Arg Glu Ala Pro Gly Lys Gly Leu Glu Trp Ile Gly Glu Ile Asn
                165                 170                 175

Asp Ser Gly Asn Thr Ile Tyr Asn Pro Ser Leu Lys Ser Arg Val Thr
            180                 185                 190

Ile Ser Arg Asp Asn Ser Lys Asn Thr Leu Tyr Leu Gln Met Asn Thr
        195                 200                 205

Leu Arg Ala Glu Asp Thr Ala Ile Tyr Tyr Cys Ala Ile Tyr Gly Gly
    210                 215                 220

Asn Ser Gly Gly Glu Tyr Trp Gly Gln Gly Thr Leu Val Thr Val Ser
225                 230                 235                 240

Ser Trp Met Glu Trp Asp Arg Glu Ile Asn Asn Tyr Thr Ser Leu Ile
                245                 250                 255

His Ser Leu Ile Glu Glu Ser Gln Asn Gln Gln Glu Lys Asn Glu Gln
            260                 265                 270
```

Glu Leu Leu Glu Leu Asp Lys Trp Ala Ser Leu Trp Asn Trp Phe
        275                 280                 285

<210> SEQ ID NO 121
<211> LENGTH: 1995
<212> TYPE: DNA
<213> ORGANISM: Artificial
<220> FEATURE:
<223> OTHER INFORMATION: Anti-HIV CAR LTG2334

<400> SEQUENCE: 121

| | | | | |
|---|---|---|---|---|
| atgcttctcc | tggtcacctc | cctgctcctc | tgcgaactgc | ctcaccctgc cttccttctg | 60 |
| attcctgaca | ccaagaaagt | cgtgtacgga | aagaagggag | acactgtgga gctgacctgt | 120 |
| accgcaagcc | agaagaagaa | catccagttc | cactggaaga | actccaacca aatcaagatc | 180 |
| ctggggaacc | agggttcctt | cctgactaag | ggaccctcaa | agctgaacga ccgcgtggat | 240 |
| agcagacgct | ccctgtggga | ccagggaaac | ttcccgctta | tcattaagaa cctcaaacct | 300 |
| gaggactcgg | atacctacat | ctgcgaagtg | gaggaccaga | aggaggaggt gcagctggtg | 360 |
| gtggtgggcg | gcggaggcgg | gtcaggtggc | ggtggtagtg | gcggtggcgg ttcaggcggt | 420 |
| ggtgggagtg | ggggaggagg | cagccaggtg | cagctggtgc | agtctggggg aggcttggta | 480 |
| cagcctggag | ggtccctgag | actctcctgt | gcagcctctg | ctttcgattt ctctgattat | 540 |
| gaaatgagct | gggtccgcga | ggctccaggg | aaggggctgg | agtggattgg gaaaatcaat | 600 |
| gatagtggaa | acaccattta | caatccgtcc | ctcaagagtc | gagtcaccat ctccagagac | 660 |
| aattccaaga | cacactgta | tctgcaaatg | aacaccctga | gagccgagga cacagccata | 720 |
| tattactgtg | cgatatatgg | tggtaactcc | ggggagagt | actggggcca gggcaccctg | 780 |
| gtcaccgtct | cctcagcggc | cgcaactacc | accctgccc | ctcggccgcc gactccggcc | 840 |
| ccaaccatcg | caagccaacc | cctctccttg | cgccccgaag | cttgccgccc ggccgcgggt | 900 |
| ggagccgtgc | ataccggggg | ctggactttt | gcctgcgata | tctacatttg gccccgctg | 960 |
| gccggcactt | gcggcgtgct | cctgctgtcg | ctggtcatca | ccctttactg caagaggggc | 1020 |
| cggaagaagc | tgctttacat | cttcaagcag | ccgttcatgc | ggcccgtgca gacgactcag | 1080 |
| gaagaggacg | gatgctcgtg | cagattccct | gaggaggaag | aggggggatg cgaactgcgc | 1140 |
| gtcaagttct | cacggtccgc | cgacgccccc | gcatatcaac | agggccagaa tcagctctac | 1200 |
| aacgagctga | acctgggaag | gagagaggag | tacgacgtgc | tggacaagcg acgcggacgc | 1260 |
| gacccggaga | tgggggggaa | ccacggcggc | aaaaaccctc | aggaaggact gtacaacgaa | 1320 |
| ctccagaaag | acaagatggc | ggaagcctac | tcagaaatcg | gatgaaggg agagcggagg | 1380 |
| aggggaaagg | gtcacgacgg | gctgtaccag | ggactgagca | ccgccactaa ggatacctac | 1440 |
| gatgccttgc | atatgcaagc | actcccaccc | cggcgcgcga | aacgcagcgg cagcggcgcg | 1500 |
| accaacttta | gcctgctgaa | acaggcgggc | gatgtggaag | aaaacccggg cccgcgagca | 1560 |
| aagaggatgg | gaattcaggg | gggttccgtg | ctctttggct | tgctcctggt cctggcagtg | 1620 |
| ttttgtcact | cgggacacag | cctgcagtgg | atggaatggg | atcgcgaaat caacaactac | 1680 |
| acctccctga | ttcactccct | gattgaggaa | tcccagaatc | aacaggagaa gaacgaacaa | 1740 |
| gagcttctgg | agctggacaa | atgggcctcc | ctgtggaact | ggttcccggc tccacgacca | 1800 |
| cccactccag | ccccaacgat | tgcgagccaa | cctctcagtc | ttcggccga ggcttgcagg | 1860 |
| ccagccgcag | gaggagcagt | gcacacccga | ggactgaatt | tcgataccgc actggcggcc | 1920 |
| gtgatctgta | gcgccctggc | caccgtgctg | ctggcgctgc | tcatccttg cgtgatctac | 1980 | tgcaagcggc agtag 1995

<210> SEQ ID NO 122
<211> LENGTH: 664
<212> TYPE: PRT
<213> ORGANISM: Artificial
<220> FEATURE:
<223> OTHER INFORMATION: Anti-HIV CAR LTG2334

<400> SEQUENCE: 122

```
Met Leu Leu Leu Val Thr Ser Leu Leu Cys Glu Leu Pro His Pro
1               5                   10                  15

Ala Phe Leu Leu Ile Pro Asp Thr Lys Lys Val Val Tyr Gly Lys Lys
            20                  25                  30

Gly Asp Thr Val Glu Leu Thr Cys Thr Ala Ser Gln Lys Lys Asn Ile
            35                  40                  45

Gln Phe His Trp Lys Asn Ser Asn Gln Ile Lys Ile Leu Gly Asn Gln
        50                  55                  60

Gly Ser Phe Leu Thr Lys Gly Pro Ser Lys Leu Asn Asp Arg Val Asp
65                  70                  75                  80

Ser Arg Arg Ser Leu Trp Asp Gln Gly Asn Phe Pro Leu Ile Ile Lys
                85                  90                  95

Asn Leu Lys Pro Glu Asp Ser Asp Thr Tyr Ile Cys Glu Val Glu Asp
            100                 105                 110

Gln Lys Glu Glu Val Gln Leu Val Val Gly Gly Gly Gly Ser
            115                 120                 125

Gly Gly Gly Gly Ser Gly Gly Gly Ser Gly Gly Gly Ser Gly
        130                 135                 140

Gly Gly Ser Gln Val Gln Leu Val Gln Ser Gly Gly Gly Leu Val
145                 150                 155                 160

Gln Pro Gly Gly Ser Leu Arg Leu Ser Cys Ala Ala Ser Ala Phe Asp
                165                 170                 175

Phe Ser Asp Tyr Glu Met Ser Trp Val Arg Glu Ala Pro Gly Lys Gly
            180                 185                 190

Leu Glu Trp Ile Gly Glu Ile Asn Asp Ser Gly Asn Thr Ile Tyr Asn
        195                 200                 205

Pro Ser Leu Lys Ser Arg Val Thr Ile Ser Arg Asp Asn Ser Lys Asn
    210                 215                 220

Thr Leu Tyr Leu Gln Met Asn Thr Leu Arg Ala Glu Asp Thr Ala Ile
225                 230                 235                 240

Tyr Tyr Cys Ala Ile Tyr Gly Gly Asn Ser Gly Gly Glu Tyr Trp Gly
                245                 250                 255

Gln Gly Thr Leu Val Thr Val Ser Ser Ala Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350
```

Met Arg Pro Val Gln Thr Thr Gln Glu Glu Asp Gly Cys Ser Cys Arg
355                 360                 365

Phe Pro Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
            435                 440                 445

Ala Tyr Ser Glu Ile Gly Met Lys Gly Glu Arg Arg Arg Gly Lys Gly
450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg Ala Lys Arg Ser
                485                 490                 495

Gly Ser Gly Ala Thr Asn Phe Ser Leu Leu Lys Gln Ala Gly Asp Val
            500                 505                 510

Glu Glu Asn Pro Gly Pro Arg Ala Lys Arg Met Gly Ile Gln Gly Gly
            515                 520                 525

Ser Val Leu Phe Gly Leu Leu Leu Val Leu Ala Val Phe Cys His Ser
            530                 535                 540

Gly His Ser Leu Gln Trp Met Glu Trp Asp Arg Glu Ile Asn Asn Tyr
545                 550                 555                 560

Thr Ser Leu Ile His Ser Leu Ile Glu Glu Ser Gln Asn Gln Gln Glu
                565                 570                 575

Lys Asn Glu Gln Glu Leu Leu Glu Leu Asp Lys Trp Ala Ser Leu Trp
            580                 585                 590

Asn Trp Phe Pro Ala Pro Arg Pro Pro Thr Pro Ala Pro Thr Ile Ala
            595                 600                 605

Ser Gln Pro Leu Ser Leu Arg Pro Glu Ala Cys Arg Pro Ala Ala Gly
610                 615                 620

Gly Ala Val His Thr Arg Gly Leu Asp Phe Asp Thr Ala Leu Ala Ala
625                 630                 635                 640

Val Ile Cys Ser Ala Leu Ala Thr Val Leu Leu Ala Leu Leu Ile Leu
                645                 650                 655

Cys Val Ile Tyr Cys Lys Arg Gln
            660

<210> SEQ ID NO 123
<211> LENGTH: 20
<212> TYPE: DNA
<213> ORGANISM: Artificial
<220> FEATURE:
<223> OTHER INFORMATION: synthetic primers

<400> SEQUENCE: 123
ggagttgaga ccagtgtagt                                          20

<210> SEQ ID NO 124
<211> LENGTH: 20
<212> TYPE: DNA
<213> ORGANISM: Artificial
<220> FEATURE:
<223> OTHER INFORMATION: synthetic primers

```
<400> SEQUENCE: 124
ccactcctga caactactct                                              20

<210> SEQ ID NO 125
<211> LENGTH: 24
<212> TYPE: DNA
<213> ORGANISM: Artificial
<220> FEATURE:
<223> OTHER INFORMATION: synthetic probe

<400> SEQUENCE: 125
cagtaggtga aggagtcgta gttg                                         24

<210> SEQ ID NO 126
<211> LENGTH: 22
<212> TYPE: DNA
<213> ORGANISM: Artificial
<220> FEATURE:
<223> OTHER INFORMATION: synthetic primers

<400> SEQUENCE: 126
tctccattcc ctatgttcat gc                                           22

<210> SEQ ID NO 127
<211> LENGTH: 22
<212> TYPE: DNA
<213> ORGANISM: Artificial
<220> FEATURE:
<223> OTHER INFORMATION: synthetic primers

<400> SEQUENCE: 127
gttcccgcag aatggtgagg tg                                           22

<210> SEQ ID NO 128
<211> LENGTH: 20
<212> TYPE: DNA
<213> ORGANISM: Artificial
<220> FEATURE:
<223> OTHER INFORMATION: synthetic probe

<400> SEQUENCE: 128
atgttcctcg gaccaacttg                                              20
```